(12) United States Patent
Smith et al.

(10) Patent No.: US 7,807,168 B2
(45) Date of Patent: Oct. 5, 2010

(54) SELECTION OF HUMAN TNFα SPECIFIC ANTIBODIES

(75) Inventors: Ernest S. Smith, Ontario, NY (US); Leslie A. Croy, Lakeville, NY (US); Maria G. M. Scrivens, Rochester, NY (US)

(73) Assignee: Vaccinex, Inc., Rochester, NY (US)

(*) Notice: Subject to any disclaimer, the term of this patent is extended or adjusted under 35 U.S.C. 154(b) by 0 days.

(21) Appl. No.: 12/100,008

(22) Filed: Apr. 9, 2008

(65) Prior Publication Data

US 2008/0267974 A1 Oct. 30, 2008

Related U.S. Application Data

(60) Provisional application No. 60/907,599, filed on Apr. 10, 2007.

(51) Int. Cl.
*A61K 39/395* (2006.01)
(52) U.S. Cl. .................. 424/145.1; 530/388.23
(58) Field of Classification Search .............. None
See application file for complete search history.

(56) References Cited

U.S. PATENT DOCUMENTS

| | | | |
|---|---|---|---|
| 4,444,887 A | 4/1984 | Hoffmann | |
| 4,474,893 A | 10/1984 | Reading | |
| 4,694,778 A | 9/1987 | Learn et al. | |
| 4,714,681 A | 12/1987 | Reading | |
| 4,716,111 A | 12/1987 | Osband et al. | |
| 4,816,397 A | 3/1989 | Boss et al. | |
| 4,816,567 A | 3/1989 | Cabilly et al. | |
| 4,925,648 A | 5/1990 | Hansen et al. | |
| 4,946,778 A | 8/1990 | Ladner et al. | |
| 5,122,464 A | 6/1992 | Wilson et al. | |
| 5,223,409 A | 6/1993 | Ladner et al. | |
| 5,258,498 A | 11/1993 | Huston et al. | |
| 5,403,484 A | 4/1995 | Ladner et al. | |
| 5,413,923 A | 5/1995 | Kucherlapati et al. | |
| 5,427,908 A | 6/1995 | Dower et al. | |
| 5,516,637 A | 5/1996 | Huang et al. | |
| 5,545,806 A | 8/1996 | Lonberg et al. | |
| 5,565,332 A | 10/1996 | Hoogenboom et al. | |
| 5,569,825 A | 10/1996 | Lonberg et al. | |
| 5,571,698 A | 11/1996 | Ladner et al. | |
| 5,573,920 A | 11/1996 | Randle | |
| 5,580,717 A | 12/1996 | Dower et al. | |
| 5,585,089 A | 12/1996 | Queen et al. | |
| 5,589,369 A | 12/1996 | Seidman et al. | |
| 5,591,669 A | 1/1997 | Krimpenfort et al. | |
| 5,601,819 A | 2/1997 | Wong et al. | |
| 5,625,126 A | 4/1997 | Lonberg et al. | |
| 5,633,425 A | 5/1997 | Lonberg et al. | |
| 5,658,570 A | 8/1997 | Newman et al. | |
| 5,658,727 A | 8/1997 | Barbas et al. | |
| 5,661,016 A | 8/1997 | Lonberg et al. | |
| 5,693,761 A | 12/1997 | Queen et al. | |
| 5,693,762 A | 12/1997 | Queen et al. | |
| 5,693,780 A | 12/1997 | Newman et al. | |
| 5,698,426 A | 12/1997 | Huse | |
| 5,731,168 A | 3/1998 | Carter et al. | |
| 5,733,743 A | 3/1998 | Johnson et al. | |
| 5,750,753 A | 5/1998 | Kimae et al. | |
| 5,756,096 A | 5/1998 | Newman et al. | |
| 5,780,225 A | 7/1998 | Wigler et al. | |
| 5,807,706 A | 9/1998 | Carter et al. | |
| 5,807,715 A | 9/1998 | Morrison et al. | |
| 5,811,524 A | 9/1998 | Brams et al. | |
| 5,814,318 A | 9/1998 | Lonberg et al. | |
| 5,821,047 A | 10/1998 | Garrard et al. | |
| 5,821,333 A | 10/1998 | Carter et al. | |
| 5,837,821 A | 11/1998 | Wu | |
| 5,859,205 A * | 1/1999 | Adair et al. ............... | 530/387.3 |
| 5,892,019 A | 4/1999 | Schlom et al. | |
| 5,939,598 A | 8/1999 | Kucherlapati et al. | |
| 5,969,108 A | 10/1999 | McCafferty et al. | |
| 6,075,181 A | 6/2000 | Kucherlapati et al. | |

(Continued)

FOREIGN PATENT DOCUMENTS

WO  WO 92/22324  12/1992

(Continued)

OTHER PUBLICATIONS

Brown et al., J Immunol. May 1, 1996;156(9):3285-91.*

(Continued)

*Primary Examiner*—Zachary Skelding
(74) *Attorney, Agent, or Firm*—Sterne, Kessler, Goldstein & Fox P.L.L.C.

(57) ABSTRACT

The invention relates to antibodies which bind to tumor necrosis factor α (TNFα) and uses thereof, in particular in the diagnosis and treatment of autoimmune diseases, e.g. rheumatoid arthritis (RA). Specific human monoclonal antibodies which inhibit TNFα-mediated signalling pathways, and variants, fragments, and derivatives thereof are provided. Also provided are specific human monoclonal antibodies which block the ability of TNFα to bind to its receptor, as well as fragments, variants and derivatives of such antibodies. The invention also includes polynucleotides encoding the above antibodies or fragments, variants or derivatives thereof, as well as vectors and host cells comprising such polynucleotides. The invention further includes methods of diagnosing and treating autoimmune diseases, e.g. rheumatoid arthritis (RA), using antibodies of the invention.

32 Claims, 14 Drawing Sheets

U.S. PATENT DOCUMENTS

Figure 1:
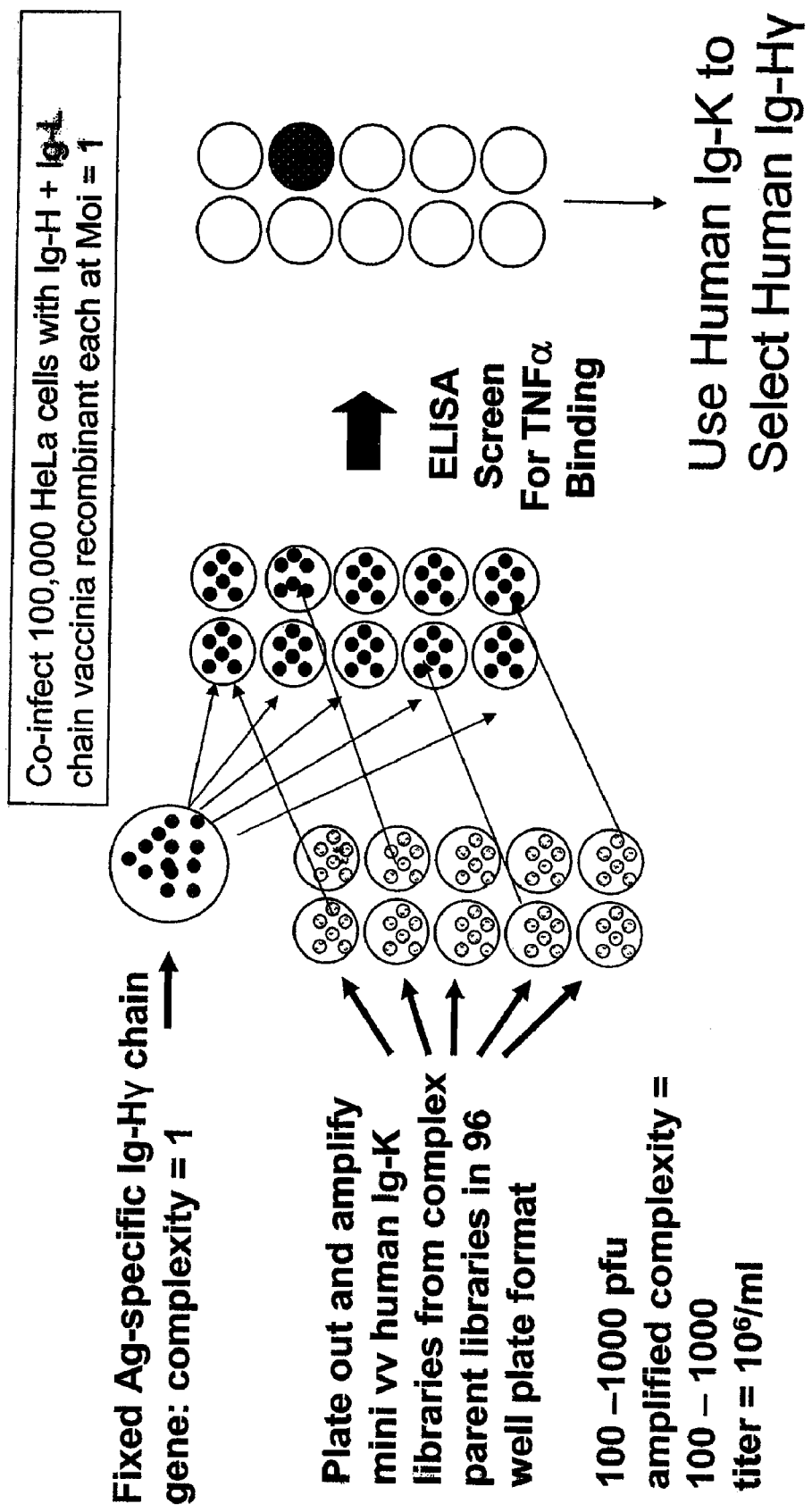

| | | | |
|---|---|---|---|
| 6,090,382 | A | 7/2000 | Salfeld et al. |
| 6,180,370 | B1 | 1/2001 | Queen et al. |
| 6,258,562 | B1 * | 7/2001 | Salfeld et al. ............ 435/69.6 |
| 6,706,477 | B2 | 3/2004 | Zauderer |
| 6,800,442 | B2 | 10/2004 | Zauderer |
| 6,872,518 | B2 | 3/2005 | Zauderer |
| 7,067,251 | B2 | 6/2006 | Zauderer et al. |
| 2002/0123057 | A1 | 9/2002 | Zauderer et al. |
| 2002/0155537 | A1 | 10/2002 | Carter et al. |
| 2006/0216293 | A1 | 9/2006 | Cuoto et al. |
| 2007/0031440 | A1 | 2/2007 | Prior et al. |

FOREIGN PATENT DOCUMENTS

| | | |
|---|---|---|
| WO | WO 00/44788 | 8/2000 |
| WO | WO 02/096948 | 12/2002 |
| WO | WO 2004/050683 A2 | 6/2004 |
| WO | WO 2007/019064 A2 | 2/2007 |

OTHER PUBLICATIONS

Harlow et al., Antibodies, Cold Spring Harbor Press, pp. 23-35 (1988).*

Eduardo Padlan, Mol Immunol. Feb. 1994;31(3):169-217.*

Portolano et al., J Immunol. Feb. 1, 1993;150(3):880-7.*

FDA Humira package insert, Sep. 26, 2003, pp. 1-18.*

Hsia et al., APLAR Journal of Rheumatology, vol. 9, No. 2, Aug. 2006, pp. 107-118.*

Janeway et al., Immunobiology, 5th Ed., Garland Science, p. 98 (2001), pp. 102-103.*

Baggiolini, M., et al., "Interleukin-8, a chemotactic and inflammatory cytokine," *FEBS Lett. 307*:97-101, Elsevier Science Publishers (May 1992).

Better, M., et al., "*Escherichia coli* secretion of an active chimeric antibody fragment," *Science 240*:1041-1043, American Association for the Advancement of Science (May 1988).

Bird, R.E., et al. "Single-chain antigen-binding proteins," *Science 242*:423-442, American Association for the Advancement of Science (Apr. 1988).

Boder, E.T., et al., "Directed evolution of antibody fragments with monovalent femtomolar antigen-binding affinity," *Proc. Natl. Acad. Sci. U.S.A. 97*:10701-05, National Academy of Sciences (Sep. 2000).

Daugherty, P.S., et al., "Flow cytometric screening of cell-based libraries," *J. Immunol. Methods 243*:211-27, Elsevier Science Publishers (Sep. 2000).

Hanes, J., et al., "Picomolar affinity antibodies from a fully synthetic naive library selected and evolved by ribosome display," *Nat. Biotechnol. 18*:1287-92, Nature Publishing Group (Dec. 2000).

Hoogenboom, H.R. and Chames, P., "Natural and designer binding sites made by phage display technology," *Immunol. Today 21*:371-78, Elsevier Science Publishers (Aug. 2000).

Huie, M.A., et al., "Antibodies to human fetal erythroid cells from a nonimmune phage antibody library," *Proc. Natl. Acad. Sci. U.S.A. 98*:2682-87, National Academy of Sciences (Feb. 2001).

Huston, J.S., et al., "Protein engineering of antibody binding sites: recovery of specific activity in an anti-digoxin single-chain Fv analogue produced in *Escherichia coli*," *Proc. Natl. Acad. Sci. U.S.A. 85*:5879-5883, National Academy of Sciences (Aug. 1988).

Irving, R.A., et al., "Ribosome display and affinity maturation: from antibodies to single V-domains and steps towards cancer therapeutics," *J. Immunol. Methods 248*:31-45, Elsevier Science Publishers (Feb. 2001).

Khabar, K.S., et al., "WEHI-13VAR: a stable and sensitive variant of WEHI 164 clone 13 fibrosarcoma for tumor necrosis factor bioassay," *Immunology Letters 46*:107-110, Elsevier Science Publishers (May 1995).

Liu, B., et al., "Towards proteome-wide production of monoclonal antibody by phage display," *J. Mol. Biol. 315*:1063-73, Elsevier Science Publishers (Feb. 2002).

Marks, J.D., et al., "By-passing immunization: building high affinity human antibodies by chain shuffling," *Biotechnology 10*:779-783, Nature Publishing Group (Jul. 1992).

Morrison, S.L., et al., "Chimeric human antibody molecules: mouse antigen-binding domains with human constant region domains," *Proc. Natl. Acad. Sci U.S.A.. 81*:6851-55, National Academy of Sciences (Nov. 1984).

Mullinax, R.L., et al., "Expression of a heterodimeric Fab antibody protein in one cloning step," *BioTechniques 12*:864-869, Informa Life Sciences Group (Jun. 1992).

Nagy, Z.A., et al., "Fully human, HLA-DR-specific monoclonal antibodies efficiently induce programmed death of malignant lymphoid cells," *Nat. Med. 8*:801-07, Nature Publishing Group (Aug. 2002).

Neuberger, M.S., et al., "Recombinant antibodies possessing novel effector functions," *Nature 312*:604-08, Nature Publishing Group (Dec. 1984).

Pennica, D., et al., "Human tumour necrosis factor: precursor structure, expression and homology to lymphotoxin," *Nature 312*:724-29, Nature Publishing Group (Jan. 1984).

Sawai, H., et al., "Direct production of the Fab fragment derived from the sperm immobilizing antibody using polymerase chain reaction and cDNA expression vectors," *Am J Reprod Immunol. 34*:26-34, Blackwell Publishing (Jul. 1995).

Scallon, B., et al., "Binding and functional comparisons of two types of tumor necrosis factor antagonists," *J Pharmacol Exp Ther. 301*:418-26, American Society for Pharmacology and Experimental Therapeutics (May 2002).

International Search Report and Written Opinion of the International Searching Authority for Intl. Appl. No. PCT/US08/04601, mailed Oct. 1, 2008.

Shu, L., et al., "Secretion of a single-gene-encoded immunoglobulin from myeloma cells," *Proc. Natl. Acad. Sci U.S.A.. 90*:7995-99, National Academy of Sciences (Sep. 1993).

Skerra, A. and Plückthun, A., "Assembly of a functional immunoglobulin Fv fragment in *Escherichia coli*," *Science 240*:1038-40, American Association for the Advancement of Science (May 1988).

Takeda, S., et al., "Construction of chimaeric processed immunoglobulin genes containing mouse variable and human constant region sequences," *Nature 314*:452-54, Nature Publishing Group (Apr. 1985).

Ward, E.S., et al., "Binding activities of a repertoire of single immunoglobulin variable domains secreted from *Escherichia coli*," *Nature 341*:544-46, Nature Publishing Group (Oct. 1989).

Wilson, D.S., et al., "The use of mRNA display to select high-affinity protein-binding peptides," *Proc. Natl. Acad. Sci. U.S.A. 98*:3750-55, National Academy of Sciences (Mar. 2001).

NCBI Database GenBank Report, Accession No. NP_000585, Jul. 20, 2008.

NCBI Database GenBank Report, Accession No. NM_000594, Jul. 20, 2008.

* cited by examiner

| MAb | ka(1/MS) | kd(1/S) | KA(1/M) | KD(pM) |
|---|---|---|---|---|
| mAb2071 | 6.92E+06 | 3.91E-05 | 1.77E+11 | 5.7 |
| mAb2090 | 6.49E+06 | 5.42E-05 | 1.20E+11 | 8.4 |
| Humira | 1.88E+06 | 5.68E-05 | 3.31E+10 | 30.3 |
| Remicade | 7.75E+06 | 9.47E-05 | 8.18E+10 | 12.2 |

FIG. 4

SEQUENCE LISTING

```
<160> NUMBER OF SEQ ID NOS: 226

<210> SEQ ID NO 1
<211> LENGTH: 1669
<212> TYPE: DNA
<213> ORGANISM: Homo sapiens

<400> SEQUENCE: 1
ctccctcagc aaggacagca gaggaccagc taagagggag agaagcaact acagaccccc      60
cctgaaaaca accctcagac gccacatccc ctgacaagct gccaggcagg ttctcttcct     120
ctcacatact gacccacggc tccaccctct ctccctgga  aaggacacca tgagcactga     180
aagcatgatc cgggacgtgg agctggccga ggaggcgctc cccaagaaga caggggggcc     240
ccagggctcc aggcggtgct tgttcctcag cctcttctcc ttcctgatcg tggcaggcgc     300
caccacgctc ttctgcctgc tgcactttgg agtgatcggc cccagaggg  aagagttccc     360 cagggacctc tctctaatca gccctctggc ccaggcagtc agatcatctt ctcgaacccc     420
gagtgacaag cctgtagccc atgttgtagc aaaccctcaa gctgaggggc agctccagtg     480
gctgaaccgc cgggccaatg ccctcctggc caatggcgtg gagctgagag ataaccagct     540
ggtggtgcca tcagagggcc tgtacctcat ctactcccag gtcctcttca agggccaagg     600
ctgcccctcc acccatgtgc tcctcaccca caccatcagc cgcatcgccg tctcctacca     660
gaccaaggtc aacctcctct ctgccatcaa gagcccctgc cagagggaga ccccagaggg     720
ggctgaggcc aagccctggt atgagcccat ctatctggga ggggtcttcc agctggagaa     780
gggtgaccga ctcagcgctg agatcaatcg gcccgactat ctcgactttg ccgagtctgg     840
gcaggtctac tttgggatca ttgccctgtg aggaggacga acatccaacc ttcccaaacg     900 cctccctgc  cccaatccct ttattacccc ctccttcaga caccctcaac ctcttctggc     960
tcaaaaagag aattggggc  ttagggtcgg aacccaagct tagaacttta agcaacaaga    1020
ccaccacttc gaaacctggg attcaggaat gtgtggcctg cacagtgaag tgctggcaac    1080
cactaagaat tcaaactggg gcctccagaa ctcactgggg cctacagctt tgatccctga    1140
catctggaat ctggagacca gggagccttt ggttctggcc agaatgctgc aggacttgag    1200
aagacctcac ctagaaattg acacaagtgg accttaggcc ttcctctctc cagatgtttc    1260
cagacttcct tgagacacgg agcccagccc tccccatgga gccagctccc tctatttatg    1320
```

```
tttgcacttg tgattattta ttatttattt attatttatt tatttacaga tgaatgtatt   1380
tatttgggag accggggtat cctgggggac ccaatgtagg agctgccttg gctcagacat   1440
gttttccgtg aaaacggagc tgaacaatag gctgttccca tgtagccccc tggcctctgt   1500
gccttctttt gattatgttt tttaaaatat ttatctgatt aagttgtcta aacaatgctg   1560
atttggtgac caactgtcac tcattgctga gcctctgctc cccagggag ttgtgtctgt    1620 aatcgcccta ctattcagtg gcgagaaata aagtttgctt agaaaagaa               1669
```

```
<210> SEQ ID NO 2
<211> LENGTH: 233
<212> TYPE: PRT
<213> ORGANISM: Homo sapiens

<400> SEQUENCE: 2

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
        50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
                100                 105                 110

Leu Ala Asn Gly Val Glu Leu Arg Asp Asn Gln Leu Val Val Pro Ser
            115                 120                 125

Glu Gly Leu Tyr Leu Ile Tyr Ser Gln Val Leu Phe Lys Gly Gln Gly
        130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
                180                 185                 190

Pro Ile Tyr Leu Gly Gly Val Phe Gln Leu Glu Lys Gly Asp Arg Leu
            195                 200                 205

Ser Ala Glu Ile Asn Arg Pro Asp Tyr Leu Asp Phe Ala Glu Ser Gly
        210                 215                 220

Gln Val Tyr Phe Gly Ile Ile Ala Leu
225                 230

<210> SEQ ID NO 3
<211> LENGTH: 117
<212> TYPE: PRT
<213> ORGANISM: Artificial Sequence
<220> FEATURE:
<223> OTHER INFORMATION: VH Sequence of variant H1192

<400> SEQUENCE: 3

Glu Val Gln Leu Leu Glu Ser Gly Gly Gly Leu Ile Gln Pro Gly Gly
1               5                   10                  15
```

```
Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Arg Thr Tyr Tyr Ala Asp Ser Val Lys
    50                  55                  60

Gly Arg Phe Thr Ile Ser Arg Asp Ser Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asn Tyr Tyr Gly Ser Thr Tyr Asp Tyr Trp Gly Gln Gly Thr Leu
            100                 105                 110

Val Thr Val Ser Ser
        115

<210> SEQ ID NO 4
<211> LENGTH: 10
<212> TYPE: PRT
<213> ORGANISM: Artificial Sequence
<220> FEATURE:
<223> OTHER INFORMATION: VH-CDR1 Sequence of variant H1192 and
      Optimized H1192

<400> SEQUENCE: 4

Gly Phe Thr Phe Ser Ser Tyr Ala Met His
1               5                   10

<210> SEQ ID NO 5
<211> LENGTH: 17
<212> TYPE: PRT
<213> ORGANISM: Artificial Sequence
<220> FEATURE:
<223> OTHER INFORMATION: VH-CDR2 Sequence of variant H1192 and
      Optimized H1192

<400> SEQUENCE: 5

Ala Ile Ser Ser Asn Gly Gly Ser Thr Tyr Tyr Ala Asp Ser Val Thr
1               5                   10                  15

Gly

<210> SEQ ID NO 6
<211> LENGTH: 9
<212> TYPE: PRT
<213> ORGANISM: Artificial Sequence
<220> FEATURE:
<223> OTHER INFORMATION: VH-CDR3 Sequence of variant H1192

<400> SEQUENCE: 6

Asn Tyr Tyr Gly Ser Thr Tyr Asp Tyr
1               5

<210> SEQ ID NO 7
<211> LENGTH: 117
<212> TYPE: PRT
<213> ORGANISM: Artificial Sequence
<220> FEATURE:
<223> OTHER INFORMATION: VH Sequence of variant H1272

<400> SEQUENCE: 7

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Val Gly Asn Asn
            20                  25                  30
```

Tyr Met Ser Trp Val Arg Gln Ala Pro Gly Lys Gly Leu Glu Trp Val
            35                  40                  45

Ser Val Ile Tyr Ser Ala Gly Ser Thr Tyr Tyr Ala Asp Ser Val Lys
        50                  55                  60

Gly Arg Phe Ile Ile Ser Arg Asp Asn Ser Lys Asp Thr Val Tyr Leu
65                  70                  75                  80

Gln Met Asn Ser Leu Arg Val Asp Asp Thr Ala Val Tyr Tyr Cys Ala
                85                  90                  95

Arg Asn Tyr Tyr Gly Ser Thr Tyr Asp Tyr Trp Gly Gln Gly Thr Leu
            100                 105                 110

Val Thr Val Ser Ser
        115

<210> SEQ ID NO 8
<211> LENGTH: 10
<212> TYPE: PRT
<213> ORGANISM: Artificial Sequence
<220> FEATURE:
<223> OTHER INFORMATION: VH-CDR1 Sequence of variant H1272 and
      Optimized H1272

<400> SEQUENCE: 8

Gly Phe Thr Val Gly Asn Asn Tyr Met Ser
1               5                   10

<210> SEQ ID NO 9
<211> LENGTH: 16
<212> TYPE: PRT
<213> ORGANISM: Artificial Sequence
<220> FEATURE:
<223> OTHER INFORMATION: VH-CDR2 Sequence of variant H1272 and
      Optimized H1272

<400> SEQUENCE: 9

Val Ile Tyr Ser Ala Gly Ser Thr Tyr Tyr Ala Asp Ser Val Lys Gly
1               5                   10                  15

<210> SEQ ID NO 10
<211> LENGTH: 9
<212> TYPE: PRT
<213> ORGANISM: Artificial Sequence
<220> FEATURE:
<223> OTHER INFORMATION: VH-CDR3 Sequence of variant H1272

<400> SEQUENCE: 10

Asn Tyr Tyr Gly Ser Thr Tyr Asp Tyr
1               5

<210> SEQ ID NO 11
<211> LENGTH: 117
<212> TYPE: PRT
<213> ORGANISM: Artificial Sequence
<220> FEATURE:
<223> OTHER INFORMATION: VH Sequence of variant H1273

<400> SEQUENCE: 11

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
            35                  40                  45

```
Ser Val Ile Tyr Ser Gly Gly Ser Thr Tyr Tyr Ala Asp Ser Val Lys
        50                  55                  60

Gly Arg Phe Thr Ile Ser Arg Asp Asn Ala Lys Asn Thr Val Tyr Leu
 65                  70                  75                  80

Gln Met Asn Ser Leu Arg Ser Glu Asp Thr Ala Val Tyr Tyr Cys Ala
                 85                  90                  95

Arg Asn Tyr Tyr Gly Ser Thr Tyr Asp Tyr Trp Gly Gln Gly Thr Leu
            100                 105                 110

Val Thr Val Ser Ser
        115

<210> SEQ ID NO 12
<211> LENGTH: 10
<212> TYPE: PRT
<213> ORGANISM: Artificial Sequence
<220> FEATURE:
<223> OTHER INFORMATION: VH-CDR1 Sequence of variant H1273

<400> SEQUENCE: 12

Gly Phe Thr Val Ser Ser Asn Tyr Met Ser
1               5                   10

<210> SEQ ID NO 13
<211> LENGTH: 16
<212> TYPE: PRT
<213> ORGANISM: Artificial Sequence
<220> FEATURE:
<223> OTHER INFORMATION: VH-CDR2 Sequence of variant H1273

<400> SEQUENCE: 13

Val Ile Tyr Ser Gly Gly Ser Thr Tyr Tyr Ala Asp Ser Val Lys Gly
1               5                   10                  15

<210> SEQ ID NO 14
<211> LENGTH: 9
<212> TYPE: PRT
<213> ORGANISM: Artificial Sequence
<220> FEATURE:
<223> OTHER INFORMATION: VH-CDR3 Sequence of variant H1273

<400> SEQUENCE: 14

Asn Tyr Tyr Gly Ser Thr Tyr Asp Tyr
1               5

<210> SEQ ID NO 15
<211> LENGTH: 117
<212> TYPE: PRT
<213> ORGANISM: Artificial Sequence
<220> FEATURE:
<223> OTHER INFORMATION: VH Sequence of variant H1278

<400> SEQUENCE: 15

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Val Ser Asn Asn
                 20                  25                  30

Tyr Met Ser Trp Val Arg Gln Ala Pro Gly Lys Gly Leu Gln Trp Val
            35                  40                  45

Ala Val Ile Tyr Ser Gly Gly Ser Thr Tyr Tyr Pro Asp Ser Met Lys
        50                  55                  60

Gly Arg Phe Thr Ile Ser Arg Asp Asn Ser Lys Asn Thr Leu Tyr Leu
 65                  70                  75                  80
```

Gln Met Asn Ser Leu Arg Ala Glu Asp Thr Ala Val Tyr Tyr Cys Ala
                85                  90                  95

Arg Asn Tyr Tyr Gly Ser Thr Tyr Asp Tyr Trp Gly Gln Gly Thr Leu
            100                 105                 110

Val Thr Val Ser Ser
        115

<210> SEQ ID NO 16
<211> LENGTH: 10
<212> TYPE: PRT
<213> ORGANISM: Artificial Sequence
<220> FEATURE:
<223> OTHER INFORMATION: VH-CDR1 Sequence of variant H1278

<400> SEQUENCE: 16

Gly Phe Thr Val Ser Asn Asn Tyr Met Ser
1               5                   10

<210> SEQ ID NO 17
<211> LENGTH: 16
<212> TYPE: PRT
<213> ORGANISM: Artificial Sequence
<220> FEATURE:
<223> OTHER INFORMATION: VH-CDR2 Sequence of variant H1278

<400> SEQUENCE: 17

Val Ile Tyr Ser Gly Gly Ser Thr Tyr Tyr Pro Asp Ser Met Lys Gly
1               5                   10                  15

<210> SEQ ID NO 18
<211> LENGTH: 9
<212> TYPE: PRT
<213> ORGANISM: Artificial Sequence
<220> FEATURE:
<223> OTHER INFORMATION: VH-CDR3 Sequence of variant H1278

<400> SEQUENCE: 18

Asn Tyr Tyr Gly Ser Thr Tyr Asp Tyr
1               5

<210> SEQ ID NO 19
<211> LENGTH: 117
<212> TYPE: PRT
<213> ORGANISM: Artificial Sequence
<220> FEATURE:
<223> OTHER INFORMATION: VH Sequence of variant H1277

<400> SEQUENCE: 19

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Arg Gly Gly Ser Thr Tyr Tyr Ala Asp Ser Val Lys
    50                  55                  60

Gly Arg Phe Thr Ile Ser Arg Asp Ile Ser Arg Asn Met Val Tyr Leu
65                  70                  75                  80

Gln Met Asn Ser Leu Arg Ala Glu Asp Thr Ala Val Tyr Tyr Cys Ala
                85                  90                  95

Arg Asn Tyr Tyr Gly Ser Thr Tyr Asp Tyr Trp Gly Gln Gly Thr Leu
            100                 105                 110

```
Val Thr Val Ser Ser
        115

<210> SEQ ID NO 20
<211> LENGTH: 10
<212> TYPE: PRT
<213> ORGANISM: Artificial Sequence
<220> FEATURE:
<223> OTHER INFORMATION: VH-CDR1 Sequence of variant H1277

<400> SEQUENCE: 20

Gly Phe Thr Val Ser Ser Asn Tyr Met Ser
1               5                   10

<210> SEQ ID NO 21
<211> LENGTH: 16
<212> TYPE: PRT
<213> ORGANISM: Artificial Sequence
<220> FEATURE:
<223> OTHER INFORMATION: VH-CDR2 Sequence of variant H1277

<400> SEQUENCE: 21

Val Ile Tyr Arg Gly Gly Ser Thr Tyr Tyr Ala Asp Ser Val Lys Gly
1               5                   10                  15

<210> SEQ ID NO 22
<211> LENGTH: 9
<212> TYPE: PRT
<213> ORGANISM: Artificial Sequence
<220> FEATURE:
<223> OTHER INFORMATION: VH-CDR3 Sequence of variant H1277

<400> SEQUENCE: 22

Asn Tyr Tyr Gly Ser Thr Tyr Asp Tyr
1               5

<210> SEQ ID NO 23
<211> LENGTH: 117
<212> TYPE: PRT
<213> ORGANISM: Artificial Sequence
<220> FEATURE:
<223> OTHER INFORMATION: VH Sequence of variant H1280

<400> SEQUENCE: 23

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
                20                  25                  30

Tyr Met Ser Trp Val Arg Gln Ala Pro Gly Lys Gly Leu Glu Trp Val
            35                  40                  45

Ser Val Ile Tyr Ser Gly Gly Ser Thr Tyr Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asn Tyr Tyr Gly Ser Thr Tyr Asp Tyr Trp Gly Gln Gly Thr Leu
            100                 105                 110

Val Thr Val Ser Ser
        115

<210> SEQ ID NO 24
<211> LENGTH: 10
```

```
<212> TYPE: PRT
<213> ORGANISM: Artificial Sequence
<220> FEATURE:
<223> OTHER INFORMATION: VH-CDR1 Sequence of variant H1280

<400> SEQUENCE: 24

Gly Phe Thr Val Ser Ser Asn Tyr Met Ser
1               5                   10

<210> SEQ ID NO 25
<211> LENGTH: 16
<212> TYPE: PRT
<213> ORGANISM: Artificial Sequence
<220> FEATURE:
<223> OTHER INFORMATION: VH-CDR2 Sequence of variant H1280

<400> SEQUENCE: 25

Val Ile Tyr Ser Gly Gly Ser Thr Tyr Tyr Ala Asp Ser Val Lys Gly
1               5                   10                  15

<210> SEQ ID NO 26
<211> LENGTH: 9
<212> TYPE: PRT
<213> ORGANISM: Artificial Sequence
<220> FEATURE:
<223> OTHER INFORMATION: VH-CDR3 Sequence of variant H1280

<400> SEQUENCE: 26

Asn Tyr Tyr Gly Ser Thr Tyr Asp Tyr
1               5

<210> SEQ ID NO 27
<211> LENGTH: 117
<212> TYPE: PRT
<213> ORGANISM: Artificial Sequence
<220> FEATURE:
<223> OTHER INFORMATION: VH Sequence of variant H1193

<400> SEQUENCE: 27

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Arg Thr Tyr Tyr Ala Asp Ser Val Lys
    50                  55                  60

Gly Arg Phe Thr Ile Ser Arg Asp Ser Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asn Tyr Tyr Gly Ser Thr Tyr Asp Tyr Trp Gly Gln Gly Thr Leu
            100                 105                 110

Val Thr Val Ser Ser
        115

<210> SEQ ID NO 28
<211> LENGTH: 10
<212> TYPE: PRT
<213> ORGANISM: Artificial Sequence
<220> FEATURE:
<223> OTHER INFORMATION: VH-CDR1 Sequence of variant H1193

<400> SEQUENCE: 28
```

```
Gly Phe Thr Val Ser Ser Asn Tyr Met Ser
1               5                   10

<210> SEQ ID NO 29
<211> LENGTH: 16
<212> TYPE: PRT
<213> ORGANISM: Artificial Sequence
<220> FEATURE:
<223> OTHER INFORMATION: VH-CDR2 Sequence of variant H1193

<400> SEQUENCE: 29

Val Ile Tyr Ser Gly Gly Arg Thr Tyr Tyr Ala Asp Ser Val Lys Gly
1               5                   10                  15

<210> SEQ ID NO 30
<211> LENGTH: 9
<212> TYPE: PRT
<213> ORGANISM: Artificial Sequence
<220> FEATURE:
<223> OTHER INFORMATION: VH-CDR3 Sequence of variant H1193

<400> SEQUENCE: 30

Asn Tyr Tyr Gly Ser Thr Tyr Asp Tyr
1               5

<210> SEQ ID NO 31
<211> LENGTH: 117
<212> TYPE: PRT
<213> ORGANISM: Artificial Sequence
<220> FEATURE:
<223> OTHER INFORMATION: VH Sequence of variant H1329

<400> SEQUENCE: 31

Glu Val Gln Leu Val Glu Ser Gly Gly Gly Leu Ile Gln Pro Gly Gly
1               5                   10                  15

Ser Leu Arg Leu Ser Cys Ala Val Ser Gly Leu Asn Val Ser Arg Asp
            20                  25                  30

Tyr Met Ser Trp Val Arg Gln Ala Pro Gly Lys Gly Leu Glu Trp Ile
        35                  40                  45

Ser Val Ile Tyr Arg Gly Gly Ala Thr Met Tyr Ala Asp Ser Val Lys
    50                  55                  60

Gly Arg Phe Thr Ile Ser Arg Asp Thr Ser Lys Asn Thr Val Phe Leu
65                  70                  75                  80

Gln Met Ser Arg Leu Lys Val Ala Asp Thr Ala Val Tyr Tyr Cys Ala
                85                  90                  95

Arg Asn Tyr Tyr Gly Ser Thr Tyr Asp Tyr Trp Gly Gln Gly Thr Leu
            100                 105                 110

Val Thr Val Ser Ser
        115

<210> SEQ ID NO 32
<211> LENGTH: 10
<212> TYPE: PRT
<213> ORGANISM: Artificial Sequence
<220> FEATURE:
<223> OTHER INFORMATION: VH-CDR1 Sequence of variant H1329 and
      Optimized H1329

<400> SEQUENCE: 32

Gly Leu Asn Val Ser Arg Asp Tyr Met Ser
1               5                   10
```

<210> SEQ ID NO 33
<211> LENGTH: 16
<212> TYPE: PRT
<213> ORGANISM: Artificial Sequence
<220> FEATURE:
<223> OTHER INFORMATION: VH-CDR2 Sequence of variant H1329 and
      Optimized H1329

<400> SEQUENCE: 33

Val Ile Tyr Arg Gly Gly Ala Thr Met Tyr Ala Asp Ser Val Lys Gly
1               5                   10                  15

<210> SEQ ID NO 34
<211> LENGTH: 9
<212> TYPE: PRT
<213> ORGANISM: Artificial Sequence
<220> FEATURE:
<223> OTHER INFORMATION: VH-CDR3 Sequence of variant H1329

<400> SEQUENCE: 34

Asn Tyr Tyr Gly Ser Thr Tyr Asp Tyr
1               5

<210> SEQ ID NO 35
<211> LENGTH: 117
<212> TYPE: PRT
<213> ORGANISM: Artificial Sequence
<220> FEATURE:
<223> OTHER INFORMATION: VH Sequence of variant H1478 (Optimized H1192)

<400> SEQUENCE: 35

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Arg Thr Tyr Tyr Ala Asp Ser Val Lys
    50                  55                  60

Gly Arg Phe Thr Ile Ser Arg Asp Ser Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Thr Tyr Tyr Gly Ser Thr Tyr Asp Tyr Trp Gly Gln Gly Thr Leu
            100                 105                 110

Val Thr Val Ser Ser
        115

<210> SEQ ID NO 36
<211> LENGTH: 9
<212> TYPE: PRT
<213> ORGANISM: Artificial Sequence
<220> FEATURE:
<223> OTHER INFORMATION: VH-CDR3 Sequence of variant H1478
      (Optimized H1192)

<400> SEQUENCE: 36

Thr Tyr Tyr Gly Ser Thr Tyr Asp Tyr
1               5

<210> SEQ ID NO 37
<211> LENGTH: 117
<212> TYPE: PRT
<213> ORGANISM: Artificial Sequence

```
<220> FEATURE:
<223> OTHER INFORMATION: VH Sequence of variant H1479 (Optimized H1192)

<400> SEQUENCE: 37

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Arg Thr Tyr Tyr Ala Asp Ser Val Lys
    50                  55                  60

Gly Arg Phe Thr Ile Ser Arg Asp Ser Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Leu Tyr Tyr Gly Ser Thr Tyr Asp Tyr Trp Gly Gln Gly Thr Leu
            100                 105                 110

Val Thr Val Ser Ser
        115

<210> SEQ ID NO 38
<211> LENGTH: 9
<212> TYPE: PRT
<213> ORGANISM: Artificial Sequence
<220> FEATURE:
<223> OTHER INFORMATION: VH-CDR3 Sequence of variant H1479
      (Optimized H1192)

<400> SEQUENCE: 38

Leu Tyr Tyr Gly Ser Thr Tyr Asp Tyr
1               5

<210> SEQ ID NO 39
<211> LENGTH: 117
<212> TYPE: PRT
<213> ORGANISM: Artificial Sequence
<220> FEATURE:
<223> OTHER INFORMATION: VH Sequence of variant H1373 (Optimized H1192)

<400> SEQUENCE: 39

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Arg Thr Tyr Tyr Ala Asp Ser Val Lys
    50                  55                  60

Gly Arg Phe Thr Ile Ser Arg Asp Ser Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asn Tyr Ala Gly Ser Thr Tyr Asp Tyr Trp Gly Gln Gly Thr Leu
            100                 105                 110

Val Thr Val Ser Ser
        115

<210> SEQ ID NO 40
```

```
<211> LENGTH: 9
<212> TYPE: PRT
<213> ORGANISM: Artificial Sequence
<220> FEATURE:
<223> OTHER INFORMATION: VH-CDR3 Sequence of variant H1373
      (Optimized H1192)

<400> SEQUENCE: 40

Asn Tyr Ala Gly Ser Thr Tyr Asp Tyr
1               5

<210> SEQ ID NO 41
<211> LENGTH: 117
<212> TYPE: PRT
<213> ORGANISM: Artificial Sequence
<220> FEATURE:
<223> OTHER INFORMATION: VH Sequence of variant H1388 (Optimized H1192)

<400> SEQUENCE: 41

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Arg Thr Tyr Tyr Ala Asp Ser Val Lys
    50                  55                  60

Gly Arg Phe Thr Ile Ser Arg Asp Ser Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asn Tyr Tyr Gly Ser Leu Tyr Asp Tyr Trp Gly Gln Gly Thr Leu
            100                 105                 110

Val Thr Val Ser Ser
        115

<210> SEQ ID NO 42
<211> LENGTH: 9
<212> TYPE: PRT
<213> ORGANISM: Artificial Sequence
<220> FEATURE:
<223> OTHER INFORMATION: VH-CDR3 Sequence of variant H1388 (Optimized
      H1192)

<400> SEQUENCE: 42

Asn Tyr Tyr Gly Ser Leu Tyr Asp Tyr
1               5

<210> SEQ ID NO 43
<211> LENGTH: 117
<212> TYPE: PRT
<213> ORGANISM: Artificial Sequence
<220> FEATURE:
<223> OTHER INFORMATION: VH Sequence of variant H1482 (Optimized H1192)

<400> SEQUENCE: 43

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45
```

```
Ser Val Ile Tyr Ser Gly Gly Arg Thr Tyr Tyr Ala Asp Ser Val Lys
        50                  55                  60

Gly Arg Phe Thr Ile Ser Arg Asp Ser Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Asn Tyr Tyr Gly Ser Thr Phe Asp Tyr Trp Gly Gln Gly Thr Leu
                100                 105                 110

Val Thr Val Ser Ser
            115

<210> SEQ ID NO 44
<211> LENGTH: 9
<212> TYPE: PRT
<213> ORGANISM: Artificial Sequence
<220> FEATURE:
<223> OTHER INFORMATION: VH-CDR3 Sequence of variant H1482 (Optimized
      H1192)

<400> SEQUENCE: 44

Asn Tyr Tyr Gly Ser Thr Phe Asp Tyr
 1               5

<210> SEQ ID NO 45
<211> LENGTH: 117
<212> TYPE: PRT
<213> ORGANISM: Artificial Sequence
<220> FEATURE:
<223> OTHER INFORMATION: VH Sequence of variant H1483 (Optimized H1192)

<400> SEQUENCE: 45

Glu Val Gln Leu Leu Glu Ser Gly Gly Gly Leu Ile Gln Pro Gly Gly
 1               5                  10                  15

Ser Leu Arg Leu Ser Cys Ala Ala Ser Gly Phe Thr Val Ser Ser Asn
             20                  25                  30

Tyr Met Ser Trp Val Arg Gln Ala Pro Gly Lys Gly Leu Glu Trp Val
         35                  40                  45

Ser Val Ile Tyr Ser Gly Gly Arg Thr Tyr Tyr Ala Asp Ser Val Lys
        50                  55                  60

Gly Arg Phe Thr Ile Ser Arg Asp Ser Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Asn Tyr Tyr Gly Ser Thr Met Asp Tyr Trp Gly Gln Gly Thr Leu
                100                 105                 110

Val Thr Val Ser Ser
            115

<210> SEQ ID NO 46
<211> LENGTH: 9
<212> TYPE: PRT
<213> ORGANISM: Artificial Sequence
<220> FEATURE:
<223> OTHER INFORMATION: VH-CDR3 Sequence of variant H1483 (Optimized
      H1192)

<400> SEQUENCE: 46

Asn Tyr Tyr Gly Ser Thr Met Asp Tyr
 1               5

<210> SEQ ID NO 47
```

```
<211> LENGTH: 117
<212> TYPE: PRT
<213> ORGANISM: Artificial Sequence
<220> FEATURE:
<223> OTHER INFORMATION: VH Sequence of variant H1487 (Optimized H1192)

<400> SEQUENCE: 47

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Arg Thr Tyr Tyr Ala Asp Ser Val Lys
    50                  55                  60

Gly Arg Phe Thr Ile Ser Arg Asp Ser Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asn Tyr Tyr Gly Ser Thr Leu Asp Tyr Trp Gly Gln Gly Thr Leu
            100                 105                 110

Val Thr Val Ser Ser
        115

<210> SEQ ID NO 48
<211> LENGTH: 9
<212> TYPE: PRT
<213> ORGANISM: Artificial Sequence
<220> FEATURE:
<223> OTHER INFORMATION: VH-CDR3 Sequence of variant H1487 (Optimized
      H1192)

<400> SEQUENCE: 48

Asn Tyr Tyr Gly Ser Thr Leu Asp Tyr
1               5

<210> SEQ ID NO 49
<211> LENGTH: 117
<212> TYPE: PRT
<213> ORGANISM: Artificial Sequence
<220> FEATURE:
<223> OTHER INFORMATION: VH Sequence of variant H1518 (Optimized H1192)

<400> SEQUENCE: 49

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Arg Thr Tyr Tyr Ala Asp Ser Val Lys
    50                  55                  60

Gly Arg Phe Thr Ile Ser Arg Asp Ser Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asn Tyr Tyr Gly Ser Thr His Asp Tyr Trp Gly Gln Gly Thr Leu
            100                 105                 110

Val Thr Val Ser Ser
        115
```

<210> SEQ ID NO 50
<211> LENGTH: 9
<212> TYPE: PRT
<213> ORGANISM: Artificial Sequence
<220> FEATURE:
<223> OTHER INFORMATION: VH-CDR3 Sequence of variant H1518 (Optimized H1192)

<400> SEQUENCE: 50

Asn Tyr Tyr Gly Ser Thr His Asp Tyr
1               5

<210> SEQ ID NO 51
<211> LENGTH: 117
<212> TYPE: PRT
<213> ORGANISM: Artificial Sequence
<220> FEATURE:
<223> OTHER INFORMATION: VH Sequence of variant H1557 (Optimized H1192)

<400> SEQUENCE: 51

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Arg Thr Tyr Tyr Ala Asp Ser Val Lys
    50                  55                  60

Gly Arg Phe Thr Ile Ser Arg Asp Ser Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asn Tyr Tyr Gly Ser Thr Val Asp Tyr Trp Gly Gln Gly Thr Leu
            100                 105                 110

Val Thr Val Ser Ser
        115

<210> SEQ ID NO 52
<211> LENGTH: 9
<212> TYPE: PRT
<213> ORGANISM: Artificial Sequence
<220> FEATURE:
<223> OTHER INFORMATION: VH-CDR3 Sequence of variant H1557 (Optimized H1192)

<400> SEQUENCE: 52

Asn Tyr Tyr Gly Ser Thr Val Asp Tyr
1               5

<210> SEQ ID NO 53
<211> LENGTH: 117
<212> TYPE: PRT
<213> ORGANISM: Artificial Sequence
<220> FEATURE:
<223> OTHER INFORMATION: VH Sequence of variant H1694 (Optimized H1329)

<400> SEQUENCE: 53

Glu Val Gln Leu Val Glu Ser Gly Gly Gly Leu Ile Gln Pro Gly Gly
1               5                   10                  15

Ser Leu Arg Leu Ser Cys Ala Val Ser Gly Leu Asn Val Ser Arg Asp
            20                  25                  30

```
Tyr Met Ser Trp Val Arg Gln Ala Pro Gly Lys Gly Leu Glu Trp Ile
            35                  40                  45

Ser Val Ile Tyr Arg Gly Gly Ala Thr Met Tyr Ala Asp Ser Val Lys
        50                  55                  60

Gly Arg Phe Thr Ile Ser Arg Asp Thr Ser Lys Asn Thr Val Phe Leu
65                  70                  75                  80

Gln Met Ser Arg Leu Lys Val Ala Asp Thr Ala Val Tyr Tyr Cys Ala
                85                  90                  95

Arg Thr Tyr Tyr Gly Ser Thr Tyr Asp Tyr Trp Gly Gln Gly Thr Leu
                100                 105                 110

Val Thr Val Ser Ser
        115

<210> SEQ ID NO 54
<211> LENGTH: 9
<212> TYPE: PRT
<213> ORGANISM: Artificial Sequence
<220> FEATURE:
<223> OTHER INFORMATION: VH-CDR3 Sequence of variant H1694 (Optimized
      H1329)

<400> SEQUENCE: 54

Thr Tyr Tyr Gly Ser Thr Tyr Asp Tyr
1               5

<210> SEQ ID NO 55
<211> LENGTH: 117
<212> TYPE: PRT
<213> ORGANISM: Artificial Sequence
<220> FEATURE:
<223> OTHER INFORMATION: VH Sequence of variant H1596 (Optimized H1329)

<400> SEQUENCE: 55

Glu Val Gln Leu Val Glu Ser Gly Gly Gly Leu Ile Gln Pro Gly Gly
1               5                   10                  15

Ser Leu Arg Leu Ser Cys Ala Val Ser Gly Leu Asn Val Ser Arg Asp
            20                  25                  30

Tyr Met Ser Trp Val Arg Gln Ala Pro Gly Lys Gly Leu Glu Trp Ile
            35                  40                  45

Ser Val Ile Tyr Arg Gly Gly Ala Thr Met Tyr Ala Asp Ser Val Lys
        50                  55                  60

Gly Arg Phe Thr Ile Ser Arg Asp Thr Ser Lys Asn Thr Val Phe Leu
65                  70                  75                  80

Gln Met Ser Arg Leu Lys Val Ala Asp Thr Ala Val Tyr Tyr Cys Ala
                85                  90                  95

Arg Asn Tyr Tyr Gly Ser Thr His Asp Tyr Trp Gly Gln Gly Thr Leu
                100                 105                 110

Val Thr Val Ser Ser
        115

<210> SEQ ID NO 56
<211> LENGTH: 9
<212> TYPE: PRT
<213> ORGANISM: Artificial Sequence
<220> FEATURE:
<223> OTHER INFORMATION: VH-CDR3 Sequence of variant H1596 (Optimized
      H1329)

<400> SEQUENCE: 56

Asn Tyr Tyr Gly Ser Thr His Asp Tyr
1               5
```

```
<210> SEQ ID NO 57
<211> LENGTH: 117
<212> TYPE: PRT
<213> ORGANISM: Artificial Sequence
<220> FEATURE:
<223> OTHER INFORMATION: VH Sequence of variant H1687 (Optimized H1329)

<400> SEQUENCE: 57

Glu Val Gln Leu Val Glu Ser Gly Gly Gly Leu Ile Gln Pro Gly Gly
1               5                   10                  15

Ser Leu Arg Leu Ser Cys Ala Val Ser Gly Leu Asn Val Ser Arg Asp
            20                  25                  30

Tyr Met Ser Trp Val Arg Gln Ala Pro Gly Lys Gly Leu Glu Trp Ile
        35                  40                  45

Ser Val Ile Tyr Arg Gly Gly Ala Thr Met Tyr Ala Asp Ser Val Lys
    50                  55                  60

Gly Arg Phe Thr Ile Ser Arg Asp Thr Ser Lys Asn Thr Val Phe Leu
65                  70                  75                  80

Gln Met Ser Arg Leu Lys Val Ala Asp Thr Ala Val Tyr Tyr Cys Ala
                85                  90                  95

Arg Asn Tyr Tyr Gly Ser Thr Met Asp Tyr Trp Gly Gln Gly Thr Leu
            100                 105                 110

Val Thr Val Ser Ser
        115

<210> SEQ ID NO 58
<211> LENGTH: 9
<212> TYPE: PRT
<213> ORGANISM: Artificial Sequence
<220> FEATURE:
<223> OTHER INFORMATION: VH-CDR3 Sequence of variant H1687 (Optimized
      H1329)

<400> SEQUENCE: 58

Asn Tyr Tyr Gly Ser Thr Met Asp Tyr
1               5

<210> SEQ ID NO 59
<211> LENGTH: 117
<212> TYPE: PRT
<213> ORGANISM: Artificial Sequence
<220> FEATURE:
<223> OTHER INFORMATION: VH Sequence of variant H1684 (Optimized H1329)

<400> SEQUENCE: 59

Glu Val Gln Leu Val Glu Ser Gly Gly Gly Leu Ile Gln Pro Gly Gly
1               5                   10                  15

Ser Leu Arg Leu Ser Cys Ala Val Ser Gly Leu Asn Val Ser Arg Asp
            20                  25                  30

Tyr Met Ser Trp Val Arg Gln Ala Pro Gly Lys Gly Leu Glu Trp Ile
        35                  40                  45

Ser Val Ile Tyr Arg Gly Gly Ala Thr Met Tyr Ala Asp Ser Val Lys
    50                  55                  60

Gly Arg Phe Thr Ile Ser Arg Asp Thr Ser Lys Asn Thr Val Phe Leu
65                  70                  75                  80

Gln Met Ser Arg Leu Lys Val Ala Asp Thr Ala Val Tyr Tyr Cys Ala
                85                  90                  95

Arg Asn Tyr Tyr Gly Ser Thr Ile Asp Tyr Trp Gly Gln Gly Thr Leu
            100                 105                 110
```

Val Thr Val Ser Ser
        115

<210> SEQ ID NO 60
<211> LENGTH: 9
<212> TYPE: PRT
<213> ORGANISM: Artificial Sequence
<220> FEATURE:
<223> OTHER INFORMATION: VH-CDR3 Sequence of variant H1684 (Optimized
      H1329)

<400> SEQUENCE: 60

Asn Tyr Tyr Gly Ser Thr Ile Asp Tyr
1               5

<210> SEQ ID NO 61
<211> LENGTH: 117
<212> TYPE: PRT
<213> ORGANISM: Artificial Sequence
<220> FEATURE:
<223> OTHER INFORMATION: VH Sequence of variant H1678 (Optimized H1329)

<400> SEQUENCE: 61

Glu Val Gln Leu Val Glu Ser Gly Gly Gly Leu Ile Gln Pro Gly Gly
1               5                   10                  15

Ser Leu Arg Leu Ser Cys Ala Val Ser Gly Leu Asn Val Ser Arg Asp
            20                  25                  30

Tyr Met Ser Trp Val Arg Gln Ala Pro Gly Lys Gly Leu Glu Trp Ile
        35                  40                  45

Ser Val Ile Tyr Arg Gly Gly Ala Thr Met Tyr Ala Asp Ser Val Lys
    50                  55                  60

Gly Arg Phe Thr Ile Ser Arg Asp Thr Ser Lys Asn Thr Val Phe Leu
65                  70                  75                  80

Gln Met Ser Arg Leu Lys Val Ala Asp Thr Ala Val Tyr Tyr Cys Ala
                85                  90                  95

Arg Asn Tyr Tyr Gly Ser Thr Phe Asp Tyr Trp Gly Gln Gly Thr Leu
            100                 105                 110

Val Thr Val Ser Ser
        115

<210> SEQ ID NO 62
<211> LENGTH: 9
<212> TYPE: PRT
<213> ORGANISM: Artificial Sequence
<220> FEATURE:
<223> OTHER INFORMATION: VH-CDR3 Sequence of variant H1678 (Optimized
      H1329)

<400> SEQUENCE: 62

Asn Tyr Tyr Gly Ser Thr Phe Asp Tyr
1               5

<210> SEQ ID NO 63
<211> LENGTH: 117
<212> TYPE: PRT
<213> ORGANISM: Artificial Sequence
<220> FEATURE:
<223> OTHER INFORMATION: VH Sequence of variant H1685 (Optimized H1329)

<400> SEQUENCE: 63

Glu Val Gln Leu Val Glu Ser Gly Gly Gly Leu Ile Gln Pro Gly Gly
1               5                   10                  15

```
Ser Leu Arg Leu Ser Cys Ala Val Ser Gly Leu Asn Val Ser Arg Asp
            20                  25                  30

Tyr Met Ser Trp Val Arg Gln Ala Pro Gly Lys Gly Leu Glu Trp Ile
            35                  40                  45

Ser Val Ile Tyr Arg Gly Gly Ala Thr Met Tyr Ala Asp Ser Val Lys
        50                  55                  60

Gly Arg Phe Thr Ile Ser Arg Asp Thr Ser Lys Asn Thr Val Phe Leu
65                  70                  75                  80

Gln Met Ser Arg Leu Lys Val Ala Asp Thr Ala Val Tyr Tyr Cys Ala
            85                  90                  95

Arg Asn Tyr Tyr Gly Ser Thr Leu Asp Tyr Trp Gly Gln Gly Thr Leu
            100                 105                 110

Val Thr Val Ser Ser
        115

<210> SEQ ID NO 64
<211> LENGTH: 9
<212> TYPE: PRT
<213> ORGANISM: Artificial Sequence
<220> FEATURE:
<223> OTHER INFORMATION: VH-CDR3 Sequence of variant H1685 (Optimized
      H1329) and Optimized H1685

<400> SEQUENCE: 64

Asn Tyr Tyr Gly Ser Thr Leu Asp Tyr
1               5

<210> SEQ ID NO 65
<211> LENGTH: 117
<212> TYPE: PRT
<213> ORGANISM: Artificial Sequence
<220> FEATURE:
<223> OTHER INFORMATION: VH Sequence of variant H1727 (Optimized H1272)

<400> SEQUENCE: 65

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Val Gly Asn Asn
            20                  25                  30

Tyr Met Ser Trp Val Arg Gln Ala Pro Gly Lys Gly Leu Glu Trp Val
            35                  40                  45

Ser Val Ile Tyr Ser Ala Gly Ser Thr Tyr Tyr Ala Asp Ser Val Lys
        50                  55                  60

Gly Arg Phe Ile Ile Ser Arg Asp Asn Ser Lys Asp Thr Val Tyr Leu
65                  70                  75                  80

Gln Met Asn Ser Leu Arg Val Asp Asp Thr Ala Val Tyr Tyr Cys Ala
            85                  90                  95

Arg Asn Tyr Tyr Gly Ser Thr His Asp Tyr Trp Gly Gln Gly Thr Leu
            100                 105                 110

Val Thr Val Ser Ser
        115

<210> SEQ ID NO 66
<211> LENGTH: 9
<212> TYPE: PRT
<213> ORGANISM: Artificial Sequence
<220> FEATURE:
<223> OTHER INFORMATION: VH-CDR3 Sequence of variant H1727 (Optimized
      H1272)

<400> SEQUENCE: 66
```

Asn Tyr Tyr Gly Ser Thr His Asp Tyr
1               5

<210> SEQ ID NO 67
<211> LENGTH: 117
<212> TYPE: PRT
<213> ORGANISM: Artificial Sequence
<220> FEATURE:
<223> OTHER INFORMATION: VH Sequence of variant H1725 (Optimized H1272)

<400> SEQUENCE: 67

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Val Gly Asn Asn
            20                  25                  30

Tyr Met Ser Trp Val Arg Gln Ala Pro Gly Lys Gly Leu Glu Trp Val
        35                  40                  45

Ser Val Ile Tyr Ser Ala Gly Ser Thr Tyr Tyr Ala Asp Ser Val Lys
    50                  55                  60

Gly Arg Phe Ile Ile Ser Arg Asp Asn Ser Lys Asp Thr Val Tyr Leu
65                  70                  75                  80

Gln Met Asn Ser Leu Arg Val Asp Asp Thr Ala Val Tyr Tyr Cys Ala
                85                  90                  95

Arg Asn Tyr Tyr Gly Ser Thr Met Asp Tyr Trp Gly Gln Gly Thr Leu
            100                 105                 110

Val Thr Val Ser Ser
        115

<210> SEQ ID NO 68
<211> LENGTH: 9
<212> TYPE: PRT
<213> ORGANISM: Artificial Sequence
<220> FEATURE:
<223> OTHER INFORMATION: VH-CDR3 Sequence of variant H1725 (Optimized
      H1272)

<400> SEQUENCE: 68

Asn Tyr Tyr Gly Ser Thr Met Asp Tyr
1               5

<210> SEQ ID NO 69
<211> LENGTH: 117
<212> TYPE: PRT
<213> ORGANISM: Artificial Sequence
<220> FEATURE:
<223> OTHER INFORMATION: VH Sequence of variant H1728 (Optimized H1272)

<400> SEQUENCE: 69

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Val Gly Asn Asn
            20                  25                  30

Tyr Met Ser Trp Val Arg Gln Ala Pro Gly Lys Gly Leu Glu Trp Val
        35                  40                  45

Ser Val Ile Tyr Ser Ala Gly Ser Thr Tyr Tyr Ala Asp Ser Val Lys
    50                  55                  60

Gly Arg Phe Ile Ile Ser Arg Asp Asn Ser Lys Asp Thr Val Tyr Leu
65                  70                  75                  80

Gln Met Asn Ser Leu Arg Val Asp Asp Thr Ala Val Tyr Tyr Cys Ala
                85                  90                  95

-continued

Arg Asn Tyr Tyr Gly Ser Thr Phe Asp Tyr Trp Gly Gln Gly Thr Leu
                100                 105                 110

Val Thr Val Ser Ser
        115

<210> SEQ ID NO 70
<211> LENGTH: 9
<212> TYPE: PRT
<213> ORGANISM: Artificial Sequence
<220> FEATURE:
<223> OTHER INFORMATION: VH-CDR3 Sequence of variant H1728 (Optimized
      H1272)

<400> SEQUENCE: 70

Asn Tyr Tyr Gly Ser Thr Phe Asp Tyr
1               5

<210> SEQ ID NO 71
<211> LENGTH: 117
<212> TYPE: PRT
<213> ORGANISM: Artificial Sequence
<220> FEATURE:
<223> OTHER INFORMATION: VH Sequence of variant H1813 (Optimized H1685)

<400> SEQUENCE: 71

Glu Val Gln Leu Val Glu Ser Gly Gly Gly Leu Ile Gln Pro Gly Gly
1               5                   10                  15

Ser Leu Arg Leu Ser Cys Ala Val Ser Gly Leu Asn Val Ser Arg Asp
            20                  25                  30

Tyr Met Ser Trp Val Arg Gln Ala Pro Gly Lys Gly Leu Glu Trp Ile
        35                  40                  45

Ser Val Ile Tyr Arg Ile Gly Ala Thr Met Tyr Ala Asp Ser Val Lys
    50                  55                  60

Gly Arg Phe Thr Ile Ser Arg Asp Thr Ser Lys Asn Thr Val Phe Leu
65                  70                  75                  80

Gln Met Ser Arg Leu Lys Val Ala Asp Thr Ala Val Tyr Tyr Cys Ala
                85                  90                  95

Arg Asn Tyr Tyr Gly Ser Thr Leu Asp Tyr Trp Gly Gln Gly Thr Leu
                100                 105                 110

Val Thr Val Ser Ser
        115

<210> SEQ ID NO 72
<211> LENGTH: 16
<212> TYPE: PRT
<213> ORGANISM: Artificial Sequence
<220> FEATURE:
<223> OTHER INFORMATION: VH-CDR2 Sequence of variant H1813 (Optimized
      H1685)

<400> SEQUENCE: 72

Val Ile Tyr Arg Ile Gly Ala Thr Met Tyr Ala Asp Ser Val Lys Gly
1               5                   10                  15

<210> SEQ ID NO 73
<211> LENGTH: 117
<212> TYPE: PRT
<213> ORGANISM: Artificial Sequence
<220> FEATURE:
<223> OTHER INFORMATION: VH Sequence of variant H1814 (Optimized H1685)

<400> SEQUENCE: 73

Glu Val Gln Leu Val Glu Ser Gly Gly Gly Leu Ile Gln Pro Gly Gly
1               5                   10                  15

Ser Leu Arg Leu Ser Cys Ala Val Ser Gly Leu Asn Val Ser Arg Asp
            20                  25                  30

Tyr Met Ser Trp Val Arg Gln Ala Pro Gly Lys Gly Leu Glu Trp Ile
            35                  40                  45

Ser Val Ile Tyr Arg Val Gly Ala Thr Met Tyr Ala Asp Ser Val Lys
50                  55                  60

Gly Arg Phe Thr Ile Ser Arg Asp Thr Ser Lys Asn Thr Val Phe Leu
65                  70                  75                  80

Gln Met Ser Arg Leu Lys Val Ala Asp Thr Ala Val Tyr Tyr Cys Ala
            85                  90                  95

Arg Asn Tyr Tyr Gly Ser Thr Leu Asp Tyr Trp Gly Gln Gly Thr Leu
            100                 105                 110

Val Thr Val Ser Ser
        115

<210> SEQ ID NO 74
<211> LENGTH: 16
<212> TYPE: PRT
<213> ORGANISM: Artificial Sequence
<220> FEATURE:
<223> OTHER INFORMATION: VH-CDR2 Sequence of variant H1814 (Optimized
      H1685)

<400> SEQUENCE: 74

Val Ile Tyr Arg Val Gly Ala Thr Met Tyr Ala Asp Ser Val Lys Gly
1               5                   10                  15

<210> SEQ ID NO 75
<211> LENGTH: 117
<212> TYPE: PRT
<213> ORGANISM: Artificial Sequence
<220> FEATURE:
<223> OTHER INFORMATION: VH Sequence of variant H1824 (Optimized H1685)

<400> SEQUENCE: 75

Glu Val Gln Leu Val Glu Ser Gly Gly Gly Leu Ile Gln Pro Gly Gly
1               5                   10                  15

Ser Leu Arg Leu Ser Cys Ala Val Ser Gly Leu Asn Val Ser Arg Asp
            20                  25                  30

Tyr Met Ser Trp Val Arg Gln Ala Pro Gly Lys Gly Leu Glu Trp Ile
            35                  40                  45

Ser Val Ile Tyr Arg Gly Gly Ile Thr Met Tyr Ala Asp Ser Val Lys
50                  55                  60

Gly Arg Phe Thr Ile Ser Arg Asp Thr Ser Lys Asn Thr Val Phe Leu
65                  70                  75                  80

Gln Met Ser Arg Leu Lys Val Ala Asp Thr Ala Val Tyr Tyr Cys Ala
            85                  90                  95

Arg Asn Tyr Tyr Gly Ser Thr Leu Asp Tyr Trp Gly Gln Gly Thr Leu
            100                 105                 110

Val Thr Val Ser Ser
        115

<210> SEQ ID NO 76
<211> LENGTH: 16
<212> TYPE: PRT
<213> ORGANISM: Artificial Sequence
<220> FEATURE:
<223> OTHER INFORMATION: VH-CDR2 Sequence of variant H1824 (Optimized

H1685)

<400> SEQUENCE: 76

Val Ile Tyr Arg Gly Gly Ile Thr Met Tyr Ala Asp Ser Val Lys Gly
1               5                   10                  15

<210> SEQ ID NO 77
<211> LENGTH: 117
<212> TYPE: PRT
<213> ORGANISM: Artificial Sequence
<220> FEATURE:
<223> OTHER INFORMATION: VH Sequence of variant H1831 (Optimized H1685)

<400> SEQUENCE: 77

Glu Val Gln Leu Val Glu Ser Gly Gly Gly Leu Ile Gln Pro Gly Gly
1               5                   10                  15

Ser Leu Arg Leu Ser Cys Ala Val Ser Gly Leu Asn Val Ser Arg Asp
            20                  25                  30

Tyr Met Ser Trp Val Arg Gln Ala Pro Gly Lys Gly Leu Glu Trp Ile
        35                  40                  45

Ser Val Ile Tyr Arg Gly Gly Ala Thr His Tyr Ala Asp Ser Val Lys
    50                  55                  60

Gly Arg Phe Thr Ile Ser Arg Asp Thr Ser Lys Asn Thr Val Phe Leu
65                  70                  75                  80

Gln Met Ser Arg Leu Lys Val Ala Asp Thr Ala Val Tyr Tyr Cys Ala
                85                  90                  95

Arg Asn Tyr Tyr Gly Ser Thr Leu Asp Tyr Trp Gly Gln Gly Thr Leu
            100                 105                 110

Val Thr Val Ser Ser
        115

<210> SEQ ID NO 78
<211> LENGTH: 16
<212> TYPE: PRT
<213> ORGANISM: Artificial Sequence
<220> FEATURE:
<223> OTHER INFORMATION: VH-CDR2 Sequence of variant H1831 (Optimized
      H1685)

<400> SEQUENCE: 78

Val Ile Tyr Arg Gly Gly Ala Thr His Tyr Ala Asp Ser Val Lys Gly
1               5                   10                  15

<210> SEQ ID NO 79
<211> LENGTH: 117
<212> TYPE: PRT
<213> ORGANISM: Artificial Sequence
<220> FEATURE:
<223> OTHER INFORMATION: VH Sequence of variant H1844 (Optimized H1685)

<400> SEQUENCE: 79

Glu Val Gln Leu Val Glu Ser Gly Gly Gly Leu Ile Gln Pro Gly Gly
1               5                   10                  15

Ser Leu Arg Leu Ser Cys Ala Val Ser Gly Leu Asn Val Ser Arg Asp
            20                  25                  30

Tyr Met Ser Trp Val Arg Gln Ala Pro Gly Lys Gly Leu Glu Trp Ile
        35                  40                  45

Ser Val Ile Tyr Arg Gly Gly Val Thr Met Tyr Ala Asp Ser Val Lys
    50                  55                  60

Gly Arg Phe Thr Ile Ser Arg Asp Thr Ser Lys Asn Thr Val Phe Leu
65                  70                  75                  80

```
Gln Met Ser Arg Leu Lys Val Ala Asp Thr Ala Val Tyr Tyr Cys Ala
                85                  90                  95

Arg Asn Tyr Tyr Gly Ser Thr Leu Asp Tyr Trp Gly Gln Gly Thr Leu
            100                 105                 110

Val Thr Val Ser Ser
        115

<210> SEQ ID NO 80
<211> LENGTH: 16
<212> TYPE: PRT
<213> ORGANISM: Artificial Sequence
<220> FEATURE:
<223> OTHER INFORMATION: VH-CDR2 Sequence of variant H1844 (Optimized
      H1685)

<400> SEQUENCE: 80

Val Ile Tyr Arg Gly Gly Val Thr Met Tyr Ala Asp Ser Val Lys Gly
1               5                   10                  15

<210> SEQ ID NO 81
<211> LENGTH: 118
<212> TYPE: PRT
<213> ORGANISM: Artificial Sequence
<220> FEATURE:
<223> OTHER INFORMATION: VH Sequence of variant H1102

<400> SEQUENCE: 81

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Thr Gly Arg Phe Thr Ile Ser Arg Asp Asn Ser Lys Asn Thr Leu His
65                  70                  75                  80

Leu Gln Met Ser Ser Leu Arg Ala Glu Asp Thr Ala Val Tyr Tyr Cys
                85                  90                  95

Ala Arg Asn Tyr Tyr Gly Ser Thr Tyr Asp Tyr Trp Gly Gln Gly Thr
            100                 105                 110

Leu Val Thr Val Ser Ser
        115

<210> SEQ ID NO 82
<211> LENGTH: 10
<212> TYPE: PRT
<213> ORGANISM: Artificial Sequence
<220> FEATURE:
<223> OTHER INFORMATION: VH-CDR1 Sequence of variant H1102

<400> SEQUENCE: 82

Gly Phe Thr Phe Ser Ser Tyr Ala Met His
1               5                   10

<210> SEQ ID NO 83
<211> LENGTH: 17
<212> TYPE: PRT
<213> ORGANISM: Artificial Sequence
<220> FEATURE:
<223> OTHER INFORMATION: VH-CDR2 Sequence of variant H1102
```

```
<400> SEQUENCE: 83

Ala Ile Ser Ser Asn Gly Gly Ser Thr Tyr Tyr Ala Asp Ser Val Thr
1               5                   10                  15

Gly

<210> SEQ ID NO 84
<211> LENGTH: 9
<212> TYPE: PRT
<213> ORGANISM: Artificial Sequence
<220> FEATURE:
<223> OTHER INFORMATION: VH-CDR3 Sequence of variant H1102

<400> SEQUENCE: 84

Asn Tyr Tyr Gly Ser Thr Tyr Asp Tyr
1               5

<210> SEQ ID NO 85
<211> LENGTH: 118
<212> TYPE: PRT
<213> ORGANISM: Artificial Sequence
<220> FEATURE:
<223> OTHER INFORMATION: VH Sequence of variant H1103

<400> SEQUENCE: 85

Glu Val Gln Leu Leu Glu Ser Gly Gly Val Val Gln Pro Gly Arg
1               5                   10                  15

Ser Leu Arg Leu Ser Cys Ala Ala Ser Gly Phe Thr Phe Asn Tyr
                20                  25                  30

Gly Met His Trp Val Arg Gln Ala Pro Gly Lys Gly Leu Glu Trp Val
            35                  40                  45

Ala Val Thr Ser Phe Asp Gly Ser His Ala Tyr Tyr Ala Asp Ser Val
        50                  55                  60

Lys Gly Arg Phe Thr Ile Ser Arg Asp Asn Ser Lys Asn Thr Val Phe
65                  70                  75                  80

Leu Gln Met Asn Asn Leu Arg Gly Asp Asp Thr Ala Val Tyr Tyr Cys
                85                  90                  95

Ala Arg Asn Tyr Tyr Gly Ser Thr Tyr Asp Tyr Trp Gly Gln Gly Thr
            100                 105                 110

Leu Val Thr Val Ser Ser
        115

<210> SEQ ID NO 86
<211> LENGTH: 10
<212> TYPE: PRT
<213> ORGANISM: Artificial Sequence
<220> FEATURE:
<223> OTHER INFORMATION: VH-CDR1 Sequence of variant H1103

<400> SEQUENCE: 86

Gly Phe Thr Val Gly Asn Asn Tyr Met Ser
1               5                   10

<210> SEQ ID NO 87
<211> LENGTH: 16
<212> TYPE: PRT
<213> ORGANISM: Artificial Sequence
<220> FEATURE:
<223> OTHER INFORMATION: VH-CDR2 Sequence of variant H1103

<400> SEQUENCE: 87

Val Ile Tyr Ser Ala Gly Ser Thr Tyr Tyr Ala Asp Ser Val Lys Gly
1               5                   10                  15
```

```
<210> SEQ ID NO 88
<211> LENGTH: 9
<212> TYPE: PRT
<213> ORGANISM: Artificial Sequence
<220> FEATURE:
<223> OTHER INFORMATION: VH-CDR3 Sequence of variant H1103

<400> SEQUENCE: 88

Asn Tyr Tyr Gly Ser Thr Tyr Asp Tyr
1               5

<210> SEQ ID NO 89
<211> LENGTH: 117
<212> TYPE: PRT
<213> ORGANISM: Artificial Sequence
<220> FEATURE:
<223> OTHER INFORMATION: VH Sequence of variant H1104

<400> SEQUENCE: 89

Glu Val Gln Leu Leu Glu Ser Gly Gly Gly Met Val Gln Thr Gly Gly
1               5                   10                  15

Ser Val Arg Leu Ser Cys Ala Val Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Thr Ser Gly Ser Thr Phe Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asn Tyr Tyr Gly Ser Thr Tyr Asp Tyr Trp Gly Gln Gly Thr Leu
            100                 105                 110

Val Thr Val Ser Ser
        115

<210> SEQ ID NO 90
<211> LENGTH: 10
<212> TYPE: PRT
<213> ORGANISM: Artificial Sequence
<220> FEATURE:
<223> OTHER INFORMATION: VH-CDR1 Sequence of variant H1104

<400> SEQUENCE: 90

Gly Phe Thr Val Ser Ser Asn Tyr Met Ser
1               5                   10

<210> SEQ ID NO 91
<211> LENGTH: 16
<212> TYPE: PRT
<213> ORGANISM: Artificial Sequence
<220> FEATURE:
<223> OTHER INFORMATION: VH-CDR2 Sequence of variant H1104

<400> SEQUENCE: 91

Val Ile Tyr Ser Gly Gly Ser Thr Tyr Tyr Ala Asp Ser Val Lys Gly
1               5                   10                  15

<210> SEQ ID NO 92
<211> LENGTH: 9
<212> TYPE: PRT
<213> ORGANISM: Artificial Sequence
```

```
<220> FEATURE:
<223> OTHER INFORMATION: VH-CDR3 Sequence of variant H1104

<400> SEQUENCE: 92

Asn Tyr Tyr Gly Ser Thr Tyr Asp Tyr
1               5

<210> SEQ ID NO 93
<211> LENGTH: 118
<212> TYPE: PRT
<213> ORGANISM: Artificial Sequence
<220> FEATURE:
<223> OTHER INFORMATION: VH Sequence of variant H1118

<400> SEQUENCE: 93

Glu Val Gln Leu Leu Glu Ser Gly Pro Gly Leu Val Lys Pro Ser Glu
1               5                   10                  15

Thr Leu Ser Leu Asn Cys Ala Val Ser Gly Asp Ser Ile Ser Ser Gly
            20                  25                  30

His Tyr Trp Gly Trp Ile Arg Gln Pro Pro Gly Lys Gly Leu Glu Trp
        35                  40                  45

Ile Gly Thr Ile Ser His Arg Gly Thr Thr Tyr Ser Asn Pro Ser Leu
    50                  55                  60

Lys Ser Arg Val Thr Ile Ser Met Asp Lys Ser Ser Asn Ser Phe Ser
65                  70                  75                  80

Leu Lys Leu Ser Ser Val Thr Ala Ala Asp Thr Ala Val Tyr Tyr Cys
                85                  90                  95

Ala Arg Asn Tyr Tyr Gly Ser Thr Tyr Asp Tyr Trp Gly Gln Gly Thr
            100                 105                 110

Leu Val Thr Val Ser Ser
        115

<210> SEQ ID NO 94
<211> LENGTH: 9
<212> TYPE: PRT
<213> ORGANISM: Artificial Sequence
<220> FEATURE:
<223> OTHER INFORMATION: VH-CDR1 Sequence of variant H1118

<400> SEQUENCE: 94

Gly Asp Ser Ile Ser Ser Gly His Tyr
1               5

<210> SEQ ID NO 95
<211> LENGTH: 16
<212> TYPE: PRT
<213> ORGANISM: Artificial Sequence
<220> FEATURE:
<223> OTHER INFORMATION: VH-CDR2 Sequence of variant H1118

<400> SEQUENCE: 95

Thr Ile Ser His Arg Gly Thr Thr Tyr Ser Asn Pro Ser Leu Lys Ser
1               5                   10                  15

<210> SEQ ID NO 96
<211> LENGTH: 9
<212> TYPE: PRT
<213> ORGANISM: Artificial Sequence
<220> FEATURE:
<223> OTHER INFORMATION: VH-CDR3 Sequence of variant H1118

<400> SEQUENCE: 96

Asn Tyr Tyr Gly Ser Thr Tyr Asp Tyr
```

-continued

```
1               5

<210> SEQ ID NO 97
<211> LENGTH: 118
<212> TYPE: PRT
<213> ORGANISM: Artificial Sequence
<220> FEATURE:
<223> OTHER INFORMATION: VH Sequence of variant H1117

<400> SEQUENCE: 97

Glu Val Gln Leu Leu Glu Ser Gly Gly Ala Leu Val Gln Pro Gly Gly
1               5                   10                  15

Ser Leu Arg Leu Ser Cys Ala Ala Ser Gly Phe Thr Phe Asp Ser Tyr
            20                  25                  30

Pro Met Asn Trp Val Arg Gln Ala Pro Gly Arg Gly Leu Glu Trp Val
        35                  40                  45

Ser Thr Ile Ser Gly Ser Gly Ile Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Arg Asn Tyr Tyr Gly Ser Thr Tyr Asp Tyr Trp Gly Gln Gly Thr
            100                 105                 110

Leu Val Thr Val Ser Ser
        115

<210> SEQ ID NO 98
<211> LENGTH: 10
<212> TYPE: PRT
<213> ORGANISM: Artificial Sequence
<220> FEATURE:
<223> OTHER INFORMATION: VH-CDR1 Sequence of variant H1117

<400> SEQUENCE: 98

Gly Phe Thr Phe Asp Ser Tyr Pro Met Asn
1               5                   10

<210> SEQ ID NO 99
<211> LENGTH: 17
<212> TYPE: PRT
<213> ORGANISM: Artificial Sequence
<220> FEATURE:
<223> OTHER INFORMATION: VH-CDR2 Sequence of variant H1117

<400> SEQUENCE: 99

Thr Ile Ser Gly Ser Gly Ile Gly Thr Tyr Tyr Ala Asp Ser Val Lys
1               5                   10                  15

Gly

<210> SEQ ID NO 100
<211> LENGTH: 9
<212> TYPE: PRT
<213> ORGANISM: Artificial Sequence
<220> FEATURE:
<223> OTHER INFORMATION: VH-CDR3 Sequence of variant H1117

<400> SEQUENCE: 100

Asn Tyr Tyr Gly Ser Thr Tyr Asp Tyr
1               5

<210> SEQ ID NO 101
```

```
<211> LENGTH: 118
<212> TYPE: PRT
<213> ORGANISM: Artificial Sequence
<220> FEATURE:
<223> OTHER INFORMATION: VH Sequence of variant H1119

<400> SEQUENCE: 101

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asn Phe Lys Lys Tyr
            20                  25                  30

Pro Met Ser Trp Val Arg Gln Thr Pro Gly Lys Gly Leu Glu Trp Val
        35                  40                  45

Ser Phe Ile Thr Gly Asn Ala Asp Arg Thr Tyr Tyr Ala Asp Ser Leu
    50                  55                  60

Lys Gly Arg Phe Thr Ile Ser Arg Asp Asn Ser Lys Asn Thr Leu Tyr
65                  70                  75                  80

Leu Gln Met Asn Ser Leu Ala Val Glu Asp Thr Ala Val Tyr Tyr Cys
                85                  90                  95

Ala Arg Asn Tyr Tyr Gly Ser Thr Tyr Asp Tyr Trp Gly Gln Gly Thr
            100                 105                 110

Leu Val Thr Val Ser Ser
        115

<210> SEQ ID NO 102
<211> LENGTH: 10
<212> TYPE: PRT
<213> ORGANISM: Artificial Sequence
<220> FEATURE:
<223> OTHER INFORMATION: VH-CDR1 Sequence of variant H1119

<400> SEQUENCE: 102

Gly Phe Asn Phe Lys Lys Tyr Pro Met Ser
1               5                   10

<210> SEQ ID NO 103
<211> LENGTH: 17
<212> TYPE: PRT
<213> ORGANISM: Artificial Sequence
<220> FEATURE:
<223> OTHER INFORMATION: VH-CDR2 Sequence of variant H1119

<400> SEQUENCE: 103

Phe Ile Thr Gly Asn Ala Asp Arg Thr Tyr Tyr Ala Asp Ser Leu Lys
1               5                   10                  15

Gly

<210> SEQ ID NO 104
<211> LENGTH: 9
<212> TYPE: PRT
<213> ORGANISM: Artificial Sequence
<220> FEATURE:
<223> OTHER INFORMATION: VH-CDR3 Sequence of variant H1119

<400> SEQUENCE: 104

Asn Tyr Tyr Gly Ser Thr Tyr Asp Tyr
1               5

<210> SEQ ID NO 105
<211> LENGTH: 118
<212> TYPE: PRT
<213> ORGANISM: Artificial Sequence
<220> FEATURE:
```

-continued

<223> OTHER INFORMATION: VH Sequence of variant H1120

<400> SEQUENCE: 105

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Gly Phe
            20                  25                  30

Ala Met His Trp Val Arg Gln Ala Pro Gly Lys Gly Leu Glu Trp Val
        35                  40                  45

Ala Val Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Val Phe
65                  70                  75                  80

Leu Gln Met Asn Ser Leu Arg Pro Glu Asp Thr Ala Val Tyr Tyr Cys
                85                  90                  95

Ala Arg Asn Tyr Tyr Gly Ser Thr Tyr Asp Tyr Trp Gly Gln Gly Thr
            100                 105                 110

Leu Val Thr Val Ser Ser
        115

<210> SEQ ID NO 106
<211> LENGTH: 10
<212> TYPE: PRT
<213> ORGANISM: Artificial Sequence
<220> FEATURE:
<223> OTHER INFORMATION: VH-CDR1 Sequence of variant H1120

<400> SEQUENCE: 106

Gly Phe Thr Phe Asn Gly Phe Ala Met His
1               5                   10

<210> SEQ ID NO 107
<211> LENGTH: 17
<212> TYPE: PRT
<213> ORGANISM: Artificial Sequence
<220> FEATURE:
<223> OTHER INFORMATION: VH-CDR2 Sequence of variant H1120

<400> SEQUENCE: 107

Val Ile Ser Tyr Asp Gly Asn Asn Lys Tyr Tyr Ala Asp Ser Val Lys
1               5                   10                  15

Gly

<210> SEQ ID NO 108
<211> LENGTH: 9
<212> TYPE: PRT
<213> ORGANISM: Artificial Sequence
<220> FEATURE:
<223> OTHER INFORMATION: VH-CDR3 Sequence of variant H1120

<400> SEQUENCE: 108

Asn Tyr Tyr Gly Ser Thr Tyr Asp Tyr
1               5

<210> SEQ ID NO 109
<211> LENGTH: 118
<212> TYPE: PRT
<213> ORGANISM: Artificial Sequence
<220> FEATURE:
<223> OTHER INFORMATION: VH Sequence of variant H1121

<400> SEQUENCE: 109

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Ala
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Tyr Tyr Gly Ser Thr Tyr Asp Tyr Trp Gly Gln Gly Thr
            100                 105                 110

Leu Val Thr Val Ser Ser
            115
```

<210> SEQ ID NO 110
<211> LENGTH: 10
<212> TYPE: PRT
<213> ORGANISM: Artificial Sequence
<220> FEATURE:
<223> OTHER INFORMATION: VH-CDR1 Sequence of variant H1121

<400> SEQUENCE: 110

```
Gly Phe Thr Phe Ser Ser Tyr Gly Met His
1               5                   10
```

<210> SEQ ID NO 111
<211> LENGTH: 17
<212> TYPE: PRT
<213> ORGANISM: Artificial Sequence
<220> FEATURE:
<223> OTHER INFORMATION: VH-CDR2 Sequence of variant H1121

<400> SEQUENCE: 111

```
Val Ile Ser Tyr Asp Gly Ser Asn Lys Tyr Tyr Ala Asp Ser Ala Lys
1               5                   10                  15

Gly
```

<210> SEQ ID NO 112
<211> LENGTH: 9
<212> TYPE: PRT
<213> ORGANISM: Artificial Sequence
<220> FEATURE:
<223> OTHER INFORMATION: VH-CDR3 Sequence of variant H1121

<400> SEQUENCE: 112

```
Asn Tyr Tyr Gly Ser Thr Tyr Asp Tyr
1               5
```

<210> SEQ ID NO 113
<211> LENGTH: 118
<212> TYPE: PRT
<213> ORGANISM: Artificial Sequence
<220> FEATURE:
<223> OTHER INFORMATION: VH Sequence of variant H1122

<400> SEQUENCE: 113

```
Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Ser Ser His
```

```
                    20                  25                  30
Pro Met His Trp Val Arg Gln Ala Pro Gly Lys Gly Leu Glu Trp Val
        35                  40                  45

Ala Val Ile Ser Tyr Asp Ala Arg Val Lys Tyr Tyr Val Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Thr Thr Glu Asp Thr Ala Val Tyr Tyr Cys
                85                  90                  95

Ala Arg Asn Tyr Tyr Gly Ser Thr Tyr Asp Tyr Trp Gly Gln Gly Thr
            100                 105                 110

Leu Val Thr Val Ser Ser
            115

<210> SEQ ID NO 114
<211> LENGTH: 10
<212> TYPE: PRT
<213> ORGANISM: Artificial Sequence
<220> FEATURE:
<223> OTHER INFORMATION: VH-CDR1 Sequence of variant H1122

<400> SEQUENCE: 114

Gly Phe Thr Phe Ser Ser His Pro Met His
1               5                   10

<210> SEQ ID NO 115
<211> LENGTH: 16
<212> TYPE: PRT
<213> ORGANISM: Artificial Sequence
<220> FEATURE:
<223> OTHER INFORMATION: VH-CDR2 Sequence of variant H1122

<400> SEQUENCE: 115

Val Ile Ser Tyr Asp Ala Arg Val Lys Tyr Tyr Val Asp Ser Val Lys
1               5                   10                  15

<210> SEQ ID NO 116
<211> LENGTH: 9
<212> TYPE: PRT
<213> ORGANISM: Artificial Sequence
<220> FEATURE:
<223> OTHER INFORMATION: VH-CDR3 Sequence of variant H1122

<400> SEQUENCE: 116

Asn Tyr Tyr Gly Ser Thr Tyr Asp Tyr
1               5

<210> SEQ ID NO 117
<211> LENGTH: 118
<212> TYPE: PRT
<213> ORGANISM: Artificial Sequence
<220> FEATURE:
<223> OTHER INFORMATION: VH Sequence of variant H1194

<400> SEQUENCE: 117

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Ile His Trp Val Arg Gln Ala Pro Gly Lys Gly Leu Glu Trp Val
        35                  40                  45

Ala Leu Ile Ser Tyr Asp Gly Ser Lys Lys Tyr Tyr Ala Asp Ser Val
```

```
                    50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Thr Glu Asp Thr Ala Val Tyr Tyr Cys
                 85                  90                  95

Ala Arg Asn Tyr Tyr Gly Ser Thr Tyr Asp Tyr Trp Gly Gln Gly Thr
                100                 105                 110

Leu Val Thr Val Ser Ser
            115

<210> SEQ ID NO 118
<211> LENGTH: 10
<212> TYPE: PRT
<213> ORGANISM: Artificial Sequence
<220> FEATURE:
<223> OTHER INFORMATION: VH-CDR1 Sequence of variant H1194

<400> SEQUENCE: 118

Gly Phe Thr Phe Ser Ser Tyr Gly Ile His
 1               5                  10

<210> SEQ ID NO 119
<211> LENGTH: 17
<212> TYPE: PRT
<213> ORGANISM: Artificial Sequence
<220> FEATURE:
<223> OTHER INFORMATION: VH-CDR2 Sequence of variant H1194

<400> SEQUENCE: 119

Leu Ile Ser Tyr Asp Gly Ser Lys Lys Tyr Tyr Ala Asp Ser Val Lys
 1               5                  10                  15

Gly

<210> SEQ ID NO 120
<211> LENGTH: 9
<212> TYPE: PRT
<213> ORGANISM: Artificial Sequence
<220> FEATURE:
<223> OTHER INFORMATION: VH-CDR3 Sequence of variant H1194

<400> SEQUENCE: 120

Asn Tyr Tyr Gly Ser Thr Tyr Asp Tyr
 1               5

<210> SEQ ID NO 121
<211> LENGTH: 118
<212> TYPE: PRT
<213> ORGANISM: Artificial Sequence
<220> FEATURE:
<223> OTHER INFORMATION: VH Sequence of variant H1195

<400> SEQUENCE: 121

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
             20                  25                  30

Asp Phe His Trp Val Arg Gln Gly Thr Gly Glu Gly Leu Glu Trp Val
         35                  40                  45

Ser Ala Ile Ser Pro Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80
```

```
Leu Gln Met Asn Ser Leu Arg Ala Glu Asp Thr Ala Val Tyr Tyr Cys
                 85                  90                  95

Ala Arg Asn Tyr Tyr Gly Ser Thr Tyr Asp Tyr Trp Gly Gln Gly Thr
            100                 105                 110

Leu Val Thr Val Ser Ser
        115

<210> SEQ ID NO 122
<211> LENGTH: 10
<212> TYPE: PRT
<213> ORGANISM: Artificial Sequence
<220> FEATURE:
<223> OTHER INFORMATION: VH-CDR1 Sequence of variant H1195

<400> SEQUENCE: 122

Gly Phe Thr Phe Ser Thr Tyr Asp Phe His
1               5                   10

<210> SEQ ID NO 123
<211> LENGTH: 17
<212> TYPE: PRT
<213> ORGANISM: Artificial Sequence
<220> FEATURE:
<223> OTHER INFORMATION: VH-CDR2 Sequence of variant H1195

<400> SEQUENCE: 123

Ala Ile Ser Pro Ser Gly Gly Ser Thr Tyr Tyr Ala Asp Ser Val Lys
1               5                   10                  15

Gly

<210> SEQ ID NO 124
<211> LENGTH: 9
<212> TYPE: PRT
<213> ORGANISM: Artificial Sequence
<220> FEATURE:
<223> OTHER INFORMATION: VH-CDR3 Sequence of variant H1195

<400> SEQUENCE: 124

Asn Tyr Tyr Gly Ser Thr Tyr Asp Tyr
1               5

<210> SEQ ID NO 125
<211> LENGTH: 107
<212> TYPE: PRT
<213> ORGANISM: Artificial Sequence
<220> FEATURE:
<223> OTHER INFORMATION: VL Sequence of variant L217

<400> SEQUENCE: 125

Asp Ile Val Met Thr Gln Ser Pro Val Ile Leu Ser Val Ser Pro Gly
1               5                   10                  15

Asp Arg Ala Thr Leu Ser Cys Arg Ala Ser Glu Ser Val Arg Gly Asn
            20                  25                  30

Val Ala Trp Tyr Gln Gln Lys Pro Gly Gln Val Pro Arg Leu Leu Ile
        35                  40                  45

Ser Gly Ala Ser Thr Arg Ala Asn Gly Ile Pro Ala Arg Phe Ser Gly
    50                  55                  60

Ser Gly Ser Gly Thr Glu Tyr Ser Leu Thr Ile Ser Ser Leu Gln Pro
65                  70                  75                  80

Glu Asp Val Ala Ile Tyr His Cys His Gln Tyr His Tyr Trp Pro Leu
                85                  90                  95
```

Thr Phe Gly Gly Gly Thr Lys Leu Glu Ile Lys
            100                 105

<210> SEQ ID NO 126
<211> LENGTH: 11
<212> TYPE: PRT
<213> ORGANISM: Artificial Sequence
<220> FEATURE:
<223> OTHER INFORMATION: VL-CDR1 Sequence of variant L217

<400> SEQUENCE: 126

Arg Ala Ser Glu Ser Val Arg Gly Asn Val Ala
1               5                   10

<210> SEQ ID NO 127
<211> LENGTH: 7
<212> TYPE: PRT
<213> ORGANISM: Artificial Sequence
<220> FEATURE:
<223> OTHER INFORMATION: VL-CDR2 Sequence of variant L217

<400> SEQUENCE: 127

Gly Ala Ser Thr Arg Ala Asn
1               5

<210> SEQ ID NO 128
<211> LENGTH: 9
<212> TYPE: PRT
<213> ORGANISM: Artificial Sequence
<220> FEATURE:
<223> OTHER INFORMATION: VL-CDR3 Sequence of variant L217

<400> SEQUENCE: 128

His Gln Tyr His Tyr Trp Pro Leu Thr
1               5

<210> SEQ ID NO 129
<211> LENGTH: 107
<212> TYPE: PRT
<213> ORGANISM: Artificial Sequence
<220> FEATURE:
<223> OTHER INFORMATION: VL Sequence of variant L218

<400> SEQUENCE: 129

Asp Ile Val Met Thr Gln Ser Pro Ala Thr Leu Ser Val Ser Pro Gly
1               5                   10                  15

Glu Arg Val Thr Leu Ser Cys Arg Ala Pro Gln Ile Leu Arg Ser Asn
            20                  25                  30

Leu Ala Trp Tyr Gln Gln Lys Pro Gly Gln Ala Pro Arg Leu Leu Ile
        35                  40                  45

Tyr Gly Ala Ser Asn Arg Val Thr Gly Val Pro Ala Arg Phe Ser Ala
    50                  55                  60

Ser Glu Ser Gly Thr Glu Phe Thr Leu Thr Ile Asn Gly Leu Gln Ser
65                  70                  75                  80

Glu Asp Phe Gly Val Tyr Phe Cys Gln Gln Tyr Asn Tyr Trp Pro Phe
                85                  90                  95

Thr Phe Gly Pro Gly Thr Lys Leu Glu Ile Lys
            100                 105

<210> SEQ ID NO 130
<211> LENGTH: 11
<212> TYPE: PRT
<213> ORGANISM: Artificial Sequence
<220> FEATURE:

```
<223> OTHER INFORMATION: VL-CDR1 Sequence of variant L218

<400> SEQUENCE: 130

Arg Ala Pro Gln Ile Leu Arg Ser Asn Leu Ala
1               5                   10

<210> SEQ ID NO 131
<211> LENGTH: 7
<212> TYPE: PRT
<213> ORGANISM: Artificial Sequence
<220> FEATURE:
<223> OTHER INFORMATION: VL-CDR2 Sequence of variant L218

<400> SEQUENCE: 131

Gly Ala Ser Asn Arg Val Thr
1               5

<210> SEQ ID NO 132
<211> LENGTH: 9
<212> TYPE: PRT
<213> ORGANISM: Artificial Sequence
<220> FEATURE:
<223> OTHER INFORMATION: VL-CDR3 Sequence of variant L218

<400> SEQUENCE: 132

Gln Gln Tyr Asn Tyr Trp Pro Phe Thr
1               5

<210> SEQ ID NO 133
<211> LENGTH: 107
<212> TYPE: PRT
<213> ORGANISM: Artificial Sequence
<220> FEATURE:
<223> OTHER INFORMATION: VL Sequence of variant L229

<400> SEQUENCE: 133

Asp Val Val Met Thr Gln Ser Pro Val Thr Leu Ser Val Ser Pro Gly
1               5                   10                  15

Glu Arg Ala Thr Leu Ser Cys Arg Pro Ser Gln Ser Ile His Asn Asn
            20                  25                  30

Leu Ala Trp Tyr Gln Gln Lys Pro Gly Gln Ala Pro Arg Val Leu Ile
        35                  40                  45

Tyr Glu Ser Ser Thr Arg Ala Lys Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Leu Tyr Tyr Cys Gln Gln Tyr Asn Arg Trp Pro Leu
                85                  90                  95

Thr Phe Gly Gln Gly Thr Lys Leu Glu Ile Lys
            100                 105

<210> SEQ ID NO 134
<211> LENGTH: 11
<212> TYPE: PRT
<213> ORGANISM: Artificial Sequence
<220> FEATURE:
<223> OTHER INFORMATION: VL-CDR1 Sequence of variant L229

<400> SEQUENCE: 134

Arg Pro Ser Gln Ser Ile His Asn Asn Leu Ala
1               5                   10

<210> SEQ ID NO 135
```

```
<211> LENGTH: 7
<212> TYPE: PRT
<213> ORGANISM: Artificial Sequence
<220> FEATURE:
<223> OTHER INFORMATION: VL-CDR2 Sequence of variant L229

<400> SEQUENCE: 135

Glu Ser Ser Thr Arg Ala Lys
1               5

<210> SEQ ID NO 136
<211> LENGTH: 9
<212> TYPE: PRT
<213> ORGANISM: Artificial Sequence
<220> FEATURE:
<223> OTHER INFORMATION: VL-CDR3 Sequence of variant L229

<400> SEQUENCE: 136

Gln Gln Tyr Asn Arg Trp Pro Leu Thr
1               5

<210> SEQ ID NO 137
<211> LENGTH: 107
<212> TYPE: PRT
<213> ORGANISM: Artificial Sequence
<220> FEATURE:
<223> OTHER INFORMATION: VL Sequence of variant L230

<400> SEQUENCE: 137

Asp Val Val Met Thr Gln Ser Pro Ala Ser Leu Ser Val Ser Pro Gly
1               5                   10                  15

Glu Arg Ala Thr Leu Ser Cys Arg Ala Ser Gln Asn Ile Arg Gly Asn
            20                  25                  30

Leu Ala Trp Tyr Gln Gln Ile Pro Gly Gln Ala Pro Arg Leu Leu Met
        35                  40                  45

Ser Gly Pro Ser Thr Arg Ala Ala Gly Ile Pro Ala Arg Phe Ser Gly
    50                  55                  60

Thr Gly Ser Gly Thr Glu Phe Thr Leu Thr Ile Ser Ser Pro Gln Ser
65                  70                  75                  80

Glu Asp Phe Ala Leu Tyr Tyr Cys Gln Gln Tyr His Phe Trp Pro Pro
                85                  90                  95

Ser Phe Gly Gln Gly Thr Lys Leu Glu Ile Lys
            100                 105

<210> SEQ ID NO 138
<211> LENGTH: 11
<212> TYPE: PRT
<213> ORGANISM: Artificial Sequence
<220> FEATURE:
<223> OTHER INFORMATION: VL-CDR1 Sequence of variant L230

<400> SEQUENCE: 138

Arg Ala Ser Gln Asn Ile Arg Gly Asn Leu Ala
1               5                   10

<210> SEQ ID NO 139
<211> LENGTH: 7
<212> TYPE: PRT
<213> ORGANISM: Artificial Sequence
<220> FEATURE:
<223> OTHER INFORMATION: VL-CDR2 Sequence of variant L230

<400> SEQUENCE: 139

Gly Pro Ser Thr Arg Ala Ala
1               5
```

-continued

```
1               5

<210> SEQ ID NO 140
<211> LENGTH: 9
<212> TYPE: PRT
<213> ORGANISM: Artificial Sequence
<220> FEATURE:
<223> OTHER INFORMATION: VL-CDR3 Sequence of variant L230

<400> SEQUENCE: 140

Gln Gln Tyr His Phe Trp Pro Pro Ser
1               5

<210> SEQ ID NO 141
<211> LENGTH: 107
<212> TYPE: PRT
<213> ORGANISM: Artificial Sequence
<220> FEATURE:
<223> OTHER INFORMATION: VL Sequence of variant L250

<400> SEQUENCE: 141

Glu Ile Val Leu Thr Gln Ser Pro Val Thr Leu Ser Val Pro Pro Gly
1               5                   10                  15

Glu Arg Ala Ser Leu Ser Cys Arg Ala Ser Gln Asn Ile Tyr Thr Ala
            20                  25                  30

Val Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Gly Gly Ser Gly Thr Asp Tyr Thr Leu Thr Ile Ser Ser Leu Glu Ser
65                  70                  75                  80

Glu Asp Phe Ala Val Tyr His Cys Gln Gln Tyr His Ser Trp Pro Leu
                85                  90                  95

Thr Phe Gly Gly Gly Thr Lys Leu Glu Ile Lys
            100                 105

<210> SEQ ID NO 142
<211> LENGTH: 11
<212> TYPE: PRT
<213> ORGANISM: Artificial Sequence
<220> FEATURE:
<223> OTHER INFORMATION: VL-CDR1 Sequence of variant L250

<400> SEQUENCE: 142

Arg Ala Ser Gln Asn Ile Tyr Thr Ala Val Ala
1               5                   10

<210> SEQ ID NO 143
<211> LENGTH: 7
<212> TYPE: PRT
<213> ORGANISM: Artificial Sequence
<220> FEATURE:
<223> OTHER INFORMATION: VL-CDR2 Sequence of variant L250

<400> SEQUENCE: 143

Gly Ala Ser Thr Arg Ala Thr
1               5

<210> SEQ ID NO 144
<211> LENGTH: 9
<212> TYPE: PRT
<213> ORGANISM: Artificial Sequence
<220> FEATURE:
<223> OTHER INFORMATION: VL-CDR3 Sequence of variant L250
```

<400> SEQUENCE: 144

Gln Gln Tyr His Ser Trp Pro Leu Thr
1               5

<210> SEQ ID NO 145
<211> LENGTH: 107
<212> TYPE: PRT
<213> ORGANISM: Artificial Sequence
<220> FEATURE:
<223> OTHER INFORMATION: VL Sequence of variant L332 (Optimized L250)

<400> SEQUENCE: 145

Glu Ile Val Leu Thr Gln Ser Pro Val Thr Leu Ser Val Pro Pro Gly
1               5                   10                  15

Glu Arg Ala Ser Leu Ser Cys Arg Ala Ser Gln Asn Ile Tyr Thr Ala
            20                  25                  30

Val Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Gly Gly Ser Gly Thr Asp Tyr Thr Leu Thr Ile Ser Ser Leu Glu Ser
65                  70                  75                  80

Glu Asp Phe Ala Val Tyr His Cys Gln Gln Trp His Ser Trp Pro Leu
                85                  90                  95

Thr Phe Gly Gly Gly Thr Lys Leu Glu Ile Lys
            100                 105

<210> SEQ ID NO 146
<211> LENGTH: 11
<212> TYPE: PRT
<213> ORGANISM: Artificial Sequence
<220> FEATURE:
<223> OTHER INFORMATION: VL-CDR1 Sequence of variant L332 (Optimized
      L250)

<400> SEQUENCE: 146

Arg Ala Ser Gln Asn Ile Tyr Thr Ala Val Ala
1               5                   10

<210> SEQ ID NO 147
<211> LENGTH: 7
<212> TYPE: PRT
<213> ORGANISM: Artificial Sequence
<220> FEATURE:
<223> OTHER INFORMATION: VL-CDR2 Sequence of variant L332 (Optimized
      L250)

<400> SEQUENCE: 147

Gly Ala Ser Thr Arg Ala Thr
1               5

<210> SEQ ID NO 148
<211> LENGTH: 9
<212> TYPE: PRT
<213> ORGANISM: Artificial Sequence
<220> FEATURE:
<223> OTHER INFORMATION: VL-CDR3 Sequence of variant L332 (Optimized
      L250)

<400> SEQUENCE: 148

Gln Gln Trp His Ser Trp Pro Leu Thr
1               5

```
<210> SEQ ID NO 149
<211> LENGTH: 107
<212> TYPE: PRT
<213> ORGANISM: Artificial Sequence
<220> FEATURE:
<223> OTHER INFORMATION: VL Sequence of variant L308 (Optimized L250)

<400> SEQUENCE: 149

Glu Ile Val Leu Thr Gln Ser Pro Val Thr Leu Ser Val Pro Pro Gly
1               5                   10                  15

Glu Arg Ala Ser Leu Ser Cys Arg Ala Ser Gln Asn Ile Tyr Thr Ala
            20                  25                  30

Val Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Gly Gly Ser Gly Thr Asp Tyr Thr Leu Thr Ile Ser Ser Leu Glu Ser
65                  70                  75                  80

Glu Asp Phe Ala Val Tyr His Cys Gln Gln Tyr Phe Ser Trp Pro Leu
                85                  90                  95

Thr Phe Gly Gly Gly Thr Lys Leu Glu Ile Lys
            100                 105

<210> SEQ ID NO 150
<211> LENGTH: 11
<212> TYPE: PRT
<213> ORGANISM: Artificial Sequence
<220> FEATURE:
<223> OTHER INFORMATION: VL-CDR1 Sequence of variant L308 (Optimized
      L250)

<400> SEQUENCE: 150

Arg Ala Ser Gln Asn Ile Tyr Thr Ala Val Ala
1               5                   10

<210> SEQ ID NO 151
<211> LENGTH: 7
<212> TYPE: PRT
<213> ORGANISM: Artificial Sequence
<220> FEATURE:
<223> OTHER INFORMATION: VL-CDR2 Sequence of variant L308 (Optimized
      L250)

<400> SEQUENCE: 151

Gly Ala Ser Thr Arg Ala Thr
1               5

<210> SEQ ID NO 152
<211> LENGTH: 9
<212> TYPE: PRT
<213> ORGANISM: Artificial Sequence
<220> FEATURE:
<223> OTHER INFORMATION: VL-CDR3 Sequence of variant L308 (Optimized
      L250)

<400> SEQUENCE: 152

Gln Gln Tyr Phe Ser Trp Pro Leu Thr
1               5

<210> SEQ ID NO 153
<211> LENGTH: 107
<212> TYPE: PRT
<213> ORGANISM: Artificial Sequence
<220> FEATURE:
```

<223> OTHER INFORMATION: VL Sequence of variant L309 (Optimized L250)

<400> SEQUENCE: 153

Glu Ile Val Leu Thr Gln Ser Pro Val Thr Leu Ser Val Pro Pro Gly
1               5                   10                  15

Glu Arg Ala Ser Leu Ser Cys Arg Ala Ser Gln Asn Ile Tyr Thr Ala
            20                  25                  30

Val Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Gly Gly Ser Gly Thr Asp Tyr Thr Leu Thr Ile Ser Ser Leu Glu Ser
65                  70                  75                  80

Glu Asp Phe Ala Val Tyr His Cys Gln Gln Tyr Met Ser Trp Pro Leu
                85                  90                  95

Thr Phe Gly Gly Gly Thr Lys Leu Glu Ile Lys
            100                 105

<210> SEQ ID NO 154
<211> LENGTH: 11
<212> TYPE: PRT
<213> ORGANISM: Artificial Sequence
<220> FEATURE:
<223> OTHER INFORMATION: VL-CDR1 Sequence of variant L309 (Optimized
      L250)

<400> SEQUENCE: 154

Arg Ala Ser Gln Asn Ile Tyr Thr Ala Val Ala
1               5                   10

<210> SEQ ID NO 155
<211> LENGTH: 7
<212> TYPE: PRT
<213> ORGANISM: Artificial Sequence
<220> FEATURE:
<223> OTHER INFORMATION: VL-CDR2 Sequence of variant L309 (Optimized
      L250)

<400> SEQUENCE: 155

Gly Ala Ser Thr Arg Ala Thr
1               5

<210> SEQ ID NO 156
<211> LENGTH: 9
<212> TYPE: PRT
<213> ORGANISM: Artificial Sequence
<220> FEATURE:
<223> OTHER INFORMATION: VL-CDR3 Sequence of variant L309 (Optimized
      L250)

<400> SEQUENCE: 156

Gln Gln Tyr Met Ser Trp Pro Leu Thr
1               5

<210> SEQ ID NO 157
<211> LENGTH: 107
<212> TYPE: PRT
<213> ORGANISM: Artificial Sequence
<220> FEATURE:
<223> OTHER INFORMATION: VL Sequence of variant L311 (Optimized L250)

<400> SEQUENCE: 157

Glu Ile Val Leu Thr Gln Ser Pro Val Thr Leu Ser Val Pro Pro Gly
1               5                   10                  15

```
Glu Arg Ala Ser Leu Ser Cys Arg Ala Ser Gln Asn Ile Tyr Thr Ala
            20                  25                  30

Val Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Gly Gly Ser Gly Thr Asp Tyr Thr Leu Thr Ile Ser Ser Leu Glu Ser
65                  70                  75                  80

Glu Asp Phe Ala Val Tyr His Cys Gln Gln Tyr His Ala Trp Pro Leu
                85                  90                  95

Thr Phe Gly Gly Gly Thr Lys Leu Glu Ile Lys
            100                 105

<210> SEQ ID NO 158
<211> LENGTH: 11
<212> TYPE: PRT
<213> ORGANISM: Artificial Sequence
<220> FEATURE:
<223> OTHER INFORMATION: VL-CDR1 Sequence of variant L311 (Optimized
      L250)

<400> SEQUENCE: 158

Arg Ala Ser Gln Asn Ile Tyr Thr Ala Val Ala
1               5                   10

<210> SEQ ID NO 159
<211> LENGTH: 7
<212> TYPE: PRT
<213> ORGANISM: Artificial Sequence
<220> FEATURE:
<223> OTHER INFORMATION: VL-CDR2 Sequence of variant L311 (Optimized
      L250)

<400> SEQUENCE: 159

Gly Ala Ser Thr Arg Ala Thr
1               5

<210> SEQ ID NO 160
<211> LENGTH: 9
<212> TYPE: PRT
<213> ORGANISM: Artificial Sequence
<220> FEATURE:
<223> OTHER INFORMATION: VL-CDR3 Sequence of variant L311 (Optimized
      L250)

<400> SEQUENCE: 160

Gln Gln Tyr His Ala Trp Pro Leu Thr
1               5

<210> SEQ ID NO 161
<211> LENGTH: 107
<212> TYPE: PRT
<213> ORGANISM: Artificial Sequence
<220> FEATURE:
<223> OTHER INFORMATION: VL Sequence of variant L459 (Optimized L332)

<400> SEQUENCE: 161

Glu Ile Val Leu Thr Gln Ser Pro Val Thr Leu Ser Val Pro Pro Gly
1               5                   10                  15

Glu Arg Ala Ser Leu Ser Cys Arg Ala Ser Gln Asn Ile Tyr Thr Ala
            20                  25                  30

Val Ala Trp Tyr Gln Gln Lys Pro Gly Gln Ala Pro Arg Leu Leu Ile
        35                  40                  45
```

Tyr Asn Ala Ser Thr Arg Ala Thr Gly Ile Pro Ala Arg Phe Ser Gly
    50                  55                  60

Gly Gly Ser Gly Thr Asp Tyr Thr Leu Thr Ile Ser Ser Leu Glu Ser
65                  70                  75                  80

Glu Asp Phe Ala Val Tyr His Cys Gln Gln Trp His Ser Trp Pro Leu
                85                  90                  95

Thr Phe Gly Gly Gly Thr Lys Leu Glu Ile Lys
            100                 105

<210> SEQ ID NO 162
<211> LENGTH: 11
<212> TYPE: PRT
<213> ORGANISM: Artificial Sequence
<220> FEATURE:
<223> OTHER INFORMATION: VL-CDR1 Sequence of variant L459 (Optimized
      L332)

<400> SEQUENCE: 162

Arg Ala Ser Gln Asn Ile Tyr Thr Ala Val Ala
1               5                   10

<210> SEQ ID NO 163
<211> LENGTH: 7
<212> TYPE: PRT
<213> ORGANISM: Artificial Sequence
<220> FEATURE:
<223> OTHER INFORMATION: VL-CDR2 Sequence of variant L459 (Optimized
      L332)

<400> SEQUENCE: 163

Asn Ala Ser Thr Arg Ala Thr
1               5

<210> SEQ ID NO 164
<211> LENGTH: 9
<212> TYPE: PRT
<213> ORGANISM: Artificial Sequence
<220> FEATURE:
<223> OTHER INFORMATION: VL-CDR3 Sequence of variant L459 (Optimized
      L332)

<400> SEQUENCE: 164

Gln Gln Trp His Ser Trp Pro Leu Thr
1               5

<210> SEQ ID NO 165
<211> LENGTH: 107
<212> TYPE: PRT
<213> ORGANISM: Artificial Sequence
<220> FEATURE:
<223> OTHER INFORMATION: VL Sequence of variant L472 (Optimized L459)

<400> SEQUENCE: 165

Glu Ile Val Leu Thr Gln Ser Pro Ala Thr Leu Ser Val Ser Pro Gly
1               5                   10                  15

Glu Arg Ala Ser Leu Ser Cys Arg Ala Ser Gln Asn Ile Tyr Thr Ala
                20                  25                  30

Val Ala Trp Tyr Gln Gln Lys Pro Gly Gln Ala Pro Arg Leu Leu Ile
            35                  40                  45

Tyr Asn Ala Ala Thr Arg Ala Thr Gly Ile Pro Ala Arg Phe Ser Gly
    50                  55                  60

Gly Gly Ser Gly Thr Asp Tyr Thr Leu Thr Ile Ser Ser Leu Glu Ser
65                  70                  75                  80

Glu Asp Phe Ala Val Tyr His Cys Gln Gln Trp His Ser Trp Pro Leu
            85                  90                  95

Thr Phe Gly Gly Gly Thr Lys Leu Glu Ile Lys
            100                 105

<210> SEQ ID NO 166
<211> LENGTH: 11
<212> TYPE: PRT
<213> ORGANISM: Artificial Sequence
<220> FEATURE:
<223> OTHER INFORMATION: VL-CDR1 Sequence of variant L471 and L472
      (Optimized L459)

<400> SEQUENCE: 166

Arg Ala Ser Gln Asn Ile Tyr Thr Ala Val Ala
1               5                   10

<210> SEQ ID NO 167
<211> LENGTH: 7
<212> TYPE: PRT
<213> ORGANISM: Artificial Sequence
<220> FEATURE:
<223> OTHER INFORMATION: VL-CDR2 Sequence of variant L471 and L472
      (Optimized L459)

<400> SEQUENCE: 167

Asn Ala Ala Thr Arg Ala Thr
1               5

<210> SEQ ID NO 168
<211> LENGTH: 9
<212> TYPE: PRT
<213> ORGANISM: Artificial Sequence
<220> FEATURE:
<223> OTHER INFORMATION: VL-CDR3 Sequence of variant L471 and L472
      (Optimized L459)

<400> SEQUENCE: 168

Gln Gln Trp His Ser Trp Pro Leu Thr
1               5

<210> SEQ ID NO 169
<211> LENGTH: 351
<212> TYPE: DNA
<213> ORGANISM: Artificial Sequence
<220> FEATURE:
<223> OTHER INFORMATION: VH Sequence of variant H1192

<400> SEQUENCE: 169
gaggtgcagc tgttggagtc tgggggaggc ttgatccagc ctgggggtc cctgagactc      60 tcctgtgcag cctctgggtt caccgtcagt agcaactaca tgagctgggt ccgccaggct    120
ccagggaagg gctggagtg gtctcagtt atttatagcg gtggtagaac atactacgca      180
gactccgtga agggccgatt caccatctcc agagacagtt ccaagaacac gctgtatctt    240
caaatgaaca gcctgagagc cgaggacacg gccgtatatt actgtgcacg gaattactac    300
ggtagtacct acgactactg gggccaggga accctggtca ccgtctcctc a             351

<210> SEQ ID NO 170
<211> LENGTH: 351
<212> TYPE: DNA
<213> ORGANISM: Artificial Sequence
<220> FEATURE:
<223> OTHER INFORMATION: VH Sequence of variant H1272

```
<400> SEQUENCE: 170
gaggtgcagc tgttggagtc tggaggaggc ttgatccagc caggggggtc cctgagactc      60
tcctgtgcag cctctgggtt caccgtcgga acaactacat tgagctgggt ccgccaggct     120
ccagggaagg ggctggagtg ggtctcagtt atttatagcg ctggaagcac atactacgca     180
gactccgtga agggccgatt catcatctcc agagacaact ccaaggacac ggtgtatctt     240
caaatgaaca gcctgagagt cgacgacacg gccgtatatt actgtgcacg gaattactac     300
ggtagtacct acgactactg gggccaggga accctggtca ccgtctcctc a             351

<210> SEQ ID NO 171
<211> LENGTH: 351
<212> TYPE: DNA
<213> ORGANISM: Artificial Sequence
<220> FEATURE:
<223> OTHER INFORMATION: VH Sequence of variant H1273

<400> SEQUENCE: 171
gaggtgcagc tgttggagtc tggaggaggc ttgatccagc ctggggggtc cctgagactc      60
tcctgtgcag cctctgggtt caccgtcagt agcaactaca tgagctgggt ccgccaggct     120
ccagggaagg ggctggagtg ggtctcagtt atttatagcg gtggtagcac atactacgca     180
gactccgtga agggccgatt caccatctcc agagacaacg ccaagaacac cgtgtatctg     240
caaatgaaca gtctgcgatc agaggacacg gccgtatatt actgtgcacg gaattactac     300
ggtagtacct acgactactg gggccaggga accctggtca ccgtctcctc a             351

<210> SEQ ID NO 172
<211> LENGTH: 351
<212> TYPE: DNA
<213> ORGANISM: Artificial Sequence
<220> FEATURE:
<223> OTHER INFORMATION: VH Sequence of variant H1278

<400> SEQUENCE: 172
gaggtgcagc tgttggagtc tggaggaggc ttgatccagc ctggggggtc cctgagactc      60
tcctgtgcag cctctgggtt caccgtcagt aacaactaca tgagctgggt ccgccaggct     120
ccagggaagg ggctgcagtg ggtcgcagtt atttatagtg gtggtagcac atactaccca     180
gactccatga agggccgatt caccatctcc agagacaatt ccaaaaacac gctttatctt     240
caaatgaaca gcctgagagc cgaggacacg gccgtatatt actgtgcacg gaattactac     300
ggtagtacct acgactactg gggccaggga accctggtca ccgtctcctc a             351

<210> SEQ ID NO 173
<211> LENGTH: 351
<212> TYPE: DNA
<213> ORGANISM: Artificial Sequence
<220> FEATURE:
<223> OTHER INFORMATION: VH Sequence of variant H1277

<400> SEQUENCE: 173
gaggtgcagc tggtggagtc tgggggaggc ttggtccagc ctggggggtc cctgaaactc      60
tcctgtgcag cctctgggtt caccgttagt agtaactaca tgagttgggt ccgccaggct     120
ccagggaagg ggctggagtg ggtctcagtt atttatagag gtggtagcac atactacgca     180
gactccgtga agggccgatt caccatctcc agagacattt ccaggaacat ggtgtatctt     240
caaatgaaca gtctgagagc cgaggacacg gccgtatatt actgtgcacg gaattactac     300
ggtagtacct acgactactg gggccaggga accctggtca ccgtctcctc a             351
```

<210> SEQ ID NO 174
<211> LENGTH: 351
<212> TYPE: DNA
<213> ORGANISM: Artificial Sequence
<220> FEATURE:
<223> OTHER INFORMATION: VH Sequence of variant H1280

<400> SEQUENCE: 174

```
gaggtgcagc tgttggagtc tggaggaggc ttgatccagc ctggggggtc cctgagactc      60
tcctgtgcag cctctgggtt caccgtcagt agcaactaca tgagctgggt ccgccaggct     120
ccagggaagg ggctggagtg ggtctcagtt atttatagcg gtggtagcac atactacgca     180
gactccgtga agggccgatt caccatctcc agagacaatt ccaagaacac gctgtatctt     240
caaatgaaca gcctgagagc cgaggacacg gccgtatatt actgtgcacg gaattactac     300
ggtagtacct acgactactg gggccaggga accctggtca ccgtctcctc a              351
```

<210> SEQ ID NO 175
<211> LENGTH: 351
<212> TYPE: DNA
<213> ORGANISM: Artificial Sequence
<220> FEATURE:
<223> OTHER INFORMATION: VH Sequence of variant H1193

<400> SEQUENCE: 175

```
gaggtgcagc tggtggagtc tggaggaggc ttgatccagc ctggggggtc cctgagactc      60
tcctgtgcag cctctgggtt caccgtcagt agcaactaca tgagctgggt ccgccaggct     120
ccagggaagg ggctggagtg ggtctcagtt atttatagcg gtggtagaac atactacgca     180
gactccgtga agggccgatt caccatctcc agagacagtt ccaagaacac gctgtatctt     240
caaatgaaca gcctgagagc cgaggacacg gccgtatatt actgtgcacg gaattactac     300
ggtagtacct acgactactg gggccaggga accctggtca ccgtctcctc a              351
```

<210> SEQ ID NO 176
<211> LENGTH: 351
<212> TYPE: DNA
<213> ORGANISM: Artificial Sequence
<220> FEATURE:
<223> OTHER INFORMATION: VH Sequence of variant H1329

<400> SEQUENCE: 176

```
gaggtgcagc tggtggagtc tggaggaggc ttgatccagc ctggggggtc cctgagactc      60
tcatgcgcag tctcggggct caatgtcagt cgcgactaca tgagctgggt ccgccaggct     120
ccagggaagg ggctagagtg gatctcagtt atttatagag gtggtgccac aatgtacgca     180
gactccgtga agggccgatt caccatctcc agagacactt ccaagaacac ggtgttcctg     240
caaatgagta gactgaaagt cgcggacacg gccgtatatt actgtgcacg gaattactac     300
ggtagtacct acgactactg gggccaggga accctggtca ccgtctcctc a              351
```

<210> SEQ ID NO 177
<211> LENGTH: 351
<212> TYPE: DNA
<213> ORGANISM: Artificial Sequence
<220> FEATURE:
<223> OTHER INFORMATION: VH Sequence of variant H1478 (Optimized H1192)

<400> SEQUENCE: 177

```
gaggtgcagc tgttggagtc tgggggaggc ttgatccagc ctggggggtc cctgagactc      60
```

-continued

```
tcctgtgcag cctctgggtt caccgtcagt agcaactaca tgagctgggt ccgccaggct      120
ccagggaagg ggctggagtg ggtctcagtt atttatagcg gtggtagaac atactacgca      180
gactccgtga agggccgatt caccatctcc agagacagtt ccaagaacac gctgtatctt      240
caaatgaaca gcctgagagc cgaggacacg gccgtatatt actgtgcacg gacttactac      300
ggtagtacct acgactactg gggccaggga accctggtca ccgtctcctc a              351
```

<210> SEQ ID NO 178
<211> LENGTH: 351
<212> TYPE: DNA
<213> ORGANISM: Artificial Sequence
<220> FEATURE:
<223> OTHER INFORMATION: VH Sequence of variant H1479 (Optimized H1192)

<400> SEQUENCE: 178

```
gaggtgcagc tgttggagtc tgggggaggc ttgatccagc ctggggggtc cctgagactc      60
tcctgtgcag cctctgggtt caccgtcagt agcaactaca tgagctgggt ccgccaggct      120
ccagggaagg ggctggagtg ggtctcagtt atttatagcg gtggtagaac atactacgca      180
gactccgtga agggccgatt caccatctcc agagacagtt ccaagaacac gctgtatctt      240
caaatgaaca gcctgagagc cgaggacacg gccgtatatt actgtgcacg gctttactac      300
ggtagtacct acgactactg gggccaggga accctggtca ccgtctcctc a              351
```

<210> SEQ ID NO 179
<211> LENGTH: 351
<212> TYPE: DNA
<213> ORGANISM: Artificial Sequence
<220> FEATURE:
<223> OTHER INFORMATION: VH Sequence of variant H1373 (Optimized H1192)

<400> SEQUENCE: 179

```
gaggtgcagc tgttggagtc tgggggaggc ttgatccagc ctggggggtc cctgagactc      60
tcctgtgcag cctctgggtt caccgtcagt agcaactaca tgagctgggt ccgccaggct      120
ccagggaagg ggctggagtg ggtctcagtt atttatagcg gtggtagaac atactacgca      180
gactccgtga agggccgatt caccatctcc agagacagtt ccaagaacac gctgtatctt      240
caaatgaaca gcctgagagc cgaggacacg gccgtatatt actgtgcacg gaattacgcg      300
ggtagtacct acgactactg gggccaggga accctggtca ccgtctcctc a              351
```

<210> SEQ ID NO 180
<211> LENGTH: 351
<212> TYPE: DNA
<213> ORGANISM: Artificial Sequence
<220> FEATURE:
<223> OTHER INFORMATION: VH Sequence of variant H1388 (Optimized H1192)

<400> SEQUENCE: 180

```
gaggtgcagc tgttggagtc tgggggaggc ttgatccagc ctggggggtc cctgagactc      60
tcctgtgcag cctctgggtt caccgtcagt agcaactaca tgagctgggt ccgccaggct      120
ccagggaagg ggctggagtg ggtctcagtt atttatagcg gtggtagaac atactacgca      180
gactccgtga agggccgatt caccatctcc agagacagtt ccaagaacac gctgtatctt      240
caaatgaaca gcctgagagc cgaggacacg gccgtatatt actgtgcacg gaattactac      300 ggtagtctttt acgactactg gggccaggga accctggtca ccgtctcctc a              351
```

<210> SEQ ID NO 181
<211> LENGTH: 351

```
<212> TYPE: DNA
<213> ORGANISM: Artificial Sequence
<220> FEATURE:
<223> OTHER INFORMATION: VH Sequence of variant H1482 (Optimized H1192)

<400> SEQUENCE: 181
gaggtgcagc tgttggagtc tgggggaggc ttgatccagc ctgggggtc cctgagactc      60 tcctgtgcag cctctgggtt caccgtcagt agcaactaca tgagctgggt ccgccaggct     120
ccagggaagg ggctggagtg ggtctcagtt atttatagcg gtggtagaac atactacgca    180
gactccgtga agggccgatt caccatctcc agagacagtt ccaagaacac gctgtatctt    240
caaatgaaca gcctgagagc cgaggacacg gccgtatatt actgtgcacg gaattactac    300
ggtagtacct ttgactactg gggccaggga accctggtca ccgtctcctc a             351

<210> SEQ ID NO 182
<211> LENGTH: 351
<212> TYPE: DNA
<213> ORGANISM: Artificial Sequence
<220> FEATURE:
<223> OTHER INFORMATION: VH Sequence of variant H1483 (Optimized H1192)

<400> SEQUENCE: 182
gaggtgcagc tgttggagtc tgggggaggc ttgatccagc ctgggggtc cctgagactc      60 tcctgtgcag cctctgggtt caccgtcagt agcaactaca tgagctgggt ccgccaggct     120
ccagggaagg ggctggagtg ggtctcagtt atttatagcg gtggtagaac atactacgca    180
gactccgtga agggccgatt caccatctcc agagacagtt ccaagaacac gctgtatctt    240
caaatgaaca gcctgagagc cgaggacacg gccgtatatt actgtgcacg gaattactac    300
ggtagtacca tggactactg ggggcaggga accctggtca ccgtctcctc a              351

<210> SEQ ID NO 183
<211> LENGTH: 351
<212> TYPE: DNA
<213> ORGANISM: Artificial Sequence
<220> FEATURE:
<223> OTHER INFORMATION: VH Sequence of variant H1487 (Optimized H1192)

<400> SEQUENCE: 183
gaggtgcagc tgttggagtc tgggggaggc ttgatccagc ctgggggtc cctgagactc      60 tcctgtgcag cctctgggtt caccgtcagt agcaactaca tgagctgggt ccgccaggct     120
ccagggaagg ggctggagtg ggtctcagtt atttatagcg gtggtagaac atactacgca    180
gactccgtga agggccgatt caccatctcc agagacagtt ccaagaacac gctgtatctt    240
caaatgaaca gcctgagagc cgaggacacg gccgtatatt actgtgcacg gaattactac    300
ggtagtaccc ttgactactg gggccaggga accctggtca ccgtctcctc a              351

<210> SEQ ID NO 184
<211> LENGTH: 351
<212> TYPE: DNA
<213> ORGANISM: Artificial Sequence
<220> FEATURE:
<223> OTHER INFORMATION: VH Sequence of variant H1518 (Optimized H1192)

<400> SEQUENCE: 184
gaggtgcagc tgttggagtc tgggggaggc ttgatccagc ctgggggtc cctgagactc      60 tcctgtgcag cctctgggtt caccgtcagt agcaactaca tgagctgggt ccgccaggct     120
ccagggaagg ggctggagtg ggtctcagtt atttatagcg gtggtagaac atactacgca    180
```

```
gactccgtga agggccgatt caccatctcc agagacagtt ccaagaacac gctgtatctt    240
caaatgaaca gcctgagagc cgaggacacg gccgtatatt actgtgcacg gaattactac    300
ggtagtaccc acgactactg gggccaggga accctggtca ccgtctcctc a             351
```

<210> SEQ ID NO 185
<211> LENGTH: 351
<212> TYPE: DNA
<213> ORGANISM: Artificial Sequence
<220> FEATURE:
<223> OTHER INFORMATION: VH Sequence of variant H1557 (Optimized H1192)

<400> SEQUENCE: 185

```
gaggtgcagc tgttggagtc tgggggaggc ttgatccagc ctgggggtc cctgagactc     60 tcctgtgcag cctctgggtt caccgtcagt agcaactaca tgagctgggt ccgccaggct   120
ccagggaagg gctggagtg gtctcagtt atttatagcg gtggtagaac atactacgca    180
gactccgtga agggccgatt caccatctcc agagacagtt ccaagaacac gctgtatctt    240
caaatgaaca gcctgagagc cgaggacacg gccgtatatt actgtgcacg gaattactac    300
ggtagtaccg tggactactg gggccaggga accctggtca ccgtctcctc a             351
```

<210> SEQ ID NO 186
<211> LENGTH: 351
<212> TYPE: DNA
<213> ORGANISM: Artificial Sequence
<220> FEATURE:
<223> OTHER INFORMATION: VH Sequence of variant H1694 (Optimized H1329)

<400> SEQUENCE: 186

```
gaggtgcagc tggtggagtc tggaggaggc ttgatccagc ctgggggtc cctgagactc     60 tcatgcgcag tctcggggct caatgtcagt cgcgactaca tgagctgggt ccgccaggct   120
ccagggaagg gctagagtg gatctcagtt atttatagag gtggtgccac aatgtacgca    180
gactccgtga agggccgatt caccatctcc agagacactt ccaagaacac ggtgttcctg    240
caaatgagta gactgaaagt cgcggacacg gccgtatatt actgtgcacg gacttactac    300
ggtagtacct acgactactg gggccaggga accctggtca ccgtctcctc a             351
```

<210> SEQ ID NO 187
<211> LENGTH: 351
<212> TYPE: DNA
<213> ORGANISM: Artificial Sequence
<220> FEATURE:
<223> OTHER INFORMATION: VH Sequence of variant H1596 (Optimized H1329)

<400> SEQUENCE: 187

```
gaggtgcagc tggtggagtc tggaggaggc ttgatccagc ctgggggtc cctgagactc     60 tcatgcgcag tctcggggct caatgtcagt cgcgactaca tgagctgggt ccgccaggct   120
ccagggaagg gctagagtg gatctcagtt atttatagag gtggtgccac aatgtacgca    180
gactccgtga agggccgatt caccatctcc agagacactt ccaagaacac ggtgttcctg    240
caaatgagta gactgaaagt cgcggacacg gccgtatatt actgtgcacg gaattactac    300
ggtagtaccc acgactactg gggccaggga accctggtca ccgtctcctc a             351
```

<210> SEQ ID NO 188
<211> LENGTH: 351
<212> TYPE: DNA
<213> ORGANISM: Artificial Sequence
<220> FEATURE:
<223> OTHER INFORMATION: VH Sequence of variant H1687 (Optimized H1329)

<400> SEQUENCE: 188

```
gaggtgcagc tggtggagtc tggaggaggc ttgatccagc ctgggggtc cctgagactc        60
tcatgcgcag tctcggggct caatgtcagt cgcgactaca tgagctgggt ccgccaggct      120
ccagggaagg ggctagagtg gatctcagtt atttatagag gtggtgccac aatgtacgca      180
gactccgtga agggccgatt caccatctcc agagacactt ccaagaacac ggtgttcctg      240
caaatgagta gactgaaagt cgcggacacg gccgtatatt actgtgcacg gaattactac      300
ggtagtacca tggactactg gggccaggga accctggtca ccgtctcctc a               351
```

<210> SEQ ID NO 189
<211> LENGTH: 351
<212> TYPE: DNA
<213> ORGANISM: Artificial Sequence
<220> FEATURE:
<223> OTHER INFORMATION: VH Sequence of variant H1684 (Optimized H1329)

<400> SEQUENCE: 189

```
gaggtgcagc tggtggagtc tggaggaggc ttgatccagc ctgggggtc cctgagactc        60
tcatgcgcag tctcggggct caatgtcagt cgcgactaca tgagctgggt ccgccaggct      120
ccagggaagg ggctagagtg gatctcagtt atttatagag gtggtgccac aatgtacgca      180
gactccgtga agggccgatt caccatctcc agagacactt ccaagaacac ggtgttcctg      240
caaatgagta gactgaaagt cgcggacacg gccgtatatt actgtgcacg gaattactac      300
ggtagtacca ttgactactg gggccaggga accctggtca ccgtctcctc a               351
```

<210> SEQ ID NO 190
<211> LENGTH: 351
<212> TYPE: DNA
<213> ORGANISM: Artificial Sequence
<220> FEATURE:
<223> OTHER INFORMATION: VH Sequence of variant H1678 (Optimized H1329)

<400> SEQUENCE: 190

```
gaggtgcagc tggtggagtc tggaggaggc ttgatccagc ctgggggtc cctgagactc        60
tcatgcgcag tctcggggct caatgtcagt cgcgactaca tgagctgggt ccgccaggct      120
ccagggaagg ggctagagtg gatctcagtt atttatagag gtggtgccac aatgtacgca      180
gactccgtga agggccgatt caccatctcc agagacactt ccaagaacac ggtgttcctg      240
caaatgagta gactgaaagt cgcggacacg gccgtatatt actgtgcacg gaattactac      300
ggtagtacct tcgactactg gggccaggga accctggtca ccgtctcctc a               351
```

<210> SEQ ID NO 191
<211> LENGTH: 351
<212> TYPE: DNA
<213> ORGANISM: Artificial Sequence
<220> FEATURE:
<223> OTHER INFORMATION: VH Sequence of variant H1685 (Optimized H1329)

<400> SEQUENCE: 191

```
gaggtgcagc tggtggagtc tggaggaggc ttgatccagc ctgggggtc cctgagactc        60
tcatgcgcag tctcggggct caatgtcagt cgcgactaca tgagctgggt ccgccaggct      120
ccagggaagg ggctagagtg gatctcagtt atttatagag gtggtgccac aatgtacgca      180
gactccgtga agggccgatt caccatctcc agagacactt ccaagaacac ggtgttcctg      240
caaatgagta gactgaaagt cgcggacacg gccgtatatt actgtgcacg gaattactac      300
```

```
ggtagtacct tggactactg gggccaggga accctggtca ccgtctcctc a          351
```

<210> SEQ ID NO 192
<211> LENGTH: 351
<212> TYPE: DNA
<213> ORGANISM: Artificial Sequence
<220> FEATURE:
<223> OTHER INFORMATION: VH Sequence of variant H1727 (Optimized H1272)

<400> SEQUENCE: 192

```
gaggtgcagc tgttggagtc tggaggaggc ttgatccagc caggggggtc cctgagactc    60
tcctgtgcag cctctgggtt caccgtcgga acaactaca tgagctgggt ccgccaggct    120
ccagggaagg ggctggagtg ggtctcagtt atttatagcg ctggaagcac atactacgca   180
gactccgtga agggccgatt catcatctcc agagacaact ccaaggacac ggtgtatctt    240
caaatgaaca gcctgagagt cgacgacacg gccgtatatt actgtgcacg gaattactac    300
ggtagtaccc acgactactg gggccaggga accctggtca ccgtctcctc a             351
```

<210> SEQ ID NO 193
<211> LENGTH: 351
<212> TYPE: DNA
<213> ORGANISM: Artificial Sequence
<220> FEATURE:
<223> OTHER INFORMATION: VH Sequence of variant H1725 (Optimized H1272)

<400> SEQUENCE: 193

```
gaggtgcagc tgttggagtc tggaggaggc ttgatccagc caggggggtc cctgagactc    60
tcctgtgcag cctctgggtt caccgtcgga acaactaca tgagctgggt ccgccaggct    120
ccagggaagg ggctggagtg ggtctcagtt atttatagcg ctggaagcac atactacgca   180
gactccgtga agggccgatt catcatctcc agagacaact ccaaggacac ggtgtatctt    240
caaatgaaca gcctgagagt cgacgacacg gccgtatatt actgtgcacg gaattactac    300
ggtagtacca tggactactg gggccaggga accctggtca ccgtctcctc a             351
```

<210> SEQ ID NO 194
<211> LENGTH: 351
<212> TYPE: DNA
<213> ORGANISM: Artificial Sequence
<220> FEATURE:
<223> OTHER INFORMATION: VH Sequence of variant H1728 (Optimized H1272)

<400> SEQUENCE: 194

```
gaggtgcagc tgttggagtc tggaggaggc ttgatccagc caggggggtc cctgagactc    60
tcctgtgcag cctctgggtt caccgtcgga acaactaca tgagctgggt ccgccaggct    120
ccagggaagg ggctggagtg ggtctcagtt atttatagcg ctggaagcac atactacgca   180
gactccgtga agggccgatt catcatctcc agagacaact ccaaggacac ggtgtatctt    240
caaatgaaca gcctgagagt cgacgacacg gccgtatatt actgtgcacg gaattactac    300
ggtagtacct tcgactactg gggccaggga accctggtca ccgtctcctc a             351
```

<210> SEQ ID NO 195
<211> LENGTH: 351
<212> TYPE: DNA
<213> ORGANISM: Artificial Sequence
<220> FEATURE:
<223> OTHER INFORMATION: VH Sequence of variant H1729 (Optimized H1272)

<400> SEQUENCE: 195

```
gaggtgcagc tgttggagtc tggaggaggc ttgatccagc caggggggtc cctgagactc    60
```

```
tcctgtgcag cctctgggtt caccgtcgga acaaactaca tgagctgggt ccgccaggct    120
ccagggaagg ggctggagtg ggtctcagtt atttatagcg ctggaagcac atactacgca    180
gactccgtga agggccgatt catcatctcc agagacaact ccaaggacac ggtgtatctt    240
caaatgaaca gcctgagagt cgacgacacg gccgtatatt actgtgcacg gaattactac    300
ggtagtaccc tcgactactg gggccaggga accctggtca ccgtctcctc a             351
```

<210> SEQ ID NO 196
<211> LENGTH: 351
<212> TYPE: DNA
<213> ORGANISM: Artificial Sequence
<220> FEATURE:
<223> OTHER INFORMATION: VH Sequence of variant H1813 (Optimized H1685)

<400> SEQUENCE: 196

```
gaggtgcagc tggtggagtc tggaggaggc ttgatccagc ctgggggtc cctgagactc      60 tcatgcgcag tctcggggct caatgtcagt cgcgactaca tgagctgggt ccgccaggct    120
ccagggaagg ggctagagtg gatctcagtt atttatagaa ttggtgccac aatgtacgca    180
gactccgtga agggccgatt caccatctcc agagacactt ccaagaacac ggtgttcctg    240
caaatgagta gactgaaagt cgcggacacg gccgtatatt actgtgcacg gaattactac    300
ggtagtaccc ttgactactg gggccaggga accctggtca ccgtctcctc a             351
```

<210> SEQ ID NO 197
<211> LENGTH: 351
<212> TYPE: DNA
<213> ORGANISM: Artificial Sequence
<220> FEATURE:
<223> OTHER INFORMATION: VH Sequence of variant H1814 (Optimized H1685)

<400> SEQUENCE: 197

```
gaggtgcagc tggtggagtc tggaggaggc ttgatccagc ctgggggtc cctgagactc      60 tcatgcgcag tctcggggct caatgtcagt cgcgactaca tgagctgggt ccgccaggct    120
ccagggaagg ggctagagtg gatctcagtt atttatagag ttggtgccac aatgtacgca    180
gactccgtga agggccgatt caccatctcc agagacactt ccaagaacac ggtgttcctg    240
caaatgagta gactgaaagt cgcggacacg gccgtatatt actgtgcacg gaattactac    300
ggtagtaccc ttgactactg gggccaggga accctggtca ccgtctcctc a             351
```

<210> SEQ ID NO 198
<211> LENGTH: 351
<212> TYPE: DNA
<213> ORGANISM: Artificial Sequence
<220> FEATURE:
<223> OTHER INFORMATION: VH Sequence of variant H1824 (Optimized H1685)

<400> SEQUENCE: 198

```
gaggtgcagc tggtggagtc tggaggaggc ttgatccagc ctgggggtc cctgagactc      60 tcatgcgcag tctcggggct caatgtcagt cgcgactaca tgagctgggt ccgccaggct    120
ccagggaagg ggctagagtg gatctcagtt atttatagag gtggtattac aatgtacgca    180
gactccgtga agggccgatt caccatctcc agagacactt ccaagaacac ggtgttcctg    240
caaatgagta gactgaaagt cgcggacacg gccgtatatt actgtgcacg gaattactac    300
ggtagtaccc ttgactactg gggccaggga accctggtca ccgtctcctc a             351
```

<210> SEQ ID NO 199

```
<211> LENGTH: 351
<212> TYPE: DNA
<213> ORGANISM: Artificial Sequence
<220> FEATURE:
<223> OTHER INFORMATION: VH Sequence of variant H1831 (Optimized H1685)

<400> SEQUENCE: 199
gaggtgcagc tggtggagtc tggaggaggc ttgatccagc ctgggggtc cctgagactc      60 tcatgcgcag tctcggggct caatgtcagt cgcgactaca tgagctgggt ccgccaggct    120
ccagggaagg ggctagagtg gatctcagtt atttatagag gtggtgccac acattacgca    180
gactccgtga agggccgatt caccatctcc agagacactt ccaagaacac ggtgttcctg    240
caaatgagta gactgaaagt cgcggacacg gccgtatatt actgtgcacg gaattactac    300
ggtagtaccc ttgactactg gggccaggga accctggtca ccgtctcctc a            351

<210> SEQ ID NO 200
<211> LENGTH: 351
<212> TYPE: DNA
<213> ORGANISM: Artificial Sequence
<220> FEATURE:
<223> OTHER INFORMATION: VH Sequence of variant H1844 (Optimized H1685)

<400> SEQUENCE: 200
gaggtgcagc tggtggagtc tggaggaggc ttgatccagc ctgggggtc cctgagactc      60 tcatgcgcag tctcggggct caatgtcagt cgcgactaca tgagctgggt ccgccaggct    120
ccagggaagg ggctagagtg gatctcagtt atttatagag gtggtgttac aatgtacgca    180
gactccgtga agggccgatt caccatctcc agagacactt ccaagaacac ggtgttcctg    240
caaatgagta gactgaaagt cgcggacacg gccgtatatt actgtgcacg gaattactac    300
ggtagtaccc ttgactactg gggccaggga accctggtca ccgtctcctc a            351

<210> SEQ ID NO 201
<211> LENGTH: 354
<212> TYPE: DNA
<213> ORGANISM: Artificial Sequence
<220> FEATURE:
<223> OTHER INFORMATION: VH Sequence of variant H1102

<400> SEQUENCE: 201
gaggtgcagc tggtggagtc tgggggaggc ttggtccagc ctgggggtc cctgagactc      60 tcctgttcag cctctggatt caccttcagt agctatgcta tgcactgggt ccgccaggct    120
ccagggaagg gactggaata tgtttcagct attagtagta tgggggtag cacatactac    180 gcagactccg tgacgggcag attcaccatc tccagagaca attccaagaa cacgctgcat    240
cttcaaatga gcagtctgag agctgaggac acggccgtat attactgtgc acggaattac    300
tacggtagta cctacgacta ctggggccag ggaaccctgg tcaccgtctc ctca          354

<210> SEQ ID NO 202
<211> LENGTH: 354
<212> TYPE: DNA
<213> ORGANISM: Artificial Sequence
<220> FEATURE:
<223> OTHER INFORMATION: VH Sequence of variant H1103

<400> SEQUENCE: 202
gaggtgcagc tgttggagtc tgggggaggc gtggtccagc ctgggaggtc cctgagactc      60
tcctgtgcag cctctggatt caccttcttt aactatggca tgcactgggt ccgccaggct    120
ccaggcaagg ggctggagtg ggtggccgtc acatcatttg atggaagtca tgcatactat    180
```

```
gcagactccg tgaagggccg attcaccatc tccagagaca attccaagaa cacggtgttc    240
ctgcaaatga acaacctgag aggtgatgac acggccgtat attactgtgc acggaattac    300
tacggtagta cctacgacta ctggggccag ggaaccctgg tcaccgtctc ctca          354
```

<210> SEQ ID NO 203
<211> LENGTH: 351
<212> TYPE: DNA
<213> ORGANISM: Artificial Sequence
<220> FEATURE:
<223> OTHER INFORMATION: VH Sequence of variant H1104

<400> SEQUENCE: 203

```
gaggtgcagc tgttggagtc tgggggaggg atggtgcaga ctgggggtc cgtgagactc      60 tcctgtgcag tctctggatt caccgtcagt agcaactaca tgagctgggt ccgccaggct    120
ccagggaagg ggctggagtg ggtctccgtt atttatacta gtggtagtac attctacgca    180
gactccgtga aggtcgatt caccatctcc agagacaatt ccaagaacac actgtatctt    240
caaatgaaca gcctgagagc cgaggacacg gccgtatatt actgtgcacg gaattactac    300
ggtagtacct acgactactg ggccaggga accctggtca ccgtctcctc a              351
```

<210> SEQ ID NO 204
<211> LENGTH: 354
<212> TYPE: DNA
<213> ORGANISM: Artificial Sequence
<220> FEATURE:
<223> OTHER INFORMATION: VH Sequence of variant H1118

<400> SEQUENCE: 204

```
gaggtgcagc tgttggagtc tggcccagga ctggtgaagc cttcggagac cctgtccctc     60
aattgcgcgg tctctggtga ctccatcagc agtggtcact attggggctg gatccggcag    120
cccccaggga aggggctgga gtggattggg actatctctc ataggggac gacctactcc     180 aacccgtccc tcaagagtcg cgtcactatt caatggaca gtccagtaa tagcttctcc     240 ttgaaactga gctctgtgac cgccgcagac acggccgtat attactgtgc acggaattac    300
tacggtagta cctacgacta ctggggccag ggaaccctgg tcaccgtctc ctca           354
```

<210> SEQ ID NO 205
<211> LENGTH: 354
<212> TYPE: DNA
<213> ORGANISM: Artificial Sequence
<220> FEATURE:
<223> OTHER INFORMATION: VH Sequence of variant H1117

<400> SEQUENCE: 205

```
gaggtgcagc tgttggagtc tgggggagcc ttggtacagc cggggggtc cctgaggctc      60 tcctgtgcag cctctggatt caccttttgac agctatccca tgaactgggt ccgccaggcc    120
ccagggaggg ggctggagtg ggtctcaact attagtggta gtggtattgg cacatactac    180
gcagactccg tgaagggtcg cttcaccatc tccagagaca actccaagaa caccctatat    240
ctgcaaatga acagcctgag agccgacgac acggccgtat attactgtgc acggaattac    300
tacggtagta cctacgacta ctggggccag ggaaccctgg tcaccgtctc ctca           354
```

<210> SEQ ID NO 206
<211> LENGTH: 354
<212> TYPE: DNA
<213> ORGANISM: Artificial Sequence
<220> FEATURE:

<223> OTHER INFORMATION: VH Sequence of variant H1119

<400> SEQUENCE: 206

```
gaggtgcagc tgttggagtc tggggggaggc ttggtgcagc cggggggtc cctgagactc    60
tcctgtgcag cctctggatt caactttaag aaatatccca tgagctgggt ccgccagact   120
ccagggaagg ggctggagtg ggtctcattt atcactggga atgctgatag gacatactac   180
gcagactcac tgaagggccg gttcactatc tccagagaca attccaagaa cacgctgtat   240
ctgcaaatga acagcctggc agtcgaggac acggccgtat attactgtgc acggaattac   300
tacggtagta cctacgacta ctggggccag ggaaccctgg tcaccgtctc ctca          354
```

<210> SEQ ID NO 207
<211> LENGTH: 354
<212> TYPE: DNA
<213> ORGANISM: Artificial Sequence
<220> FEATURE:
<223> OTHER INFORMATION: VH Sequence of variant H1120

<400> SEQUENCE: 207

```
gaggtgcagc tggtggagtc tggggggaggc gtggtccagc ctgggaggtc cctgagactc    60
tcctgtgcag cctctggatt caccttcaat ggctttgcca tgcactgggt ccgccaggct   120
ccaggcaagg ggctggagtg ggtggcggtt atatcatatg atggaaataa taaatactat   180
gcagactccg tgaagggccg gttcaccatc tccagagaca attccaagaa cacggtgttc   240
ctacaaatga acagcctgag acctgaggac acggccgtat attactgtgc acggaattac   300
tacggtagta cctacgacta ctggggccag ggaaccctgg tcaccgtctc ctca          354
```

<210> SEQ ID NO 208
<211> LENGTH: 354
<212> TYPE: DNA
<213> ORGANISM: Artificial Sequence
<220> FEATURE:
<223> OTHER INFORMATION: VH Sequence of variant H1121

<400> SEQUENCE: 208

```
gaggtgcagc tggtggagtc tggggggaggc gtggtccagc ctgggaggtc cctgagactc    60
tcctgtgcag cctctggatt caccttcagt agctatggca tgcactgggt ccgccaggct   120
ccaggcaagg ggctggagtg ggtggcagtt atatcatatg atggaagtaa taaatactat   180
gcagactccg cgaagggccg attcaccatc tccagagaca attccaagaa cacgctgtat   240
ctgcaaatga acagcctgag agctgaggac acggccgtat attactgtgc acggaattac   300
tacggtagta cctacgacta ctggggccag ggaaccctgg tcaccgtctc ctca          354
```

<210> SEQ ID NO 209
<211> LENGTH: 354
<212> TYPE: DNA
<213> ORGANISM: Artificial Sequence
<220> FEATURE:
<223> OTHER INFORMATION: VH Sequence of variant H1122

<400> SEQUENCE: 209

```
gaggtgcagc tgttggagtc tggggggaggc gtggtccagc cgggggggtc cctgagactg    60
tcctgtgcag cctctggatt caccttcagt agtcatccta tgcactgggt ccgccaggct   120
ccaggcaagg ggctggagtg ggtggcagtt atatcatatg atgcaagggt taaatactat   180
gtagactccg tgaagggccg attcaccatc tccagagacg actccaagaa cacgctgtat   240
ctgcaaatga acagcctgac aactgaggac acggccgtat attactgtgc acggaattac   300
```
tacggtagta cctacgacta ctggggccag ggaaccctgg tcaccgtctc ctca    354

<210> SEQ ID NO 210
<211> LENGTH: 354
<212> TYPE: DNA
<213> ORGANISM: Artificial Sequence
<220> FEATURE:
<223> OTHER INFORMATION: VH Sequence of variant H1194

<400> SEQUENCE: 210
gaggtgcagc tggtggagtc tgggggaggc gtggtccagc ctgggggtc cctgagactc    60 tcctgtgcag cctctggatt caccttcagt agttatggca tacactgggt ccgccaggct   120
ccaggcaagg gctggagtg gtggcactt atatcatatg atggaagtaa gaaatactat    180
gcagactccg tgaagggccg attcaccatc tccagagaca attccaagaa cacgctgtat   240
ctgcaaatga acagcctgag aactgaggac acggccgtat attactgtgc acggaattac   300
tacggtagta cctacgacta ctggggccag ggaaccctgg tcaccgtctc ctca         354

<210> SEQ ID NO 211
<211> LENGTH: 354
<212> TYPE: DNA
<213> ORGANISM: Artificial Sequence
<220> FEATURE:
<223> OTHER INFORMATION: VH Sequence of variant H1195

<400> SEQUENCE: 211
gaggtgcagc tggtggagtc tgggggaggc ctggtacagc ctgggggtc cctgagactc    60 tcctgtgcag cctctggatt caccttcagt acctacgact ccactgggt ccgccaaggt   120 acaggagaag gtctggagtg gtctcagct attagtccta gtggtggtag cacatactac   180
gcagactccg tgaagggccg gttcaccatc tccagagaca attccaagaa cacgctttat   240
ctgcaaatga acagcctgag agccgaggac acggccgtat attactgtgc acggaattac   300
tacggtagta cctacgacta ctggggccag ggaaccctgg tcaccgtctc ctca         354

<210> SEQ ID NO 212
<211> LENGTH: 321
<212> TYPE: DNA
<213> ORGANISM: Artificial Sequence
<220> FEATURE:
<223> OTHER INFORMATION: VL Sequence of variant L217

<400> SEQUENCE: 212
gacatcgtga tgacccagtc tcctgtcatc ttgtctgtgt ctccagggga cagagccacc    60
ctctcctgca gggccagtga gagtgtcaga ggcaacgtag cctggtatca acaaaaaccc   120
ggacaggttc ccaggctcct catctctggt gcatccacca gggccaatgg gatcccagcc   180
aggttcagtg gcagtgggtc tgggaccgag tacagtctca ccatcagcag cctgcagcct   240
gaagatgttg caatttatca ttgtcatcag tatcattatt ggccgctcac tttcggcgga   300
gggaccaagc tcgagatcaa a                                              321

<210> SEQ ID NO 213
<211> LENGTH: 321
<212> TYPE: DNA
<213> ORGANISM: Artificial Sequence
<220> FEATURE:
<223> OTHER INFORMATION: VL Sequence of variant L218

<400> SEQUENCE: 213

```
gacatcgtga tgacccagtc tccagccacc ctctctgtgt ctcctgggga aagagtcacc    60
ctctcctgca gggcccctca aattctgaga agcaacttag cctggtacca gcagaagcct   120
ggccaggctc ccaggctcct catctacggt gcatccaaca gggtcactgg tgtcccagcc   180
aggttcagtg ccagtgagtc tgggacagag ttcactctca ccatcaacgg ccttcaatct   240
gaggattttg agtttatttc tgtcagcaa tataattact ggccattcac tttcggccct    300
gggaccaaac tcgagatcaa a                                              321

<210> SEQ ID NO 214
<211> LENGTH: 321
<212> TYPE: DNA
<213> ORGANISM: Artificial Sequence
<220> FEATURE:
<223> OTHER INFORMATION: VL Sequence of variant L229

<400> SEQUENCE: 214
gatgttgtga tgactcagtc tccagtcacc ctgtctgtgt ctccagggga aagagccacc    60
ctctcctgca ggcccagtca gagtattcac aacaacttag cctggtacca gcagaaacct   120
gggcaggctc ccaggtcct catctatgaa tcatccacca gggccaaagg tatcccagcc    180
aggttcagtg gcagtgggtc tgggacagag ttcactctca ccatcagcag cctgcagtcg   240
gaagactttg cactttatta ctgtcagcag tataataggt gcctctcac tttcggccaa    300 gggaccaagc tcgagatcaa a                                              321

<210> SEQ ID NO 215
<211> LENGTH: 321
<212> TYPE: DNA
<213> ORGANISM: Artificial Sequence
<220> FEATURE:
<223> OTHER INFORMATION: VL Sequence of variant L230

<400> SEQUENCE: 215
gatgttgtga tgactcagtc tccagccagt ttgtctgtgt ctccagggga aagagccacc    60
ctctcctgta gggccagtca gaatattaga ggtaacttag cctggtatca gcagataacct  120 gggcaggctc ccaggctcct tatgtctggt ccatccacca gggccgctgg tatcccagct   180
aggttcagtg gcactgggtc tgggacagag ttcactctca ccatcagcag cccgcagtct   240
gaagattttg cactttatta ttgtcaacag tatcattct ggccccccag cttcggccaa    300
gggaccaagc tcgagatcaa a                                              321

<210> SEQ ID NO 216
<211> LENGTH: 321
<212> TYPE: DNA
<213> ORGANISM: Artificial Sequence
<220> FEATURE:
<223> OTHER INFORMATION: VL Sequence of variant L250

<400> SEQUENCE: 216
gaaattgtgt tgacgcagtc tccagtcacc ctgtctgtgc tccagggga gagagcctcc    60 ctctcctgta gggccagtca gaatatatac accgccgtgg cctggtacca gcagaaacct   120
ggccaggctc ccaggctcct catctatggc gcatccacca gggccactgg tatcccagcc   180
aggttcagtg gcgtgggtc tgggacagac tacactctca ccatcagcag tctggagtct    240
gaagattttg cagtttatca ctgtcagcag tatcatagct ggcccctcac tttcggcgga   300
gggaccaagc tcgagatcaa a                                              321
```

<210> SEQ ID NO 217
<211> LENGTH: 321
<212> TYPE: DNA
<213> ORGANISM: Artificial Sequence
<220> FEATURE:
<223> OTHER INFORMATION: VL Sequence of variant L332 (Optimized L250)

<400> SEQUENCE: 217

```
gaaattgtgt tgacgcagtc tccagtcacc ctgtctgtgc ctccagggga gagagcctcc      60
ctctcctgta gggccagtca gaatatatac accgccgtgg cctggtacca gcagaaacct    120
ggccaggctc ccaggctcct catctatggc gcatccacca gggccactgg tatcccagcc    180
aggttcagtg gcggtgggtc tgggacagac tacactctca ccatcagcag tctggagtct    240
gaagattttg cagtttatca ctgtcagcag tggcatagct ggcccctcac tttcggcgga    300
gggaccaagc tcgagatcaa a                                              321
```

<210> SEQ ID NO 218
<211> LENGTH: 321
<212> TYPE: DNA
<213> ORGANISM: Artificial Sequence
<220> FEATURE:
<223> OTHER INFORMATION: VL Sequence of variant L308 (Optimized L250)

<400> SEQUENCE: 218

```
gaaattgtgt tgacgcagtc tccagtcacc ctgtctgtgc ctccagggga gagagcctcc      60
ctctcctgta gggccagtca gaatatatac accgccgtgg cctggtacca gcagaaacct    120
ggccaggctc ccaggctcct catctatggc gcatccacca gggccactgg tatcccagcc    180
aggttcagtg gcggtgggtc tgggacagac tacactctca ccatcagcag tctggagtct    240
gaagattttg cagtttatca ctgtcagcag tattttagct ggcccctcac tttcggcgga    300
gggaccaagc tcgagatcaa a                                              321
```

<210> SEQ ID NO 219
<211> LENGTH: 321
<212> TYPE: DNA
<213> ORGANISM: Artificial Sequence
<220> FEATURE:
<223> OTHER INFORMATION: VL Sequence of variant L309 (Optimized L250)

<400> SEQUENCE: 219

```
gaaattgtgt tgacgcagtc tccagtcacc ctgtctgtgc ctccagggga gagagcctcc      60
ctctcctgta gggccagtca gaatatatac accgccgtgg cctggtacca gcagaaacct    120
ggccaggctc ccaggctcct catctatggc gcatccacca gggccactgg tatcccagcc    180
aggttcagtg gcggtgggtc tgggacagac tacactctca ccatcagcag tctggagtct    240
gaagattttg cagtttatca ctgtcagcag tatatgagct ggcccctcac tttcggcgga    300
gggaccaagc tcgagatcaa a                                              321
```

<210> SEQ ID NO 220
<211> LENGTH: 321
<212> TYPE: DNA
<213> ORGANISM: Artificial Sequence
<220> FEATURE:
<223> OTHER INFORMATION: VL Sequence of variant L311 (Optimized L250)

<400> SEQUENCE: 220

```
gaaattgtgt tgacgcagtc tccagtcacc ctgtctgtgc ctccagggga gagagcctcc      60
ctctcctgta gggccagtca gaatatatac accgccgtgg cctggtacca gcagaaacct    120
```

```
ggccaggctc ccaggctcct catctatggc gcatccacca gggccactgg tatcccagcc    180
aggttcagtg gcggtgggtc tgggacagac tacactctca ccatcagcag tctggagtct    240
gaagattttg cagtttatca ctgtcagcag tatcatgcgt ggccccctca ctttcggcgga   300 gggaccaagc tcgagatcaa a                                              321
```

<210> SEQ ID NO 221
<211> LENGTH: 321
<212> TYPE: DNA
<213> ORGANISM: Artificial Sequence
<220> FEATURE:
<223> OTHER INFORMATION: VL Sequence of variant L459 (Optimized L332)

<400> SEQUENCE: 221

```
gaaattgtgt tgacgcagtc tccagtcacc ctgtctgtgc tccaggggga gagagcctcc     60
ctctcctgta gggccagtca gaatatatac accgccgtgg cctggtacca gcagaaacct    120
ggccaggctc ccaggctcct catctataat gcatccacca gggccactgg tatcccagcc    180
aggttcagtg gcggtgggtc tgggacagac tacactctca ccatcagcag tctggagtct    240
gaagattttg cagtttatca ctgtcagcag tggcatagct ggccccctca ctttcggcgga   300 gggaccaagc tcgagatcaa a                                              321
```

<210> SEQ ID NO 222
<211> LENGTH: 321
<212> TYPE: DNA
<213> ORGANISM: Artificial Sequence
<220> FEATURE:
<223> OTHER INFORMATION: VL Sequence of variant L471

<400> SEQUENCE: 222

```
gaaattgtgt tgacgcagtc tccagccacc ctgtctgtgt ctccagggga gagagcctcc     60
ctctcctgta gggccagtca gaatatatac accgccgtgg cctggtacca gcagaaacct    120
ggccaggctc ccaggctcct catctataat gcatccacca gggccactgg tatcccagcc    180
aggttcagtg gcggtgggtc tgggacagac tacactctca ccatcagcag tctggagtct    240
gaagattttg cagtttatca ctgtcagcag tggcatagct ggccccctca ctttcggcgga   300 gggaccaagc tcgagatcaa a                                              321
```

<210> SEQ ID NO 223
<211> LENGTH: 321
<212> TYPE: DNA
<213> ORGANISM: Artificial Sequence
<220> FEATURE:
<223> OTHER INFORMATION: VL Sequence of variant L472 (Optimized L459)

<400> SEQUENCE: 223

```
gaaattgtgt tgacgcagtc tccagccacc ctgtctgtgt ctccagggga gagagcctcc     60
ctctcctgta gggccagtca gaatatatac accgccgtgg cctggtacca gcagaaacct    120
ggccaggctc ccaggctcct catctataat gcagccacca gggccactgg tatcccagcc    180
aggttcagtg gcggtgggtc tgggacagac tacactctca ccatcagcag tctggagtct    240
gaagattttg cagtttatca ctgtcagcag tggcatagct ggccccctca ctttcggcgga   300 gggaccaagc tcgagatcaa a                                              321
```

<210> SEQ ID NO 224
<211> LENGTH: 107
<212> TYPE: PRT
<213> ORGANISM: Artificial Sequence

```
<220> FEATURE:
<223> OTHER INFORMATION: VL Sequence of variant L471

<400> SEQUENCE: 224

Glu Ile Val Leu Thr Gln Ser Pro Ala Thr Leu Ser Val Ser Pro Gly
1               5                   10                  15

Glu Arg Ala Ser Leu Ser Cys Arg Ala Ser Gln Asn Ile Tyr Thr Ala
            20                  25                  30

Val Ala Trp Tyr Gln Gln Lys Pro Gly Gln Ala Pro Arg Leu Leu Ile
        35                  40                  45

Tyr Asn Ala Ser Thr Arg Ala Thr Gly Ile Pro Ala Arg Phe Ser Gly
50                  55                  60

Gly Gly Ser Gly Thr Asp Tyr Thr Leu Thr Ile Ser Ser Leu Glu Ser
65                  70                  75                  80

Glu Asp Phe Ala Val Tyr His Cys Gln Gln Trp His Ser Trp Pro Leu
                85                  90                  95

Thr Phe Gly Gly Gly Thr Lys Leu Glu Ile Lys
            100                 105

<210> SEQ ID NO 225
<211> LENGTH: 117
<212> TYPE: PRT
<213> ORGANISM: Artificial Sequence
<220> FEATURE:
<223> OTHER INFORMATION: VH Sequence of variant H1729 (Optimized H1272)

<400> SEQUENCE: 225

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Val Gly Asn Asn
            20                  25                  30

Tyr Met Ser Trp Val Arg Gln Ala Pro Gly Lys Gly Leu Glu Trp Val
        35                  40                  45

Ser Val Ile Tyr Ser Ala Gly Ser Thr Tyr Tyr Ala Asp Ser Val Lys
50                  55                  60

Gly Arg Phe Ile Ile Ser Arg Asp Asn Ser Lys Asp Thr Val Tyr Leu
65                  70                  75                  80

Gln Met Asn Ser Leu Arg Val Asp Asp Thr Ala Val Tyr Tyr Cys Ala
                85                  90                  95

Arg Asn Tyr Tyr Gly Ser Thr Leu Asp Tyr Trp Gly Gln Gly Thr Leu
            100                 105                 110

Val Thr Val Ser Ser
        115

<210> SEQ ID NO 226
<211> LENGTH: 16
<212> TYPE: PRT
<213> ORGANISM: Artificial Sequence
<220> FEATURE:
<223> OTHER INFORMATION: VH-CDR2 Sequence of variant H1729 (Optimized
      H1272)

<400> SEQUENCE: 226

Val Ile Tyr Ser Ala Gly Ser Thr Tyr Tyr Ala Asp Ser Val Lys Gly
1               5                   10                  15
```

SELECTION OF HUMAN TNFα SPECIFIC ANTIBODIES

CROSS-REFERENCE TO RELATED APPLICATIONS

This application claims the benefit of U.S. Prov. App. No. 60/907,599, filed Apr. 10, 2007, which is herein incorporated by reference in its entirety.

REFERENCE TO A SEQUENCE LISTING SUBMITTED ELECTRONICALLY VIA EFS-WEB

The content of the electronically submitted sequence listing (Name: Sequence_listing_ascii.txt, Size: 121 kilobytes; and Date of Creation: Apr. 7, 2008) filed herewith the application is incorporated by reference in its entirety.

BACKGROUND OF THE INVENTION

Field of the Invention

Arthritis is a chronic multifactorial disease induced when the immune system attacks and begins degrading body joints. The disease is present in all races and exists in many forms, most commonly osteoarthritis (OA) and rheumatoid arthritis (RA). RA is an autoimmune disease where the immune system, for unknown reasons, attacks the synovium (tissue lining the joint capsule) causing local inflammation. As inflammation progresses, the self-reacting immune cells divide abnormally and cause destruction of the cartilage and bone within the joint. This inflammatory response ultimately results in the destruction of ligaments, tendons and muscles that support the joint. RA distribution is more evenly spread across the population, however, its main period of onset is between 35 and 55 years of age and it therefore imposes enormous societal costs. In addition to causing significant morbidity and economic burden, an increasing number of patient-based studies have shown that RA leads to premature mortality, which is associated with both rheumatoid complications and an increase in non-specific causes of death (e.g., infections). The exact mechanism of disease pathogenesis is not yet known, however, RA is strongly associated with genetic predisposition. The U.S. has an estimated prevalence of RA of just under 1%. It is estimated that the global prevalence of RA is approximately 0.5%-0.75%, representing between 30-40 million people with the disease world-wide.

TNFα is a key mediator of RA. TNFα is synthesized primarily by cells of the monocyte/macrophage lineage in response to immunological insults (bacterial lipopolysaccharides, viral infection, etc), but can also be synthesized by T and B cells, endothelial cells, and fibroblasts. TNFα is synthesized as a 26 kDa membrane bound protein that is then cleaved into 17 kDa monomers. These monomers assemble into biologically active homotrimers. TNFα homotrimers exist in both soluble and transmembrane forms and exert many of their effects by binding (in either form) to a 55 kDa cell membrane receptor termed TNF receptor-1 (TNFR-1) or a 75 kDa cell membrane receptor termed TNFR-2. The binding of TNFα to its receptors leads to signal transduction and a variety of cellular activities including apoptosis, proliferation, activation, recruitment and differentiation. Many of the TNFα-induced events can be identified as relevant to the inflammatory and pathological processes of RA.

TNFα appears early in the inflammatory response. One of the mechanisms by which TNFα promotes inflammation is through the induction of synthesis of other proinflammatory cytokines, such as interleukin (IL)-1, IL-6, IL-8, and granulocyte-monocyte colony-stimulating factor (GM-CSF). TNFα may also sustain inflammation by facilitating the infiltration of leukocytes into areas of tissue damage. TNFα has also been shown to increase the expression of synovial vessel adhesion molecules that interact with leukocyte cell-surface receptors. The interactions between such adhesion molecules and receptors are required for leukocyte extravasation into inflamed tissues. Thus, TNFα activates normal diploid target cells (e.g., fibroblasts and neutrophils) leading to synthesis of other pro-inflammatory cytokines such as (IL1, IL6, IL8), increased expression of adhesion molecules, and increased expression of inflammatory response enzymes. Furthermore, TNFα recruits and activates leukocytes, stimulates cell proliferation, increases prostaglandin synthesis, and stimulates bone and cartilage resorption.

In addition to initiating and sustaining inflammation in RA, TNFα likely plays a critical role in the degradation of bone and cartilage. The imbalance between bone resorption and bone formation that leads to focal bone loss in RA is driven primarily by osteoclasts. TNFα acts both indirectly and directly to promote osteoclast differentiation. Bone-lining cells respond to TNFα by releasing factors that promote the differentiation of osteoclast precurosors. TNFα acts directly on osteoclasts by enhancing their resorbin activity and has been shown to increase the expression of receptor activator of NF-κB ligand, a potent regulator of osteoclastogenesis. TNFα further enhances bone loss in RA by inducing osteoblast apoptosis.

TNFα also appears to play a critical role in cartilage loss in RA by stimulating the production of matrix metalloproteinases and other tissue-degrading substance such as nitric oxide, while decreasing the synthesis of cartilage-specific collages and proteoglycans.

In patients with RA, it is thought that angiogenesis is one factor that ensures the development and persistence of the pannus by increasing the supply of nutrients, cytokines, and inflammatory cells to the synovial membrane. There is emerging evidence that TNFα also plays a role in angiogenesis and the resultant increase in vascularity which is observed early in the development of RA. TNFα is also known to play a role in other inflammatory conditions, including sepsis, inflammatory bowel disease and Jarisch-Herxheimer reaction.

Treatment with murine TNFα specific monoclonal antibodies can prevent the development of RA in animal models, and treatment of humans with chimeric (Remicade®) or human (Humira®) TNFα specific monoclonal antibodies can reduce the severity of RA. Experimental approaches utilizing such antibodies to inhibit TNFα function and prevent the development of RA have provided encouraging results, but their safety and effectiveness for treating RA, and for autoimmune diseases in general, have yet to be optimized.

Dramatic advances in genomics have greatly increased the number of targets that may be the basis for development of valuable new therapeutics including human antibodies specific for novel human proteins. A fundamental challenge to selection of human antibodies against these human products is the natural tolerance of the immune system to protein antigens normally expressed in the organism.

The use of human immunoglobulin transgenic mice has provided only a limited solution to this problem because of the extensive homology (on average 90% at the protein level) between important human and mouse gene products. This limitation of in vivo antibody selection can be overcome by strategies based on in vitro antibody selection from unbiased and unselected libraries of immunoglobulin genes.

To date, the major implementation of such a strategy has been phage display libraries expressing fragments of antibody molecules synthesized in bacterial cells. While this has given rise to many useful research reagents, the value of phage display antibodies for clinical applications is limited by the selection of many low-affinity antibodies. It is possible that the functional titer of phage display libraries is severely limited by the difficulty of properly folding mammalian proteins in the abnormal physiological environment of a bacterial cell.

Because antibody-based therapies have achieved notable success in clinical trials and regulatory acceptance, they are a major focus of new drug development efforts in the biopharmaceutical industry. The technology of the present invention offers important advantages because of its potential to generate high affinity, human monoclonal antibodies against a broad range of disease targets. The present invention has focused on a strategy in which separate libraries of immunoglobulin heavy and light chains are constructed in its proprietary vaccinia virus-based mammalian expression vector. See e.g., U.S. Publ. No. 2002/0123057 A1.

The present invention utilitizes technology for generating human monoclonal antibodies. The human monoclonal antibody technology is based on the monoclonal expression of recombinant antibodies in mammalian cells. Separate libraries of human heavy and light chain immunoglobulin variable genes are constructed in a vaccinia virus-based vector employing a novel and very efficient method for generating recombinants. The strategy for construction of cDNA libraries in vaccinia virus is described as Tri-Molecular Recombination. In sharp contrast to the low frequency of recombinants obtained employing conventional methods, >99% of infectious vaccinia virus produced by Tri-Molecular Recombination is recombinant. See e.g., U.S. Pat. Nos. 6,706,477; 6,800,442 and 7,067,251.

Mammalian cells infected with the vaccinia immunoglobulin gene recombinant vectors produce fully functional, bivalent antibodies. Ig-Hγ libraries in a vaccinia expression vector that encodes the secretory form of the IgG1 heavy chain constant region have been generated. When combined with Ig-K light chains, immunoglobulin heavy chain gene libraries constructed in this vector give rise to secreted products permitting screening by ELISA or other functional assay to select antibodies specific for TNFα.

There remains a need in the art for TNFα antibodies with different or improved binding, efficacy, and safety characteristics for the treatment of various diseases, including autoimmune diseases such as RA.

BRIEF SUMMARY OF THE INVENTION

The present invention is based on the important role of TNFα as a key mediator of autoimmune diseases or disorders, such as rheumatoid arthritis (RA). The invention relates generally to human anti-TNFα antibodies, antigen binding fragments or derivatives thereof. Certain human anti-TNFα antibodies and antigen-binding fragments inhibit TNFα function or block the biological functions of TNFα-mediated signaling. Additionally, the invention generally relates to methods for treating various autoimmune diseases and disorders, or inflammatory conditions, e.g., RA, sepsis, Crohn's Disease, Ankylosing Spondylitis, Psoriatic Arthritis, Plaque Psoriasis, and Ulcerative Colitis.

In certain embodiments, the invention provides an isolated antibody or antigen-binding fragment thereof which specifically binds to the same TNFα epitope as a reference monoclonal antibody selected from the group consisting of 696, 698, 699, 715, 714, 716, 695, 805, 855, 812, 813, 815, 1028, 1029, 874, 892, 1037, 1038, 1066, 1132, 1036, 1042, 1043, 1067, 1131, 1210, 1371, 1775, 1777, 1714, 1780, 1850, 1874, 1851, 1852, 1895, 1896, 1988, 1989, 1999, 2006, 2019, 2060, 2071 and 2090. In further embodiments, the reference monoclonal antibody is selected from the group consisting of 2071 and 2090.

Certain embodiments of the invention include an isolated polypeptide comprising an immunoglobulin heavy chain variable region (VH) wherein the CDR1, CDR2 and CDR3 regions are selected from the polypeptide sequences shown in Tables 6-7, or at least 80%, 85%, 90 or 95% identical to the polypeptide sequences shown in Tables 6-7.

Certain embodiments of the invention include an isolated polypeptide comprising an immunoglobulin light chain variable region (VL) wherein the CDR1, CDR2 and CDR3 regions are selected from the polypeptide sequences shown in Table or at least 80%, 85%, 90% or 95% identical to the polypeptide sequences shown in Table 8.

Certain embodiments of the invention include an isolated polypeptide comprising an immunoglobulin heavy chain variable region (VH) selected from the group consisting of SEQ ID NOs: 3, 7, 11, 15, 19, 23, 27, 31, 35, 37, 39, 41, 43, 45, 47, 49, 51, 53, 55, 57, 59, 61, 63, 65, 67, 69, 225, 71, 73, 75, 75, 77, 79, 81, 85, 89, 93, 97, 101, 105, 109, 113, 117 and 121, as shown in Tables 6-7, or at least 80%, 85%, 90% or 95% identical to said SEQ ID NOs: 3, 7, 11, 15, 19, 23, 27, 31, 35, 37, 39, 41, 43, 45, 47, 49, 51, 53, 55, 57, 59, 61, 63, 65, 67, 69, 225, 71, 73, 75, 75, 77, 79, 81, 85, 89, 93, 97, 101, 105, 109, 113, 117 and 121, as shown in Tables 6-7.

Certain embodiments of the invention include an isolated polypeptide comprising an immunoglobulin light chain variable region (VL) selected from the group consisting of SEQ ID NOs: 125, 129, 133, 137, 141, 145, 149, 153, 157, 161, 165 and 224, as shown in Table 8, or at least 80%, 85%, 90% or 95% identical to said SEQ ID NOs: 125, 129, 133, 137, 141, 145, 149, 153, 157, 161, 165 or 224, as shown in Table 8.

In additional embodiments, the invention includes an isolated polynucleotide comprising a nucleic acid encoding an immunoglobulin heavy chain variable region (VH) wherein the CDR1, CDR2 and CDR3 regions are selected from the group selected from the polynucleotide sequences shown in Table 4 or at least 80%, 85%, 90 or 95% identical to the polynucleotide sequences shown in Tables 6-7.

In other embodiments, the invention includes an isolated polynucleotide comprising a nucleic acid encoding an immunoglobulin light chain variable region (VL) wherein the CDR1, CDR2 and CDR3 regions are selected from the polynucleotide sequences shown in Table 8 or at least 80%, 85%, 90% or 95% identical to the polynucleotide sequences shown in Table 8.

Other embodiments of the invention include, an isolated polynucleotide comprising a nucleic acid encoding an immunoglobulin heavy chain variable region (VH) selected from the group consisting of SEQ ID NOs: 3, 7, 11, 15, 19, 23, 27, 31, 35, 37, 39, 41, 43, 45, 47, 49, 51, 53, 55, 57, 59, 61, 63, 65, 67, 69, 225, 71, 73, 75, 75, 77, 79, 81, 85, 89, 93, 97, 101, 105, 109, 113, 117 and 121, as shown in Tables 6-7, or at least 80%, 85%, 90% or 95% identical to said SEQ ID NOs: 3, 7, 11, 15, 19, 23, 27, 31, 35, 37, 39, 41, 43, 45, 47, 49, 51, 53, 55, 57, 59, 61, 63, 65, 67, 69, 225, 71, 73, 75, 75, 77, 79, 81, 85, 89, 93, 97, 101, 105, 109, 113, 117 or 121, as shown in Tables 6-7.

Other embodiments of the invention include, an isolated polynucleotide comprising a nucleic acid encoding an immunoglobulin light chain variable region (VL) selected from the group consisting of SEQ ID NOs: 125, 129, 133, 137, 141, 145, 149, 153, 157, 161, 165 and 224, as shown in Table 8, or at least 80%, 85%, 90% or 95% identical to said SEQ ID NOs: 125, 129, 133, 137, 141, 145, 149, 153, 157, 161, 165 or 224, as shown in Table 8.

In certain embodiments, the invention includes compositions comprising the antibodies or antigen binding fragments described herein.

In additional embodiments, the invention includes methods for treating autoimmune diseases or disorders, e.g., RA, or a method for treating an inflammatory condition such as sepsis, Crohn's Disease, Ankylosing Spondylitis, Psoriatic Arthritis, Plaque Psoriasis, and Ulcerative Colitiscomprising administering to an animal in need of said treatment an effective amount of an agent selected from the group consisting of an isolated human anti-TNFα antibody or fragment thereof or compositions comprising said antibody or fragment thereof.

Other embodiments of the present invention include a method of inhibiting signal transduction by TNFα, comprising contacting the TNFα with an effective amount of an agent selected from the group consisting of the isolated human anti-TNFα antibody or fragment thereof or compositions comprising said antibody or fragment thereof.

BRIEF DESCRIPTION OF THE DRAWINGS/FIGURES

FIG. 1: Identification scheme for human MAbs.

Figure 2A:
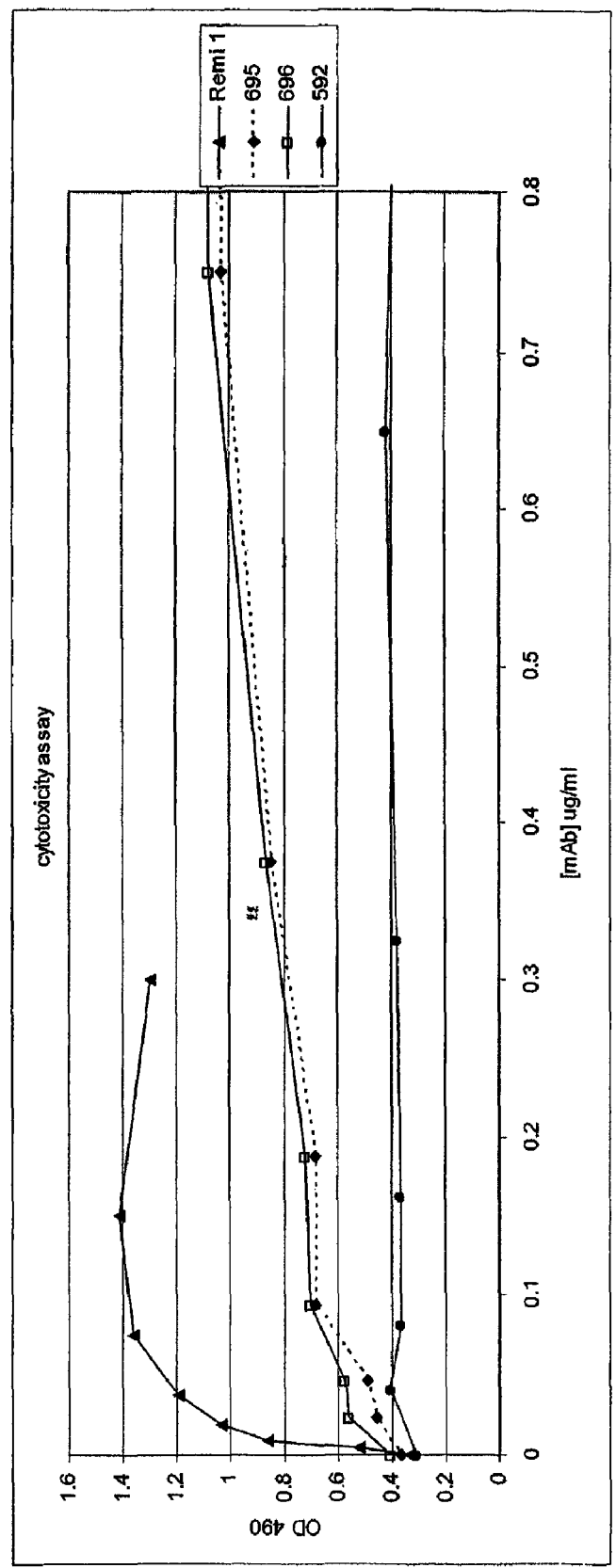
Figure 2B:
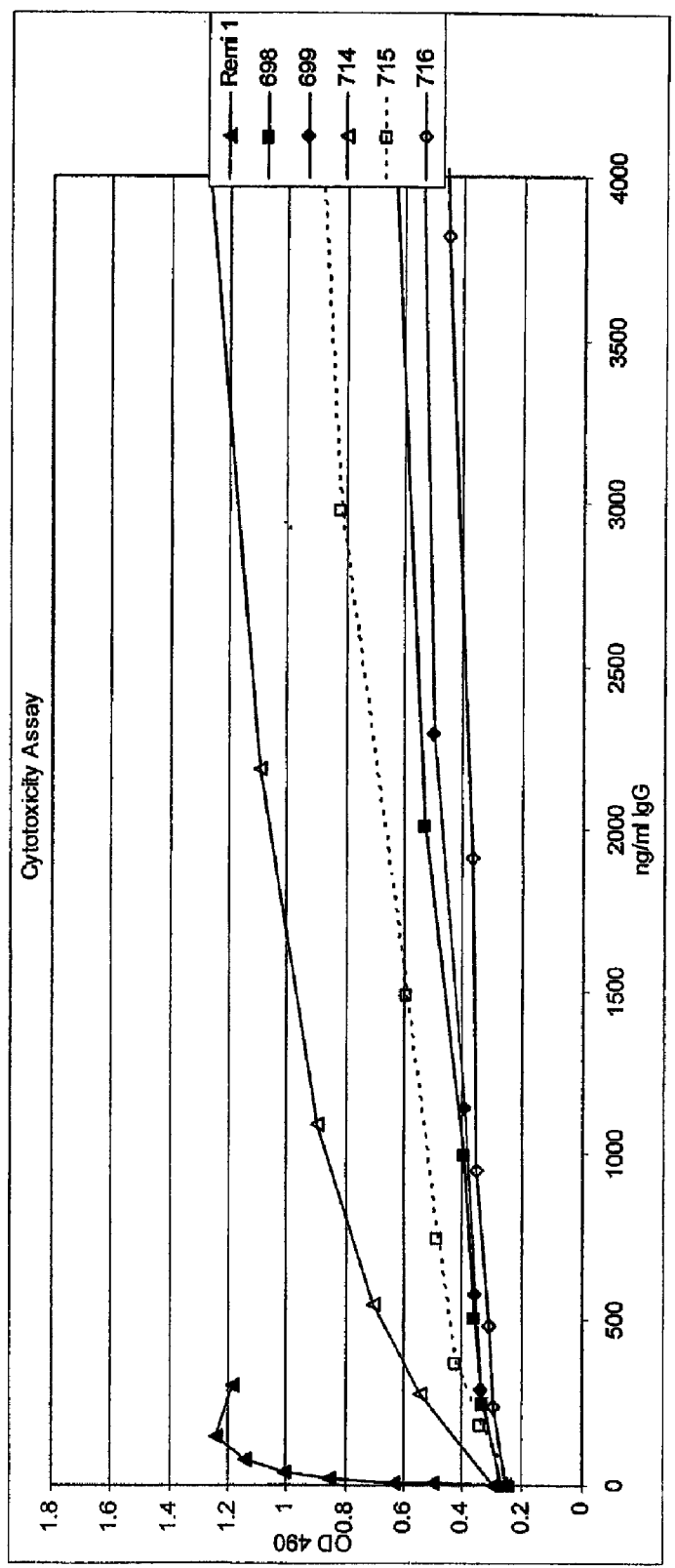
Figure 2C:
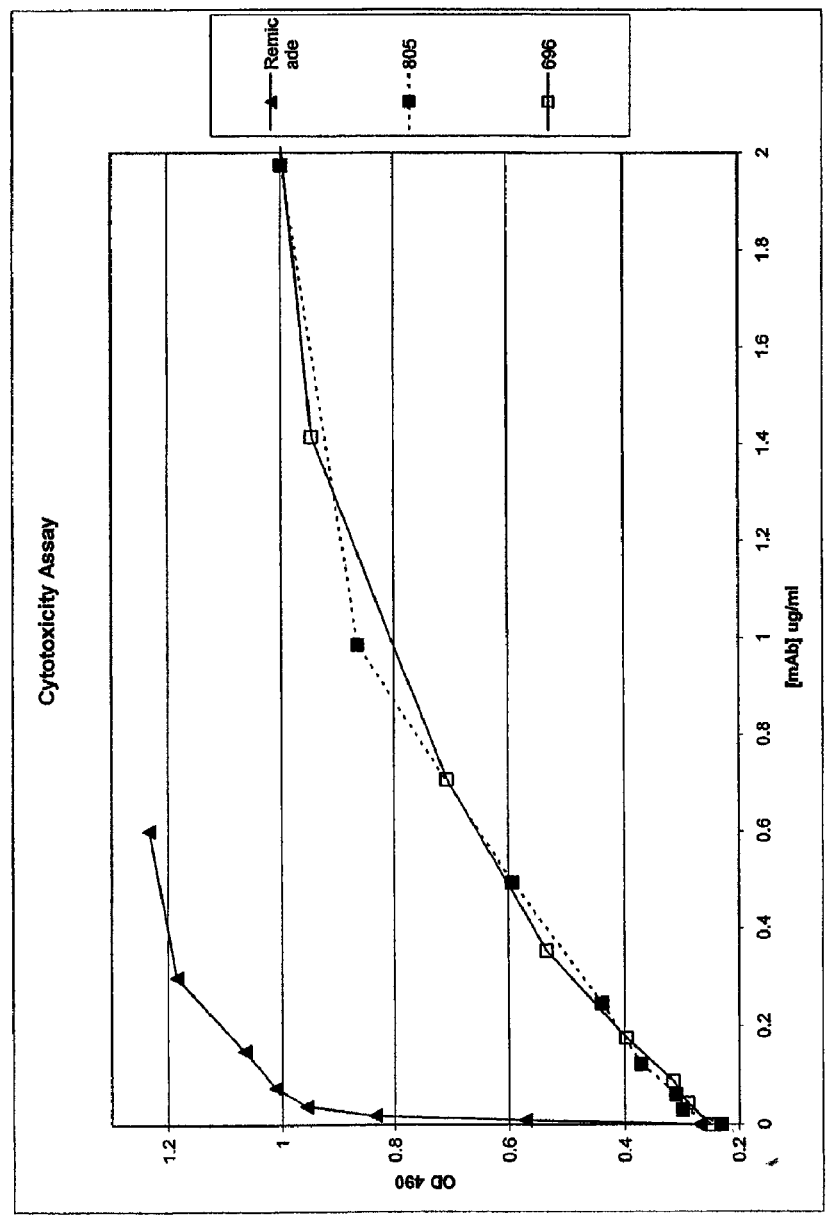

FIGS. 2A-C: Cytotoxicity Assay with Primary Antibodies. A. TNFα-specific human MAbs 695, 696 and 592 compared with Remicade®. B. anti-TNFα MAbs 698, 699, 714. 715 and 716 compared with Remicade®. C. anti-TNFα MAbs 805 and 696 compared with Remicade®. Levels of cytotoxicity were measured in WEHI-13 VAR cells. These cells are sensitive to TNFα treatment in the presence of Actinomycin D. Cells treated with TNFα were assayed after incubation with or without TNFα antibodies. Viable cells were assayed using a standard non-radioactive cell proliferation assay.

FIGS. 3A-F: Cytotoxicity assay with Optimized Monoclonal Antibodies. A. Anti-TNFα human MAbs 855 and 696 compared with Remicade®. B. Anti-TNFα human MAbs 1775, 1777, 1714, 1749, 1780, 1651, 1371 805 and 1007 compared with Remicade®. C. Anti-TNFα human MAbs 1895, 1371, 1896 and 1780 compared with Remicade®. D. Anti-TNFα human MAbs 1988, 1989, 1999, 1896, 2006 and 2019 compared with Remicade®. E. Anti-TNFα human MAbs 2071 and 2060 compared with Remicade®. F. Anti-TNFα human MAbs 2071 and 2090 compared with Remicade® and Humira®.

FIG. 4: BIAcore Comparison among anti-TNFα mAbs 2071 and 2091 as compared with Remicade® and Humira®. In this assay the human antibody (Mab 2071, 2090, Remicade® or Humira®) is captured using a goat anti-human IgG polyclonal antibody that is immobilized on the biacore chip. The TNFα was then used as the analyte and binding of Mab to the TNF was measured by Biacore.

Figure 5:
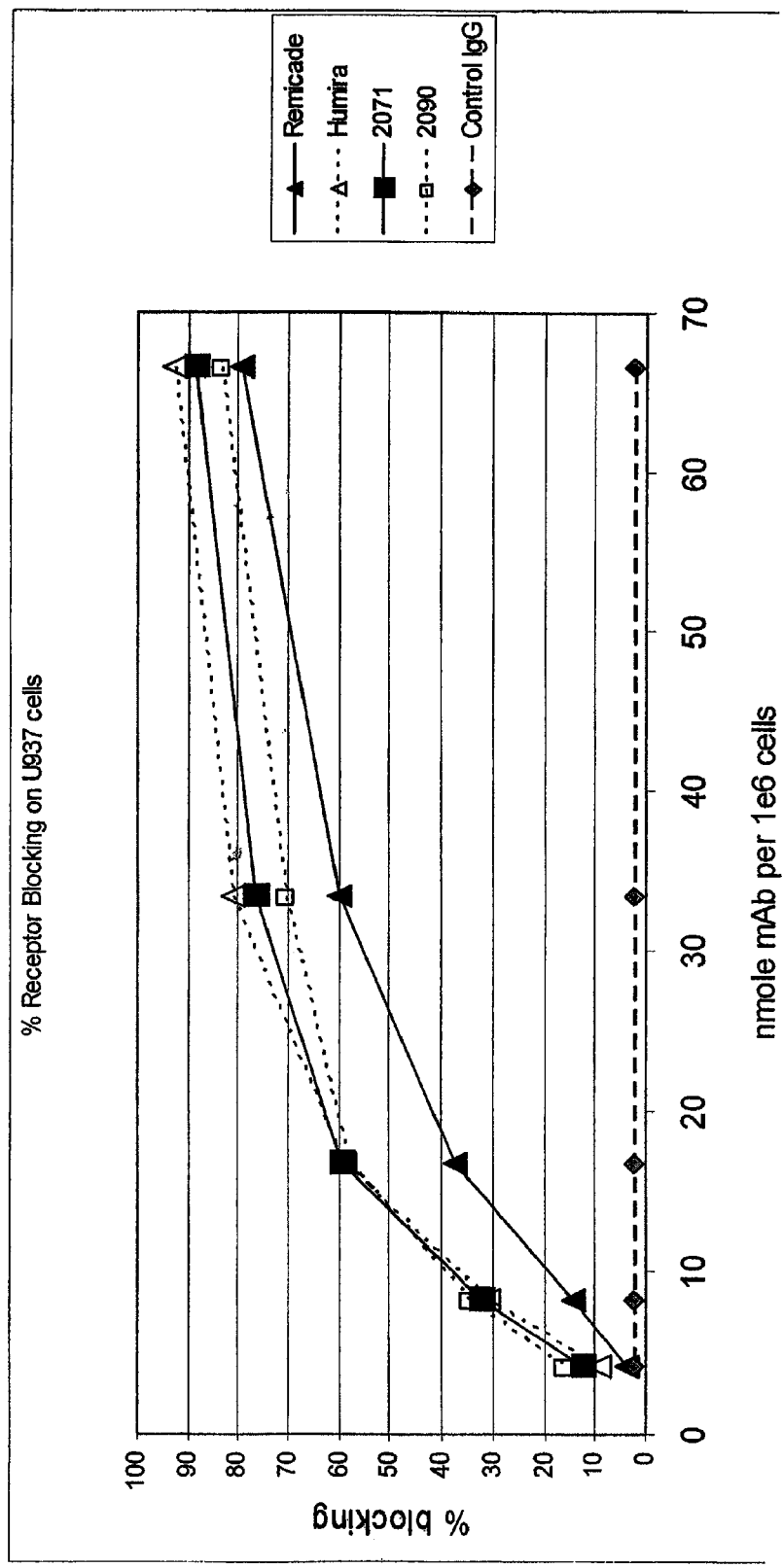

FIG. 5: TNFα receptor blocking assay. Results of the TNFα receptor blocking assay comparing control TNFα antibodies Remicade® and Humira® and anti-TNFα human MAbs 2071 and 2090, and control IgG.

Figure 6:
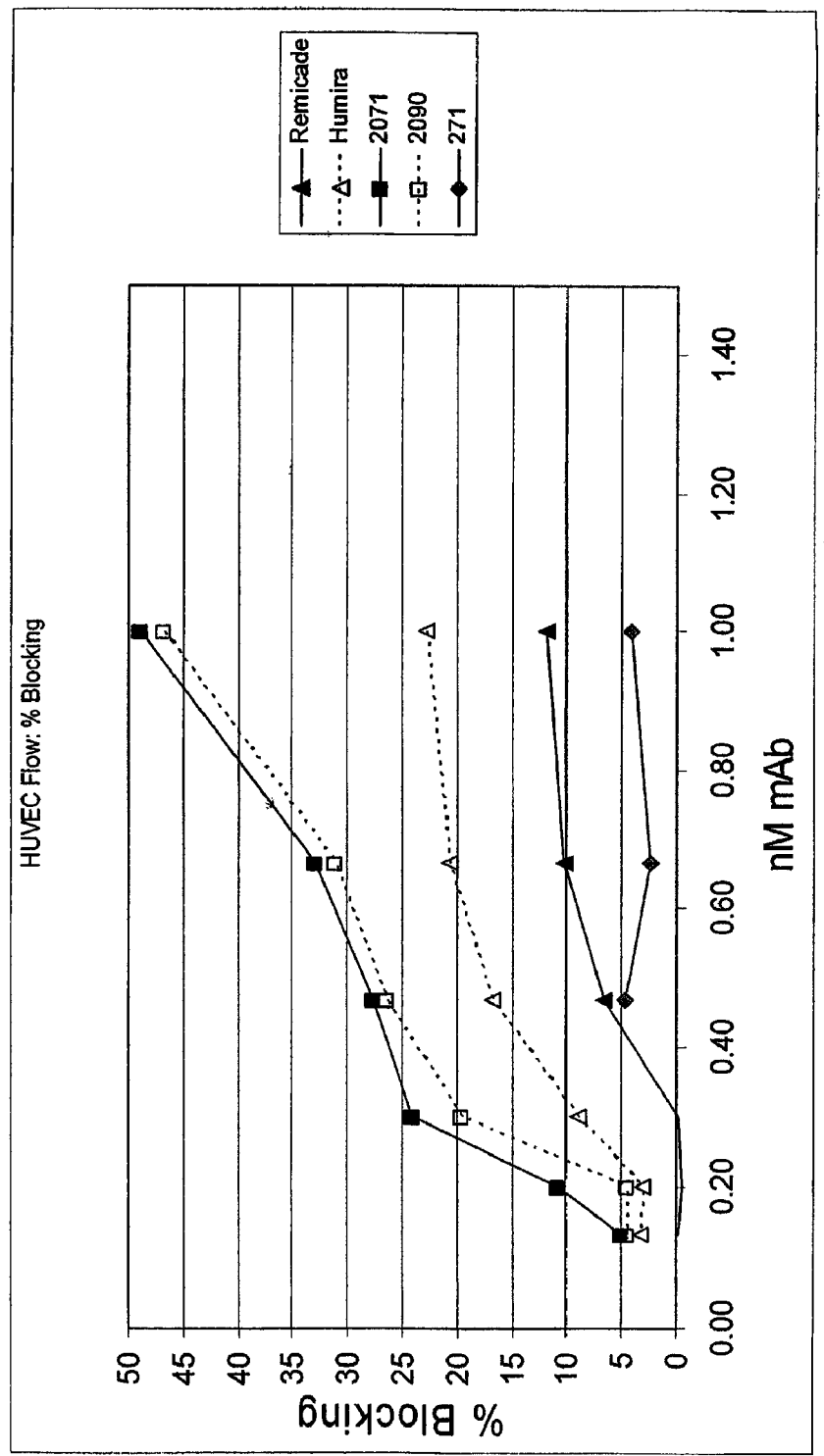

FIG. 6: HUVEC assay. Comparison of inhibition of the TNFα-induced cell surface expression of adhesion molecules with human umbilical vein endothelial cells (HUVEC) using control TNFα antibodies Remicade® and Humira® and anti-TNFα human MAbs 2071, 2090 and 271.

Figure 7:
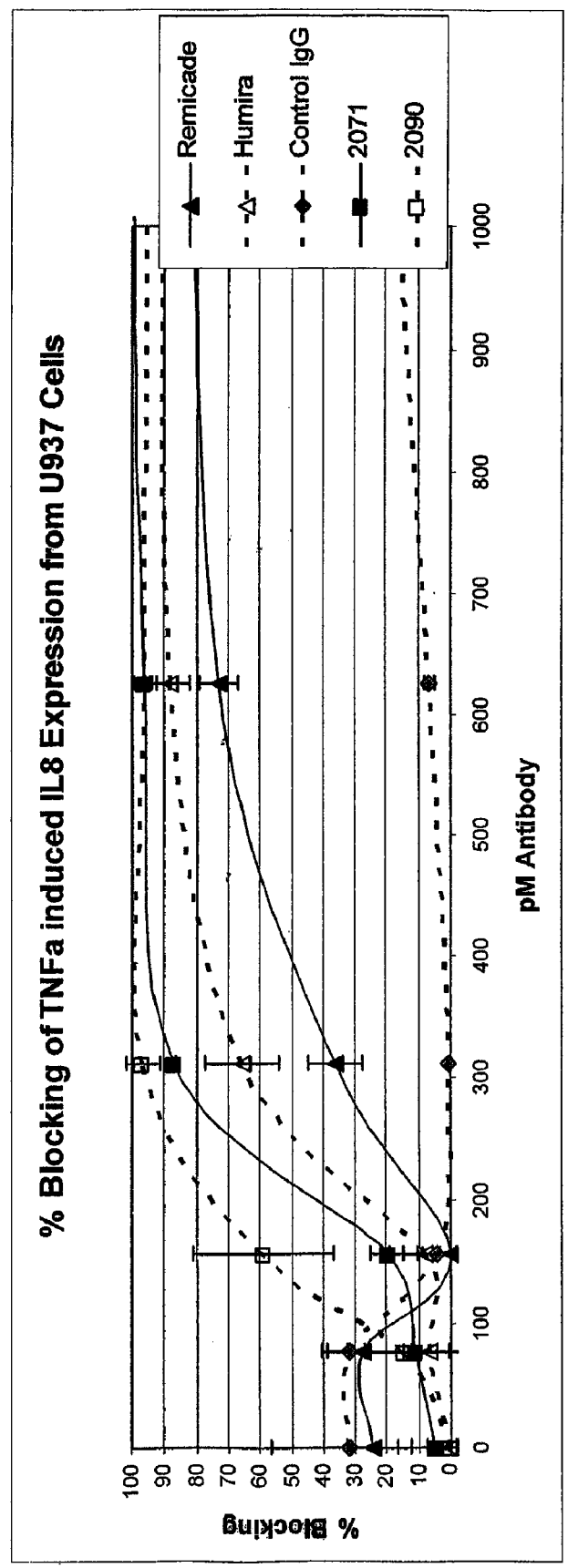

FIG. 7: IL8 assay. Measurement of TNFα-induced expression of IL-8 by human monocytes using control TNFα antibodies Remicade® and Humira® and anti-TNFα human MAbs 22071 and 2090, and control IgG.

DETAILED DESCRIPTION OF THE INVENTION

I. Definitions

It is to be noted that the term "a" or "an" entity refers to one or more of that entity; for example, "a TNFα antibody," is understood to represent one or more TNFα antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

Also included as polypeptides of the present invention are fragments, derivatives, analogs, or variants of the foregoing polypeptides, and any combination thereof. The terms "fragment," "variant," "derivative" and "analog" when referring to TNFα antibodies or antibody polypeptides of the present invention include any polypeptides which retain at least some of the antigen-binding properties of the corresponding native antibody or polypeptide. Fragments of polypeptides of the present invention include proteolytic fragments, as well as deletion fragments, in addition to specific antibody fragments discussed elsewhere herein. Variants of TNFα antibodies and antibody polypeptides of the present invention include fragments as described above, and also polypeptides with altered amino acid sequences due to amino acid substitutions, deletions, or insertions. Variants may occur naturally or be non-naturally occurring Non-naturally occurring variants may be produced using art-known mutagenesis techniques. Variant polypeptides may comprise conservative or non-conservative amino acid substitutions, deletions or additions. Derivatives of TNFα antibodies and antibody polypeptides of the present invention, are polypeptides which have been altered so as to exhibit additional features not found on the native polypeptide. Examples include fusion proteins. Variant polypeptides may also be referred to herein as "polypeptide analogs." As used herein a "derivative" of a TNFα antibody or antibody polypeptide refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refer to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding a TNFα antibody contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, polynucleotide or a nucleic acid may be or may include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid of the invention may encode heterologous coding regions, either fused or unfused to a nucleic acid encoding a TNFα antibody or fragment, variant, or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA).

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated.

Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

The present invention is directed to human TNFα antibodies, or antigen-binding fragments, variants, or derivatives thereof. Unless specifically referring to full-sized antibodies such as naturally-occurring antibodies, the term "TNFα antibodies" encompasses full-sized antibodies as well as antigen-binding fragments, variants, analogs, or derivatives of such antibodies, e.g., naturally occurring antibody or immunoglobulin molecules or engineered antibody molecules or fragments that bind antigen in a manner similar to antibody molecules.

As used herein, "human" or "fully human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example in, U.S. Pat. No. 5,939,598 by Kucherlapati et al. "Human" or "fully human" antibodies also include antibodies comprising at least the variable domain of a heavy chain, or at least the variable domains of a heavy chain and a light chain, where the variable domain(s) have the amino acid sequence of human immunoglobulin variable domain(s).

"Human" or "fully human" antibodies also include "human" or "fully human" antibodies, as described above, that comprise, consist essentially of, or consist of, variants (including derivatives) of antibody molecules (e.g., the VH regions and/or VL regions) described herein, which antibodies or fragments thereof immunospecifically bind to a TNFα polypeptide or fragment or variant thereof. Standard techniques known to those of skill in the art can be used to introduce mutations in the nucleotide sequence encoding a human anti-TNFα antibody, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH region, VHCDR1, VHCDR2, VHCDR3, VL region, VLCDR1, VLCDR2, or VLCDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind a TNFα polypeptide). Such variants (or derivatives thereof) of "human" or "fully human" antibodies can also be referred to as human or fully human antibodies that are "optimized" or "optimized for antigen binding" and include antibodies that have improved affinity to antigen.

The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgA_1$, etc. are well characterized and are known to confer functional specialization. Modified versions of each of these classes and isotypes are readily discernable to the skilled artisan in view of the instant disclosure and, accordingly, are within the scope of the instant invention. All immunoglobulin classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light ($V_L$) and heavy ($V_H$) chain portions determine antigen recognition and specificity. Conversely, the constant domains of the light chain ($C_L$) and the heavy chain ($C_H1$, $C_H2$ or $C_H3$) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the $C_H3$ and $C_L$ domains actually comprise the carboxy-terminus of the heavy and light chain, respectively.

As indicated above, the variable region allows the antibody to selectively recognize and specifically bind epitopes on antigens. That is, the $V_L$ domain and $V_H$ domain, or subset of the complementarity determining regions (CDRs), of an antibody combine to form the variable region that defines a three dimensional antigen binding site. This quaternary antibody structure forms the antigen binding site present at the end of each arm of the Y. More specifically, the antigen binding site is defined by three CDRs on each of the $V_H$ and $V_L$ chains. In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., *Nature* 363:446-448 (1993).

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see, "Sequences of Proteins of Immunological Interest," Kabat, E., et al., U.S. Department of Health and Human Services, (1983); and Chothia and Lesk, *J. Mol. Biol.*, 196: 901-917 (1987), which are incorporated herein by reference in their entireties).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., *J. Mol. Biol.* 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table 1 as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

CDR Definitions[1]

| | Kabat | Chothia |
|---|---|---|
| $V_H$ CDR1 | 31-35 | 26-32 |
| $V_H$ CDR2 | 50-65 | 52-58 |
| $V_H$ CDR3 | 95-102 | 95-102 |
| $V_L$ CDR1 | 24-34 | 26-32 |
| $V_L$ CDR2 | 50-56 | 50-52 |
| $V_L$ CDR3 | 89-97 | 91-96 |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in a TNFα antibody or antigen-binding fragment, variant, or derivative thereof of the present invention are according to the Kabat numbering system.

In camelid species, the heavy chain variable region, referred to as $V_HH$, forms the entire antigen-binding domain. The main differences between camelid $V_HH$ variable regions and those derived from conventional antibodies ($V_H$) include (a) more hydrophobic amino acids in the light chain contact surface of $V_H$ as compared to the corresponding region in $V_HH$, (b) a longer CDR3 in $V_HH$, and (c) the frequent occurrence of a disulfide bond between CDR1 and CDR3 in $V_HH$.

Human antibodies or antigen-binding fragments, variants, or derivatives thereof of the invention include, but are not limited to, polyclonal, monoclonal, multispecific, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a $V_L$ or $V_H$ domain, fragments produced by a Fab expression library, and anti-idiotypic (anti-Id) antibodies (including, e.g., anti-Id antibodies to TNFα antibodies disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Antibody fragments, including single-chain antibodies, may comprise the variable region(s) alone or in combination with the entirety or a portion of the following: hinge region, $C_H1$, $C_H2$, and $C_H3$ domains. Also included in the invention are antigen-binding fragments also comprising any combination of variable region(s) with a hinge region, $C_H1$, $C_H2$, and $C_H3$ domains. Antibodies or immunospecific fragments thereof for use in the diagnostic and therapeutic methods disclosed herein include human or fully human antibodies, but also include antibodies where at least all of the CDRs within the variable domain(s) have the amino acid sequence of a human immunoglobulin variable domain or the amino acid sequence of a human immunoglobulin CDR. The non-CDR regions of such antibodies may be from any animal origin including birds and mammals and can comprise primate, murine, donkey, rabbit, goat, guinea pig, camel, llama, horse, or chicken non-CDR immunoglobulin regions. In another embodiment, the non-CDR regions may be condricthoid in origin (e.g., from sharks).

As used herein, the term "heavy chain portion" includes amino acid sequences derived from an immunoglobulin heavy chain. A polypeptide comprising a heavy chain portion comprises at least one of: a $C_H1$ domain, a hinge (e.g., upper, middle, and/or lower hinge region) domain, a $C_H2$ domain, a $C_H3$ domain, or a variant or fragment thereof. For example, a binding polypeptide for use in the invention may comprise a polypeptide chain comprising a $C_H1$ domain; a polypeptide chain comprising a $C_H1$ domain, at least a portion of a hinge domain, and a $C_H2$ domain; a polypeptide chain comprising a $C_H1$ domain and a $C_H3$ domain; a polypeptide chain comprising a $C_H1$ domain, at least a portion of a hinge domain, and a $C_H3$ domain, or a polypeptide chain comprising a $C_H1$ domain, at least a portion of a hinge domain, a $C_H2$ domain, and a $C_H3$ domain. In another embodiment, a polypeptide of the invention comprises a polypeptide chain comprising a $C_H3$ domain. Further, a binding polypeptide for use in the invention may lack at least a portion of a $C_H2$ domain (e.g., all or part of a $C_H2$ domain). As set forth above, it will be understood by one of ordinary skill in the art that these domains (e.g., the heavy chain portions) may be modified such that they vary in amino acid sequence from the naturally occurring immunoglobulin molecule.

In certain human TNFα antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the invention are not identical. For example, each monomer may comprise a different target binding site, forming, for example, a bispecific antibody.

The heavy chain portions of a binding polypeptide for use in the diagnostic and treatment methods disclosed herein may be derived from different immunoglobulin molecules. For example, a heavy chain portion of a polypeptide may comprise a $C_H1$ domain derived from an IgG1 molecule and a hinge region derived from an IgG3 molecule. In another example, a heavy chain portion can comprise a hinge region derived, in part, from an Ig1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain. Preferably, the light chain portion comprises at least one of a $V_L$ or $C_L$ domain.

Human TNFα antibodies, or antigen-binding fragments, variants, or derivatives thereof disclosed herein may be described or specified in terms of the epitope(s) or portion(s) of an antigen, e.g., a target polypeptide (TNFα) that they recognize or specifically bind. The portion of a target polypeptide which specifically interacts with the antigen binding domain of an antibody is an "epitope," or an "antigenic determinant." A target polypeptide may comprise a single epitope, but typically comprises at least two epitopes, and can include any number of epitopes, depending on the size, conformation, and type of antigen. Furthermore, it should be noted that an "epitope" on a target polypeptide may be or include non-polypeptide elements, e.g., an "epitope" may include a carbohydrate side chain.

The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. In the present invention, peptide or polypeptide epitope recognized by human TNFα antibodies of the present invention contains a sequence of at least 4, at least 5, at least 6, at least 7, more preferably at least 8, at least 9, at least 10, at least 15, at least 20, at least 25, or between about 15 to about 30 contiguous or non-contiguous amino acids of TNFα.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

By way of non-limiting example, an antibody may be considered to bind a first epitope preferentially if it binds said first epitope with a dissociation constant ($K_D$) that is less than the antibody's $K_D$ for the second epitope. In another non-limiting example, an antibody may be considered to bind a first antigen preferentially if it binds the first epitope with an affinity that is at least one order of magnitude less than the antibody's $K_D$ for the second epitope. In another non-limiting example, an antibody may be considered to bind a first epitope preferentially if it binds the first epitope with an affinity that is at least two orders of magnitude less than the antibody's $K_D$ for the second epitope.

In another non-limiting example, an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope.

An antibody or antigen-binding fragment, variant, or derivative disclosed herein may be said to bind a target polypeptide disclosed herein or a fragment or variant thereof with an off rate (k(off)) of less than or equal to $5 \times 10^{-2}$ sec$^{-1}$, $10^{-2}$ sec$^{-1}$, $5 \times 10^{-3}$ sec$^{-1}$ or $10^{-3}$ sec$^{-1}$. More preferably, an antibody of the invention may be said to bind a target polypeptide disclosed herein or a fragment or variant thereof with an off rate (k(off)) less than or equal to $5 \times 10^4$ sec$^{-1}$, $10^{-4}$ sec$^{-1}$, $5 \times 10^{-5}$ sec$^{-1}$, or $10^{-5}$ sec$^{-1}$ $5 \times 10^{-6}$ sec$^{-1}$, $10^{-6}$ sec$^{-1}$, $5 \times 10^{-7}$ sec$^{-1}$ or $10^{-7}$ sec$^{-1}$.

An antibody or antigen-binding fragment, variant, or derivative disclosed herein may be said to bind a target polypeptide disclosed herein or a fragment or variant thereof with an on rate (k(on)) of greater than or equal to $10^3$ M$^{-1}$ sec$^{-1}$, $5\times10^3$ M$^{-1}$ sec$^{-1}$, $10^4$ M$^{-1}$ sec$^{-1}$ or $5\times10^4$ M$^{-1}$ sec$^{-1}$. More preferably, an antibody of the invention may be said to bind a target polypeptide disclosed herein or a fragment or variant thereof with an on rate (k(on)) greater than or equal to $10^5$ M$^{-1}$ sec$^{-1}$, $5\times10^5$ M$^{-1}$ sec$^{-1}$, $10^6$ M$^{-1}$ sec$^{-1}$, or $5\times10^6$ M$^{-1}$ sec$^{-1}$ or $10^7$ M$^{-1}$ sec$^{-1}$.

An antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al., Antibodies: A Laboratory Manual, (Cold Spring Harbor Laboratory Press, 2nd ed. 1988) at pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

Human TNFα antibodies or antigen-binding fragments, variants or derivatives thereof of the invention may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

Human TNFα antibodies or antigen-binding fragments, variants or derivatives thereof of the invention may also be described or specified in terms of their binding affinity to a polypeptide of the invention. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

Human TNFα antibodies or antigen-binding fragments, variants or derivatives thereof of the invention may be "multispecific," e.g., bispecific, trispecific or of greater multispecificity, meaning that it recognizes and binds to two or more different epitopes present on one or more different antigens (e.g., proteins) at the same time. Thus, whether a TNFα antibody is "monospecfic" or "multispecific," e.g., "bispecific," refers to the number of different epitopes with which a binding polypeptide reacts. Multispecific antibodies may be specific for different epitopes of a target polypeptide described herein or may be specific for a target polypeptide as well as for a heterologous epitope, such as a heterologous polypeptide or solid support material.

As used herein the term "valency" refers to the number of potential binding domains, e.g., antigen binding domains, present in a TNFα antibody, binding polypeptide or antibody. Each binding domain specifically binds one epitope. When a TNFα antibody, binding polypeptide or antibody comprises more than one binding domain, each binding domain may specifically bind the same epitope, for an antibody with two binding domains, termed "bivalent monospecific," or to different epitopes, for an antibody with two binding domains, termed "bivalent bispecific." An antibody may also be bispecific and bivalent for each specificity (termed "bispecific tetravalent antibodies"). In another embodiment, tetravalent minibodies or domain deleted antibodies can be made.

Bispecific bivalent antibodies, and methods of making them, are described, for instance in U.S. Pat. Nos. 5,731,168; 5,807,706; 5,821,333; and U.S. Appl. Publ. Nos. 2003/020734 and 2002/0155537, the disclosures of all of which are incoporated by reference herein. Bispecific tetravalent antibodies, and methods of making them are described, for instance, in WO 02/096948 and WO 00/44788, the disclosures of both of which are incorporated by reference herein. See generally, PCT publications WO 93/17715; WO 92/08802; WO 91/00360; WO 92/05793; Tutt et al., J. Immunol. 147:60-69 (1991); U.S. Pat. Nos. 4,474,893; 4,714,681; 4,925,648; 5,573,920; 5,601,819; Kostelny et al., *J. Immunol.* 148:1547-1553 (1992).

As previously indicated, the subunit structures and three dimensional configuration of the constant regions of the various immunoglobulin classes are well known. As used herein, the term "V$_H$ domain" includes the amino terminal variable domain of an immunoglobulin heavy chain and the term "C$_H$1 domain" includes the first (most amino terminal) constant region domain of an immunoglobulin heavy chain. The C$_H$1 domain is adjacent to the V$_H$ domain and is amino terminal to the hinge region of an immunoglobulin heavy chain molecule.

As used herein the term "C$_H$2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al. op. cit. The C$_H$2 domain is unique in that it is not closely paired with another domain. Rather, two N-linked branched carbohydrate chains are interposed between the two C$_H$2 domains of an intact native IgG molecule. It is also well documented that the C$_H$3 domain extends from the C$_H$2 domain to the C-terminal of the IgG molecule and comprises approximately 108 residues.

As used herein, the term "hinge region" includes the portion of a heavy chain molecule that joins the $C_H1$ domain to the $C_H2$ domain. This hinge region comprises approximately 25 residues and is flexible, thus allowing the two N-terminal antigen binding regions to move independently. Hinge regions can be subdivided into three distinct domains: upper, middle, and lower hinge domains (Roux et al., *J. Immunol.* 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the $C_H1$ and $C_L$ regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant invention) is obtained from a second species. In preferred embodiments the target binding region or site will be from a non-human source (e.g. mouse or primate) and the constant region is human.

As used herein, the term "engineered antibody" refers to an antibody in which the variable domain in either the heavy and light chain or both is altered by at least partial replacement of one or more CDRs from an antibody of known specificity and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. Preferred engineered antibodies of the present invention include those in which one or more "donor" CDRs is from a human antibody of known specificity and is grafted into a non-human heavy or light chain framework region. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered antibody.

As used herein the term "properly folded polypeptide" includes polypeptides (e.g., TNFα antibodies) in which all of the functional domains comprising the polypeptide are distinctly active. As used herein, the term "improperly folded polypeptide" includes polypeptides in which at least one of the functional domains of the polypeptide is not active. In one embodiment, a properly folded polypeptide comprises polypeptide chains linked by at least one disulfide bond and, conversely, an improperly folded polypeptide comprises polypeptide chains not linked by at least one disulfide bond.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques).

As used herein, the terms "linked," "fused" or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two ore more segments that correspond to polypeptides encoded by the original ORFs (which segments are not normally so joined in nature.) Although the reading frame is thus made continuous throughout the fused segments, the segments may be physically or spatially separated by, for example, in-frame linker sequence. For example, polynucleotides encoding the CDRs of an immunoglobulin variable region may be fused, in-frame, but be separated by a polynucleotide encoding at least one immunoglobulin framework region or additional CDR regions, as long as the "fused" CDRs are co-translated as part of a continuous polypeptide.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, the terms "treat" or "treatment" refer to both therapeutic treatment and prophylactic or preventative measures, wherein the object is to prevent or slow down (lessen) an undesired physiological change or disorder, such as the progression of multiple sclerosis. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, and so on.

As used herein, phrases such as "a subject that would benefit from administration of a TNFα antibody" and "an animal in need of treatment" includes subjects, such as mammalian subjects, that would benefit from administration of a TNFα antibody used, e.g., for detection of a TNFα polypeptide (e.g., for a diagnostic procedure) and/or from treatment, i.e., palliation or prevention of a disease, with a TNFα antibody. As described in more detail herein, the TNFα antibody can be used in unconjugated form or can be conjugated, e.g., to a drug, prodrug, or an isotope.

TNFα antibodies of the present invention may be used to treat autoimmune disorders, such as OA and RA, and may be used to treat inflammatory conditions such as sepsis, inflammatory bowel disease and Jarisch-Herxheimer reaction. Such conditions in which cells begin to express, over-express, or abnormally express TNFα, are particularly treatable by the methods of the present invention.

II. TNFα

Naturally occurring tumor necrosis factor alpha (TNFα) is a multifunctional proinflammatory cytokine that belongs to the tumor necrosis factor (TNF) superfamily. Pennica, D., et al., Nature 312: 724-729 (1984). TNFα is mainly secreted by macrophages. It can bind to, and thus functions through its receptors TNFR-1 and TNFR-2. TNFα is involved in the regulation of a wide spectrum of biological processes including cell proliferation, differentiation, apoptosis, lipid metabolism, and coagulation. TNFα has been implicated in a variety of diseases, including autoimmune diseases, insulin resistance, and cancer. Knockout studies in mice also suggested the neuroprotective function of TNFα. The nucleic acid sequence of the human TNFα mRNA is available under GenBank Accession Number NM_000594, and is presented herein as SEQ ID NO:1.

```
SEQ ID NO: 1
> gi|25952110|ref|NM_000594.2|[25952110] Homo
sapiens tumor necrosis factor (TNF superfamily,
member 2) (TNF), mRNA
ctccctcagc aaggacagca gaggaccagc taagagggag agaagcaact acagacccc cctgaaaaca accctcagac gccacatccc ctgacaagct gccaggcagg ttctcttcct ctcacatact gacccacggc tccaccctct ctccctgga aaggacacca tgagcactga aagcatgatc cgggacgtgg agctggccga ggaggcgctc cccaagaaga caggggggcc ccagggctcc aggcggtgct tgttcctcag cctcttctcc ttcctgatcg tggcaggcgc caccacgctc ttctgcctgc tgcactttgg agtgatcggc ccccagaggg aagagttccc cagggacctc tctctaatca gccctctggc ccaggcagtc agatcatctt ctcgaacccc gagtgacaag cctgtagccc atgttgtagc aaaccctcaa gctgaggggc agctccagtg gctgaaccgc cgggccaatg ccctcctggc caatggcgtg gagctgagag ataaccagct ggtggtgcca tcagagggcc tgtacctcat ctactcccag gtcctcttca agggccaagg ctgcccctcc acccatgtgc tcctcaccca caccatcagc cgcatcgccg tctcctacca gaccaaggtc aacctcctct ctgccatcaa gagcccctgc cagagggaga ccccagaggg ggctgaggcc aagccctggt atgagcccat ctatctggga ggggtcttcc agctggagaa gggtgaccga ctcagcgctg agatcaatcg gcccgactat ctcgactttg ccgagtctgg gcaggtctac tttgggatca ttgccctgtg aggaggacga
```

```
acatccaacc ttcccaaacg cctcccctgc cccaatccct ttattacccc ctccttcaga caccctcaac ctcttctggc tcaaaaagag aattgggggc ttagggtcgg aacccaagct tagaacttta agcaacaaga ccaccacttc gaaacctggg attcaggaat gtgtggcctg cacagtgaag tgctggcaac cactaagaat tcaaactggg gcctccagaa ctcactgggg cctacagctt tgatccctga catctggaat ctggagacca gggagccttt ggttctggcc agaatgctgc aggacttgag aagacctcac ctagaaattg acacaagtgg accttaggcc ttcctctctc cagatgtttc cagacttcct tgagacacgg agcccagccc tcccatgga gccagctccc tctatttatg tttgcacttg tgattattta ttatttattt attatttatt tatttacaga tgaatgtatt tatttgggag accggggtat cctgggggac ccaatgtagg agctgccttg gctcagacat gttttccgtg aaaacggagc tgaacaatag gctgttccca tgtagcccc tggcctctgt gccttctttt gattatgttt tttaaaatat ttatctgatt aagttgtcta aacaatgctg atttggtgac caactgtcac tcattgctga gcctctgctc cccaggggag ttgtgtctgt aatcgcccta ctattcagtg gcgagaaata aagtttgctt agaaaagaa
```

The precursor polypeptide sequence is available under GenBank Accession Number NP_000585, and is presented herein as SEQ ID NO:2.

```
SEQ ID NO: 2
>gi|25952111|ref|NP_000585.2| tumor necrosis
factor alpha [Homo sapiens]
MSTESMIRDVELAEEALPKKTGGPQGSRRCLFLSLFSFLIVAGATTLFCL

LHFGVIGPQREEFPRDLSLISPLAQAVRSSSRTPSDKPVAHVVANPQAEG

QLQWLNRRANALLANGVELRDNQLVVPSEGLYLIYSQVLFKGQGCPSTHV

LLTHTISRIAVSYQTKVNLLSAIKSPCQRETPEGAEAKPWYEPIYLGGVF

QLEKGDRLSAEINRPDYLDFAESGQVYFGIIAL
```

The present invention is also directed to TNFα antibodies, or antigen-binding fragments, variants, or derivatives thereof which bind specifically, preferentially, or competitively to non-human TNFα proteins, e.g., TNFα from rodents or non-human primates.

III. TNFα Antibodies

In one embodiment, the present invention is directed to human TNFα antibodies, or antigen-binding fragments, variants, or derivatives thereof. For example, the present invention includes at least the antigen-binding domains of certain monoclonal antibodies, and fragments, variants, and derivatives thereof shown in Table 3. The present invention also includes at least the antigen-binding domains of certain monoclonal antibodies, and fragments, variants, and derivatives thereof, where VL and VH sequences are shown in Table 4.

Tables 3 and 4 describe the binding affinities of the named monoclonal antibodies or Fab fragments in TNFα binding assays using known monoclonal antibodies, such as Remicade® and Humira® as controls. Monoclonal Fab fragments listed in Table 3 were isolated from two different human immunoglobulin libraries using techniques known in the art. Monoclonal Fab fragments listed in Table 4 were produced by mutagenenesis of CDR1, CDR2 and/or CDR3 regions of VH or VL sequences isolated from two different human immunoglobulin libraries using techniques known in the art.

TABLE 3

| Clone Name | VH Number | VL Number | MAb Number | Affinity (nM) |
|---|---|---|---|---|
| 121 E1B | H1193 | L250 | 696 | 0.6 |
| 131 E11 | H1272 | L250 | 698 | 2.3 |
| 183 E9 | H1273 | L250 | 699 | 7.3 |
| 141 F2 | H1278 | L250 | 715 | 0.6 |
| 141 A10 | H1277 | L250 | 714 | 0.4 |
| 142 F2 | H1280 | L250 | 716 | >10 |
| 121 D11 | H1192 | L250 | 695 | 0.6 |
| 156 H7 | H1329 | L250 | 805 | 0.6 |

TABLE 4

| VH Number | VL Number | MAb Number | Affinity (nM) |
|---|---|---|---|
| H1192 | L332 | 855 | 0.25 |
| H1192 | L308 | 812 | 0.32 |
| H1192 | L309 | 813 | 0.42 |
| H1192 | L311 | 815 | 0.36 |
| H1478 | L250 | 1028 | 0.32 |
| H1479 | L250 | 1029 | 0.36 |
| H1373 | L250 | 874 | 0.56 |
| H1388 | L250 | 892 | 0.43 |
| H1482 | L250 | 1037 | 0.12 |
| H1483 | L250 | 1038 | 0.25 |
| H1487 | L250 | 1066 | 0.13 |
| H1518 | L250 | 1132 | 0.10 |
| H1478 | L332 | 1036 | 0.18 |
| H1482 | L332 | 1042 | 0.07 |
| H1483 | L332 | 1043 | 0.31 |
| H1487 | L332 | 1067 | 0.12 |
| H1518 | L332 | 1131 | 0.13 |
| H1557 | L332 | 1210 | 0.14 |
| H1596 | L332 | 1371 | 0.20 |
| H1687 | L332 | 1775 | 0.22 |
| H1684 | L332 | 1777 | 0.18 |
| H1678 | L332 | 1714 | 0.16 |
| H1685 | L332 | 1780 | 0.23 |
| H1727 | L332 | 1850 | 0.59 |
| H1725 | L332 | 1874 | 0.38 |
| H1728 | L332 | 1851 | 0.26 |
| H1729 | L332 | 1852 | 0.41 |
| H1596 | L459 | 1895 | 0.09 |
| H1685 | L459 | 1896 | 0.08 |
| H1813 | L459 | 1988 | 0.04 |
| H1814 | L459 | 1989 | 0.05 |
| H1824 | L459 | 1999 | 0.04 |
| H1831 | L459 | 2006 | 0.04 |
| H1844 | L459 | 2019 | 0.04 |
| H1844 | L471 | 2060 | 0.02 |
| H1844 | L472 | 2071 | 0.01 |
| H1813 | L472 | 2090 | 0.02 |

Table 5 describes the binding affinity of the named monoclonal antibodies in cytotoxicity assays using Remicade®, and in some cases, both Remicade® and Humira® as controls. These experiments are described in more detail in the Examples; results of these assays are also presented in FIGS. 2A-C and 3A-F.

TABLE 5

| MAb Number | IC50 (nM) (IC50 of control antibody indicated in parenthesis)* |
|---|---|
| 695 | 22.9 (0.14) |
| 696 | 22.2 (0.14)** |
|  | 1.7 (1.0) |
|  | 19 (0.15) |
| 592 | 50.3 (0.14) |
| 698 | 152 (0.18) |
| 699 | 350 (0.18) |
| 714 | 7.75 (0.18) |
| 715 | 21.4 (0.18) |
| 716 | 31.4 (0.18) |
| 805 | 4.8 (0.1) |
|  | 10.3 (0.1) |
| 855 | 3.5 (0.15) |
| 1775 | 6.5 (0.1) |
| 1777 | 7.0 (0.1) |
| 1714 | 1.3 (0.1) |
| 1749 | 2.5 (0.1) |
| 1780 | 1.6 (0.1) |
| 1651 | 4.0 (0.1) |
| 1371 | 2.0 (0.1) |
| 1007 | 12.2 (0.1) |
| 1895 | 0.89 (0.34) |
| 1371 | 3.08 (0.34) |
| 1896 | 0.79 (0.34) |
|  | 0.9 (0.35) |
| 1780 | 3.18 (0.34) |
| 1988 | 0.2 (0.35) |
| 1989 | 0.2 (0.35) |
| 1999 | 0.3 (0.35) |
| 2006 | 0.3 (0.35) |
| 2019 | 0.3 (0.35) |
| 2060 | 0.14 (0.16) |
| 2071 | 0.03 (0.16) |
|  | 0.04 (0.11-Remicade ®; 0.18-Humira) |
| 2090 | 0.09 (0.11-Remicade ®; 0.18-Humira) |

*MAbs 2071 and 2090 were assayed in an experiment using both Remicade ® and Humira ® as controls. The IC50 of both control antibodies are indicated. For all other antibodies listed in Table 5, Remicade ® was used as the control antibody.
**Several antibodies listed in Table 5 above were assayed in more than one experiment. Results of each experiment are indicated together with the corresponding control.

As used herein, the term "antigen binding domain" includes a site that specifically binds an epitope on an antigen (e.g., an epitope of TNFα). The antigen binding domain of an antibody typically includes at least a portion of an immunoglobulin heavy chain variable region and at least a portion of an immunoglobulin light chain variable region. The binding site formed by these variable regions determines the specificity of the antibody.

The present invention is more specifically directed to a human TNFα antibody, or antigen-binding fragment, variant or derivatives thereof, where the TNFα antibody binds to the same epitope as a monoclonal antibody selected from the group consisting of 696, 698, 699, 715, 714, 716, 695, 805, 855, 812, 813, 815, 1028, 1029, 874, 892, 1037, 1038, 1066, 1132, 1036, 1042, 1043, 1067, 1131, 1210, 1371, 1775, 1777, 1714, 1780, 1850, 1874, 1851, 1852, 1895, 1896, 1988, 1989, 1999, 2006, 2019 and 2060. In certain embodiments, the TNFα antibody binds to the same epitope as a monoclonal antibody selected from the group consisting of 2071 and 2090.

The invention is further drawn to a human TNFα antibody, or antigen-binding fragment, variant or derivatives thereof where the human TNFα antibody comprises at least the antigen binding region of a monoclonal antibody selected from the group consisting of 696, 698, 699, 715, 714, 716, 695, 805, 855, 812, 813, 815, 1028, 1029, 874, 892, 1037, 1038, 1066, 1132, 1036, 1042, 1043, 1067, 1131, 1210, 1789, 1371, 1775, 1777, 1714, 1780, 1850, 1874, 1851, 1852, 1895, 1896, 1988, 1989, 1999, 2006, 2019 and 2060. In certain embodiments, the human TNFα antibody comprises at least the antigen binding region of a monoclonal antibody selected from the group consisting of 2071 and 2090.

The invention is also drawn to a human TNFα antibody, or antigen-binding fragment, variant or derivatives thereof, where the human TNFα antibody comprises at least the antigen binding region of a monoclonal antibody selected from the group consisting of 696, 698, 699, 715, 714, 716, 695, 805, 855, 812, 813, 815, 1028, 1029, 874, 892, 1037, 1038, 1066, 1132, 1036, 1042, 1043, 1067, 1131, 1210, 1789, 1371, 1775, 1777, 1714, 1780, 1850, 1874, 1851, 1852, 1895, 1896, 1988, 1989, 1999, 2006, 2019, and 2060. In certain embodiments, the human TNFα antibody comprises at least the antigen binding region of a monoclonal antibody selected from the group consisting of 2071 and 2090.

In certain embodiments, the present invention is directed to a human antibody, or antigen-binding fragment, variant, or derivative thereof which specifically or preferentially binds to a particular TNFα polypeptide fragment or domain. Such TNFα polypeptide fragments include, but are not limited to, a TNFα polypeptide comprising, consisting essentially of, or consisting of the polypeptide of SEQ ID NO:2, or a TNFα variant polypeptide at least 70%, 75%, 80%, 85%, 90%, or 95% identical to the polypeptide of SEQ ID NO:2.

As known in the art, "sequence identity" between two polypeptides is determined by comparing the amino acid sequence of one polypeptide to the sequence of a second polypeptide. When discussed herein, whether any particular polypeptide is at least about 70%, 75%, 80%, 85%, 90% or 95% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2:482-489 (1981), to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

Methods of making antibodies are well known in the art and described herein. Once antibodies to various fragments of, or to the full-length TNFα without the signal sequence, have been produced, determining which amino acids, or epitope, of TNFα to which the antibody or antigen binding fragment binds can be determined by eptiope mapping protocols as described herein as well as methods known in the art (e.g. double antibody-sandwich ELISA as described in "Chapter 11—Immunology," *Current Protocols in Molecular Biology*, Ed. Ausubel et al., v.2, John Wiley & Sons, Inc. (1996)). Additional eiptope mapping protocols may be found in Morris, G. *Epitope Mapping Protocols*, New Jersey: Humana Press (1996), which are both incorporated herein by reference in their entireties. Epitope mapping can also be performed by commercially available means (i.e. Proto-PROBE, Inc. (Milwaukee, Wis.)).

Additionally, antibodies produced which bind to any portion of TNFα can then be screened for their ability to act as an antagonist of TNFα.

In other embodiments, the present invention includes a human antibody, or antigen-binding fragment, variant, or derivative thereof which specifically or preferentially binds to at least one epitope of TNFα, where the epitope comprises, consists essentially of, or consists of at least about four to five amino acids of SEQ ID NO:2, at least seven, at least nine, or between at least about 15 to about 30 amino acids of SEQ ID NO:2. The amino acids of a given epitope of SEQ ID NO:2 as described may be, but need not be contiguous or linear. In certain embodiments, the at least one epitope of TNFα comprises, consists essentially of, or consists of a non-linear epitope formed by the extracellular domain of TNFα as expressed on the surface of a cell or as a soluble fragment, e.g., fused to an IgG Fc region. Thus, in certain embodiments the at least one epitope of TNFα comprises, consists essentially of, or consists of at least 4, at least 5, at least 6, at least 7, at least 8, at least 9, at least 10, at least 15, at least 20, at least 25, between about 15 to about 30, or at least 10, 15, 20, 25, 30, 35, 40, 45, 50, 55, 60, 65, 70, 75, 80, 85, 90, 95, or 100 contiguous or non-contiguous amino acids of SEQ ID NO:2, where non-contiguous amino acids form an epitope through protein folding.

In other embodiments, the present invention includes a human antibody, or antigen-binding fragment, variant, or derivative thereof which specifically or preferentially binds to at least one epitope of TNFα, where the epitope comprises, consists essentially of, or consists of, in addition to one, two, three, four, five, six or more contiguous or non-contiguous amino acids of SEQ ID NO:2 as described above, and an additional moiety which modifies the protein, e.g., a carbohydrate moiety may be included such that the TNFα antibody binds with higher affinity to modified target protein than it does to an unmodified version of the protein. Alternatively, the TNFα antibody does not bind the unmodified version of the target protein at all.

In certain aspects, the present invention is directed to a human antibody, or antigen-binding fragment, variant, or derivative thereof which specifically binds to a TNFα polypeptide or fragment thereof, or a TNFα variant polypeptide, with an affinity characterized by a dissociation constant ($K_D$) which is less than the $K_D$ for said reference monoclonal antibody.

In certain embodiments, a human antibody, or antigen-binding fragment, variant, or derivative thereof of the invention binds specifically to at least one epitope of TNFα or fragment or variant described above, i.e., binds to such an epitope more readily than it would bind to an unrelated, or random epitope; binds preferentially to at least one epitope of TNFα or fragment or variant described above, i.e., binds to such an epitope more readily than it would bind to a related, similar, homologous, or analogous epitope; competitively inhibits binding of a reference antibody which itself binds specifically or preferentially to a certain epitope of TNFα or fragment or variant described above; or binds to at least one epitope of TNFα or fragment or variant described above with an affinity characterized by a dissociation constant $K_D$ of less than about $5 \times 10^{-2}$ M, about $10^{-2}$ M, about $5 \times 10^{-3}$ M, about $10^{-3}$ M, about $5 \times 10^{-4}$ M, about $10^{-4}$ M, about $5 \times 10^{-5}$ M, about $10^{-5}$ M, about $5 \times 10^{-4}$ M, about $10^{-4}$ M, about $5 \times 10^{-7}$ M, about $10^{-7}$ M, about $5 \times 10^{-8}$ M, about $10^{-8}$ M, about $5 \times 10^{-9}$ M, about $10^{-9}$ M, about $5 \times 10^{-10}$ M, about $10^{-10}$ M, about $5 \times 10^{-11}$ M, about $10^{-11}$ M, about $5 \times 10^{-12}$ M, about $10^{-12}$ M, about $5 \times 10^{-13}$ M, about $5.7 \times 10^{-12}$ M, about $8.4 \times 10^{-12}$ M, about $10^{-13}$ M, about $5 \times 10^{-14}$ M, about $10^{-14}$ M, about $5\times10^{-15}$ M, or about $10^{-15}$ M. In a particular aspect, the antibody or fragment thereof preferentially binds to a human TNFα polypeptide or fragment thereof, relative to a murine TNFα polypeptide or fragment thereof.

As used in the context of antibody binding dissociation constants, the term "about" allows for the degree of variation inherent in the methods utilized for measuring antibody affinity. For example, depending on the level of precision of the instrumentation used, standard error based on the number of samples measured, and rounding error, the term "about $10^{-2}$ M" might include, for example, from 0.05 M to 0.005 M.

In specific embodiments, a human antibody, or antigen-binding fragment, variant, or derivative thereof of the invention binds TNFα polypeptides or fragments or variants thereof with an off rate (k(off)) of less than or equal to $5\times10^{-2}$ sec$^{-1}$, $10^{-2}$ sec$^{-1}$, $5\times10^{-3}$ sec$^{-1}$ or $10^{-3}$ sec$^{-1}$. Alternatively, an antibody, or antigen-binding fragment, variant, or derivative thereof of the invention binds TNFα polypeptides or fragments or variants thereof with an off rate (k(off)) of less than or equal to $5\times10^{-4}$ sec$^{-1}$, $10^{-4}$ sec$^{-1}$, $5\times10^{-5}$ sec$^{-1}$, or $10^{-5}$ sec$^{-1}$, $5\times10^{-6}$ sec$^{-1}$, $10^{-6}$ sec$^{-1}$, $5\times10^{-7}$ sec$^{-1}$ or $10^{-7}$ sec$^{-1}$.

In other embodiments, a human antibody, or antigen-binding fragment, variant, or derivative thereof of the invention binds TNFα polypeptides or fragments or variants thereof with an on rate (k(on)) of greater than or equal to $10^3$ M$^{-1}$ sec$^{-1}$, $5\times10^3$ M$^{-1}$ sec$^{-1}$, $10^4$ M$^{-1}$ sec$^{-1}$ or $5\times10^4$ M$^{-1}$ sec$^{-1}$. Alternatively, an antibody, or antigen-binding fragment, variant, or derivative thereof of the invention binds TNFα polypeptides or fragments or variants thereof with an on rate (k(on)) greater than or equal to $10^5$ M$^{-1}$ sec$^{-1}$, $5\times10^5$ M$^{-1}$ sec$^{-1}$, $10^6$ M$^{-1}$ sec$^{-1}$, or $5\times10^6$ M$^{-1}$ sec$^{-1}$ or $10^7$ M$^{-1}$ sec$^{-1}$.

In various embodiments, a human TNFα antibody, or antigen-binding fragment, variant, or derivative thereof as described herein is an antagonist of TNFα activity.

Unless it is specifically noted, as used herein a "fragment thereof" in reference to an antibody refers to an antigen-binding fragment, i.e., a portion of the antibody which specifically binds to the antigen. In one embodiment, a human TNFα antibody, e.g., an antibody of the invention is a bispecific TNFα antibody, binding polypeptide, or antibody, e.g., a bispecific antibody, minibody, domain deleted antibody, or fusion protein having binding specificity for more than one epitope, e.g., more than one antigen or more than one epitope on the same antigen. In one embodiment, a bispecific TNFα antibody, binding polypeptide, or antibody has at least one binding domain specific for at least one epitope on a target polypeptide disclosed herein, e.g., TNFα. In another embodiment, a bispecific TNFα antibody, binding polypeptide, or antibody has at least one binding domain specific for an epitope on a target polypeptide and at least one target binding domain specific for a drug or toxin. In yet another embodiment, a bispecific TNFα antibody, binding polypeptide, or antibody has at least one binding domain specific for an epitope on a target polypeptide disclosed herein, and at least one binding domain specific for a prodrug. A bispecific TNFα antibody, binding polypeptide, or antibody may be a tetravalent antibody that has two target binding domains specific for an epitope of a target polypeptide disclosed herein and two target binding domains specific for a second target. Thus, a tetravalent bispecific TNFα antibody, binding polypeptide, or antibody may be bivalent for each specificity.

Human TNFα antibodies, or antigen-binding fragments, variants, or derivatives thereof of the invention, as known by those of ordinary skill in the art, can comprise a constant region which mediates one or more effector functions. For example, binding of the C1 component of complement to an antibody constant region may activate the complement system. Activation of complement is important in the opsonisation and lysis of cell pathogens. The activation of complement also stimulates the inflammatory response and may also be involved in autoimmune hypersensitivity. Further, antibodies bind to receptors on various cells via the Fc region, with a Fc receptor binding site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

Accordingly, certain embodiments of the invention include a human TNFα antibody, or antigen-binding fragment, variant, or derivative thereof, in which at least a fraction of one or more of the constant region domains has been deleted or otherwise altered so as to provide desired biochemical characteristics such as reduced effector functions, the ability to non-covalently dimerize, increased ability to localize at the site of a tumor, reduced serum half-life, or increased serum half-life when compared with a whole, unaltered antibody of approximately the same immunogenicity. For example, certain antibodies for use in the diagnostic and treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the $C_H2$ domain will be deleted.

In certain human TNFα antibodies, or antigen-binding fragments, variants, or derivatives thereof described herein, the Fc portion may be mutated to decrease effector function using techniques known in the art. For example, the deletion or inactivation (through point mutations or other means) of a constant region domain may reduce Fc receptor binding of the circulating modified antibody thereby increasing tumor localization. In other cases it may be that constant region modifications consistent with the instant invention moderate complement binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, may easily be measured and quantified using well know immunological techniques without undue experimentation.

Modified forms of human TNFα antibodies, or antigen-binding fragments, variants, or derivatives thereof of the invention can be made from whole precursor or parent antibodies using techniques known in the art.

Human TNFα antibodies, or antigen-binding fragments, variants, or derivatives thereof of the invention can be made or manufactured using techniques that are known in the art. In certain embodiments, antibody molecules or fragments thereof are "recombinantly produced," i.e., are produced using recombinant DNA technology. Exemplary techniques for making antibody molecules or fragments thereof are discussed in more detail elsewhere herein.

Human TNFα antibodies, or antigen-binding fragments, variants, or derivatives thereof of the invention also include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: *A Laboratory Manual*, Cold Spring Harbor Laboratory Press, 2nd ed. (1988); Hammerling et al., in: *Monoclonal Antibodies and T-Cell Hybridomas* Elsevier, N.Y., 563-681 (1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology. Monoclonal antibodies can be prepared using TNFα knockout mice to increase the regions of epitope recognition. Monoclonal antibodies can be prepared using a wide variety of techniques known in the art including the use of hybridoma and recombinant and display technologies as described elsewhere herein.

Antibody fragments that recognize specific epitopes may be generated by known techniques. For example, Fab and F(ab')$_2$ fragments may be produced by proteolytic cleavage of immunoglobulin molecules, using enzymes such as papain (to produce Fab fragments), or pepsin (to produce F(ab')$_2$ fragments). F(ab')$_2$ fragments contain the variable region, the light chain constant region and the $C_H1$ domain of the heavy chain.

Those skilled in the art will also appreciate that DNA encoding antibodies or antibody fragments (e.g., antigen binding sites) may also be derived from antibody libraries made from various display technologies.

In display technologies based on expression from vaccinia virus libraries in mammalian cells, human antibodies can be identified or selected using one of two methods to select antibodies, one based on membrane-bound antibody expression and one employing secreted antibodies. Vaccinia virus-based vectors are used to express antibodies in mammalian cells and to achieve extremely high levels of combinatorial diversity of immunoglobulin heavy and light chains. The use of such methods results in the identification of antibodies with high-affinity, high specificity, and the desired function. Technologies to construct large cDNA libraries using vaccinia vectors has been described. See e.g., U.S. Pat. Nos. 6,706,477, 6,800,442, and 6,872,518.

The membrane antibody selection process utilizes separate cDNA libraries containing diverse Ig heavy and light chain genes that have been constructed in a vaccinia virus-based vector. These libaries are introduced, via infection, into human cells engineered to allow for high levels of expression of fully assembled antibodies on their cell surface. A fluorescently tagged antigen binds to the minority of cells that express a specific antibody for this antigen. These antigen-binding cells can be isolated in a high-throughput process using a combination of magnetic bead technology and high-speed cell sorting. The recombinant viruses encoding the relevant heavy and light chains can then be extracted and characterized.

In the secreted antibody selection process, separate cDNA libraries containing diverse Ig heavy and light chain genes that have been constructed in a vaccinia virus-based vector are again utilized. These libraries are introduced, via infection, into human cells engineered to allow for high levels of expression of fully assembled, secreted antibodies. The libraries are divided into pools and the supernatants from the pools are screened for antibodies with the proper binding characteristics. Pools in which binding is detected are then further divided into subpools and screened, and so on, until the culture is highly enriched for vaccinia viruses which express antibodies with the desired characteristics.

In one variation of the vaccinia virus library-based antibody selection technology, a nonhuman VH gene is used to select human VL genes. Once these human VL genes are identified, they can be used to select human VH genes, thereby creating a human antibody specific to the same antigen and, in many cases, the same functional epitope as the original non-human antibody. In a related variation, a human VH library, except for a non-human CDR3 region from a known antibody, is used to select human VL genes, and once these VL genes are identified, they can be used to select human VH genes.

These vaccinia virus library-based display technologies, which provide the selection of human antibodies in mammalian cells are particularly suitable for use in the present invention. human antibodies have the advantage of having a lower chance of immune rejection when used therapeutically as compared to a humanized or murine antibody counterpart. Furthermore, the technologies allow the selection or identification of antibodies that would be difficult or impossible to identify with other systems, such as phage display. For example, antibodies that specifically bind to highly conserved proteins or multi-pass membrane receptors. Furthermore, these technologies can utilize previously-identified non-human antibodies to select human antibodies while retaining desired epitope specificity and function. Finally, these methods involve direct expression and produce complete IgG antibodies.

Phage display can also be utilized to display antigen-binding domains expressed from a repertoire or combinatorial antibody library (e.g., human or murine). Exemplary methods are set forth, for example, in EP 368 684 B1; U.S. Pat. No. 5,969,108, Hoogenboom, H. R. and Chames, *Immunol. Today* 21:371 (2000); Nagy et al. Nat. Med. 8:801 (2002); Huie et al., *Proc. Natl. Acad. Sci. USA* 98:2682 (2001); Lui et al., *J. Mol. Biol.* 315:1063 (2002), each of which is incorporated herein by reference. Several publications (e.g., Marks et al., *Bio/Technology* 10:779-783 (1992)) have described the production of high affinity human antibodies by chain shuffling, as well as combinatorial infection and in vivo recombination as a strategy for constructing large phage libraries. In another embodiment, Ribosomal display can be used to replace bacteriophage as the display platform (see, e.g., Hanes et al., *Nat. Biotechnol.* 18:1287 (2000); Wilson et al., *Proc. Natl. Acad. Sci. USA* 98:3750 (2001); or Irving et al., *J. Immunol. Methods* 248:31 (2001)). In yet another embodiment, cell surface libraries can be screened for antibodies (Boder et al., *Proc. Natl. Acad. Sci. USA* 97:10701 (2000); Daugherty et al., *J. Immunol. Methods* 243:211 (2000)). Such procedures provide alternatives to traditional hybridoma techniques for the isolation and subsequent cloning of monoclonal antibodies.

Additional examples of phage display methods that can be used to make the antibodies include those disclosed in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187:9-18 (1997); Burton et al., *Advances in Immunology* 57:191-280 (1994); PCT Application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

Antibody coding regions obtained from the methods described above can be isolated and used to generate whole antibodies, including human antibodies, or any other desired antigen binding fragment, and expressed in any desired host, including mammalian cells, insect cells, plant cells, yeast, and bacteria. For example, techniques to recombinantly produce Fab, Fab' and F(ab')$_2$ fragments can also be employed using methods known in the art such as those disclosed in PCT publication WO 92/22324; Mullinax et al., *BioTechniques* 12(6):864-869 (1992); and Sawai et al., *AJRI* 34:26-34 (1995); and Better et al., *Science* 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46-88 (1991); Shu et al., *PNAS* 90:7995-7999 (1993); and Skerra et al., *Science* 240:1038-1040 (1988). For some uses, including in vivo use of antibodies in humans and in vitro detection assays, it may be preferable to use chimeric or human antibodies. A chimeric antibody is a molecule in which different portions of the antibody are derived from different animal species, such as antibodies having a variable region derived from a human monoclonal antibody and a non-human immunoglobulin constant region. Methods for producing chimeric antibodies are known in the art. See, e.g., Morrison, *Science* 229:1202 (1985); Oi et al., *BioTechniques* 4:214 (1986); Gillies et al., *J. Immunol. Methods* 125:191-202 (1989); U.S. Pat. Nos. 5,807,715; 4,816,567; and 4,816,397, which are incorporated herein by reference in their entireties.

Completely human antibodies are particularly desirable for therapeutic treatment of human patients. Human antibodies can be made by a variety of methods known in the art including display technologies described above that provide for the selection of fully-human antibodies by utilizing, e.g. a membrane-bound antibody expression technology, or a technology employing secreted antibodies. Additional methods include phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered nonfunctional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a desired target polypeptide. Monoclonal antibodies directed against the antigen can be obtained from the immunized, transgenic mice using conventional hybridoma technology. The human immunoglobulin transgenes harbored by the transgenic mice rearrange during B-cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar *Int. Rev. Immunol.* 13:65-93 (1995). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and GenPharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., *Bio/Technology* 12:899-903 (1988). See also, U.S. Pat. No. 5,565,332.)

Further, antibodies to target polypeptides of the invention can, in turn, be utilized to generate anti-idiotype antibodies that "mimic" target polypeptides using techniques well known to those skilled in the art. (See, e.g., Greenspan & Bona, *FASEB J* 7(5):437-444 (1989) and Nissinoff, *J. Immunol.* 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a desired target polypeptide and/or to bind its ligands/receptors, and thereby block its biological activity.

In another embodiment, DNA encoding desired monoclonal antibodies may be readily isolated and sequenced using conventional procedures (e.g., by using oligonucleotide probes that are capable of binding specifically to genes encoding the heavy and light chains of human antibodies). The isolated and subcloned hybridoma cells serve as a preferred source of such DNA. Once isolated, the DNA may be placed into expression vectors, which are then transfected into prokaryotic or eukaryotic host cells such as *E. coli* cells, simian COS cells, Chinese Hamster Ovary (CHO) cells or myeloma cells that do not otherwise produce immunoglobulins. More particularly, the isolated DNA (which may be synthetic as described herein) may be used to clone constant and variable region sequences for the manufacture antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

In one embodiment, a human TNFα antibody of the invention comprises at least one human heavy or light chain CDR of an antibody molecule. In another embodiment, a TNFα antibody of the invention comprises at least two human CDRs from one or more antibody molecules. In another embodiment, a TNFα antibody of the invention comprises at least three human CDRs from one or more antibody molecules. In another embodiment, a TNFα antibody of the invention comprises at least four human CDRs from one or more antibody molecules. In another embodiment, a TNFα antibody of the invention comprises at least five human CDRs from one or more antibody molecules. In another embodiment, a TNFα antibody of the invention comprises at least six human CDRs from one or more antibody molecules. Exemplary antibody molecules comprising at least one human CDR that can be included in the subject TNFα antibodies are described herein.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the human CDRs may be inserted within framework regions, e.g., into primate framework regions to "primatize" a human antibody. The framework regions may be naturally occurring or consensus framework regions (see, e.g., Chothia et al., *J. Mol. Biol.* 278:457-479 (1998) for a listing of human framework regions). Preferably, the polynucleotide generated by the combination of the framework regions and CDRs encodes an antibody that specifically binds to at least one epitope of a desired polypeptide, e.g., TNFα. Preferably, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., *Proc. Natl. Acad. Sci.* 81:851-855 (1984); Neuberger et al., *Nature* 312:604-608 (1984); Takeda et al., *Nature* 314:452-454 (1985)) by splicing genes from a mouse antibody molecule of appropriate antigen specificity together with genes from a human antibody molecule of appropriate biological activity can be used. As used herein, a chimeric antibody is a molecule in which different portions are derived from different animal species, such as those having a variable region derived from a human monoclonal antibody and a primate immunoglobulin constant region, e.g., primatized antibodies.

Alternatively, techniques described for the production of single chain antibodies (U.S. Pat. No. 4,694,778; Bird, *Science* 242:423-442 (1988); Huston et al., *Proc. Natl. Acad. Sci. USA* 85:5879-5883 (1988); and Ward et al., *Nature* 334:544-554 (1989)) can be adapted to produce single chain antibodies. Single chain antibodies are formed by linking the heavy and light chain fragments of the Fv region via an amino acid bridge, resulting in a single chain antibody. Techniques for the assembly of functional Fv fragments in *E coli* may also be used (Skerra et al., *Science* 242:1038-1041 (1988)).

Yet other embodiments of the present invention comprise the generation of human or fully human antibodies in transgenic animals (e.g., mice) that are incapable of endogenous immunoglobulin production (see e.g., U.S. Pat. Nos. 6,075,181, 5,939,598, 5,591,669 and 5,589,369 each of which is incorporated herein by reference). For example, it has been described that the homozygous deletion of the antibody heavy-chain joining region in chimeric and germ-line mutant mice results in complete inhibition of endogenous antibody production. Transfer of a human immunoglobulin gene array to such germ line mutant mice will result in the production of human antibodies upon antigen challenge. Another preferred means of generating human antibodies using SCID mice is disclosed in U.S. Pat. No. 5,811,524 which is incorporated herein by reference. It will be appreciated that the genetic material associated with these human antibodies may also be isolated and manipulated as described herein.

Yet another highly efficient means for generating recombinant antibodies is disclosed by Newman, *Biotechnology* 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

In another embodiment, lymphocytes can be selected by micromanipulation and the variable genes isolated. For example, peripheral blood mononuclear cells can be isolated from an immunized mammal and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the $V_H$ and $V_L$ genes can be amplified using, e.g., RT-PCR. The $V_H$ and $V_L$ genes can be cloned into an antibody expression vector and transfected into cells (e.g., eukaryotic or prokaryotic cells) for expression.

Alternatively, antibody-producing cell lines may be selected and cultured using techniques well known to the skilled artisan. Such techniques are described in a variety of laboratory manuals and primary publications. In this respect, techniques suitable for use in the invention as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

Antibodies for use in the diagnostic and therapeutic methods disclosed herein can be produced by any method known in the art for the synthesis of antibodies, in particular, by chemical synthesis or preferably, by recombinant expression techniques as described herein.

In one embodiment, a human TNFα antibody, or antigen-binding fragment, variant, or derivative thereof of the invention comprises a synthetic constant region wherein one or more domains are partially or entirely deleted ("domain-deleted antibodies"). In certain embodiments compatible modified antibodies will comprise domain deleted constructs or variants wherein the entire $C_H2$ domain has been removed ($\Delta C_H2$ constructs). For other embodiments a short connecting peptide may be substituted for the deleted domain to provide flexibility and freedom of movement for the variable region. Those skilled in the art will appreciate that such constructs are particularly preferred due to the regulatory properties of the $C_H2$ domain on the catabolic rate of the antibody.

In certain embodiments, human TNFα antibodies, or antigen-binding fragments, variants, or derivatives thereof of the invention are minibodies. Minibodies can be made using methods described in the art (see, e.g., see e.g., U.S. Pat. No. 5,837,821 or WO 94/09817A1).

In one embodiment, a human TNFα antibody, or antigen-binding fragment, variant, or derivative thereof of the invention comprises an immunoglobulin heavy chain having deletion or substitution of a few or even a single amino acid as long as it permits association between the monomeric subunits. For example, the mutation of a single amino acid in selected areas of the $C_H2$ domain may be enough to substantially reduce Fc binding and thereby increase tumor localization. Similarly, it may be desirable to simply delete that part of one or more constant region domains that control the effector function (e.g. complement binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be synthetic through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. Yet other embodiments comprise the addition of one or more amino acids to the constant region to enhance desirable characteristics such as effector function or provide for more cytotoxin or carbohydrate attachment. In such embodiments it may be desirable to insert or replicate specific sequences derived from selected constant region domains.

The present invention also provides antibodies that comprise, consist essentially of, or consist of, variants (including derivatives) of human antibody molecules (e.g., the $V_H$ regions and/or $V_L$ regions) described herein, which antibodies or fragments thereof immunospecifically bind to a TNFα polypeptide or fragment or variant thereof. Standard techniques known to those of skill in the art can be used to introduce mutations in the nucleotide sequence encoding a TNFα antibody, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference $V_H$ region, $V_H$CDR1, $V_H$CDR2, $V_H$CDR3, $V_L$ region, $V_L$CDR1, $V_L$CDR2, or $V_L$CDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind a TNFα polypeptide).

For example, it is possible to introduce mutations only in framework regions or only in CDR regions of an antibody molecule. Introduced mutations may be silent or neutral missense mutations, i.e., have no, or little, effect on an antibody's ability to bind antigen. These types of mutations may be useful to optimize codon usage, or improve a hybridoma's antibody production. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein may routinely be expressed and the functional and/or biological activity of the encoded protein, (e.g., ability to immunospecifically bind at least one epitope of a TNFα polypeptide) can be determined using techniques described herein or by routinely modifying techniques known in the art.

IV. Polynucleotides Encoding TNFα Antibodies

The present invention also provides for nucleic acid molecules encoding TNFα antibodies, or antigen-binding fragments, variants, or derivatives thereof of the invention.

In one embodiment, the present invention provides an isolated polynucleotide comprising, consisting essentially of, or consisting of a nucleic acid encoding an immunoglobulin heavy chain variable region (VH), where at least one of the CDRs of the heavy chain variable region or at least two of the VH-CDRs of the heavy chain variable region are at least 80%, 85%, 90% or 95% identical to reference heavy chain VH-CDR1, VH-CDR2, or VH-CDR3 amino acid sequences from monoclonal TNFα antibodies disclosed herein. Alternatively, the VH-CDR1, VH-CDR2, and VH-CDR3 regions of the VH are at least 80%, 85%, 90% or 95% identical to reference heavy chain VH-CDR1, VH-CDR2, and VH-CDR3 amino acid sequences from monoclonal TNFα antibodies disclosed herein. Thus, according to this embodiment a heavy chain variable region of the invention has VH-CDR1, VH-CDR2, or VH-CDR3 polypeptide sequences related to the polypeptide sequences shown in Table 6:

TABLE 6

Reference VH-CDR1, VH-CDR2, and VH-CDR3 amino acid sequences

| VH | Germline Gene | VH NUCLEOTIDE AND AMINO ACID SEQUENCE (VH-CDR1, VH-CDR2, and VH-CDR3 underlined) | VH CDR1 | VH CDR2 | VH CDR3 |
|---|---|---|---|---|---|
| H1192 | VH3-53 | GAGGTGCAGCTGTTGGAGTCTGGGGG AGGCTTGATCCAGCCTGGGGGGTCCC TGAGACTCTCCTGTGCAGCCTCTGGG TTCACCGTCAGTAGCAACTACATGAG CTGGGTCCGCCAGGCTCCAGGGAAGG GGCTGGAGTGGGTCTCAGTTATTTAT AGCGGTGGTAGAACATACTACGCAG ACTCCGTGAAGGGCCGATTCACCATC TCCAGAGACAGTTCCAAGAACACGCT GTATCTTCAAATGAACAGCCTGAGAG CCGAGGACACGGCCGTATATTACTGT GCACGGAATTACTACGGTAGTACCTA CGACTACTGGGGCCAGGGAACCCTGG TCACCGTCTCCTCA (SEQ ID NO: 169) EVQLLESGGGLIQPGGSLRLSCAAS<u>GFT VSSNYMS</u>WVRQAPGKGLEWVS<u>VIYSG GRTYYADSVKG</u>RFTISRDSSKNTLYLQ MNSLRAEDTAVYYCAR<u>NYYGSTYDY</u> WGQGTLVTVSS (SEQ ID NO: 3) | GFTFSS YAMH (SEQ ID NO: 4) | AISSNG GSTYY ADSVT G (SEQ ID NO: 5) | NYYGS TYDY (SEQ ID NO: 6) |
| H1272 | VH3-53 | GAGGTGCAGCTGTTGGAGTCTGGAGG AGGCTTGATCCAGCCAGGGGGGTCCC TGAGACTCTCCTGTGCAGCCTCTGGG TTCACCGTCGGAAACAACTACATGAG CTGGGTCCGCCAGGCTCCAGGGAAGG GGCTGGAGTGGGTCTCAGTTATTTAT AGCGCTGGAAGCACATACTACGCAG ACTCCGTGAAGGGCCGATTCATCATC TCCAGAGACAACTCCAAGGACACGGT GTATCTTCAAATGAACAGCCTGAGAG TCGACGACACGGCCGTATATTACTGT GCACGGAATTACTAGGGTAGTACCTA CGACTACTGGGGCCAGGGAACCCTGG TCACCGTCTCCTCA (SEQ ID NO: 170) EVQLLESGGGLIQPGGSLRLSCAAS<u>GFT VGNNYMS</u>WVRQAPGKGLEWVS<u>VIYS AGSTYYADSVKG</u>RFIISRDNSKDTVYL QMNSLRVDDTAVYYCAR<u>NYYGSTYD Y</u>WGQGTLVTVSS (SEQ ID NO: 7) | GFTVG NNYMS (SEQ ID NO: 8) | VIYSAG STYYA DSVKG (SEQ ID NO: 9) | NYYGS TYDY (SEQ ID NO: 10) |
| H1273 | VH3-53 | GAGGTGCAGCTGTTGGAGTCTGGAGG AGGCTTGATCCAGCCTGGGGGGTCCC TGAGACTCTCCTGTGCAGCCTCTGGG TTCACCGTCAGTAGCAACTACATGAG CTGGGTCCGCCAGGCTCCAGGGAAGG GGCTGGAGTGGGTCTCAGTTATTTAT AGCGGTGGTAGCACATACTACGCAGA CTCCGTGAAGGGCCGATTCACCATCT CCAGAGACAACGCCAAGAACACCGT GTATCTGCAAATGAACAGTCTGCGAT CAGAGGACACGGCCGTATATTACTGT GCACGGAATTACTACGGTAGTACCTA CGACTACTGGGGCCAGGGAACCCTGG TCACCGTCTCCTCA (SEQ ID NO: 171) EVQLLESGGGLIQPGGSLRLSCAAS<u>GFT VSSNYMS</u>WVRQAPGKGLEWVS<u>VIYSG GSTYYADSVKG</u>RFTISRDNAKNTVYLQ MNSLRSEDTAVYYCAR<u>NYYGSTYDY</u> WGQGTLVTVSS (SEQ ID NO: 11) | GFTVSS NYMS (SEQ ID NO: 12) | VIYSGG STYYA DSVKG (SEQ ID NO: 13) | NYYGS TYDY (SEQ ID NO: 14) |
| H1278 | VH3-53 | GAGGTGCAGCTGTTGGAGTCTGGAGG AGGCTTGATCCAGCCTGGGGGGTCCC TGAGACTCTCCTGTGCAGCCTCTGGG TTCACCGTCAGTAACAACTACATGAG CTGGGTCCGCCAGGCTCCAGGGAAGG GGCTGCAGTGGGTCGCAGTTATTTAT AGTGGTGGTAGCACATACTACCCAGA | GFTVSN NYMS (SEQ ID NO: 16) | VIYSGG STYYPD SMKG (SEQ ID NO: 17) | NYYGS TYDY (SEQ ID NO: 18) |

TABLE 6-continued

Reference VH-CDR1, VH-CDR2, and VH-CDR3 amino acid sequences

| VH | Germline Gene | VH NUCLEOTIDE AND AMINO ACID SEQUENCE (VH-CDR1, VH-CDR2, and VH-CDR3 underlined) | VH CDR1 | VH CDR2 | VH CDR3 |
|---|---|---|---|---|---|
| | | CTCCATGAAGGGCCGATTCACCATCT<br>CCAGAGACAATTCCAAAAACACGCTT<br>TATCTTCAAATGAACAGCCTGAGAGC<br>CGAGGACACGGCCGTATATTACTGTG<br>CACGGAATTACTACGGTAGTACCTAC<br>GACTACTGGGGCCAGGGAACCCTGGT<br>CACCGTCTCCTCA<br>(SEQ ID NO: 172)<br>EVQLLESGGGLIQPGGSLRLSCAAS<u>GFT</u><br><u>VSNNYMS</u>WVRQAPGKGLQWVA<u>VIYS</u><br><u>GGSTYYPDSMKG</u>RFTISRDNSKNTLYL<br>QMNSLRAEDTAVYYCAR<u>NYYGSTYDY</u><br>WGQGTLVTVSS<br>(SEQ ID NO: 15) | | | |
| H1277 | VH3-53 | GAGGTGCAGCTGGTGGAGTCTGGGGG<br>AGGCTTGGTCCAGCCTGGGGGGTCCC<br>TGAAACTCTCCTGTGCAGCCTCTGGG<br>TTCACCGTTAGTAGTAACTACATGAG<br>TTGGGTCCGCCAGGCTCCAGGGAAGG<br>GGCTGGAGTGGGTCTCAGTTATTTAT<br>AGAGGTGGTAGCACATACTACGCAG<br>ACTCCGTGAAGGGCCGATTCACCATC<br>TCCAGAGACATTTCCAGGAACATGGT<br>GTATCTTCAAATGAACAGTCTGAGAG<br>CCGAGGACACGGCCGTATATTACTGT<br>GCACGGAATTACTACGGTAGTACCTA<br>CGACTACTGGGGCCAGGGAACCCTGG<br>TCACCGTCTCCTCA<br>(SEQ ID NO: 173)<br>EVQLVESGGGLVQPGGSLKLSCAAS<u>GF</u><br><u>TVSSNYMS</u>WVRQAPGKGLEWVS<u>VIYR</u><br><u>GGSTYYADSVKG</u>RFTISRDISRNMVYL<br>QMNSLRAEDTAVYYCAR<u>NYYGSTYDY</u><br>WGQGTLVTVSS<br>(SEQ ID NO: 19) | GFTVSS<br>NYMS<br>(SEQ ID<br>NO: 20) | VIYRGG<br>STYYA<br>DSVKG<br>(SEQ ID<br>NO: 21) | NYYGS<br>TYDY<br>(SEQ ID<br>NO: 22) |
| H1280 | VH3-53 | GAGGTGCAGCTGTTGGAGTCTGGAGG<br>AGGCTTGATCCAGCCTGGGGGGTCCC<br>TGAGAGTCTCCTGTGCAGCCTCTGGG<br>TTCACCGTCAGTAGCAACTACATGAG<br>CTGGGTCCGCCAGGCTCCAGGGAAGG<br>GGCTGGAGTGGGTCTCAGTTATTTAT<br>AGCGGTGGTAGCACATACTACGCAGA<br>CTCCGTGAAGGGCCGATTCACCATCT<br>CCAGAGACAATTCCAAGAACAGGCTG<br>TATCTTCAAATGAACAGCCTGAGAGC<br>CGAGGACACGGCCGTATATTACTGTG<br>CACGGAATTACTACGGTAGTACCTAC<br>GACTACTGGGGCCAGGGAACCCTGGT<br>CACCGTCTCCTCA<br>(SEQ ID NO: 174)<br>EVQLLESGGGLIQPGGSLRLSCAAS<u>GFT</u><br><u>VSSNYMS</u>WVRQAPGKGLEWVS<u>VIYSG</u><br><u>GSTYYADSVKG</u>RFTISRDNSKNTLYLQ<br>MNSLRAEDTAVYYCAR<u>NYYGSTYDY</u><br>WGQGTLVTVSS<br>(SEQ ID NO: 23) | GFTVSS<br>NYMS<br>(SEQ ID<br>NO: 24) | VIYSGG<br>STYYA<br>DSVKG<br>(SEQ ID<br>NO: 25) | NYYGS<br>TYDY<br>(SEQ ID<br>NO: 26) |
| H1193 | VH3-53 | GAGGTGCAGCTGGTGGAGTCTGGAGG<br>AGGCTTGATCCAGCCTGGGGGGTCCC<br>TGAGACTCTCCTGTGCAGCCTCTGGG<br>TTCACCGTCAGTAGCAACTACATGAG<br>CTGGGTCCGCCAGGCTCCAGGGAAGG<br>GGCTGGAGTGGGTCTCAGTTATTTAT<br>AGCGGTGGTAGAACATACTACGCAG<br>ACTCCGTGAAGGGCCGATTCACCATC<br>TCCAGAGACAGTTCCAAGAACACGCT<br>GTATCTTCAAATGAACAGCCTGAGAG<br>CCGAGGACACGGCCGTATATTACTGT<br>GCACGGAATTACTACGGTAGTACCTA | GFTVSS<br>NYMS<br>(SEQ ID<br>NO: 28) | VIYSGG<br>RTYYA<br>DSVKG<br>(SEQ ID<br>NO: 29) | NYYGS<br>TYDY<br>(SEQ ID<br>NO: 30) |

TABLE 6-continued

Reference VH-CDR1, VH-CDR2, and VH-CDR3 amino acid sequences

| VH | Germline Gene | VH NUCLEOTIDE AND AMINO ACID SEQUENCE (VH-CDR1, VH-CDR2, and VH-CDR3 underlined) | VH CDR1 | VH CDR2 | VH CDR3 |
|---|---|---|---|---|---|
| | | CGACTACTGGGGCCAGGGAACCCTGG<br>TCACCGTGTCCTCA<br>(SEQ ID NO: 175)<br>EVQLVESGGGLIQPGGSLRLSCAAS<u>GFT</u><br><u>VSSNYMS</u>WVRQAPGKGLEWVS<u>VIYSG</u><br><u>GRTYYADSVKG</u>RFTISRDSSKNTLYLQ<br>MNSLRAEDTAVYYCAR<u>NYYGSTYDY</u><br>WGQGTLVTVSS<br>(SEQ ID NO: 27) | | | |
| H1329 | VH3-53 | GAGGTGCAGCTGGTGGAGTCTGGAGG<br>AGGCTTGATCCAGCCTGGGGGGTCCC<br>TGAGACTCTCATGCGCAGTCTCGGGG<br>CTCAATGTCAGTCGCGACTACATGAG<br>CTGGGTCCGCCAGGCTCCAGGGAAGG<br>GGCTAGAGTGGATCTCAGTTATTTAT<br>AGAGGTGGTGCCACAATGTACGCAG<br>ACTCCGTGAAGGGCCGATTCACCATC<br>TCCAGAGACACTTCCAAGAACACGGT<br>GTTCCTGCAAATGAGTAGACTGAAAG<br>TCGCGGACACGGCCGTATATTACTGT<br>GCACGGAATTACTACGGTAGTACCTA<br>CGACTACTGGGGCCAGGGAACCCTGG<br>TCACCGTCTCCTCA<br>(SEQ ID NO: 176)<br>EVQLVESGGGLIQPGGSLRLSCAVS<u>GL</u><br><u>NVSRDYMS</u>WVRQAPGKGLEWIS<u>VIYR</u><br><u>GGATMYADSVKG</u>RFTISRDTSKNTVFL<br>QMSRLKVADTAVYYCAR<u>NYYGSTYD</u><br><u>Y</u>WGQGTLVTVSS<br>(SEQ ID NO: 31) | GLNVS RDYMS (SEQ ID NO: 32) | VIYRGG ATMYA DSVKG (SEQ ID NO: 33) | NYYGS TYDY (SEQ ID NO: 34) |
| H1478 (Optimized H1192) | | GAGGTGCAGCTGTTGGAGTCTGGGGG<br>AGGCTTGATCCAGCCTGGGGGGTCCC<br>TGAGACTCTCCTGTGCAGCCTCTGGG<br>TTCACCGTCAGTAGCAACTACATGAG<br>CTGGGTCCGCCAGGCTCCAGGGAAGG<br>GGCTGGAGTGGGTCTCAGTTATTTAT<br>AGCGGTGGTAGAACATACTACGCAG<br>ACTCCGTGAAGGGCCGATTCACCATC<br>TCCAGAGACAGTTCCAAGAACACGCT<br>GTATCTTCAAATGAACAGCCTGAGAG<br>CCGAGGACACGGCCGTATATTACTGT<br>GCACGGACTTACTACGGTAGTACCTA<br>CGACTACTGGGGCCAGGGAACCCTGG<br>TCACCGTCTCCTCA<br>(SEQ ID NO: 177)<br>EVQLLESGGGLIQPGGSLRLSCAAS<u>GFT</u><br><u>VSSNYMS</u>WVRQAPGKGLEWVS<u>VIYSG</u><br><u>GRTYYADSVKG</u>RFTISRDSSKNTLYLQ<br>MNSLRAEDTAVYYCAR<u>TYYGSTYDY</u><br>WGQGTLVTVSS<br>(SEQ ID NO: 35) | GFTFSS YAMH (SEQ ID NO: 4) | AISSNG GSTYY ADSVT G (SEQ ID NO: 5) | TYYGS TYDY (SEQ ID NO: 36) |
| H1479 (Optimized H1192) | | GAGGTGCAGCTGTTGGAGTCTGGGGG<br>AGGCTTGATCCAGCCTGGGGGGTCCC<br>TGAGAGTCTCCTGTGCAGCCTCTGGG<br>TTCACCGTCAGTAGCAACTACATGAG<br>CTGGGTCCGCCAGGCTCCAGGGAAGG<br>GGCTGGAGTGGGTCTCAGTTATTTAT<br>AGCGGTGGTAGAACATACTACGCAG<br>ACTCCGTGAAGGGCCGATTCACCATC<br>TCCAGAGACAGTTCCAAGAACACGCT<br>GTATCTTCAAATGAACAGCCTGAGAG<br>CCGAGGACACGGCCGTATATTACTGT<br>GCACGGCTTTACTACGGTAGTACCTA<br>CGACTACTGGGGCCAGGGAACCCTGG<br>TCACCGTCTCCTCA<br>(SEQ ID NO: 178) | GFTFSS YAMH (SEQ ID NO: 4) | AISSNG GSTYY ADSVT G (SEQ ID NO: 5) | LYYGS TYDY (SEQ ID NO: 38) |

TABLE 6-continued

Reference VH-CDR1, VH-CDR2, and VH-CDR3 amino acid sequences

| VH | Germline Gene | VH NUCLEOTIDE AND AMINO ACID SEQUENCE (VH-CDR1, VH-CDR2, and VH-CDR3 underlined) | VH CDR1 | VH CDR2 | VH CDR3 |
|---|---|---|---|---|---|
| | | EVQLLESGGGLIQPGGSLRLSCAAS<u>GFT VSSNYMS</u>WVRQAPGKGLEWVS<u>VIYSG GRTYYADSVKG</u>RFTISRDSSKNTLYLQ MNSLRAEDTAVYYCAR<u>LYYGSTYDY</u> WGQGTLVTVSS (SEQ ID NO: 37) | | | |
| H1373 (Optimized H1192) | | GAGGTGCAGCTGTTGGAGTCTGGGGG AGGCTTGATCCAGCCTGGGGGGTCCC TGAGACTCTCCTGTGCAGCCTCTGGG TTCACCGTCAGTAGCAACTACATGAG CTGGGTCCGCCAGGCTCCAGGGAAGG GGCTGGAGTGGGTCTCAGTTATTTAT AGCGGTGGTAGAACATACTACGCAG ACTCCGTGAAGGGCCGATTCACCATC TCCAGAGACAGTTCCAAGAACACGCT GTATCTTCAAATGAACAGCCTGAGAG CCGAGGACACGGCCGTATATTACTGT GCACGGAATTACGCGGGTAGTACCTA CGACTACTGGGGCCAGGGAACCCTGG TCACCGTCTCCTCA (SEQ ID NO: 179) EVQLLESGGGLIQPGGSLRLSCAAS<u>GFT VSSNYMS</u>WVRQAPGKGLEWVS<u>VIYSG GRTYYADSVKG</u>RFTISRDSSKNTLYLQ MNSLRAEDTAVYYCAR<u>NYAGSTYDY</u> WGQGTLVTVSS (SEQ ID NO: 39) | GFTFSS YAMH (SEQ ID NO: 4) | AISSNG GSTYY ADSVT G (SEQ ID NO: 5) | NYAGS TYDY (SEQ ID NO: 40) |
| H1388 (Optimized H1192) | | GAGGTGCAGCTGTTGGAGTCTGGGGG AGGCTTGATCCAGCCTGGGGGGTCCC TGAGACTCTCCTGTGGAGCCTCTGGG TTCACCGTCAGTAGCAACTACATGAG CTGGGTCCGCCAGGCTCCAGGGAAGG GGCTGGAGTGGGTCTCAGTTATTTAT AGCGGTGGTAGAACATACTACGCAG ACTCCGTGAAGGGCCGATTCACCATC TCCAGAGACAGTTCCAAGAACACGCT GTATCTTCAAATGAACAGCCTGAGAG CCGAGGACACGGCCGTATATTACTGT GCACGGAATTACTACGGTAGTCTTTA CGACTACTGGGGCCAGGGAACCCTGG TCACCGTCTCCTCA (SEQ ID NO: 180) EVQLLESGGGLIQPGGSLRLSCAAS<u>GFT VSSNYMS</u>WVRQAPGKGLEWVS<u>VIYSG GRTYYADSVKG</u>RFTISRDSSKNTLYLQ MNSLRAEDTAVYYCAR<u>NYYGSLYDY</u> WGQGTLVTVSS (SEQ ID NO: 41) | GFTFSS YAMH (SEQ ID NO: 4) | AISSNG GSTYY ADSVT G (SEQ ID NO: 5) | NYYGS LYDY (SEQ ID NO: 42) |
| H1482 (Optimized H1192) | | GAGGTGCAGCTGTTGGAGTCTGGGGG AGGCTTGATCCAGCCTGGGGGGTCCC TGAGACTCTCCTGTGCAGCCTCTGGG TTCACCGTCAGTAGCAACTACATGAG CTGGGTCCGCCAGGCTCCAGGGAAGG GGCTGGAGTGGGTCTCAGTTATTTAT AGCGGTGGTAGAACATAGTACGCAG ACTCCGTGAAGGGCCGATTCACCATC TCCAGAGACAGTTCCAAGAACACGCT GTATCTTCAAATGAACAGCCTGAGAG CCGAGGACACGGCCGTATATTACTGT GCACGGAATTACTACGGTAGTACCTT TGACTACTGGGGCCAGGGAACCCTGG TCACCGTCTCCTCA (SEQ ID NO: 181) EVQLLESGGGLIQPGGSLRLSCAAS<u>GFT VSSNYMS</u>WVRQAPGKGLEWVS<u>VIYSG GRTYYADSVKG</u>RFTISRDSSKNTLYLQ MNSLRAEDTAVYYCAR<u>NYYGSTFDY</u> WGQGTLVTVSS (SEQ ID NO: 43) | GFTFSS YAMH (SEQ ID NO: 4) | AISSNG GSTYY ADSVT G (SEQ ID NO: 5) | NYYGS TFDY (SEQ ID NO: 44) |

TABLE 6-continued

Reference VH-CDR1, VH-CDR2, and VH-CDR3 amino acid sequences

| VH | Germline Gene | VH NUCLEOTIDE AND AMINO ACID SEQUENCE (VH-CDR1, VH-CDR2, and VH-CDR3 underlined) | VH CDR1 | VH CDR2 | VH CDR3 |
|---|---|---|---|---|---|
| H1483 (Optimized H1192) | | GAGGTGCAGCTGTTGGAGTCTGGGGG AGGCTTGATCCAGCCTGGGGGTCCC TGAGACTCTCCTGTGCAGCCTCTGGG TTCACCGTCAGTAGCAACTACATGAG CTGGGTCCGCCAGGCTCCAGGGAAGG GGCTGGAGTGGGTCTCAGTTATTTAT AGCGGTGGTAGAACATACTACGCAG ACTCCGTGAAGGGCCGATTCACCATC TCCAGAGACAGTTCCAAGAACACGCT GTATCTTCAAATGAACAGCCTGAGAG CCGAGGACACGGCCGTATATTACTGT GGACGGAATTACTACGGTAGTACCAT GGACTACTGGGGCAGGGAACCCTG GTCAGCGTCTCCTCA (SEQ ID NO: 182) EVQLLESGGGLIQPGGSLRLSCAAS<u>GFT VSSNYMS</u>WVRQAPGKGLEWVS<u>VIYSG GRTYYADSVK</u>GRFTISRDSSKNTLYLQ MNSLRAEDTAVYYCAR<u>NYYGSTMDY</u> WGQGTLVTSS (SEQ ID NO: 45) | GFTFSS YAMH (SEQ ID NO: 4) | AISSNG GSTYY ADSVT G (SEQ ID NO: 5) | NYYGS TMDY (SEQ ID NO: 46) |
| H1487 (Optimized H1192) | | GAGGTGCAGCTGTTGGAGTCTGGGGG AGGCTTGATCCAGCCTGGGGGGTCCC TGAGACTCTCCTGTGCAGCCTCTGGG TTCACCGTCAGTAGCAACTACATGAG CTGGGTCCGCCAGGCTCCAGGGAAGG GGCTGGAGTGGGTCTCAGTTATTTAT AGCGGTGGTAGAACATACTACGCAG ACTCCGTGAAGGGCCGATTCACCATC TCCAGAGACAGTTCCAAGAACACGCT GTATCTTCAAATGAAGAGCCTGAGAG CCGAGGACACGGCCGTATATTACTGT GCACGGAATTACTACGGTAGTACCCT TGACTACTGGGGCAGGGAACCCTGG TCACCGTCTCCTCA EVQLLESGGGLIQPGGSLRLSCAAS<u>GFT VSSNYMS</u>WVRQAPGKGLEWVS<u>VIYSG GRTYYADSVK</u>GRFTISRDSSKNTLYLQ MNSLRAEDTAVYYCAR<u>NYYGSTLDY</u> WGQGTLVTSS (SEQ ID NO: 47) | GFTFSS YAMH (SEQ ID NO: 4) | AISSNG GSTYY ADSVT G (SEQ ID NO: 5) | NYYGS TLDY (SEQ ID NO: 48) |
| H1518 (Optimized H1192) | | GAGGTGCAGCTGTTGGAGTCTGGGGG AGGCTTGATCCAGCCTGGGGGGTCCC TGAGACTCTCCTGTGCAGCCTCTGGG TTCACCGTCAGTAGCAACTACATGAG CTGGGTCCGCCAGGCTCCAGGGAAGG GGCTGGAGTGGGTCTCAGTTATTTAT AGCGGTGGTAGAACATACTACGCAG ACTCCGTGAAGGGCCGATTCACCATC TCCAGAGACAGTTCCAAGAACACGCT GTATCTTCAAATGAACAGCCTGAGAG CCGAGGACACGGCCGTATATTACTGT GCACGGAATTACTACGGTAGTACCCA CGACTACTGGGGCCAGGGAACCCTGG TCACCGTCTCCTCA (SEQ ID NO: 184) EVQLLESGGGLIQPGGSLRISCAAS<u>GFT VSSNYMS</u>WVRQAPGKGLEWVS<u>VIYSG GRTYYADSVK</u>GRFTISRDSSKNTLYLQ MNSLRAEDTAVYYCAR<u>NYYGSTHDY</u> WGQGTLVTSS (SEQ ID NO: 49) | GFTFSS YAMH (SEQ ID NO: 4) | AISSNG GSTYY ADSVT G (SEQ ID NO: 5) | NYYGS THDY (SEQ ID NO: 50) |
| H1557 (Optimized H1192) | | GAGGTGCAGCTGTTGGAGTCTGGGGG AGGCTTGATCCAGCCTGGGGGGTCCC TGAGACTCTCCTGTGCAGCCTCTGGG TTCACCGTCAGTAGGAACTACATGAG CTGGGTCCGCCAGGCTCCAGGGAAGG GGCTGGAGTGGGTCTCAGTTATTTAT AGCGGTGGTAGAACATACTACGCAG ACTCCGTGAAGGGCCGATTCACCATC | GFTFSS YAMH (SEQ ID NO: 4) | AISSNG GSTYY ADSVT G (SEQ ID NO: 5) | NYYGS TVDY (SEQ ID NO: 52) |

TABLE 6-continued

Reference VH-CDR1, VH-CDR2, and VH-CDR3 amino acid sequences

| VH | Germline Gene | VH NUCLEOTIDE AND AMINO ACID SEQUENCE (VH-CDR1, VH-CDR2, and VH-CDR3 underlined) | VH CDR1 | VH CDR2 | VH CDR3 |
|---|---|---|---|---|---|
| | | TCCAGAGACAGTTCCAAGAACACGCT<br>GTATCTTCAAATGAACAGCCTGAGAG<br>CCGAGGACACGGCCGTATATTACTGT<br>GCACGGAATTACTACGGTAGTACCGT<br>GGACTACTGGGGCCAGGGAACCCTG<br>GTCACCGTCTCCTCA<br>(SEQ ID NO: 185)<br>EVQLLESGGGLIQPGGSLRLSCAAS<u>GFT<br>VSSNYMS</u>WVRQAPGKGLEWVS<u>VIYSG<br>GRTYYADSVKG</u>RFTISRDSSKNTLYLQ<br>MNSLRAEDTAVYYCAR<u>NYYGSTVDY</u><br>WGQGTLVTSS<br>(SEQ ID NO: 51) | | | |
| H1694<br>(Optimized H1329) | | GAGGTGCAGCTGGTGGAGTCTGGAGG<br>AGGCTTGATCCAGCCTGGGGGGTCCC<br>TGAGACTCTCATGCGCAGTCTCGGGG<br>CTCAATGTCAGTCGCGACTACATGAG<br>CTGGGTCCGCCAGGGTCCAGGGAAGG<br>GGCTAGAGTGGATCTCAGTTATTTAT<br>AGAGGTGGTGCCACAATGTACGCAG<br>ACTCCGTGAAGGGCCGATTCACCATC<br>TCCAGAGACACTTCCAAGAACACGGT<br>GTTCCTGCAAATGAGTAGACTGAAAG<br>TCGCGGACACGGCCGTATATTACTGT<br>GCACGGACTTACTACGGTAGTACCTA<br>CGACTACTGGGGCCAGGGAACCCTGG<br>TCACCGTCTCCTCA<br>(SEQ ID NO: 186)<br>EVQLVESGGGLIQPGGSLRLSCAVS<u>GL<br>NVSRDYMS</u>WVRQAPGKGLEWIS<u>VIYR<br>GGATMYADSVKG</u>RFTISRDTSKNTVFL<br>QMSRLKVADTAVYYCAR<u>TYYGSTYDY</u><br>WGQGTLVTVSS<br>(SEQ ID NO: 53) | GLNVS RDYMS (SEQ ID NO: 32) | VIYRGG ATMYA DSVKG (SEQ ID NO: 33) | TYYGS TYDY (SEQ ID NO: 54) |
| H1596<br>(Optimized H1329) | | GAGGTGCAGCTGGTGGAGTCTGGAGG<br>AGGCTTGATCCAGCCTGGGGGGTCCC<br>TGAGACTCTCATGCGCAGTCTCGGGG<br>CTCAATGTCAGTCGCGACTACATGAG<br>CTGGGTCCGCCAGGCTCCAGGGAAGG<br>GGCTAGAGTGGATCTCAGTTATTTAT<br>AGAGGTGGTGCCACAATGTACGCAG<br>ACTCCGTGAAGGGCCGATTCACCATC<br>TCCAGAGACACTTCCAAGAACACGGT<br>GTTCCTGCAAATGAGTAGACTGAAAG<br>TCGCGGACACGGCCGTATATTACTGT<br>GCACGGAATTACTACGGTAGTACCCA<br>CGACTACTGGGGCCAGGGAACCCTGG<br>TCACCGTCTCCTCA<br>(SEQ ID NO: 187)<br>EVQLVESGGGLIQPGGSLRLSCAVS<u>GL<br>NVSRDYMS</u>WVRQAPGKGLEWIS<u>VIYR<br>GGATMYADSVKG</u>RFTISRDTSKNTVFL<br>QMSRLKVADTAVYYCAR<u>NYYGSTHD<br>Y</u>WGQGTLVTVSS<br>(SEQ ID NO: 55) | GLNVS RDYMS (SEQ ID NO: 32) | VIYRGG ATMYA DSVKG (SEQ ID NO: 33) | NYYGS THDY (SEQ ID NO: 56) |
| H1687<br>(Optimized H1329) | | GAGGTGCAGCTGGTGGAGTCTGGAGG<br>AGGCTTGATCCAGCCTGGGGGGTCCC<br>TGAGACTCTCATGCGCAGTCTCGGGG<br>CTCAATGTCAGTCGCGACTACATGAG<br>CTGGGTCGCCCAGGCTCCAGGGAAGG<br>GGCTAGAGTGGATCTCAGTTATTTAT<br>AGAGGTGGTGCCACAATGTACGCAG<br>ACTCCGTGAAGGGCCGATTCACCATC<br>TCCAGAGACACTTCCAAGAACACGGT<br>GTTCCTGCAAATGAGTAGACTGAAAG<br>TCGCGGACACGGCCGTATATTACTGT<br>GCACGGAATTACTACGGTAGTACCAT<br>GGACTACTGGGGCCAGGGAACCCTG<br>GTCACCGTCTCCTCA<br>(SEQ ID NO: 188) | GLNVS RDYMS (SEQ ID NO: 32) | VIYRGG ATMYA DSVKG (SEQ ID NO: 33) | NYYGS TMDY (SEQ ID NO: 58) |

TABLE 6-continued

Reference VH-CDR1, VH-CDR2, and VH-CDR3 amino acid sequences

| VH | Germline Gene | VH NUCLEOTIDE AND AMINO ACID SEQUENCE (VH-CDR1, VH-CDR2, and VH-CDR3 underlined) | VH CDR1 | VH CDR2 | VH CDR3 |
|---|---|---|---|---|---|
| | | EVQLVESGGGLIQPGGSLRLSCAVS<u>GL NVSRDYMS</u>WVRQAPGKGLEWIS<u>VIYR GGATMYADS</u>VKGRFTISRDTSKNTVFL QMSRLKVADTAVYYCAR<u>NYYGSTMD YW</u>GQGTLVTVSS (SEQ ID NO: 57) | | | |
| H1684 (Optimized H1329) | | GAGGTGCAGCTGGTGGAGTCTGGAGG AGGCTTGATCCAGCCTGGGGGGTCCC TGAGACTCTCATGCGCAGTCTCGGGG CTCAATGTCAGTCGCGACTACATGAG CTGGGTCCGCCAGGCTCCAGGGAAGG GGCTAGAGTGGATCTCAGTTATTTAT AGAGGTGGTGCCACAATGTACGCAG ACTCCGTGAAGGGCCGATTCACCATC TCCAGAGACACTTCCAAGAACACGGT GTTCCTGCAAATGAGTAGACTGAAAG TCGCGGACACGGCCGTATATTACTGT GCACGGAATTACTACGGTAGTACCAT TGACTAGTGGGGCCAGGGAACCCTGG TCACCGTCTCCTCA (SEQ ID NO: 189) EVQLVESGGGLIQPGGSLRLSCAVS<u>GL NVSRDYMS</u>WVRQAPGKGLEWIS<u>VIYR GGATMYADS</u>VKGRFTISRDTSKNTVFL QMSRLKVADTAVYYCAR<u>NYYGSTIDY</u> WGQGTLVTVSS (SEQ ID NO: 59) | GLNVS RDYMS (SEQ ID NO: 32) | VIYRGG ATMYA DSVKG (SEQ ID NO: 33) | NYYGS TIDY (SEQ ID NO: 60) |
| H1678 (Optimized H1329) | | GAGGTGCAGCTGGTGGAGTCTGGAGG AGGCTTGATCCAGCCTGGGGGGTCCC TGAGACTCTCATGCGCAGTCTCGGGG CTCAATGTCAGTCGCGACTAGATGAG CTGGGTCCGCCAGGCTCCAGGGAAGG GGCTAGAGTGGATCTCAGTTATTTAT AGAGGTGGTGCCACAATGTACGCAG ACTCCGTGAAGGGCCGATTCACCATC TCCAGAGACACTTCCAAGAACACGGT GTTCCTGCAAATGAGTAGACTGAAAG TCGCGGACACGGCCGTATATTACTGT GCACGGAATTACTACGGTAGTACCTT CGACTACTGGGGCCAGGGAACCCTGG TCACCGTCTCCTCA (SEQ ID NO: 190) EVQLVESGGGLIQPGGSLRLSCAVS<u>GL NVSRDYMS</u>WVRQAPGKGLEWIS<u>VIYR GGATMYADS</u>VKGRFTISRDTSKNTVFL QMSRLKVADTAVYYCAR<u>NYYGSTFDY</u> WGQGTLVTVSS (SEQ ID NO: 61) | GLNVS RDYMS (SEQ ID NO: 32) | VIYRGG ATMYA DSVKG (SEQ ID NO: 33) | NYYGS TFDY (SEQ ID NO: 62) |
| H1685 (Optimized H1329) | | GAGGTGCAGCTGGTGGAGTGTGGAGG AGGCTTGATCCAGGCTGGGGGGTCCC TGAGACTCTCATGCGCAGTGTCGGGG CTCAATGTCAGTCGCGACTACATGAG CTGGGTCCGCCAGGCTCCAGGGAAGG GGCTAGAGTGGATCTCAGTTATTTAT AGAGGTGGTGCCAGAATGTACGCAG ACTCCGTGAAGGGCCGATTCACCATC TCCAGAGACACTTCCAAGAACACGGT GTTCCTGCAAATGAGTAGACTGAAAG TGGCGGACACGGCCGTATATTACTGT GCACGGAATTACTACGGTAGTACCTT GGACTACTGGGGCCAGGGAACCCTG GTCACCGTCTCCTCA (SEQ ID NO: 191) EVQLVESGGGLIQPGGSLRLSCAVS<u>GL NVSRDYMS</u>WVRQAPGKGLEWIS<u>VIYR GGATMYADS</u>VKGRFTISRDTSKNTVFL QMSRLKVADTAVYYCAR<u>NYYGSTLDY</u> WGQGTLVTVSS (SEQ ID NO: 63) | GLNVS RDYMS (SEQ ID NO: 32) | VIYRGG ATMYA DSVKG (SEQ ID NO: 33) | NYYGS TLDY (SEQ ID NO: 64) |

TABLE 6-continued

Reference VH-CDR1, VH-CDR2, and VH-CDR3 amino acid sequences

| VH | Germline Gene | VH NUCLEOTIDE AND AMINO ACID SEQUENCE (VH-CDR1, VH-CDR2, and VH-CDR3 underlined) | VH CDR1 | VH CDR2 | VH CDR3 |
|---|---|---|---|---|---|
| H1727 (Optimized H1272) | | GAGGTGCAGCTGTTGGAGTCTGGAGG AGGCTTGATGCAGCCAGGGGGTCCC TGAGACTCTCCTGTGCAGCCTCTGGG TTCACCGTCGGAAACAACTACATGAG CTGGGTCCGCCAGGCTCCAGGGAAGG GGCTGGAGTGGGTCTCAGTTATTTAT AGCGCTGGAAGCACATACTACGCAG ACTCCGTGAAGGGCCGATTCATCATC TCCAGAGACAACTCCAAGGACACGGT GTATCTTCAAATGAACAGCCTGAGAG TCGACGACACGGCCGTATATTACTGT GCACGGAATTACTACGGTAGTACCCA CGACTACTGGGGCCAGGGAACCCTGG TCACCGTCTCCTCA (SEQ ID NO: 192) EVQLLESGGGLIQPGGSLRLSCAAS<u>GFT VGNNYMS</u>WVRQAPGKGLEWVS<u>VIYS AGSTYYA</u>DSVKGRFIISRDNSKDTVYL QMNSLRVDDTAVYYCAR<u>NYYGSTHD Y</u>WGQGTLVTVSS (SEQ ID NO: 65) | GFTVG NNYMS (SEQ ID NO: 8) | VIYSAG STYYA DSVKG (SEQ ID NO: 9) | NYYGS THDY (SEQ ID NO: 66) |
| H1725 (Optimized H1272) | | GAGGTGCAGCTGTTGGAGTCTGGAGG AGGCTTGATCCAGCCAGGGGGGTCCC TGAGACTCTCCTGTGCAGCCTCTGGG TTCACCGTCGGAAACAACTACATGAG CTGGGTCCGCCAGGCTCCAGGGAAGG GGCTGGAGTGGGTCTCAGTTATTTAT AGCGCTGGAAGCACATACTACGCAG ACTCCGTGAAGGGCCGATTCATCATC TCCAGAGACAACTCCAAGGACACGGT GTATCTTCAAATGAACAGCCTGAGAG TCGACGACACGGCCGTATATTACTGT GCACGGAATTACTACGGTAGTACCAT GGACTACTGGGGCCAGGGAACCCTG GTCACC GTCTCCTCA (SEQ ID NO: 193) EVQLLESGGGLIQPGGSLRLSCAAS<u>GFT VGNNYMS</u>WVRQAPGKGLEWVS<u>VIYS AGSTYYA</u>DSVKGRFIISRDNSKDTVYL QMNSLRVDDTAVYYCAR<u>NYYGSTMD Y</u>WGQGTLVTVSS (SEQ ID NO: 67) | GFTVG NNYMS (SEQ ID NO: 8) | VIYSAG STYYA DSVKG (SEQ ID NO: 9) | NYYGS TMDY (SEQ ID NO: 68) |
| H1728 (Optimized H1272) | | GAGGTGCAGCTGTTGGAGTCTGGAGG AGGCTTGATCCAGCCAGGGGGGTCCC TGAGACTCTCCTGTGCAGCCTCTGGG TTCACCGTCGGAAACAACTACATGAG CTGGGTCCGCCAGGCTCCAGGGAAGG GGCTGGAGTGGGTCTCAGTTATTTAT AGCGCTGGAAGCACATACTACGCAG ACTCCGTGAAGGGCCGATTCATCATC TCCAGAGACAACTCCAAGGACACGGT GTATCTTCAAATGAACAGCCTGAGAG TCGACGACACGGCCGTATATTACTGT GCACGGAATTACTACGGTAGTACCTT CGACTACTGGGGCCAGGGAACCCTGG TCACC GTCTCCTCA (SEQ ID NO: 194) EVQLLESGGGLIQPGGSLRLSCAAS<u>GFT VGNNYMS</u>WVRQAPGKGLEWVS<u>VIYS AGSTYYA</u>DSVKGRFIISRDNSKDTVYL QMNSLRVDDTAVYYCAR<u>NYYGSTFDY</u> WGQGTLVTVSS (SEQ ID NO: 69) | GFTVG NNYMS (SEQ ID NO: 8) | VIYSAG STYYA DSVKG (SEQ ID NO: 9) | NYYGS TFDY (SEQ ID NO: 70) |
| H1729 (Optimized H1272) | | GAGGTGCAGCTGTTGGAGTCTGGAGG AGGCTTGATCCAGCCAGGGGGGTCCC TGAGACTCTCCTGTGCAGCCTCTGGG TTCACCGTCGGAAACAACTACATGAG CTGGGTCCGCCAGGCTCCAGGGAAGG GGCTGGAGTGGGTCTCAGTTATTTAT AGCGCTGGAAGCACATACTACGCAG | GFTVG NNYMS (SEQ ID NO: 8) | VIYSAG STYYA DSVKG (SEQ ID NO: 226) | NYYGS TLDY (SEQ ID NO: 64) |

TABLE 6-continued

Reference VH-CDR1, VH-CDR2, and VH-CDR3 amino acid sequences

| VH | Germline Gene | VH NUCLEOTIDE AND AMINO ACID SEQUENCE (VH-CDR1, VH-CDR2, and VH-CDR3 underlined) | VH CDR1 | VH CDR2 | VH CDR3 |
|---|---|---|---|---|---|
| | | ACTCCGTGAAGGGCCGATTCATCATC TCCAGAGACAACTCCAAGGACACGGT GTATCTTCAAATGAACAGCCTGAGAG TCGACGACACGGCCGTATATTACTGT GCACGGAATTACTACGGTAGTACCCT CGACTACTGGGGCCAGGGAACCCTGG TCACC GTCTCCTCA (SEQ ID NO: 195) EVQLLESGGGLIQPGGSLRLSCAAS<u>GFT VGNNYMS</u>WVRQAPGKGLEWVS<u>VIYS AGSTYYADSVKG</u>RFIISRDNSKDTVYL QMNSLRVDDTAVYYCAR<u>NYYGSTLDY</u> WGQGTLVTVSS (SEQ ID NO: 225) | | | |
| H1813 (Optimized H1685) | | GAGGTGCAGCTGGTGGAGTCTGGAGG AGGCTTGATCCAGCCTGGGGGGTCCC TGAGACTCTCATGCGCAGTCTCGGGG CTCAATGTCAGTCGCGACTACATGAG CTGGGTCCGCCAGGCTCCAGGGAAGG GGCTAGAGTGGATCTCAGTTATTTAT AGAATTGGTGCCACAATGTACGCAGA CTCCGTGAAGGGCCGATTCACCATCT CCAGAGACACTTCCAAGAACACGGTG TTCCTGCAAATGAGTAGACTGAAAGT CGCGGACACGGCCGTATATTACTGTG CACGGAATTACTACGGTAGTACCCTT GACTACTGGGGCCAGGGAACCCTGGT CACC GTCTCCTCA (SEQ ID NO: 196) EVQLVESGGGLIQPGGSLRLSCAVS<u>GL NVSRDYMS</u>WVRQAPGKGLEWIS<u>VIYRI GATMYADSVKG</u>RFTISRDTSKNTVFLQ MSRLKVADTAVYYCAR<u>NYYGSTLDY</u> WGQGTLVTVSS (SEQ ID NO: 71) | GFTVG NNYMS (SEQ ID NO: 32) | VIYRIG ATMYA DSVKG (SEQ ID NO: 72) | NYYGS TLDY (SEQ ID NO: 64) |
| H1814 (Optimized H1685) | | GAGGTGCAGCTGGTGGAGTCTGGAGG AGGCTTGATCCAGCCTGGGGGGTCCC TGAGACTCTCATGCGCAGTCTCGGGG CTCAATGTCAGTCGCGACTACATGAG CTGGGTCCGCCAGGCTCCAGGGAAGG GGCTAGAGTGGATCTCAGTTATTTAT AGAGTTGGTGCCACAATGTACGCAGA CTCCGTGAAGGGCCGATTCACCATCT CCAGAGACACTTCCAAGAACACGGTG TTCCTGCAAATGAGTAGACTGAAAGT CGCGGACACGGCCGTATATTACTGTG CACGGAATTACTACGGTAGTACCCTT GACTACTGGGGCCAGGGAACCCTGGT CACCGTCTCCTCA (SEQ ID NO: 197) EVQLVESGGGLIQPGGSLRLSCAVS<u>GL NVSRDYMS</u>WVRQAPGKGLEWIS<u>VIYR VGATMYADSVKG</u>RFTISRDTSKNTVFL QMSRLKVADTAVYYCAR<u>NYYGSTLDY</u> WGQGTLVTVSS (SEQ ID NO: 73) | GFTVG NNYMS (SEQ ID NO: 32) | VIYRVG ATMYA DSVKG (SEQ ID NO: 74) | NYYGS TLDY (SEQ ID NO: 64) |
| H1824 (Optimized H1685) | | GAGGTGCAGCTGGTGGAGTCTGGAGG AGGCTTGATCCAGCCTGGGGGGTCCC TGAGACTCTCATGCGCAGTCTCGGGG CTCAATGTCAGTCGCGACTAGATGAG CTGGGTCCGCCAGGCTCCAGGGAAGG GGCTAGAGTGGATCTCAGTTATTTAT AGAGGTGGTATTACAATGTACGCAGA GTCCGTGAAGGGCCGATTCACCATCT CCAGAGACACTTCCAAGAACACGGTG TTCCTGCAAATGAGTAGACTGAAAGT | GFTVG NNYMS (SEQ ID NO: 32) | VIYRGG ITMYA DSVKG (SEQ ID NO: 76) | NYYGS TLDY (SEQ ID NO: 64) |

TABLE 6-continued

Reference VH-CDR1, VH-CDR2, and VH-CDR3 amino acid sequences

| VH | Germline Gene | VH NUCLEOTIDE AND AMINO ACID SEQUENCE (VH-CDR1, VH-CDR2, and VH-CDR3 underlined) | VH CDR1 | VH CDR2 | VH CDR3 |
|---|---|---|---|---|---|
| | | CGCGGACACGGCCGTATATTACTGTG<br>CACGGAATTACTACGGTAGTACGCTT<br>GACTACTGGGGCCAGGGAACCCTGGT<br>CACC GTCTCCTCA<br>(SEQ ID NO: 198)<br>EVQLVESGGGLIQPGGSLRLSCAVS<u>GL</u><br><u>NVSRDYMS</u>WVRQAPGKGLEWIS<u>VIYR</u><br><u>GGITMYADSVKG</u>RFTISRDTSKNTVFL<br>QMSRLKVADTAVYYCAR<u>NYYGSTLDY</u><br>WGQGTLVTVSS<br>(SEQ ID NO: 75) | | | |
| H1831<br>(Optimized<br>H1685) | | GAGGTGCAGCTGGTGGAGTCTGGAGG<br>AGGCTTGATCCAGCCTGGGGGGTCCC<br>TGAGACTCTCATGCGCAGTCTCGGGG<br>CTCAATGTCAGTCGCGACTACATGAG<br>CTGGGTCCGCCAGGCTCCAGGGAAGG<br>GGCTAGAGTGGATCTCAGTTATTTAT<br>AGAGGTGGTGCCACACATTACGCAGA<br>CTCCGTGAAGGGCCGATTCACCATCT<br>CCAGAGACACTTCCAAGAACACGGTG<br>TTCCTGCAAATGAGTAGACTGAAAGT<br>GGCGGACACGGCCGTATATTACTGTG<br>CACGGAATTACTACGGTAGTACCCTT<br>GACTACTGGGGCCAGGGAACCCTGGT<br>CACC GTCTCCTCA<br>(SEQ ID NO: 199)<br>EVQLVESGGGLIQPGGSLRLSCAVS<u>GL</u><br><u>NVSRDYMS</u>WVRQAPGKGLEWIS<u>VIYR</u><br><u>GGATHYADSVKG</u>RFTISRDTSKNTVFL<br>QMSRLKVADTAVYYCAR<u>NYYGSTLDY</u><br>WGQGTLVTVSS<br>(SEQ ID NO: 77) | GFTVG<br>NNYMS<br>(SEQ ID<br>NO: 32) | VIYRGG<br>ATHYA<br>DSVKG<br>(SEQ ID<br>NO: 78) | NYYGS<br>TLDY<br>(SEQ ID<br>NO: 64) |
| H1844<br>(Optimized<br>H1685) | | GAGGTGCAGCTGGTGGAGTCTGGAGG<br>AGGCTTGATCCAGCCTGGGGGGTCCC<br>TGAGACTCTCATGCGCAGT<u>CTCGGGG</u><br><u>CTCAATGTCAGTCGCGACTACATGAG</u><br><u>C</u>TGGGTCCGCCAGGCTCCAGGGAAGG<br>GGCTAGAGTGGATCTCA<u>GTTATTTAT</u><br><u>AGAGGTGGTGTTACAATGTACGCAGA</u><br><u>CTCCGTGAAGGGC</u>CGATTCACCATCT<br>CCAGAGACACTTCCAAGAACACGGTG<br>TTCCTGCAAATGAGTAGACTGAAAGT<br>CGCGGACACGGCCGTATATTACTGTG<br>CACGG<u>AATTACTACGGTAGTACCCTT</u><br><u>GACTAC</u>TGGGGCCAGGGAACCCTGGT<br>CACCGTCTCCTCA<br>(SEQ ID NO: 200)<br>EVQLVESGGGLIQPGGSLRLSCAVS<u>GL</u><br><u>NVSRDYMS</u>WVRQAPGKGLEWIS<u>VIYR</u><br><u>GGVTMYADSVKG</u>RFTISRDTSKNTVFL<br>QMSRLKVADTAVYYCAR<u>NYYGSTLDY</u><br>WGQGTLVTVSS<br>(SEQ ID NO: 79) | GFTVG<br>NNYMS<br>(SEQ ID<br>NO: 32) | VIYRGG<br>VTMYA<br>DSVKG<br>(SEQ ID<br>NO: 80) | NYYGS<br>TLDY<br>(SEQ ID<br>NO: 64) |

*Determined by the Kabat system (see supra).
N = nucleotide sequence, P = polypeptide sequence.

In other embodiments, a heavy chain variable region of the invention has VH-CDR1, VH-CDR2, or VH-CDR3 polypeptide sequences related to the polypeptide sequences shown in Table 7:

TABLE 7

Reference VH-CDR1, VH-CDR2, and VH-CDR3 amino acid sequences*

| VH | Germline Gene | VH NUCLEOTIDE AND AMINO ACID SEQUENCE (VH-CDR1, VH-CDR2, and VH-CDR3 underlined) | VH CDR1 | VH CDR2 | VH CDR3 |
|---|---|---|---|---|---|
| H1102 | VH3-64 | GAGGTGCAGCTGGTGGAGTCTGGGGG AGGCTTGGTCCAGCCTGGGGGGTCCCT GAGACTCTCCTGTTCAGCCTCTGGATT CACCTTCAGTAGCTATGCTATGCACTG GGTCCGCCAGGCTCCAGGGAAGGGAC TGGAATATGTTTCAGCTATTAGTAGTA ATGGGGGTAGCACATACTACGCAGAC TCCGTGACGGGCAGATTCACCATCTCC AGAGACAATTCCAAGAACACGCTGCA TCTTCAAATGAGCAGTCTGAGAGCTGA GGACACGGCCGTATATTACTGTGCACG GAATTACTACGGTAGTACCTACGACTA CTGGGGCCAGGGAACCCTGGTCACC GTCTCCTCA (SEQ ID NO: 201) EVQLVESGGGLVQPGGSLRLSCSAS<u>GFT FSSYAMH</u>WVRQAPGKGLEYVS<u>AISSNG GSTYYADSVTG</u>RFTISRDNSKNTLHLQM SSLRAEDTAVYYCAR<u>NYYGSTYDY</u>WG QGTLVTVSS (SEQ ID NO: 81) | GFTFSS YAMH (SEQ ID NO: 82) | AISSNG GSTYY ADSVT G (SEQ ID NO: 83) | NYYGS TYDY (SEQ ID NO: 84) |
| H1103 | VH3-30 | GAGGTGCAGCTGTTGGAGTCTGGGGG AGGCGTGGTCCAGCCTGGGAGGTCCCT GAGACTCTCCTGTGCAGCCTCTGGATT CACCTTCTTTAACTATGGCATGCACTG GGTCCGCCAGGCTCCAGGCAAGGGGC TGGAGTGGGTGGCCGTCACATCATTTG ATGGAAGTCATGCATACTATGCAGACT CCGTGAAGGGCCGATTCACCATCTCCA GAGACAATTCCAAGAACACGGTGTTCC TGCAAATGAACAACCTGAGAGGTGAT GACACGGCCGTATATTACTGTGCACGG AATTACTACGGTAGTACCTACGACTAC TGGGGCCAGGGAACCCTGGTCACC GTCTCCTCA (SEQ ID NO: 202) EVQLLESGGGVVQPGRSLRLSCAAS<u>GFT FFNYGMH</u>WVRQAPGKGLEWVA<u>VTSFD GSHAYYADSVKG</u>RFTISRDNSKNTVFLQ MNNLRGDDTAVYYCAR<u>NYYGSTYDY</u>W GQGTLVTVSS (SEQ ID NO: 85) | GFTVG NNYMS (SEQ ID NO: 86) | VIYSAG STYYA DSVKG (SEQ ID NO: 87) | NYYGS TYDY (SEQ ID NO: 88) |
| H1104 | VH3-53 | GAGGTGCAGCTGTTGGAGTCTGGGGG AGGGATGGTGCAGACTGGGGGGTCCG TGAGACTCTCCTGTGCAGTCTCTGGAT TCACCGTCAGTAGCAACTACATGAGCT GGGTCCGCCAGGCTCCAGGGAAGGGG CTGGAGTGGGTCTCCGTTATTTATACT AGTGGTAGTACATTCTACGCAGACTCC GTGAAGGGTCGATTCACCATCTCCAGA GACAATTCCAAGAACACACTGTATCTT CAAATGAACAGCCTGAGAGCCGAGGA CACGGCCGTATATTACTGTGCACGGAA TTACTACGGTAGTACCTACGACTACTG GGGCCAGGGAACCCTGGTCACC GTCTCCTCA (SEQ ID NO: 203) EVQLLESGGGMVQTGGSVRLSCAVS<u>GF TVSSNYMS</u>WVRQAPGKGLEWVS<u>VIYTS GSTFYADSVKG</u>RFTISRDNSKNTLYLQM NSLRAEDTAVYYCARNYYGSTYDYWG QGTLVTVSS (SEQ ID NO: 89) | GFTVSS NYMS (SEQ ID NO: 90) | VIYSGG STYYA DSVKG (SEQ ID NO: 91) | NYYGS TYDY (SEQ ID NO: 92) |

TABLE 7-continued

Reference VH-CDR1, VH-CDR2, and VH-CDR3 amino acid sequences*

| VH | Germline Gene | VH NUCLEOTIDE AND AMINO ACID SEQUENCE (VH-CDR1, VH-CDR2, and VH-CDR3 underlined) | VH CDR1 | VH CDR2 | VH CDR3 |
|---|---|---|---|---|---|
| H1118 | VH4-39 | GAGGTGCAGCTGTTGGAGTCTGGCCCA GGACTGGTGAAGCCTTCGGAGACCCTG TCCCTCAATTGCGCGGTCTCTGGTGAC TCCATCAGCAGTGGTCACTATTGGGGC TGGATCCGGCAGCCCCCAGGGAAGGG GCTGGAGTGGATTGGGACTATCTCTCA TAGGGGGACGACCTACTCCAACCCGTC CCTCAAGAGTCGCGTGACTATTTCAAT GGACAAGTCCAGTAATAGCTTCTCCTT GAAACTGAGCTCTGTGACCGCCGCAG ACACGGCCGTATATTACTGTGCACGGA ATTACTACGGTAGTACCTACGACTACT GGGGCCAGGGAACCCTGGTCACC GTCTCCTCA (SEQ ID NO: 204) EVQLLESGPGLVKPSETLSLNCAVS<u>GDSI SSGHY</u>WGWIRQPPGKGLEWIG<u>TISHRGT TYSNPSLKS</u>RVTISMDKSSNSFSLKLSSV TAADTAVYYCAR<u>NYYGSTYDY</u>WGQGT LVTVSS (SEQ ID NO: 93) | GDSISS GHY (SEQ ID NO: 94) | TISHRG TTYSNP SLKS (SEQ ID NO: 95) | NYYGS TYDY (SEQ ID NO: 96) |
| H1117 | VH3-23 | GAGGTGCAGCTGTTGGAGTCTGGGGG AGCCTTGGTACAGCCGGGGGGGTCCCT GAGGCTCTCCTGTGCAGCCTCTGGATT CACCTTTGACAGCTATCCCATGAACTG GGTCCGCCAGGCCCCAGGGAGGGGGC TGGAGTGGGTCTCAACTATTAGTGGTA GTGGTATTGGCACATACTACGCAGACT CCGTGAAGGGTCGCTTCACCATCTCCA GAGACAACTCCAAGAACACCCTATATC TGCAAATGAACAGCCTGAGAGCCGAC GACACGGCCGTATATTACTGTGCACGG AATTACTACGGTAGTACCTACGACTAC TGGGGCCAGGGAACCCTGGTCACC GTCTCCTCA (SEQ ID NO: 205) EVQLLESGGALVQPGGSLRLSCAAS<u>GFT FDSYPMN</u>WVRQAPGRGLEWVS<u>TISGSGI GTYYADSVKG</u>RFTISRDNSKNTLYLQM NSLRADDTAVYYCAR<u>NYYGSTYDY</u>WG QGTLVTVSS (SEQ ID NO: 97) | GFTFDS YPMN (SEQ ID NO: 98) | TISGSGI GTYYA DSVKG (SEQ ID NO: 99) | NYYGS TYDY (SEQ ID NO: 100) |
| H1119 | VH3-23 | GAGGTGCAGCTGTTGGAGTCTGGGGG AGGCTTGGTGCAGCCGGGGGGGTCCCT GAGACTCTCCTGTGCAGCCTCTGGATT CAACTTTAAGAAATATCCCATGAGCTG GGTCCGCCAGACTCCAGGGAAGGGGC TGGAGTGGGTCTCATTTATCACTGGGA ATGCTGATAGGACATACTACGCAGACT CACTGAAGGGCCGGTTCACTATCTCCA GAGACAATTCCAAGAACACGCTGTATC TGCAAATGAACAGCCTGGCAGTCGAG GACACGGCCGTATATTACTGTGCACGG AATTACTACGGTAGTACCTACGACTAC TGGGGCCAGGGAACCCTGGTCACC GTCTCCTCA (SEQ ID NO: 206) EVQLLESGGGLVQPGGSLRLSCAAS<u>GFN FKKYPMS</u>WVRQTPGKGLEWVS<u>FITGNA DRTYYADSLKG</u>RFTISRDNSKNTLYLQM NSLAVEDTAVYYCAR<u>NYYGSTYDY</u>WG QGTLVTVSS (SEQ ID NO: 101) | GFNFK KYPMS (SEQ ID NO: 102) | FITGNA DRTYY ADSLK G (SEQ ID NO: 103) | NYYGS TYDY (SEQ ID NO: 104) |
| H1120 | VH3-30 | GAGGTGCAGCTGGTGGAGTCTGGGGG AGGCGTGGTCCAGCCTGGGAGGTCCCT GAGACTCTCCTGTGCAGCCTCTGGATT CACCTTCAATGGCTTTGCCATGCACTG GGTCCGCCAGGCTCCAGGCAAGGGGC TGGAGTGGGTGGCGGTTATATCATATG | GFTFNG FAMH (SEQ ID NO: 106) | VISYDG NNKYY ADSVK G (SEQ ID NO: 107) | NYYGS TYDY (SEQ ID NO: 108) |

TABLE 7-continued

Reference VH-CDR1, VH-CDR2, and VH-CDR3 amino acid sequences*

| VH | Germline Gene | VH NUCLEOTIDE AND AMINO ACID SEQUENCE (VH-CDR1, VH-CDR2, and VH-CDR3 underlined) | VH CDR1 | VH CDR2 | VH CDR3 |
|---|---|---|---|---|---|
| | | ATGGAAATAATAAATACTATGCAGACT<br>CCGTGAAGGGCCGGTTCACCATCTCCA<br>GAGACAATTCCAAGAACACGGTGTTCC<br>TACAAATGAACAGCCTGAGACCTGAG<br>GACACGGCCGTATATTACTGTGCACGG<br>AATTACTACGGTAGTACCTACGACTAC<br>TGGGGCCAGGGAACCCTGGTCACC<br>GTCTCCTCA<br>(SEQ ID NO: 207)<br>EVQLVESGGGVVQPGRSLRLSCAAS<u>GFT</u><br><u>FNGFAMH</u>WVRQAPGKGLEWVA<u>VISYD</u><br><u>GNNKYYADSVKG</u>RFTISRDNSKNTVFLQ<br>MNSLRPEDTAVYYCAR<u>NYYGSTYDY</u>W<br>GQGTLVTVSS<br>(SEQ ID NO: 105) | | | |
| H1121 | VH3-30 | GAGGTGCAGCTGGTGGAGTCTGGGGG<br>AGGCGTGGTCCAGCCTGGGAGGTCCCT<br>GAGACTCTCCTGTGCAGCCTCTGGATT<br>CACCTTCAGTAGCTATGGCATGCACTG<br>GGTCCGCCAGGCTCCAGGCAAGGGGC<br>TGGAGTGGGTGGCAGTTATATCATATG<br>ATGGAAGTAATAAATACTATGCAGACT<br>CCGCGAAGGGCCGATTCACCATCTCCA<br>GAGACAATTCCAAGAACACGCTGTATC<br>TGCAAATGAACAGCCTGAGAGCTGAG<br>GACACGGCCGTATATTACTGTGCACGG<br>AATTACTACGGTAGTACCTACGACTAC<br>TGGGGCCAGGGAACCCTGGTCACC<br>GTCTCCTCA<br>(SEQ ID NO: 208)<br>EVQLVESGGGVVQPGRSLRLSCAAS<u>GFT</u><br><u>FSSYGMH</u>WVRQAPGKGLEWVA<u>VISYD</u><br><u>GSNKYYADSAKG</u>RFTISRDNSKNTLYLQ<br>MNSLRAEDTAVYYCAR<u>NYYGSTYDY</u>W<br>GQGTLVTVSS<br>(SEQ ID NO: 109) | GFTFSS<br>YGMH<br>(SEQ ID<br>NO: 110) | VISYDG<br>SNKYY<br>ADSAK<br>G<br>(SEQ ID<br>NO: 111) | NYYGS<br>TYDY<br>(SEQ ID<br>NO: 112) |
| H1122 | VH3-30 | GAGGTGCAGCTGTTGGAGTCTGGGGG<br>AGGCGTGGTCCAGCCGGGGGGGTCCC<br>TGAGACTGTCCTGTGCAGCCTCTGGAT<br>TCACCTTCAGTAGTCATCCATATGCACT<br>GGGTCCGCCAGGCTCGAGGCAAGGGG<br>CTGGAGTGGGTGGCAGTTATATCATAT<br>GATGCAAGGGTTAAATACTATGTAGAC<br>TCCGTGAAGGGCCGATTCACCATCTCC<br>AGAGACGACTCCAAGAACACGCTGTA<br>TCTGCAAATGAACAGCCTGACAACTGA<br>GGACACGGCCGTATATTACTGTGCACG<br>GAATTACTACGGTAGTACCTACGACTA<br>CTGGGGCCAGGGAACCCTGGTCACC<br>GTCTCCTCA<br>(SEQ ID NO: 209)<br>EVQLLESGGGVVQPGGSLRLSCAAS<u>GFT</u><br><u>FSSHPMH</u>WVRQAPGKGLEWVA<u>VISYDA</u><br><u>RVKYYVDSVK</u>GRFTISRDDSKNTLYLQ<br>MNSLTTEDTAVYYCAR<u>NYYGSTYDY</u>W<br>GQGTLVTVSS<br>(SEQ ID NO: 113) | GFTFSS<br>HPMH<br>(SEQ ID<br>NO: 114) | VISYDA<br>RVKYY<br>VDSVK<br>(SEQ ID<br>NO: 115) | NYYGS<br>TYDY<br>(SEQ ID<br>NO: 116) |
| H1194 | VH3-30 | GAGGTGCAGCTGGTGGAGTCTGGGGG<br>AGGCGTGGTCCAGCCTGGGGGGTCCCT<br>GAGACTCTCCTGTGCAGCCTCTGGATT<br>CACCTTCAGTAGTTATGGCATACACTG<br>GGTCCGCCAGGCTCCAGGCAAGGGGC<br>TGGAGTGGGTGGCACTTATATCATATG<br>ATGGAAGTAAGAAATACTATGCAGAC<br>TCCGTGAAGGGCCGATTCACCATCTCC<br>AGAGACAATTCCAAGAACACGCTGTA<br>TCTGCAAATGAACAGCCTGAGAACTG<br>AGGACACGGCCGTATATTACTGTGCAC<br>GGAATTACTACGGTAGTACCTACGACT | GFTFSS<br>YGIH<br>(SEQ ID<br>NO: 118) | LISYDG<br>SKKYY<br>ADSVK<br>G<br>(SEQ ID<br>NO: 119) | NYYGS<br>TYDY<br>(SEQ ID<br>NO: 120) |

TABLE 7-continued

Reference VH-CDR1, VH-CDR2, and VH-CDR3 amino acid sequences*

| VH | Germline Gene | VH NUCLEOTIDE AND AMINO ACID SEQUENCE (VH-CDR1, VH-CDR2, and VH-CDR3 underlined) | VH CDR1 | VH CDR2 | VH CDR3 |
|---|---|---|---|---|---|
| | | ACTGGGGCCAGGGAACCCTGGTCACC<br>GTCTCCTCA<br>(SEQ ID NO: 210)<br>EVQLVESGGGVVQPGGSLRLSCAAS<u>GFT</u><br><u>FSSYGIH</u>WVRQAPGKGLEWVA<u>LISYDGS</u><br><u>KKYYADSVKG</u>RFTISRDNSKNTLYLQM<br>NSLRTEDTAVYYCAR<u>NYYGSTYDY</u>WG<br>QGTLVTVSS<br>(SEQ ID NO: 117) | | | |
| H1195 | VH3-23 | GAGGTGCAGCTGGTGGAGTCTGGGGG<br>AGGCCTGGTACAGCCTGGGGGGTCCCT<br>GAGACTCTCCTGTGCAGCCTCTGGATT<br>CACCTTCAGTACCTACGACTTCCACTG<br>GGTCCGCCAAGGTACAGGAGAAGGTC<br>TGGAGTGGGTCTCAGCTATTAGTCCTA<br>GTGGTGGTAGCACATACTACGCAGACT<br>CCGTGAAGGGCCGGTTCACCATCTCCA<br>GAGACAATTCCAAGAACACGCTTTATC<br>TGCAAATGAACAGCCTGAGAGCCGAG<br>GACACGGCCGTATATTACTGTGCACGG<br>AATTACTACGGTAGTACCTACGACTAC<br>TGGGGCCAGGGAACCCTGGTCACC<br>GTCTCCTCA<br>(SEQ ID NO: 211)<br>EVQLVESGGGLVQPGGSLRLSCAAS<u>GFT</u><br><u>FSTYDFH</u>WVRQGTGEGLEWVS<u>AISPSGG</u><br><u>STYYADSVKG</u>RFTISRDNSKNTLYLQMN<br>SLRAEDTAVYYCAR<u>NYYGSTYDY</u>WGQ<br>GTLVTVSS<br>(SEQ ID NO: 121) | GFTFST<br>YDFH<br>(SEQ ID<br>NO: 122) | AISPSG<br>GSTYY<br>ADSVK<br>G<br>(SEQ ID<br>NO: 123) | NYYGS<br>TYDY<br>(SEQ ID<br>NO: 124) |

*Determined by the Kabat system (see supra).
N = nucleotide sequence, P = polypeptide sequence.

As known in the art, "sequence identity" between two polypeptides or two polynucleotides is determined by comparing the amino acid or nucleic acid sequence of one polypeptide or polynucleotide to the sequence of a second polypeptide or polynucleotide. When discussed herein, whether any particular polypeptide is at least about 40%, 45%, 50%, 55%, 60%, 65%, 70%, 75%, 80%, 85%, 90% or 95% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2:482-489 (1981), to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

In certain embodiments, a human antibody or antigen-binding fragment comprising the VH encoded by the polynucleotide specifically or preferentially binds to TNFα. In certain embodiments the nucleotide sequence encoding the VH polypeptide is altered without altering the amino acid sequence encoded thereby. For instance, the sequence may be altered for improved codon usage in a given species, to remove splice sites, or the remove restriction enzyme sites. Sequence optimizations such as these are described in the examples and are well known and routinely carried out by those of ordinary skill in the art.

In another embodiment, the present invention provides an isolated polynucleotide comprising, consisting essentially of, or consisting of a nucleic acid encoding an immunoglobulin heavy chain variable region (VH) in which the VH-CDR1, VH-CDR2, and VH-CDR3 regions have polypeptide sequences which are identical to the VH-CDR1, VH-CDR2, and VH-CDR3 groups shown in Tables 6 and 7. In certain embodiments, an antibody or antigen-binding fragment comprising the VH encoded by the polynucleotide specifically or preferentially binds to TNFα.

In certain embodiments, a human antibody or antigen-binding fragment thereof comprising, consisting essentially of, or consisting of a VH encoded by one or more of the polypeptides described above specifically or preferentially binds to the same TNFα epitope as a reference monoclonal Fab antibody fragment selected from the group consisting of 696, 698, 699, 715, 714, 716, 695, 805, 855, 812, 813, 815, 1028, 1029, 874, 892, 1037, 1038, 1066, 1132, 1036, 1042, 1043, 1067, 1131, 1210, 1789, 1371, 1775, 1777, 1714, 1780, 1850, 1874, 1851, 1852, 1895, 1896, 1988, 1989, 1999, 2006, 2019, and 2060, or will competitively inhibit such a monoclonal antibody or fragment from binding to TNFα. In certain other embodiments, a human antibody or antigen-binding fragment thereof comprising, consisting essentially of, or consisting of a VH encoded by one or more of the polypeptides described above specifically or preferentially binds to the same TNFα epitope as a reference monoclonal Fab antibody fragment selected from the group consisting of 2071 and 2090, or will competitively inhibit such a monoclonal antibody or fragment from binding to TNFα.

In certain embodiments, a human antibody or antigen-binding fragment thereof comprising, consisting essentially of, or consisting of a VH encoded by one or more of the polypeptides described above specifically or preferentially binds to a TNFα polypeptide or fragment thereof, or a TNFα variant polypeptide, with an affinity characterized by a dissociation constant ($K_D$) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

In another embodiment, the present invention provides an isolated polynucleotide comprising, consisting essentially of, or consisting of a nucleic acid encoding an immunoglobulin light chain variable region (VL), where at least one of the VL-CDRs of the light chain variable region or at least two of the VL-CDRs of the light chain variable region are at least 80%, 85%, 90% or 95% identical to reference light chain VL-CDR1, VL-CDR2, or VL-CDR3 amino acid sequences from monoclonal TNFα antibodies disclosed herein. Alternatively, the VL-CDR1, VL-CDR2, and VL-CDR3 regions of the VL are at least 80%, 85%, 90% or 95% identical to reference light chain VL-CDR1, VL-CDR2, and VL-CDR3 amino acid sequences from monoclonal TNFα antibodies disclosed herein. Thus, according to this embodiment a light chain variable region of the invention has VL-CDR1, VL-CDR2, or VL-CDR3 polypeptide sequences related to the polypeptide sequences shown in Table 8:

TABLE 8

Reference VL-CDR1, VL-CDR2, and VL-CDR3 amino acid sequences*

| VL | Germline Gene | VL NUCLEOTIDE AND AMINO ACID SEQUENCE (VH-CDR1, VH-CDR2, and VH-CDR3 underlined) | VL CDR1 | VL CDR2 | VL CDR3 |
|---|---|---|---|---|---|
| L217 | L2 | GACATCGTGATGACCCAGTCTCCTGT CATCTTGTCTGTGTCTCCAGGGGACA GAGCCACCCTCTCCTGCAGGGCCAGT GAGAGTGTCAGAGGCAACGTAGCCT GGTATCAACAAAAACCCGGACAGGTT CCCAGGCTCCTCATCTCTGGTGCATC CACCAGGGCCAATGGGATCCCAGCCA GGTTCAGTGGCAGTGGGTCTGGGACC GAGTACAGTCTCACCATCAGCAGCCT GCAGCCTGAAGATGTTGCAATTTATC ATTGTCATCAGTATCATTATTGGCCGC TCACTTTCGGCGGAGGGACCAAGCTC GAGATCAAA (SEQ ID NO: 212) DIVMTQSPVILSVSPGDRATLSC<u>RASES VRGNVA</u>WYQQKPGQVPRLLIS<u>GASTR AN</u>GIPARFSGSGSGTEYSLTISSLQPEDV AIYHC<u>HQYHYWPLT</u>FGGGTKLEIK (SEQ ID NO: 125) | RASESV RGNVA (SEQ ID NO: 126) | GASTR AN (SEQ ID NO: 127) | HQYHY WPLT (SEQ ID NO: 128) |
| L218 | L2 | GACATCGTGATGACCCAGTCTCCAGC CACCCTCTCTGTGTCTCCTGGGGAAA GAGTCACCCTCTCCTGCAGGGCCCCT CAAATTCTGAGAAGCAACTTAGCCTG GTACCAGCAGAAGCCTGGCCAGGCTC CCAGGCTCCTCATCTACGGTGCATCC AACAGGGTCACTGGTGTCCCAGCCAG GTTCAGTGCCAGTGAGTCTGGGACAG AGTTCACTCTCACCATCAACGGCCTT CAATCTGAGGATTTTGGAGTTTATTTC TGTCAGCAATATAATTACTGGCCATT CACTTTCGGCCCTGGGACCAAACTCG AGATCAAA (SEQ ID NO: 213) DIVMTQSPATLSVSPGERVTLSC<u>RAPQI LRSNLA</u>WYQQKPGQAPRLLIY<u>GASNR VT</u>GVPARFSASESGTEFTLTINGLQSED FGVYFC<u>QQYNYWPFT</u>FGPGTKLEIK (SEQ ID NO: 129) | RAPQIL RSNLA (SEQ ID NO: 130) | GASNR VT (SEQ ID NO: 131) | QQYNY WPFT (SEQ ID NO: 132) |
| L229 | L2 | GATGTTGTGATGACTCAGTCTCCAGT CAGCCTGTCTGTGTCTCCAGGGGAAA GAGCCACCCTCTCCTGCAGGCCCAGT CAGAGTATTCACAACAACTTAGCCTG GTAGCAGGAGAAACCTGGGCAGGCTC CCAGGGTGCTCATCTATGAATCATCC ACCAGGGCCAAAGGTATCCCAGCCA GGTTCAGTGGCAGTGGGTCTGGGACA GAGTTCACTCTCACCATCAGCAGCCT GCAGTCGGAAGACTTTGCACTTTATT ACTGTCAGCAGTATAATAGGTGGCCT | RPSQSI HNNLA (SEQ ID NO: 134) | ESSTRA K (SEQ ID NO: 135) | QQYNR WPLT (SEQ ID NO: 136) |

TABLE 8-continued

Reference VL-CDR1, VL-CDR2, and VL-CDR3 amino acid sequences*

| VL | Germline Gene | VL NUCLEOTIDE AND AMINO ACID SEQUENCE (VH-CDR1, VH-CDR2, and VH-CDR3 underlined) | VL CDR1 | VL CDR2 | VL CDR3 |
|---|---|---|---|---|---|
| | | CTCACTTTCGGCCAAGGGACCAAGCT CGAGATCAAA (SEQ ID NO: 214) DVVMTQSPVTLSVSPGERATLSCRPSQ SIHNNLAWYQQKPGQAPRVLIYESSTR AKGIPARFSGSGSGTEFTLTISSLQSEDF ALYYCQQYNRWPLTFGQGTKLEIK (SEQ ID NO: 133) | | | |
| L230 | L2 | GATGTTGTGATGACTCAGTCTCCAGC CAGTTTGTCTGTGTCTCCAGGGGAAA GAGCCACCCTCTCCTGTAGGGCCAGT CAGAATATTAGAGGTAACTTAGCCTG GTATCAGCAGATACCTGGGCAGGCTC CCAGGCTCCTTATGTCTGGTCCATCC ACCAGGGCCGCTGGTATCCCAGCTAG GTTCAGTGGCACTGGGTCTGGGACAG AGTTCACTCTCACCATCAGCAGCCCG CAGTCTGAAGATTTTGCACTTTATTAT TGTCAACAGTATCATTTCTGGCCCCC CAGCTTCGGCCAAGGGACCAAGCTCG AGATCAAA (SEQ ID NO: 215) DVVMTQSPASLSVSPGERATLSCRASQ NIRGNLAWYQQIPGQAPRLLMSGPSTR AAGIPARFSGTGSGTEFTLTISSPQSEDF ALYYCQQYHFWPPSFGQGTKLEIK (SEQ ID NO: 137) | RASQNI RGNLA (SEQ ID NO: 138) | GPSTRA A (SEQ ID NO: 139) | QQYHF WPPS (SEQ ID NO: 140) |
| L250 | L2 | GAAATTGTGTTGACGCAGTCTCCAGT CACCCTGTCTGTGCCTCCAGGGGAGA GAGCCTCCCTCTCCTGTAGGGCCAGT CAGAATATATACACCGCCGTGGCCTG GTACCAGCAGAAACCTGGCCAGGCTC CCAGGCTCCTCATCTATGGCGCATCC ACCAGGGCCACTGGTATCCCAGCCAG GTTCAGTGGCGGTGGGTCTGGGACAG ACTACACTCTCACCATCAGCAGTCTG GAGTCTGAAGATTTTGCAGTTTATCA CTGTCAGCAGTATCATAGCTGGCCCC TCACTTTGGGCGGAGGGACCAAGCTC GAGATCAAA (SEQ ID NO: 216) EIVLTQSPVTLSVPPGERASLSCRASQNI YTAVAWYQQKPGQAPRLLIYGASTRA TGIPARFSGGGSGTDYTLTISSLESEDFA VYHGQQYHSWPLTFGGGTKLEIK (SEQ ID NO: 141) | RASQNI YTAVA (SEQ ID NO: 142) | GASTR AT (SEQ ID NO: 143) | QQYHS WPLT (SEQ ID NO: 144) |
| L332 (Optimized L250) | | GAAATTGTGTTGACGCAGTCTCCAGT CACCCTGTCTGTGCCTCCAGGGGAGA GAGCCTCCCTCTCCTGTAGGGCCAGT CAGAATATATACACCGCCGTGGCCTG GTACCAGCAGAAACCTGGCCAGGCTC CCAGGCTCCTCATCTATGGCGCATCC ACCAGGGCCACTGGTATCCCAGCCAG GTTCAGTGGCGGTGGGTCTGGGACAG ACTACACTCTCACCATCAGCAGTCTG GAGTCTGAAGATTTTGCAGTTTATCA CTGTCAGCAGTGGCATAGCTGGCCCC TCACTTTCGGCGGAGGGACCAAGCTC GAGATCAAA (SEQ ID NO: 217) EIVLTQSPVTLSVPPGERASLSCRASQNI YTAVAWYQQKPGQAPRLLIYGASTRA TGIPARFSGGGSGTDYTLTISSLESEDFA VYHCQQWHSWPLTFGGGTKLEIK (SEQ ID NO: 145) | RASQNI YTAVA (SEQ ID NO: 146) | GASTR AT (SEQ ID NO: 147) | QQWHS WPLT (SEQ ID NO: 148) |
| L308 (Optimized L250) | | GAAATTGTGTTGACGCAGTCTCCAGT CACCCTGTCTGTGCCTCCAGGGGAGA GAGCCTCCCTCTCCTGTAGGGCCAGT CAGAATATATACACCGCCGTGGCCTG | RASQNI YTAVA (SEQ ID NO: 150) | GASTR AT (SEQ ID NO: 151) | QQYFS WPLT (SEQ ID NO: 152) |

TABLE 8-continued

Reference VL-CDR1, VL-CDR2, and VL-CDR3 amino acid sequences*

| VL | Germline Gene | VL NUCLEOTIDE AND AMINO ACID SEQUENCE (VH-CDR1, VH-CDR2, and VH-CDR3 underlined) | VL CDR1 | VL CDR2 | VL CDR3 |
|---|---|---|---|---|---|
| | | GTACCAGCAGAAACCTGGCCAGGCTC<br>CCAGGCTCCTCATCTATGGCGCATCC<br>ACCAGGGCCACTGGTATCCCAGCCAG<br>GTTCAGTGGCGGTGGGTCTGGGACAG<br>ACTACACTCTCACCATCAGCAGTCTG<br>GAGTCTGAAGATTTTGCAGTTTATCA<br>CTGTCAGCAGTATTTTAGCTGGCCCC<br>TCACTTTCGGCGGAGGGACCAAGCTC<br>GAGATCAAA<br>(SEQ ID NO: 218)<br>EIVLTQSPVTLSVPPGERASLSC<u>RASQNI</u><br><u>YTAVA</u>WYQQKPGQAPRLLIY<u>GASTRA</u><br><u>T</u>GIPARFSGGGSGTDYTLTISSLESEDFA<br>VYHC<u>QQYFSWPLT</u>FGGGTKLEIK<br>(SEQ ID NO: 149) | | | |
| L309<br>(Optimized<br>L250) | | GAAATTGTGTTGACGCAGTCTCCAGT<br>CACCCTGTCTGTGCCTCCAGGGGAGA<br>GAGCCTCCCTCTCCTGTAGGGCCAGT<br>CAGAATATATACACCGCCGTGGCCTG<br>GTACCAGCAGAAACCTGGCCAGGCTC<br>CCAGGCTCCTCATCTATGGCGCATCC<br>ACCAGGGCCACTGGTATCCCAGCCAG<br>GTTCAGTGGCGGTGGGTCTGGGACAG<br>ACTACACTCTCACCATCAGCAGTCTG<br>GAGTCTGAAGATTTTGCAGTTTATCA<br>CTGTCAGGAGTATATGAGCTGGCCCC<br>TCACTTTCGGCGGAGGGACCAAGCTC<br>GAGATCAAA<br>(SEQ ID NO: 219)<br>EIVLTQSPVTLSVPPGERASLSC<u>RASQNI</u><br><u>YTAVA</u>WYQQKPGQAPRLLIY<u>GASTRA</u><br><u>T</u>GIPARFSGGGSGTDYTLTISSLESEDFA<br>VYHC<u>QQYMSWPLT</u>FGGGTKLEIK<br>(SEQ ID NO: 153) | RASQNI<br>YTAVA<br>(SEQ ID<br>NO: 154) | GASTR<br>AT<br>(SEQ ID<br>NO: 155) | QQYMS<br>WPLT<br>(SEQ ID<br>NO: 156) |
| L311<br>(Optimized<br>L250) | | GAAATTGTGTTGACGCAGTCTCCAGT<br>CACCCTGTCTGTGCCTCCAGGGGAGA<br>GAGCCTCCCTCTCCTGTAGGGCCAGT<br>CAGAATATATACAGCGCCGTGGCCTG<br>GTACCAGCAGAAACCTGGCCAGGCTC<br>CCAGGCTCCTCATCTATGGCGCATCC<br>ACCAGGGCCACTGGTATCCCAGCCAG<br>GTTCAGTGGCGGTGGGTCTGGGACAG<br>ACTACACTCTCACCATCAGCAGTCTG<br>GAGTCTGAAGATTTTGCAGTTTATCA<br>CTGTCAGCAGTATCATGCGTGGCCCC<br>TCACTTTCGGCGGAGGGACCAAGCTC<br>GAGATCAAA<br>(SEQ ID NO: 220)<br>EIVLTQSPVTLSVPPGERASLSC<u>RASQNI</u><br><u>YTAVA</u>WYQQKPGQAPRLLIY<u>GASTRA</u><br><u>T</u>GIPARFSGGGSGTDYTLTISSLESEDFA<br>VYHC<u>QQYHAWPLT</u>FGGGTKLEIK<br>(SEQ ID NO: 157) | RASQNI<br>YTAVA<br>(SEQ ID<br>NO: 158) | GASTR<br>AT<br>(SEQ ID<br>NO: 159) | QQYHA<br>WPLT<br>(SEQ ID<br>NO: 160) |
| L459<br>(Optimized<br>L332) | | GAAATTGTGTTGACGCAGTCTCCAGT<br>CACCCTGTCTGTGCCTCCAGGGGAGA<br>GAGCCTCCCTCTCCTGTAGGGCCAGT<br>CAGAATATATACACCGCGGTGGCCTG<br>GTACCAGCAGAAACCTGGCCAGGCTC<br>CCAGGCTCCTCATCTATAATGCATCC<br>ACCAGGGCCACTGGTATCCCAGCCAG<br>GTTCAGTGGCGGTGGGTCTGGGACAG<br>ACTACACTCTCACCATCAGCAGTCTG<br>GAGTCTGAAGATTTTGCAGTTTATCA<br>CTGTCAGCAGTGGCATAGCTGGCCCC<br>TCACTTTCGGCGGAGGGACCAAGCTC<br>GAGATCAAA<br>(SEQ ID NO: 221)<br>EIVLTQSPVTLSVPPGERASLSC<u>RASQNI</u><br><u>YTAVA</u>WYQQKPGQAPRLLIY<u>NASTRA</u> | RASQNI<br>YTAVA<br>(SEQ ID<br>NO: 162) | NASTR<br>AT<br>(SEQ ID<br>NO: 163) | QQWHS<br>WPLT<br>(SEQ ID<br>NO: 164) |

TABLE 8-continued

Reference VL-CDR1, VL-CDR2, and VL-CDR3 amino acid sequences*

| VL | Germline Gene | VL NUCLEOTIDE AND AMINO ACID SEQUENCE (VH-CDR1, VH-CDR2, and VH-CDR3 underlined) | VL CDR1 | VL CDR2 | VL CDR3 |
|---|---|---|---|---|---|
| | | TGIPARFSGGGSGTDYTLTISSLESEDFA VYHCQQWHSWPLTFGGGTKLEIK (SEQ ID NO: 161) | | | |
| L471 | | GAAATTGTGTTGACGCAGTCTCCAGC CACCCTGTCTGTGTCTCCAGGGGAGA GAGCCTCCCTCTCCTGTAGGGCCAGT CAGAATATATACACCGCCGTGGCCTG GTACCAGCAGAAACCTGGCCAGGCTC CCAGGCTCCTCATCTATAATGCATCC ACCAGGGCCACTGGTATCCCAGCCAG GTTCAGTGGCGGTGGGTCTGGGACAG ACTACACTCTCACCATCAGCAGTCTG GAGTCTGAAGATTTTGCAGTTTATCA CTGTCAGCAGTGGCATAGCTGGCCCC TCACTTTCGGCGGAGGGACCAAGCTC GAG ATCAAA (SEQ ID NO: 222) EIVLTQSPATLSVSPGERASLSCRASQNI YTAVAWYQQKPGQAPRLLIYNASTRA TGIPARFSGGGSGTDYTLTISSLESEDFA VYHCQQWHSWPLTFGGGTKLEIK (SEQ ID NO: 224) | RASQNI YTAVA (SEQ ID NO: 166) | NASTR AT (SEQ ID NO: 163) | QQWHS WPLT (SEQ ID NO: 168) |
| L472 (Optimized L459) | | GAAATTGTGTTGACGCAGTCTCCAGC CACCCTGTCTGTGTCTCCAGGGGAGA GAGCCTCCCTCTCCTGT<u>AGGGCCAGT CAGAATATATACACCGCCGTGGCCTG</u> GTACCAGCAGAAACCTGGCCAGGCTC CCAGGCTCCTCATCTAT<u>AATGCAGCC ACCAGGGCCACTGGTATCCCAGCCAG</u> GTTCAGTGGCGGTGGGTCTGGGACAG ACTACACTCTCACCATCAGCAGTCTG GAGTGTGAAGATTTTGCAGTTTATCA CTGT<u>CAGCAGTGGCATAGCTGGCCCC TCAC</u>TTTCGGCGGAGGGACCAAGCTC GAGATCAAA (SEQ ID NO: 223) EIVLTQSPATLSVSPGERASLSCRASQNI YTAVAWYQQKPGQAPRLLIYNAATRA TGIPARFSGGGSGTDYTLTISSLESEDFA VYHCQQWHSWPLTFGGGTKLEIK (SEQ ID NO: 165) | RASQNI YTAVA (SEQ ID NO: 166) | NAATR AT (SEQ ID NO: 167) | QQWHS WPLT (SEQ ID NO: 168) |

*Determined by the Kabat system (see supra).
PN = nucleotide sequence, PP = polypeptide sequence.

In certain embodiments, a human antibody or antigen-binding fragment comprising the VL encoded by the polynucleotide specifically or preferentially binds to TNFα.

In another embodiment, the present invention provides an isolated polynucleotide comprising, consisting essentially of, or consisting of a nucleic acid encoding an immunoglobulin light chain variable region (VL) in which the VL-CDR1, VL-CDR2, and VL-CDR3 regions have polypeptide sequences which are identical to the VL-CDR1, VL-CDR2, and VL-CDR3 groups shown in Table 8. In certain embodiments, an antibody or antigen-binding fragment comprising the VL encoded by the polynucleotide specifically or preferentially binds to TNFα.

In a further aspect, the present invention provides an isolated polynucleotide comprising, consisting essentially of, or consisting of a nucleic acid encoding an immunoglobulin light chain variable region (VL) in which the VL-CDR1, VL-CDR2, and VL-CDR3 regions are encoded by polypeptide sequences which encode the VL-CDR1, VL-CDR2, and VL-CDR3 groups shown in Table 8. In certain embodiments, an antibody or antigen-binding fragment comprising the VL encoded by the polypeptide specifically or preferentially binds to TNFα.

In certain embodiments, a human antibody or antigen-binding fragment thereof comprising, consisting essentially of, or consisting of a VL encoded by one or more of the polypeptides described above specifically or preferentially binds to the same TNFα epitope as a reference monoclonal Fab antibody fragment selected from the group consisting of 696, 698, 699, 715, 714, 716, 695, 805, 855, 812, 813, 815, 1028, 1029, 874, 892, 1037, 1038, 1066, 1132, 1036, 1042, 1043, 1067, 1131, 1210, 1789, 1371, 1775, 1777, 1714, 1780, 1850, 1874, 1851, 1852, 1895, 1896, 1988, 1989, 1999, 2006, 2019, 2060, 2071 and 2090, or will competitively inhibit such a monoclonal antibody or fragment from binding to TNFα. In certain other embodiments, a human antibody or antigen-binding fragment thereof comprising, consisting essentially of, or consisting of a VL encoded by one or more of the polypeptides described above specifically or preferentially binds to the same TNFα epitope as a reference monoclonal Fab antibody fragment selected from the group consisting of 2071 and 2090, or will competitively inhibit such a monoclonal antibody or fragment from binding to TNFα.

In certain embodiments, a human antibody or antigen-binding fragment thereof comprising, consisting essentially of, or consisting of a VL encoded by one or more of the polynucleotides described above specifically or preferentially binds to an TNFα polypeptide or fragment thereof, or a TNFα variant polypeptide, with an affinity characterized by a dissociation constant ($K_D$) no greater than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

In a further embodiment, the present invention includes an isolated polynucleotide comprising, consisting essentially of, or consisting of a nucleic acid encoding a VH at least 80%, 85%, 90% 95% or 100% identical to a reference VH polypeptide sequence selected from the group consisting of SEQ ID NOs: 3, 7, 11, 15, 19, 23, 27, 31, 35, 37, 39, 41, 43, 45, 47, 49, 51, 53, 57, 59, 61, 63, 65, 67, 69, 225, 71, 73, 75, 77, 79, 81, 85, 89, 93, 97, 101, 105, 109, 113, 117 and 121. In certain embodiments, the reference VH polypeptide sequence is selected from the group consisting of SEQ ID NOs: 71 and 79. In further embodiments, an antibody or antigen-binding fragment comprising the VH encoded by the polynucleotide specifically or preferentially binds to TNFα.

In another aspect, the present invention includes an isolated polynucleotide comprising, consisting essentially of, or consisting of a nucleic acid sequence encoding a VH having a polypeptide sequence selected from the group consisting of SEQ ID NOs: 3, 7, 11, 15, 19, 23, 27, 31, 35, 37, 39, 41, 43, 45, 47, 49, 51, 53, 57, 59, 61, 63, 65, 67, 69, 225, 71, 73, 75, 77, 79, 81, 85, 89, 93, 97, 101, 105, 109, 113, 117 and 121. In certain embodiments, the nucleic acid sequence encoding a VH has a polypeptide sequence selected from the group consisting of SEQ ID NOs: 71 and 79. In further embodiments, an antibody or antigen-binding fragment comprising the VH encoded by the polynucleotide specifically or preferentially binds to TNFα.

In a further embodiment, the present invention includes an isolated polynucleotide comprising, consisting essentially of, or consisting of a VH-encoding nucleic acid at least 80%, 85%, 90% 95% or 100% identical to a reference nucleic acid sequence selected from the group consisting of SEQ ID NOs: 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210 and 211. In certain embodiments, an antibody or antigen-binding fragment comprising the VH encoded by such polynucleotides specifically or preferentially binds to TNFα.

In another aspect, the present invention includes an isolated polynucleotide comprising, consisting essentially of, or consisting of a nucleic acid sequence encoding a VH of the invention, where the amino acid sequence of the VH is selected from the group consisting of SEQ ID NOs: 3, 7, 11, 15, 19, 23, 27, 31, 35, 37, 39, 41, 43, 45, 47, 49, 51, 53, 57, 59, 61, 63, 65, 67, 69, 225, 71, 73, 75, 77, 79, 81, 85, 89, 93, 97, 101, 105, 109, 113, 117 and 121. The present invention further includes an isolated polynucleotide comprising, consisting essentially of, or consisting of a nucleic acid sequence encoding a VH of the invention, where the sequence of the nucleic acid is selected from the group consisting of SEQ ID NOs: 71 and 79. In certain embodiments, an antibody or antigen-binding fragment comprising the VH encoded by such polynucleotides specifically or preferentially binds to TNFα.

In certain embodiments, a human antibody or antigen-binding fragment thereof comprising, consisting essentially of, or consisting of a VH encoded by one or more of the polynucleotides described above specifically or preferentially binds to the same TNFα epitope as a reference monoclonal Fab antibody fragment selected from the group consisting of 696, 698, 699, 715, 714, 716, 695, 805, 855, 812, 813, 815, 1028, 1029, 874, 892, 1037, 1038, 1066, 1132, 1036, 1042, 1043, 1067, 1131, 1210, 1789, 1371, 1775, 1777, 1714, 1780, 1850, 1874, 1851, 1852, 1895, 1896, 1988, 1989, 1999, 2006, 2019, 2060, 2071 and 2090, or will competitively inhibit such a monoclonal antibody or fragment from binding to TNFα. In further embodiments, the VH encoded by one or more of the polynucleotides described above specifically or preferentially binds to the same TNFα epitope as a reference monoclonal Fab antibody fragment selected from the group consisting of 2071 and 2090, or will competitively inhibit such a monoclonal antibody or fragment from binding to TNFα.

In certain embodiments, an antibody or antigen-binding fragment thereof comprising, consisting essentially of, or consisting of a VH encoded by one or more of the polynucleotides described above specifically or preferentially binds to a TNFα polypeptide or fragment thereof, or a TNFα variant polypeptide, with an affinity characterized by a dissociation constant ($K_D$) no greater than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

In a further embodiment, the present invention includes an isolated polynucleotide comprising, consisting essentially of, or consisting of a nucleic acid encoding a VL at least 80%, 85%, 90% 95% or 100% identical to a reference VL polypeptide sequence having an amino acid sequence selected from the group consisting of SEQ ID NOs: 125, 129, 133, 137, 141, 145, 149, 153, 157, 161, 165 and 224. In certain embodiments, the isolated polynucleotide comprises, consists essentially of, or consists of a nucleic acid encoding a VL at least 80%, 85%, 90% 95% or 100% identical to a reference VL polypeptide sequence having the amino acid sequence selected from the group consisting of SEQ ID NOs:165 and 224.

In a further embodiment, the present invention includes an isolated polynucleotide comprising, consisting essentially of, or consisting of a VL-encoding nucleic acid at least 80%, 85%, 90% 95% or 100% identical to a reference nucleic acid sequence selected from the group consisting of SEQ ID NOs: 212, 213, 214, 215, 216, 217, 218, 219, 220, 221, 222 and 223. In certain embodiments, an antibody or antigen-binding fragment comprising the VL encoded by such polynucleotides specifically or preferentially binds to TNFα.

In another aspect, the present invention includes an isolated polynucleotide comprising, consisting essentially of, or consisting of a nucleic acid sequence encoding a VL having a polypeptide sequence selected from the group consisting of SEQ ID NOs: 125, 129, 133, 137, 141, 145, 149, 153, 157, 161, 165 and 224. In certain embodiments, the isolated polynucleotide comprises, consists essentially of, or consists of a nucleic acid sequence encoding a VL having a polypeptide sequence selected from the group consisting of SEQ ID NOs: 165 and 224. The present invention further includes an isolated polynucleotide comprising, consisting essentially of, or consisting of a nucleic acid sequence encoding a VL of the invention, where the sequence of the nucleic acid is selected from the group consisting of SEQ ID NOs: 222 and 223. In certain embodiments, an antibody or antigen-binding fragment comprising the VL encoded by such polynucleotides specifically or preferentially binds to TNFα.

In certain embodiments, an antibody or antigen-binding fragment thereof comprising, consisting essentially of, or consisting of a VL encoded by one or more of the polynucleotides described above specifically or preferentially binds to the same TNFα epitope as a reference monoclonal Fab antibody fragment selected from the group consisting of 696, 698, 699, 715, 714, 716, 695, 805, 855, 812, 813, 815, 1028, 1029, 874, 892, 1037, 1038, 1066, 1132, 1036, 1042, 1043, 1067, 1131, 1210, 1789, 1371, 1775, 1777, 1714, 1780, 1850, 1874, 1851, 1852, 1895, 1896, 1988, 1989, 1999, 2006, 2019, 2060, 2071 and 2090, or will competitively inhibit such a monoclonal antibody or fragment from binding to TNFα. In further embodiments, the VL encoded by one or more of the polynucleotides described above specifically or preferentially binds to the same TNFα epitope as a reference monoclonal Fab antibody fragment selected from the group consisting of 2071 and 2090, or will competitively inhibit such a monoclonal antibody or fragment from binding to TNFα.

In certain embodiments, an antibody or antigen-binding fragment thereof comprising, consisting essentially of, or consisting of a VL encoded by one or more of the polynucleotides described above specifically or preferentially binds to a TNFα polypeptide or fragment thereof, or a TNFα variant polypeptide, with an affinity characterized by a dissociation constant ($K_D$) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $5.7 \times 10^{-12}$ M, $8.4 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

Any of the polynucleotides described above may further include additional nucleic acids, encoding, e.g., a signal peptide to direct secretion of the encoded polypeptide, antibody constant regions as described herein, or other heterologous polypeptides as described herein.

Also, as described in more detail elsewhere herein, the present invention includes compositions comprising the polynucleotides comprising one or more of the polynucleotides described above. In one embodiment, the invention includes compositions comprising a first polynucleotide and second polynucleotide wherein said first polynucleotide encodes a VH polypeptide as described herein and wherein said second polynucleotide encodes a VL polypeptide as described herein. Specifically a composition which comprises, consists essentially of, or consists of a VH polynucleotide, and a VL polynucleotide, wherein the VH polynucleotide and the VL polynucleotide encode polypeptides, respectively at least 80%, 85%, 90% 95% or 100% identical to reference VH and VL polypeptide amino acid sequences selected from the group consisting of SEQ ID NOs: 3 and 141, 7 and 141, 11 and 141, 15 and 141, 19 and 141, 23 and 141, 27 and 141, 31 and 141, 3 and 145, 3 and 149, 3 and 153, 3 and 157, 35 and 141, 37 and 141, 39 and 141, 41 and 141, 43 and 141, 45 and 141, 47 and 141, 49 and 141, 35 and 145, 43 and 145, 45 and 145, 47 and 145, 49 and 145, 51 and 145, 53 and 145, 55 and 145, 57 and 145, 59 and 145, 61 and 145, 63 and 145, 65 and 145, 67 and 145, 69 and 145, 225 and 145, 55 and 161, 63 and 161, 71 and 161, 73 and 161, 75 and 161, 77 and 161, and 79 and 161, 79 and 165, 71 and 165, and 79 and 224. In certain embodiments, the VH polynucleotide and the VL polynucleotide encode polypeptides, respectively at least 80%, 85%, 90% 95% or 100% identical to reference VH and VL polypeptide amino acid sequences selected from the group consisting of 79 and 165, 71 and 165, and 79 and 224. Or alternatively, a composition which comprises, consists essentially of, or consists of a VH polynucleotide, and a VL polynucleotide at least 80%, 85%, 90% 95% or 100% identical, respectively, to reference VH and VL nucleic acid sequences selected from the group consisting of SEQ ID NOs: 175 and 217, 170 and 216, 171 and 216, 172 and 216, 173 and 216, 174 and 216, 169 and 216, 176 and 216, 169 and 217, 169 and 218, 169 and 219, 169 and 220, 177 and 216, 178 and 216, 179 and 216, 180 and 216, 181 and 216, 182 and 216, 183 and 216, 184 and 216, 177 and 217, 181 and 217, 182 and 217, 183 and 217, 184 and 217, 185 and 217, 186 and 217, 187 and 217, 188 and 217, 189 and 217, 190 and 217, 191 and 217, 192 and 217, 193 and 217, 194 and 217, 195 and 217, 187 and 221, 191 and 221, 196 and 221, 197 and 221, 198 and 221, 199 and 221, 200 and 221, 200 and 222, 200 and 223, and 196 and 223. In certain embodiments, an antibody or antigen-binding fragment comprising the VH and VL encoded by the polynucleotides in such compositions specifically or preferentially binds to TNFα.

The present invention also includes fragments of the polynucleotides of the invention, as described elsewhere. Additionally polynucleotides which encode fusion polynucleotides, Fab fragments, and other derivatives, as described herein, are also contemplated by the invention.

The polynucleotides may be produced or manufactured by any method known in the art. For example, if the nucleotide sequence of the antibody is known, a polynucleotide encoding the antibody may be assembled from chemically synthesized oligonucleotides (e.g., as described in Kutmeier et al., *BioTechniques* 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding a TNFα antibody, or antigen-binding fragment, variant, or derivative thereof may be generated from nucleic acid from a suitable source. If a clone containing a nucleic acid encoding a particular antibody is not available, but the sequence of the antibody molecule is known, a nucleic acid encoding the antibody may be chemically synthesized or obtained from a suitable source (e.g., an antibody cDNA library, or a cDNA library generated from, or nucleic acid, preferably poly A+RNA, isolated from, any tissue or cells expressing the antibody or other TNFα antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody or other TNFα antibody. Amplified nucleic acids generated by PCR may then be cloned into replicable cloning vectors using any method well known in the art.

Once the nucleotide sequence and corresponding amino acid sequence of the TNFα antibody, or antigen-binding fragment, variant, or derivative thereof is determined, its nucleotide sequence may be manipulated using methods well known in the art for the manipulation of nucleotide sequences, e.g., recombinant DNA techniques, site directed mutagenesis, PCR, etc. (see, for example, the techniques described in Sambrook et al., *Molecular Cloning, A Laboratory Manual*, 2d Ed., Cold Spring Harbor Laboratory, Cold Spring Harbor, N.Y. (1990) and Ausubel et al., eds., *Current Protocols in Molecular Biology*, John Wiley & Sons, NY (1998), which are both incorporated by reference herein in their entireties), to generate antibodies having a different amino acid sequence, for example to create amino acid substitutions, deletions, and/or insertions.

A polynucleotide encoding a TNFα antibody, or antigen-binding fragment, variant, or derivative thereof can be composed of any polyribonucleotide or polydeoxyribonucleotide, which may be unmodified RNA or DNA or modified RNA or DNA. For example, a polynucleotide encoding TNFα antibody, or antigen-binding fragment, variant, or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, a polynucleotide encoding a TNFα antibody, or antigen-binding fragment, variant, or derivative thereof can be composed of triple-stranded regions comprising RNA or DNA or both RNA and DNA. A polynucleotide encoding a TNFα antibody, or antigen-binding fragment, variant, or derivative thereof may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

An isolated polynucleotide encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. Preferably, conservative amino acid substitutions are made at one or more non-essential amino acid residues.

V. TNFα Antibody Polypeptides

The present invention is further directed to isolated polypeptides which make up TNFα antibodies, and polynucleotides encoding such polypeptides. TNFα antibodies of the present invention comprise polypeptides, e.g., amino acid sequences encoding TNFα-specific antigen binding regions derived from immunoglobulin molecules. A polypeptide or amino acid sequence "derived from" a designated protein refers to the origin of the polypeptide having a certain amino acid sequence. In certain cases, the polypeptide or amino acid sequence which is derived from a particular starting polypeptide or amino acid sequence has an amino acid sequence that is essentially identical to that of the starting sequence, or a portion thereof, wherein the portion consists of at least 10-20 amino acids, at least 20-30 amino acids, at least 30-50 amino acids, or which is otherwise identifiable to one of ordinary skill in the art as having its origin in the starting sequence.

In one embodiment, the present invention provides an isolated polypeptide comprising, consisting essentially of, or consisting of an immunoglobulin heavy chain variable region (VH), where at least one of VH-CDRs of the heavy chain variable region or at least two of the VH-CDRs of the heavy chain variable region are at least 80%, 85%, 90% or 95% identical to reference heavy chain VH-CDR1, VH-CDR2 or VH-CDR3 amino acid sequences from monoclonal TNFα antibodies disclosed herein. Alternatively, the VH-CDR1, VH-CDR2 and VH-CDR3 regions of the VH are at least 80%, 85%, 90% or 95% identical to reference heavy chain VH-CDR1, VH-CDR2 and VH-CDR3 amino acid sequences from monoclonal TNFα disclosed herein. Thus, according to this embodiment a heavy chain variable region of the invention has VH-CDR1, VH-CDR2 and V-H-CDR3 polypeptide sequences related to the groups shown in Table 6, supra. While Table 6 shows VH-CDRs defined by the Kabat system, other CDR definitions, e.g., VH-CDRs defined by the Chothia system, are also included in the present invention. In certain embodiments, an antibody or antigen-binding fragment comprising the VH specifically or preferentially binds to TNFα.

In another embodiment, the present invention provides an isolated polypeptide comprising, consisting essentially of, or consisting of an immunoglobulin heavy chain variable region (VH) in which the VH-CDR1, VH-CDR2 and VH-CDR3 regions have polypeptide sequences which are identical to the VH-CDR1, VH-CDR2 and VH-CDR3 groups shown in Table 6. In certain embodiments, an antibody or antigen-binding fragment comprising the VH specifically or preferentially binds to TNFα.

In another embodiment, the present invention provides an isolated polypeptide comprising, consisting essentially of, or consisting of an immunoglobulin heavy chain variable region (VH) in which the VH-CDR1, VH-CDR2 and VH-CDR3 regions have polypeptide sequences which are identical to the VH-CDR1, VH-CDR2 and VH-CDR3 groups shown in Table 6, except for one, two, three, four, five, or six amino acid substitutions in any one VH-CDR. In larger CDRs, e.g., VH-CDR-3, additional substitutions may be made in the CDR, as long as the a VH comprising the VH-CDR specifically or preferentially binds to TNFα. In certain embodiments the amino acid substitutions are conservative. In certain embodiments, an antibody or antigen-binding fragment comprising the VH specifically or preferentially binds to TNFα.

In a further embodiment, the present invention includes an isolated polypeptide comprising, consisting essentially of, or consisting of a VH polypeptide at least 80%, 85%, 90% 95% or 100% identical to a reference VH polypeptide amino acid sequence selected from the group consisting of SEQ ID NOs: 3, 7, 11, 15, 19, 23, 27, 31, 35, 37, 39, 41, 43, 45, 47, 49, 51, 53, 57, 59, 61, 63, 65, 67, 69, 225, 71, 73, 75, 77, 79, 81, 85, 89, 93, 97, 101, 105, 109, 113, 117 and 121. In certain embodiments, the VH polypeptide at least 80%, 85%, 90% 95% or 100% identical to a reference VH polypeptide amino acid sequence selected from the group consisting of SEQ ID NOs: 71 and 79. In further embodiments, an antibody or antigen-binding fragment comprising the VH polypeptide specifically or preferentially binds to TNFα.

In another aspect, the present invention includes an isolated polypeptide comprising, consisting essentially of, or consisting of a VH polypeptide selected from the group consisting of SEQ ID NOs: 3, 7, 11, 15, 19, 23, 27, 31, 35, 37, 39, 41, 43, 45, 47, 49, 51, 53, 57, 59, 61, 63, 65, 67, 69, 225, 71, 73, 75, 77, 79, 81, 85, 89, 93, 97, 101, 105, 109, 113, 117 and 121. In certain embodiments, the isolated polypeptide comprises, consists essentially of, or consists of a VH polypeptide selected from the group consisting of SEQ ID NOs: 71 and 79. In further embodiments, an antibody or antigen-binding fragment comprising the VH polypeptide specifically or preferentially binds to TNFα.

In certain embodiments, an antibody or antigen-binding fragment thereof comprising, consisting essentially of, or consisting of a one or more of the VH polypeptides described above specifically or preferentially binds to the same TNFα epitope as a reference monoclonal Fab antibody fragment selected from the group consisting of 696, 698, 699, 715, 714, 716, 695, 805, 855, 812, 813, 815, 1028, 1029, 874, 892, 1037, 1038, 1066, 1132, 1036, 1042, 1043, 1067, 1131, 1210, 1789, 1371, 1775, 1777, 1714, 1780, 1850, 1874, 1851, 1852, 1895, 1896, 1988, 1989, 1999, 2006, 2019, 2060, 2071 and 2090, or will competitively inhibit such a monoclonal antibody or fragment from binding to TNFα. In certain embodiments, the one or more of the VH polypeptides described above specifically or preferentially binds to the same TNFα epitope as a reference monoclonal Fab antibody fragment selected from the group consisting of 2071 and 2090, or will competitively inhibit such a monoclonal antibody or fragment from binding to TNFα.

In certain embodiments, an antibody or antigen-binding fragment thereof comprising, consisting essentially of, or consisting of one or more of the VH polypeptides described above specifically or preferentially binds to a TNFα polypeptide or fragment thereof, or a TNFα variant polypeptide, with an affinity characterized by a dissociation constant ($K_D$) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $5.7 \times 10^{-12}$ M, $8.4 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

In another embodiment, the present invention provides an isolated polypeptide comprising, consisting essentially of, or consisting of an immunoglobulin light chain variable region (VL), where at least one of the VL-CDRs of the light chain variable region or at least two of the VL-CDRs of the light chain variable region are at least 80%, 85%, 90% or 95% identical to reference light chain VL-CDR1, VL-CDR2 or VL-CDR3 amino acid sequences from monoclonal TNFα antibodies disclosed herein. Alternatively, the VL-CDR1, VL-CDR2 and VL-CDR3 regions of the VL are at least 80%, 85%, 90% or 95% identical to reference light chain VL-CDR1, VL-CDR2 and VL-CDR3 amino acid sequences from monoclonal TNFα antibodies disclosed herein. Thus, according to this embodiment a light chain variable region of the invention has VL-CDR1, VL-CDR2 and VL-CDR3 polypeptide sequences related to the polypeptides shown in Table 7, supra. While Table 7 shows VL-CDRs defined by the Kabat system, other CDR definitions, e.g., VL-CDRs defined by the Chothia system, are also included in the present invention. In certain embodiments, an antibody or antigen-binding fragment comprising the VL polypeptide specifically or preferentially binds to TNFα.

In another embodiment, the present invention provides an isolated polypeptide comprising, consisting essentially of, or consisting of an immunoglobulin light chain variable region (VL) in which the VL-CDR1, VL-CDR2 and VL-CDR3 regions have polypeptide sequences which are identical to the VL-CDR1, VL-CDR2 and VL-CDR3 groups shown in Table 7. In certain embodiments, an antibody or antigen-binding fragment comprising the VL polypeptide specifically or preferentially binds to TNFα.

In another embodiment, the present invention provides an isolated polypeptide comprising, consisting essentially of, or consisting of an immunoglobulin heavy chain variable region (VL) in which the VL-CDR1, VL-CDR2 and VL-CDR3 regions have polypeptide sequences which are identical to the VL-CDR1, VL-CDR2 and VL-CDR3 groups shown in Table 7, except for one, two, three, four, five, or six amino acid substitutions in any one VL-CDR. In larger CDRs, additional substitutions may be made in the VL-CDR, as long as the a VL comprising the VL-CDR specifically or preferentially binds to TNFα. In certain embodiments the amino acid substitutions are conservative. In certain embodiments, an antibody or antigen-binding fragment comprising the VL specifically or preferentially binds to TNFα.

In a further embodiment, the present invention includes an isolated polypeptide comprising, consisting essentially of, or consisting of a VL polypeptide at least 80%, 85%, 90% 95% or 100% identical to a reference VL polypeptide sequence selected from the group consisting of SEQ ID NOs: 125, 129, 133, 137, 141, 145, 149, 153, 157, 161, 165, and 224. In certain embodiments, the isolated polypeptide comprises, consists essentially of, or consists of a VL polypeptide at least 80%, 85%, 90% 95% or 100% identical to the reference VL polypeptide sequence selected from the group consisting of SEQ ID NOs: 165 and 224. In further embodiments, an antibody or antigen-binding fragment comprising the VL polypeptide specifically or preferentially binds to TNFα.

In another aspect, the present invention includes an isolated polypeptide comprising, consisting essentially of, or consisting of a VL polypeptide selected from the group consisting of SEQ ID NOs: 125, 129, 133, 137, 141, 145, 149, 153, 157, 161, 165 and 224. In certain embodiments, the isolated polypeptide comprises, consists essentially of, or consists of a VL polypeptide that is selected from the group consisting of SEQ ID NOs: 165 and 224. In further embodiments, an antibody or antigen-binding fragment comprising the VL polypeptide specifically or preferentially binds to TNFα.

In certain embodiments, an antibody or antigen-binding fragment thereof comprising, consisting essentially of, one or more of the VL polypeptides described above specifically or preferentially binds to the same TNFα epitope as a reference monoclonal Fab antibody fragment selected from the group consisting of 696, 698, 699, 715, 714, 716, 695, 805, 855, 812, 813, 815, 1028, 1029, 874, 892, 1037, 1038, 1066, 1132, 1036, 1042, 1043, 1067, 1131, 1210, 1789, 1371, 1775, 1777, 1714, 1780, 1850, 1874, 1851, 1852, 1895, 1896, 1988, 1989, 1999, 2006, 2019, 2060, 2071 and 2090, or will competitively inhibit such a monoclonal antibody or fragment from binding to TNFα. In further embodiments, the one or more of the VL polypeptides described above specifically or preferentially binds to the same TNFα epitope as a reference monoclonal Fab antibody fragment selected from the group consisting of 2071 and 2090, or will competitively inhibit such a monoclonal antibody or fragment from binding to TNFα.

In certain embodiments, an antibody or antigen-binding fragment thereof comprising, consisting essentially of, or consisting of a one or more of the VL polypeptides described above specifically or preferentially binds to a TNFα polypeptide or fragment thereof, or a TNFα variant polypeptide, with an affinity characterized by a dissociation constant ($K_D$) no greater than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $5.7 \times 10^{-12}$ M, $8.4 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

In other embodiments, an antibody or antigen-binding fragment thereof comprises, consists essentially of or consists of a VH polypeptide, and a VL polypeptide, where the VH polypeptide and the VL polypeptide, respectively are at least 80%, 85%, 90% 95% or 100% identical to reference VH and VL polypeptide amino acid sequences selected from the group consisting of SEQ ID NOs: 3 and 141, 7 and 141, 11 and 141, 15 and 141, 19 and 141, 23 and 141, 27 and 141, 31 and 141, 3 and 145, 3 and 149, 3 and 153, 3 and 157, 35 and 141, 37 and 141, 39 and 141, 41 and 141, 43 and 141, 45 and 141, 47 and 141, 49 and 141, 35 and 145, 43 and 145, 45 and 145, 47 and 145, 49 and 145, 51 and 145, 53 and 145, 55 and 145, 57 and 145, 59 and 145, 61 and 145, 63 and 145, 65 and 145, 67 and 145, 69 and 145, 225 and 145, 55 and 161, 63 and 161, 71 and 161, 73 and 161, 75 and 161, 77 and 161, 79 and 161, and 79 and 224. In certain embodiments, the VH polynucleotide and the VL polynucleotide encode polypeptides, respectively at least 80%, 85%, 90% 95% or 100% identical to reference VH and VL polypeptide amino acid sequences selected from the group consisting of SEQ ID NOs: 79 and 165, 71 and 165, and 79 and 224. Or alternatively, a composition which comprises, consists essentially of, or consists of a VH polynucleotide, and a VL polynucleotide at least 80%, 85%, 90% 95% or 100% identical, respectively, to reference VH and VL nucleic acid sequences selected from the group consisting of SEQ ID NOs: 175 and 216, 170 and 216, 171 and 216, 172 and 216, 173 and 216, 174 and 216, 169 and 216, 176 and 216, 169 and 217, 169 and 218, 169 and 219, 169 and 220, 177 and 216, 178 and 216, 179 and 216, 180 and 216, 181 and 216, 182 and 216, 183 and 216, 184 and 216, 177 and 217, 181 and 217, 182 and 217, 183 and 217, 184 and 217, 185 and 217, 186 and 217, 187 and 217, 188 and 217, 189 and 217, 190 and 217, 191 and 217, 192 and 217, 193 and 217, 194 and 217, 195 and 217, 187 and 221, 191 and 221, 196 and 221, 197 and 221, 198 and 221, 199 and 221, 200 and 221, 200 and 222, 200 and 223, and 196 and 223. In certain embodiments, an antibody or antigen-binding fragment comprising these VH and VL polypeptides specifically or preferentially binds to TNFα.

Any of the polypeptides described above may further include additional polypeptides, e.g., a signal peptide to direct secretion of the encoded polypeptide, antibody constant regions as described herein, or other heterologous polypeptides as described herein. Additionally, polypeptides of the invention include polypeptide fragments as described elsewhere. Additionally polypeptides of the invention include fusion polypeptide, Fab fragments, and other derivatives, as described herein.

Also, as described in more detail elsewhere herein, the present invention includes compositions comprising the polypeptides described above.

It will also be understood by one of ordinary skill in the art that TNFα antibody polypeptides as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, or 95% identical to the starting sequence.

Furthermore, nucleotide or amino acid substitutions, deletions, or insertions leading to conservative substitutions or changes at "non-essential" amino acid regions may be made. For example, a polypeptide or amino acid sequence derived from a designated protein may be identical to the starting sequence except for one or more individual amino acid substitutions, insertions, or deletions, e.g., one, two, three, four, five, six, seven, eight, nine, ten, fifteen, twenty or more individual amino acid substitutions, insertions, or deletions. a polypeptide or amino acid sequence derived from a designated protein may be identical to the starting sequence except for one or more individual amino acid substitutions, insertions, or deletions, e.g., one, two, three, four, five, six, seven, eight, nine, ten, fifteen, twenty or more individual amino acid substitutions, insertions, or deletions. In other embodiments, a polypeptide or amino acid sequence derived from a designated protein may be identical to the starting sequence except for two or fewer, three or fewer, four or fewer, five or fewer, six or fewer, seven or fewer, eight or fewer, nine or fewer, ten or fewer, fifteen or fewer, or twenty or fewer individual amino acid substitutions, insertions, or deletions. In certain embodiments, a polypeptide or amino acid sequence derived from a designated protein has one to five, one to ten, one to fifteen, or one to twenty individual amino acid substitutions, insertions, or deletions relative to the starting sequence.

Certain TNFα antibody polypeptides of the present invention comprise, consist essentially of, or consist of an amino acid sequence derived from a human amino acid sequence. However, certain TNFα antibody polypeptides comprise one or more contiguous amino acids derived from another mammalian species. For example, a TNFα antibody of the present invention may include a primate heavy chain portion, hinge portion, or antigen binding region. In another example, one or more murine-derived amino acids may be present in a non-murine antibody polypeptide, e.g., in an antigen binding site of a TNFα antibody. In another example, the antigen binding site of a TNFα antibody is fully murine. In certain therapeutic applications, TNFα-specific antibodies, or antigen-binding fragments, variants, or analogs thereof are designed so as to not be immunogenic in the animal to which the antibody is administered.

In certain embodiments, a TNFα antibody polypeptide comprises an amino acid sequence or one or more moieties not normally associated with an antibody. Exemplary modifications are described in more detail below. For example, a single-chain fv antibody fragment of the invention may comprise a flexible linker sequence, or may be modified to add a functional moiety (e.g., PEG, a drug, a toxin, or a label).

A TNFα antibody polypeptide of the invention may comprise, consist essentially of, or consist of a fusion protein. Fusion proteins are chimeric molecules which comprise, for example, an immunoglobulin antigen-binding domain with at least one target binding site, and at least one heterologous portion, i.e., a portion with which it is not naturally linked in nature. The amino acid sequences may normally exist in separate proteins that are brought together in the fusion polypeptide or they may normally exist in the same protein but are placed in a new arrangement in the fusion polypeptide. Fusion proteins may be created, for example, by chemical synthesis, or by creating and translating a polynucleotide in which the peptide regions are encoded in the desired relationship.

The term "heterologous" as applied to a polynucleotide or a polypeptide, means that the polynucleotide or polypeptide is derived from a distinct entity from that of the rest of the entity to which it is being compared. For instance, as used herein, a "heterologous polypeptide" to be fused to a TNFα antibody, or an antigen-binding fragment, variant, or analog thereof is derived from a non-immunoglobulin polypeptide of the same species, or an immunoglobulin or non-immunoglobulin polypeptide of a different species.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a non-essential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Alternatively, in another embodiment, mutations may be introduced randomly along all or part of the immunoglobulin coding sequence, such as by saturation mutagenesis, and the resultant mutants can be incorporated into TNFα antibodies for use in the diagnostic and treatment methods disclosed herein and screened for their ability to bind to the desired antigen, e.g., TNFα.

VI. Fusion Proteins and Antibody Conjugates

As discussed in more detail elsewhere herein, TNFα antibodies, or antigen-binding fragments, variants, or derivatives thereof of the invention may further be recombinantly fused to a heterologous polypeptide at the N- or C-terminus or chemically conjugated (including covalent and non-covalent conjugations) to polypeptides or other compositions. For example, anti-TNFα antibodies may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

TNFα antibodies, or antigen-binding fragments, variants, or derivatives thereof of the invention include derivatives that are modified, i.e., by the covalent attachment of any type of molecule to the antibody such that covalent attachment does not prevent the antibody binding TNFα. For example, but not by way of limitation, the antibody derivatives include antibodies that have been modified, e.g., by glycosylation, acetylation, pegylation, phosphylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

TNFα antibodies, or antigen-binding fragments, variants, or derivatives thereof of the invention can be composed of amino acids joined to each other by peptide bonds or modified peptide bonds, i.e., peptide isosteres, and may contain amino acids other than the 20 gene-encoded amino acids. TNFα-specific antibodies may be modified by natural processes, such as posttranslational processing, or by chemical modification techniques which are well known in the art. Such modifications are well described in basic texts and in more detailed monographs, as well as in a voluminous research literature. Modifications can occur anywhere in the TNFα-specific antibody, including the peptide backbone, the amino acid side-chains and the amino or carboxyl termini, or on moieties such as carbohydrates. It will be appreciated that the same type of modification may be present in the same or varying degrees at several sites in a given TNFα-specific antibody. Also, a given TNFα-specific antibody may contain many types of modifications. TNFα-specific antibodies may be branched, for example, as a result of ubiquitination, and they may be cyclic, with or without branching. Cyclic, branched, and branched cyclic TNFα-specific antibodies may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, *Proteins—Structure And Molecular Properties*, T. E. Creighton, W. H. Freeman and Company, New York 2nd Ed., (1993); *Posttranslational Covalent Modification Of Proteins*, B. C. Johnson, Ed., Academic Press, New York, pgs. 1-12 (1983); Seifter et al., *Meth Enzymol* 182:626-646 (1990); Rattan et al., *Ann NY Acad Sci* 663:48-62 (1992)).

The present invention also provides for fusion proteins comprising a TNFα antibody, or antigen-binding fragment, variant, or derivative thereof, and a heterologous polypeptide. The heterologous polypeptide to which the antibody is fused may be useful for function or is useful to target the TNFα polypeptide expressing cells. In one embodiment, a fusion protein of the invention comprises, consists essentially of, or consists of, a polypeptide having the amino acid sequence of any one or more of the $V_H$ regions of an antibody of the invention or the amino acid sequence of any one or more of the $V_L$ regions of an antibody of the invention or fragments or variants thereof, and a heterologous polypeptide sequence. In another embodiment, a fusion protein for use in the diagnostic and treatment methods disclosed herein comprises, consists essentially of, or consists of a polypeptide having the amino acid sequence of any one, two, three of the $V_H$ CDRs of a TNFα-specific antibody, or fragments, variants, or derivatives thereof, or the amino acid sequence of any one, two, three of the $V_L$ CDRs of a TNFα-specific antibody, or fragments, variants, or derivatives thereof, and a heterologous polypeptide sequence. In one embodiment, the fusion protein comprises a polypeptide having the amino acid sequence of a $V_H$ CDR3 of a TNFα-specific antibody of the present invention, or fragment, derivative, or variant thereof, and a heterologous polypeptide sequence, which fusion protein specifically binds to at least one epitope of TNFα. In another embodiment, a fusion protein comprises a polypeptide having the amino acid sequence of at least one $V_H$ region of a TNFα-specific antibody of the invention and the amino acid sequence of at least one $V_L$ region of a TNFα-specific antibody of the invention or fragments, derivatives or variants thereof, and a heterologous polypeptide sequence. Preferably, the $V_H$ and $V_L$ regions of the fusion protein correspond to a single source antibody (or scFv or Fab fragment) which specifically binds at least one epitope of TNFα. In yet another embodiment, a fusion protein for use in the diagnostic and treatment methods disclosed herein comprises a polypeptide having the amino acid sequence of any one, two, three or more of the $V_H$ CDRs of a TNFα-specific antibody and the amino acid sequence of any one, two, three or more of the $V_L$ CDRs of a TNFα-specific antibody, or fragments or variants thereof, and a heterologous polypeptide sequence. Preferably, two, three, four, five, six, or more of the $V_H$CDR(s) or $V_L$CDR(s) correspond to single source antibody (or scFv or Fab fragment) of the invention. Nucleic acid molecules encoding these fusion proteins are also encompassed by the invention.

Exemplary fusion proteins reported in the literature include fusions of the T cell receptor (Gascoigne et al., *Proc. Natl. Acad. Sci. USA* 84:2936-2940 (1987)); CD4 (Capon et al., *Nature* 337:525-531 (1989); Traunecker et al., *Nature* 339:68-70 (1989); Zettmeissl et al., *DNA Cell Biol. USA* 9:347-353 (1990); and Byrn et al., *Nature* 344:667-670

(1990)); L-selectin (homing receptor) (Watson et al., *J. Cell. Biol.* 110:2221-2229 (1990); and Watson et al., *Nature* 349: 164-167 (1991)); CD44 (Aruffo et al., *Cell* 61:1303-1313 (1990)); CD28 and B7 (Linsley et al., *J. Exp. Med.* 173:721-730 (1991)); CTLA-4 (Lisley et al., *J. Exp. Med.* 174:561-569 (1991)); CD22 (Stamenkovic et al., *Cell* 66:1133-1144 (1991)); TNF receptor (Ashkenazi et al., *Proc. Natl. Acad. Sci. USA* 88:10535-10539 (1991); Lesslauer et al., *Eur. J. Immunol.* 27:2883-2886 (1991); and Peppel et al., *J. Exp. Med.* 174:1483-1489 (1991)); and IgE receptor a (Ridgway and Gorman, *J. Cell. Biol.* Vol. 115, Abstract No. 1448 (1991)).

As discussed elsewhere herein, TNFα antibodies, or antigen-binding fragments, variants, or derivatives thereof of the invention may be fused to heterologous polypeptides to increase the in vivo half life of the polypeptides or for use in immunoassays using methods known in the art. For example, in one embodiment, PEG can be conjugated to the TNFα antibodies of the invention to increase their half-life in vivo. Leong, S. R., et al., *Cytokine* 16:106 (2001); *Adv. in Drug Deliv. Rev.* 54:531 (2002); or Weir et al., *Biochem. Soc. Transactions* 30:512 (2002).

Moreover, TNFα antibodies, or antigen-binding fragments, variants, or derivatives thereof of the invention can be fused to marker sequences, such as a peptide to facilitate their purification or detection. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., *Cell* 37:767 (1984)) and the "flag" tag.

Fusion proteins can be prepared using methods that are well known in the art (see for example U.S. Pat. Nos. 5,116,964 and 5,225,538). The precise site at which the fusion is made may be selected empirically to optimize the secretion or binding characteristics of the fusion protein. DNA encoding the fusion protein is then transfected into a host cell for expression.

TNFα antibodies of the present invention may be used in non-conjugated form or may be conjugated to at least one of a variety of molecules, e.g., to improve the therapeutic properties of the molecule, to facilitate target detection, or for imaging or therapy of the patient. TNFα antibodies, or antigen-binding fragments, variants, or derivatives thereof of the invention can be labeled or conjugated either before or after purification, when purification is performed.

In particular, TNFα antibodies, or antigen-binding fragments, variants, or derivatives thereof of the invention may be conjugated to therapeutic agents, prodrugs, peptides, proteins, enzymes, viruses, lipids, biological response modifiers, pharmaceutical agents, or PEG.

Those skilled in the art will appreciate that conjugates may also be assembled using a variety of techniques depending on the selected agent to be conjugated. For example, conjugates with biotin are prepared e.g. by reacting a binding polypeptide with an activated ester of biotin such as the biotin N-hydroxysuccinimide ester. Similarly, conjugates with a fluorescent marker may be prepared in the presence of a coupling agent, e.g. those listed herein, or by reaction with an isothiocyanate, preferably fluorescein-isothiocyanate. Conjugates of the TNFα antibodies, or antigen-binding fragments, variants, or derivatives thereof of the invention are prepared in an analogous manner.

The present invention further encompasses TNFα antibodies, or antigen-binding fragments, variants, or derivatives thereof of the invention conjugated to a diagnostic or therapeutic agent. The TNFα antibodies can be used diagnostically to, for example, monitor the development or progression of a disease as part of a clinical testing procedure to, e.g., determine the efficacy of a given treatment and/or prevention regimen. Detection can be facilitated by coupling the TNFα antibody, or antigen-binding fragment, variant, or derivative thereof to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present invention. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

A TNFα antibody, or antigen-binding fragment, variant, or derivative thereof also can be detectably labeled by coupling it to a chemiluminescent compound. The presence of the chemiluminescent-tagged TNFα antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

One of the ways in which a TNFα antibody, or antigen-binding fragment, variant, or derivative thereof can be detectably labeled is by linking the same to an enzyme and using the linked product in an enzyme immunoassay (EIA) (Voller, A., "The Enzyme Linked Immunosorbent Assay (ELISA)" Microbiological Associates Quarterly Publication, Walkersville, Md., *Diagnostic Horizons* 2:1-7 (1978)); Voller et al., *J. Clin. Pathol.* 31:507-520 (1978); Butler, J. E., *Meth. Enrymol.* 73:482-523 (1981); Maggio, E. (ed.), *Enzyme Immunoassay*, CRC Press, Boca Raton, Fla., (1980); Ishikawa, E. et al., (eds.), *Enzyme Immunoassay*, Kgaku Shoin, Tokyo (1981). The enzyme, which is bound to the TNFα antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the TNFα antibody, or antigen-binding fragment, variant, or derivative thereof, it is possible to detect the antibody through the use of a radioimmunoassay (RIA) (see, for example, Weintraub, B., *Principles of Radioimmunoassays, Seventh Training Course on Radioligand Assay Techniques*, The Endocrine Society, (March, 1986)), which is incorporated by reference herein). The radioactive isotope can be detected by means including, but not limited to, a gamma counter, a scintillation counter, or autoradiography.

A TNFα antibody, or antigen-binding fragment, variant, or derivative thereof can also be detectably labeled using fluorescence emitting metals such as 152Eu, or others of the lanthanide series. These metals can be attached to the antibody using such metal chelating groups as diethylenetriaminepentacetic acid (DTPA) or ethylenediaminetetraacetic acid (EDTA).

Techniques for conjugating various moieties to a TNFα antibody, or antigen-binding fragment, variant, or derivative thereof are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in *Controlled Drug Delivery* (2nd Ed.), Robinson et al. (eds.), Marcel Dekker, Inc., pp. 623-53 (1987); Thorpe, "Antibody Carriers Of Cytotoxic Agents In Cancer Therapy: A Review", in *Monoclonal Antibodies '84: Biological And Clinical Applications*, Pinchera et al. (eds.), pp. 475-506 (1985); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), Academic Press pp. 303-16 (1985), and Thorpe et al., "The Preparation And Cytotoxic Properties Of Antibody-Toxin Conjugates", *Immunol. Rev.* 62:119-58 (1982).

VII. Expression of Antibody Polypeptides

As is well known, RNA may be isolated from the original hybridoma cells or from other transformed cells by standard techniques, such as guanidinium isothiocyanate extraction and precipitation followed by centrifugation or chromatography. Where desirable, mRNA may be isolated from total RNA by standard techniques such as chromatography on oligo dT cellulose. Suitable techniques are familiar in the art.

In one embodiment, cDNAs that encode the light and the heavy chains of the antibody may be made, either simultaneously or separately, using reverse transcriptase and DNA polymerase in accordance with well known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis.

Following manipulation of the isolated genetic material to provide TNFα antibodies, or antigen-binding fragments, variants, or derivatives thereof of the invention, the polynucleotides encoding the TNFα antibodies are typically inserted in an expression vector for introduction into host cells that may be used to produce the desired quantity of TNFα antibody.

Recombinant expression of an antibody, or fragment, derivative or analog thereof, e.g., a heavy or light chain of an antibody which binds to a target molecule described herein, e.g., TNFα, requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The term "vector" or "expression vector" is used herein to mean vectors used in accordance with the present invention as a vehicle for introducing into and expressing a desired gene in a host cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

For the purposes of this invention, numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. Additional elements may also be needed for optimal synthesis of mRNA. These elements may include signal sequences, splice signals, as well as transcriptional promoters, enhancers, and termination signals.

In particularly preferred embodiments the cloned variable region genes are inserted into an expression vector along with the heavy and light chain constant region genes (preferably human) synthetic as discussed above. Of course, any expression vector which is capable of eliciting expression in eukaryotic cells may be used in the present invention. Examples of suitable vectors include, but are not limited to plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). In general, screening large numbers of transformed cells for those which express suitably high levels if immunoglobulin heavy and light chains is routine experimentation which can be carried out, for example, by robotic systems.

More generally, once the vector or DNA sequence encoding a monomeric subunit of the TNFα antibody has been prepared, the expression vector may be introduced into an appropriate host cell. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "Mammalian Expression Vectors" Vectors, Rodriguez and Denhardt, Eds., Butterworths, Boston, Mass., Chapter 24.2, pp. 470-472 (1988). Typically, plasmid introduction into the host is via electroporation. The host cells harboring the expression construct are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

The expression vector is transferred to a host cell by conventional techniques and the transfected cells are then cultured by conventional techniques to produce an antibody for use in the methods described herein. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

As used herein, "host cells" refers to cells which harbor vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

A variety of host-expression vector systems may be utilized to express antibody molecules for use in the methods described herein. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene* 45:101 (1986); Cockett et al., *Bio/Technology* 8:2 (1990)).

The host cell line used for protein expression is often of mammalian origin; those skilled in the art are credited with ability to preferentially determine particular host cell lines which are best suited for the desired gene product to be expressed therein. Exemplary host cell lines include, but are not limited to, CHO (Chinese Hamster Ovary), DG44 and DUXB11 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, 293, WI38, R1610 (Chinese hamster fibroblast) BALBC/3T3 (mouse fibroblast), HAK (hamster kidney line), SP2/O (mouse myeloma), P3x63-Ag3.653 (mouse myeloma), BFA-1c1BPT (bovine endothelial cells), RAJI (human lymphocyte) and 293 (human kidney). Host cell lines are typically available from commercial services, the American Tissue Culture Collection or from published literature.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 1980) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); TIB TECH 11(5):155-215 (May, 1993); and hygro, which confers resistance to hygromycin (Santerre et al., Gene 30:147 (1984). Methods commonly known in the art of recombinant DNA technology which can be used are described in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Prolocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Academic Press, New York, Vol. 3. (1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein.

Genes encoding TNFα antibodies, or antigen-binding fragments, variants, or derivatives thereof of the invention can also be expressed non-mammalian cells such as bacteria or yeast or plant cells. Bacteria which readily take up nucleic acids include members of the enterobacteriaceae, such as strains of Escherichia coli or Salmonella; Bacillaceae, such as Bacillus subtilis; Pneumococcus; Streptococcus, and Haemophilus influenzae. It will further be appreciated that, when expressed in bacteria, the heterologous polypeptides typically become part of inclusion bodies. The heterologous polypeptides must be isolated, purified and then assembled into functional molecules. Where tetravalent forms of antibodies are desired, the subunits will then self-assemble into tetravalent antibodies (WO02/096948A2).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the E. coli expression vector pUR278 (Ruther et al., EMBO J. 2:1791 (1983)), in which the antibody coding sequence may be ligated individually into the vector in frame with the lacZ coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes may also be used. Saccharomyces cerevisiae, or common baker's yeast, is the most commonly used among eukaryotic microorganisms although a number of other strains are commonly available, e.g., Pichia pastoris.

For expression in Saccharomyces, the plasmid YRp7, for example, (Stinchcomb et al., Nature 282:39 (1979); Kingsman et al., Gene 7:141 (1979); Tschemper et al., Gene 10:157 (1980)) is commonly used. This plasmid already contains the TRP1 gene which provides a selection marker for a mutant strain of yeast lacking the ability to grow in tryptophan, for example ATCC No. 44076 or PEP4-1 (Jones, Genetics 85:12 (1977)). The presence of the trp1 lesion as a characteristic of the yeast host cell genome then provides an effective environment for detecting transformation by growth in the absence of tryptophan.

In an insect system, Autographa californica nuclear polyhedrosis virus (AcNPV) is typically used as a vector to express foreign genes. The virus grows in Spodoptera frugiperda cells. The antibody coding sequence may be cloned individually into non-essential regions (for example the polyhedrin gene) of the virus and placed under control of an AcNPV promoter (for example the polyhedrin promoter).

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Alternatively, a preferred method for increasing the affinity of antibodies of the invention is disclosed in US 2002 0123057 A1.

VIII. Treatment Methods Using Therapeutic TNFα Antibodies, or Immunospecific Fragments Thereof One embodiment of the present invention provides methods for treating a autoimmune disease or disorder, e.g., RA, or a method for treating an inflammatory condition such as sepsis or Crohn's Disease, Ankylosing Spondylitis, Psoriatic Arthritis, Plaque Psoriasis, and Ulcerative Colitis in an animal suffering from such disease or condition, or predisposed to contract such disease or condition, the method comprising, consisting essentially of, or consisting of administering to the animal an effective amount of an antibody or immunospecific fragment thereof, that binds to TNFα or a variant of TNFα. Suitable antibodies include all antibodies and antigen-specific fragments thereof described herein. Examples include, but are not limited to, an isolated antibody or antigen-binding fragment thereof which specifically binds to the same TNFα epitope as a reference monoclonal Fab antibody fragment selected from the group consisting of 696, 698, 699, 715, 714, 716, 695, 805, 855, 812, 813, 815, 1028, 1029, 874, 892, 1037, 1038, 1066, 1132, 1036, 1042, 1043, 1067, 1131, 1210, 1371, 1775, 1777, 1714, 1780, 1850, 1874, 1851, 1852, 1895, 1896, 1988, 1989, 1999, 2006, 2019, 2060, 2071 and 2090, an isolated antibody or antigen-binding fragment thereof which specifically binds to TNFα, where the antibody or fragment thereof competitively inhibits a reference monoclonal Fab antibody fragment selected from the group consisting of 696, 698, 699, 715, 714, 716, 695, 805, 855, 812, 813, 815, 1028, 1029, 874, 892, 1037, 1038, 1066, 1132, 1036, 1042, 1043, 1067, 1131, 1210, 1371, 1775, 1777, 1714, 1780, 1850, 1874, 1851, 1852, 1895, 1896, 1988, 1989, 1999, 2006, 2019, 2060, 2071 and 2090, from binding to TNFα, or an isolated antibody or antigen-binding fragment thereof which specifically binds to TNFα, where the antibody or fragment thereof comprises an antigen binding domain identical to that of a monoclonal Fab antibody fragment selected from the group consisting of 696, 698, 699, 715, 714, 716, 695, 805, 855, 812, 813, 815, 1028, 1029, 874, 892, 1037, 1038, 1066, 1132, 1036, 1042, 1043, 1067, 1131, 1210, 1789, 1371, 1775, 1777, 1714, 1780, 1850, 1874, 1851, 1852, 1895, 1896, 1988, 1989, 1999, 2006, 2019, 2060, 2071 and 2090. In certain embodiments, the monoclonal Fab antibody fragment, or reference monoclonal Fab antibody fragment is selected from the group consisting of 2071 and 2090.

In certain embodiments an antibody of the present invention which specifically binds to TNFα or a variant thereof inhibits TNFα from binding to its receptor. In a further embodiment, an antibody of the present invention which specifically binds to TNFα or a variant thereof expressed on a cell, inhibits downstream signal transduction molecules involved in immune responses. In a further embodiment, an antibody of the present invention which specifically binds to TNFα or a variant thereof.

An antibody of the present invention which specifically binds to TNFα or a variant thereof, to be used in treatment methods disclosed herein can be prepared and used as a therapeutic agent that stops, reduces, prevents, or inhibits cellular activities involved in autoimmune responses, or are often associated with mechanisms involved in autoimmune diseases or disorders.

Antibodies or immunospecific fragments thereof of the present invention include, but are not limited to monoclonal, chimeric or humanized antibodies, and fragments of antibodies that bind specifically to tumor-associated proteins such as TNFα. The antibodies may be monovalent, bivalent, polyvalent, or bifunctional antibodies, and the antibody fragments include Fab F(ab')$_2$, and Fv.

Therapeutic antibodies according to the invention can be used in unlabeled or unconjugated form, or can be coupled or linked to cytotoxic moieties such as radiolabels and biochemical cytotoxins to produce agents that exert therapeutic effects.

In certain embodiments, an antibody, or immunospecific fragment thereof of the invention includes an antigen binding domain. An antigen binding domain is formed by antibody variable regions that vary from one antibody to another. Naturally occurring antibodies comprise at least two antigen binding domains, i.e., they are at least bivalent. As used herein, the term "antigen binding domain" includes a site that specifically binds an epitope on an antigen (e.g., a cell surface or soluble antigen). The antigen binding domain of an antibody typically includes at least a portion of an immunoglobulin heavy chain variable region and at least a portion of an immunoglobulin light chain variable region. The binding site formed by these variable regions determines the specificity of the antibody.

The present invention provides methods for treating various autoimmune disorders, e.g., by inhibiting cytokine induction, in a mammal, comprising, consisting essentially of, or consisting of administering to the mammal an effective amount of a antibody or antigen-binding fragment thereof which specifically or preferentially binds to TNFα, e.g., human TNFα.

The present invention is more specifically directed to a method of treating an autoimmune disease in an animal, e.g., a mammal, e.g., a human, comprising, consisting essentially of, or consisting of administering to an animal in need thereof an effective amount of a an antibody or immunospecific fragment thereof, which specifically or preferentially binds to one or more epitopes of TNFα.

In other embodiments, the present invention includes a method for treating an autoimmune disease in an animal, e.g., a human patient, where the method comprises administering to an animal in need of such treatment an effective amount of a composition comprising, consisting essentially of, or consisting of, in addition to a pharmaceutically acceptable carrier, an antibody, or immunospecific fragment thereof, which specifically binds to at least one epitope of TNFα, where the epitope comprises, consists essentially of, or consists of at least about four to five amino acids amino acids of SEQ ID NO:2, at least seven, at least nine, or between at least about 15 to about 30 amino acids of SEQ ID NO:2. The amino acids of a given epitope of SEQ ID NO:2 as described may be, but need not be contiguous. In certain embodiments, the at least one epitope of TNFα comprises, consists essentially of, or consists of a non-linear epitope formed by the extracellular domain of TNFα as expressed on the surface of a cell. Thus, in certain embodiments the at least one epitope of TNFα comprises, consists essentially of, or consists of at least 4, at least 5, at least 6, at least 7, at least 8, at least 9, at least 10, at least 15, at least 20, at least 25, between about 15 to about 30, or at least 10, 15, 20, 25, 30, 35, 40, 45, 50, 55, 60, 65, 70, 75, 80, 85, 90, 95, or 100 contiguous or non-contiguous amino acids of SEQ ID NO:2, where non-contiguous amino acids form an epitope through protein folding.

In other embodiments, the present invention includes a method for treating a autoimmune disease in an animal, e.g., a human patient, where the method comprises administering to an animal in need of such treatment an effective amount of a composition comprising, consisting essentially of, or consisting of, in addition to a pharmaceutically acceptable carrier, an antibody, or immunospecific fragment thereof, which specifically binds to at least one epitope of TNFα, where the epitope comprises, consists essentially of, or consists of, in addition to one, two, three, four, five, six or more contiguous or non-contiguous amino acids of SEQ ID NO:2 as described above, and an additional moiety which modifies the protein, e.g., a carbohydrate moiety may be included such that the binding molecule binds with higher affinity to modified target protein than it does to an unmodified version of the protein.

Alternatively, the binding molecule does not bind the unmodified version of the target protein at all.

More specifically, the present invention provides a method of treating autoimmune disease in a human, comprising administering to a human in need of treatment a composition comprising an effective amount of an TNFα-specific antibody or immunospecific fragment thereof, and a pharmaceutically acceptable carrier. Types of autoimmune diseases to be treated include, but are not limited to, OA and RA.

In certain embodiments, an antibody or fragment thereof binds specifically to at least one epitope of TNFα or fragment or variant described above, i.e., binds to such an epitope more readily than it would bind to an unrelated, or random epitope; binds preferentially to at least one epitope of TNFα or fragment or variant described above, i.e., binds to such an epitope more readily than it would bind to a related, similar, homologous, or analogous epitope; competitively inhibits binding of a reference antibody which itself binds specifically or preferentially to a certain epitope of TNFα or fragment or variant described above; or binds to at least one epitope of TNFα or fragment or variant described above with an affinity characterized by a dissociation constant $K_D$ of less than about $5 \times 10^{-2}$ M, about $10^{-2}$ M, about $5 \times 10^{-3}$ M, about $10^{-3}$ M, about $5 \times 10^{-4}$ M, about $10^{-4}$ M, about $5 \times 10^{-5}$ M, about $10^{-5}$ M, about $5 \times 10^{-6}$ M, about $10^{-6}$ M, about $5 \times 10^{-7}$ M, about $10^{-7}$ M, about $5 \times 10^{-8}$ M, about $10^{-8}$ M, about $5 \times 10^{-9}$ M, about $10^{-9}$ M, about $5 \times 10^{-10}$ M, about $10^{-10}$ M, about $5 \times 10^{-11}$ M, about $10^{-11}$ M, about $5 \times 10^{-12}$ M, about $10^{-12}$ M, about $5 \times 10^{-13}$ M, about $10^{-13}$ M, about $5 \times 10^{-14}$ M, about $10^{-14}$ M, about $5 \times 10^{-15}$ M, or about $10^{-15}$ M. As used in the context of antibody binding dissociation constants, the term "about" allows for the degree of variation inherent in the methods utilized for measuring antibody affinity. For example, depending on the level of precision of the instrumentation used, standard error based on the number of samples measured, and rounding error, the term "about $10^{-2}$ M" might include, for example, from 0.05 M to 0.005 M. In certain embodiments, antibodies and fragments thereof of the present invention cross-react with TNFα proteins of other species from which they were raised, e.g., an antibody or fragment thereof which specifically binds to human TNFα also binds to primate TNFα and/or murine TNFα. Other suitable antibodies or fragments thereof of the present invention include those that are highly species specific.

In specific embodiments, antibodies or immunospecific fragments thereof disclosed herein bind TNFα polypeptides or fragments or variants thereof with an off rate (k(off)) of less than or equal to $5 \times 10^{-2}$ sec$^{-1}$, $10^{-2}$ sec$^{-1}$, $5 \times 10^{-3}$ sec$^{-1}$ or $10^{-3}$ sec$^{-1}$. Other antibodies or immunospecific fragments thereof disclosed herein bind TNFα polypeptides or fragments or variants thereof with an off rate (k(off)) of less than or equal to $5 \times 10^{-4}$ sec$^{-1}$, $10^{-4}$ sec$^{-1}$, $5 \times 10^{-5}$ sec$^{-1}$, or $10^{-5}$ sec$^{-1}$ $5 \times 10^{-6}$ sec$^{-1}$, $10^{-6}$ sec$^{-1}$, $5 \times 10^{-7}$ sec$^{-1}$ or $10^{-7}$ sec$^{-1}$.

In other embodiments, bantibodies or immunospecific fragments thereof disclosed herein bind TNFα polypeptides or fragments or variants thereof with an on rate (k(on)) of greater than or equal to $10^3$ M$^{-1}$ sec$^{-1}$, $5 \times 10^3$ M$^{-1}$ sec$^{-1}$, $10^4$ M$^{-1}$ sec$^{-1}$ or $5 \times 10^4$ M$^{-1}$ sec$^{-1}$. Other antibodies or immunospecific fragments thereof for use in the diagnostic and treatment methods disclosed herein bind TNFα polypeptides or fragments or variants thereof with an on rate (k(on)) greater than or equal to $10^5$ M$^{-1}$ sec$^{-1}$, $5 \times 10^5$ M$^{-1}$ sec$^{-1}$, $10^6$ M$^{-1}$ sec$^{-1}$, or $5 \times 10^6$ M$^{-1}$ sec$^{-1}$ or $10^7$ M$^{-1}$ sec$^{-1}$.

In various embodiments, one or more binding molecules as described above is an antagonist of TNFα activity, for example, binding of an antagonist TNFα antibody to TNFα as expressed on an immune cell inhibits induction of cytokines, e.g., IL-8, thereby inhibiting its signal transduction capability, inhibits activation of molecules downstream in the signal transduction pathway, or inhibits an autoimmune response.

IX. Pharmaceutical Compositions and Administration Methods

Methods of preparing and administering TNFα antibodies, or antigen-binding fragments, variants, or derivatives thereof of the invention to a subject in need thereof are well known to or are readily determined by those skilled in the art. The route of administration of the TNFα antibody, or antigen-binding fragment, variant, or derivative thereof may be, for example, oral, parenteral, by inhalation or topical. The term parenteral as used herein includes, e.g., intravenous, intraarterial, intraperitoneal, intramuscular, subcutaneous, rectal or vaginal administration. While all these forms of administration are clearly contemplated as being within the scope of the invention, a form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc. However, in other methods compatible with the teachings herein, TNFα antibodies, or antigen-binding fragments, variants, or derivatives thereof of the invention can be delivered directly to the site of the adverse cellular population thereby increasing the exposure of the diseased tissue to the therapeutic agent.

As previously discussed, TNFα antibodies, or antigen-binding fragments, variants, or derivatives thereof of the invention may be administered in a pharmaceutically effective amount for the in vivo treatment of an autoimmune disease, e.g. RA. In this regard, it will be appreciated that the disclosed antibodies will be formulated so as to facilitate administration and promote stability of the active agent. Preferably, pharmaceutical compositions in accordance with the present invention comprise a pharmaceutically acceptable, non-toxic, sterile carrier such as physiological saline, non-toxic buffers, preservatives and the like. For the purposes of the instant application, a pharmaceutically effective amount of a TNFα antibody, or antigen-binding fragment, variant, or derivative thereof, conjugated or unconjugated, shall be held to mean an amount sufficient to achieve effective binding to a target and to achieve a benefit, e.g., to ameliorate symptoms of a disease or disorder or to detect a substance or a cell.

The pharmaceutical compositions used in this invention comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Preparations for parenteral administration includes sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences, Mack Publishing Co., 16th ed. (1980).

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., a TNFα antibody, or antigen-binding fragment, variant, or derivative thereof, by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in co-pending U.S. Ser. No. 09/259,337 (US-2002-0102208 A1), which is incorporated herein by reference in its entirety. Such articles of manufacture will preferably have labels or package inserts indicating that the associated compositions are useful for treating a subject suffering from, or predisposed to a disease or disorder.

Parenteral formulations may be a single bolus dose, an infusion or a loading bolus dose followed with a maintenance dose. These compositions may be administered at specific fixed or variable intervals, e.g., once a day, or on an "as needed" basis.

Certain pharmaceutical compositions used in this invention may be orally administered in an acceptable dosage form including, e.g., capsules, tablets, aqueous suspensions or solutions. Certain pharmaceutical compositions also may be administered by nasal aerosol or inhalation. Such compositions may be prepared as solutions in saline, employing benzyl alcohol or other suitable preservatives, absorption promoters to enhance bioavailability, and/or other conventional solubilizing or dispersing agents.

The amount of a TNFα antibody, or fragment, variant, or derivative thereof that may be combined with the carrier materials to produce a single dosage form will vary depending upon the host treated and the particular mode of administration. The composition may be administered as a single dose, multiple doses or over an established period of time in an infusion. Dosage regimens also may be adjusted to provide the optimum desired response (e.g., a therapeutic or prophylactic response).

In keeping with the scope of the present disclosure, TNFα antibodies, or antigen-binding fragments, variants, or derivatives thereof of the invention may be administered to a human or other animal in accordance with the aforementioned methods of treatment in an amount sufficient to produce a therapeutic effect. The TNFα antibodies, or antigen-binding fragments, variants, or derivatives thereof of the invention can be administered to such human or other animal in a conventional dosage form prepared by combining the antibody of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of TNFα antibodies, or antigen-binding fragments, variants, or derivatives thereof of the invention may prove to be particularly effective.

Effective doses of the compositions of the present invention, for treatment of an autoimmune disease, e.g. RA, vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages may be titrated using routine methods known to those of skill in the art to optimize safety and efficacy.

For treatment of an autoimmune disease, e.g. RA, with a TNFα antibody, or antigen-binding fragment, variant, or derivative thereof, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated.

TNFα antibodies, or antigen-binding fragments, variants, or derivatives thereof of the invention can be administered on multiple occasions. Intervals between single dosages can be daily, weekly, monthly or yearly. Intervals can also be irregular as indicated by measuring blood levels of target polypeptide or target molecule in the patient. In some methods, dosage is adjusted to achieve a plasma polypeptide concentration of 1-1000 µg/ml and in some methods 25-300 µg/ml. Alternatively, TNFα antibodies, or antigen-binding fragments, variants, or derivatives thereof of the invention can be administered as a sustained release formulation, in which case less frequent administration is required. Dosage and frequency vary depending on the half-life of the antibody in the patient. The half-life of a TNFα antibody can also be prolonged via fusion to a stable polypeptide or moeity, e.g., albumin or PEG. In general, humanized antibodies show the longest half-life, followed by chimeric antibodies and nonhuman antibodies. In one embodiment, the TNFα antibodies, or antigen-binding fragments, variants, or derivatives thereof of the invention can be administered in unconjugated form, In another embodiment, the TNFα antibodies, or antigen-binding fragments, variants, or derivatives thereof of the invention can be administered multiple times in conjugated form. In still another embodiment, TNFα antibodies, or antigen-binding fragments, variants, or derivatives thereof of the invention can be administered in unconjugated form, then in conjugated form, or vice versa.

The compositions of the present invention may be administered by any suitable method, e.g., parenterally, intraventricularly, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

The compositions may also comprise a TNFα antibody dispersed in a biocompatible carrier material that functions as a suitable delivery or support system for the compounds. Suitable examples of sustained release carriers include semipermeable polymer matrices in the form of shaped articles such as suppositories or capsules. Implantable or microcapsular sustained release matrices include polylactides (U.S. Pat. No. 3,773,319; EP 58,481), copolymers of L-glutamic acid and gamma-ethyl-L-glutamate (Sidman et al., Biopolymers 22:547-56 (1985)); poly(2-hydroxyethyl-methacrylate), ethylene vinyl acetate (Langer et al., J. Biomed. Mater. Res. 15:167-277 (1981); Langer, Chem. Tech. 12:98-105 (1982)) or poly-D-(−)-3hydroxybutyric acid (EP 133,988).

TNFα antibodies, or antigen-binding fragments, variants, or derivatives thereof of the invention can optionally be administered in combination with other agents that are effective in treating the disorder or condition in need of treatment (e.g., prophylactic or therapeutic).

X. Diagnostics

The invention further provides a diagnostic method useful during diagnosis of an autoimmune disease, e.g. RA, which involves measuring the expression level of TNFα protein or transcript in tissue or other cells or body fluid from an individual and comparing the measured expression level with a standard TNFα expression levels in normal tissue or body fluid, whereby an increase in the expression level compared to the standard is indicative of a disorder.

TNFα-specific antibodies can be used to assay protein levels in a biological sample using classical immunohistological methods known to those of skill in the art (e.g., see Jalkanen, et al., J. Cell. Biol. 101:976-985 (1985); Jalkanen, et al., J. Cell Biol. 105:3087-3096 (1987)). Other antibody-based methods useful for detecting protein expression include immunoassays, such as the enzyme linked immunosorbent assay (ELISA), immunoprecipitation, or western blotting. Suitable assays are described in more detail elsewhere herein.

By "assaying the expression level of TNFα polypeptide" is intended qualitatively or quantitatively measuring or estimating the level of TNFα polypeptide in a first biological sample either directly (e.g., by determining or estimating absolute protein level) or relatively (e.g., by comparing to the disease associated polypeptide level in a second biological sample). Preferably, TNFα polypeptide expression level in the first biological sample is measured or estimated and compared to a standard TNFα polypeptide level, the standard being taken from a second biological sample obtained from an individual not having the disorder or being determined by averaging levels from a population of individuals not having the disorder. As will be appreciated in the art, once the "standard" TNFα polypeptide level is known, it can be used repeatedly as a standard for comparison.

By "biological sample" is intended any biological sample obtained from an individual, cell line, tissue culture, or other source of cells potentially expressing TNFα. Methods for obtaining tissue biopsies and body fluids from mammals are well known in the art.

TNFα antibodies for use in the diagnostic methods described above include any TNFα antibody which specifically binds to a TNFα gene product, as described elsewhere herein.

XI. Immunoassays

TNFα antibodies, or antigen-binding fragments, variants, or derivatives thereof of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, Current Protocols in Molecular Biology, John Wiley & Sons, Inc., New York, Vol. 1 (1994), which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4.degree. C., adding protein A and/or protein G sepharose beads to the cell lysate, incubating for about an hour or more at 4.degree. C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds, *Current Protocols in Molecular Biology*, John Wiley & Sons, Inc., New York, Vol. 1 (1994) at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g. PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32p or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al., eds, *Current Protocols in Molecular Biology*, John Wiley & Sons, Inc., New York Vol. 1 (1994) at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al., eds, *Current Protocols in Molecular Biology*, John Wiley & Sons, Inc., New York, Vol. 1 (1994) at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest is conjugated to a labeled compound (e.g., $^3$H or $^{125}$I) in the presence of increasing amounts of an unlabeled second antibody.

TNFα antibodies, or antigen-binding fragments, variants, or derivatives thereof of the invention, additionally, be employed histologically, as in immunofluorescence, immunoelectron microscopy or non-immunological assays, for in situ detection of cancer antigen gene products or conserved variants or peptide fragments thereof. In situ detection may be accomplished by removing a histological specimen from a patient, and applying thereto a labeled TNFα antibody, or antigen-binding fragment, variant, or derivative thereof, preferably applied by overlaying the labeled antibody (or fragment) onto a biological sample. Through the use of such a procedure, it is possible to determine not only the presence of TNFα protein, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for TNFα gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of binding to TNFα or conserved variants or peptide fragments thereof, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled TNFα antibody, or antigen-binding fragment, variant, or derivative thereof. The solid phase support may then be washed with the buffer a second time to remove unbound antibody. Optionally the antibody is subsequently labeled. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of TNFα antibody, or antigen-binding fragment, variant, or derivative thereof may be determined according to well known methods. Those skilled in the art will be able to determine operative and optimal assay conditions for each determination by employing routine experimentation.

There are a variety of methods available for measuring the affinity of an antibody-antigen interaction, but relatively few for determining rate constants. Most of the methods rely on either labeling antibody or antigen, which inevitably complicates routine measurements and introduces uncertainties in the measured quantities.

Surface plasmon reasonance (SPR) as performed on BIAcore offers a number of advantages over conventional methods of measuring the affinity of antibody-antigen interactions: (i) no requirement to label either antibody or antigen; (ii) antibodies do not need to be purified in advance, cell culture supernatant can be used directly; (iii) real-time measurements, allowing rapid semi-quantitative comparison of different monoclonal antibody interactions, are enabled and are sufficient for many evaluation purposes; (iv) biospecific surface can be regenerated so that a series of different monoclonal antibodies can easily be compared under identical conditions; (v) analytical procedures are fully automated, and extensive series of measurements can be performed without user intervention. BIAapplications Handbook, version AB (reprinted 1998), BIACORE code No. BR-1001-86; BIAtechnology Handbook, version AB (reprinted 1998), BIACORE code No. BR-1001-84.

SPR based binding studies require that one member of a binding pair be immobilized on a sensor surface. The binding partner immobilized is referred to as the ligand. The binding partner in solution is referred to as the analyte. In some cases, the ligand is attached indirectly to the surface through binding to another immobilized molecule, which is referred as the capturing molecule. SPR response reflects a change in mass concentration at the detector surface as analytes bind or dissociate.

Based on SPR, real-time BIAcore measurements monitor interactions directly as they happen. The technique is well suited to determination of kinetic parameters. Comparative affinity ranking is extremely simple to perform, and both kinetic and affinity constants can be derived from the sensorgram data.

When analyte is injected in a discrete pulse across a ligand surface, the resulting sensorgram can be divided into three essential phases: (i) Association of analyte with ligand during sample injection; (ii) Equilibrium or steady state during sample injection, where the rate of analyte binding is balanced by dissociation from the complex; (iii) Dissociation of analyte from the surface during buffer flow.

The association and dissociation phases provide information on the kinetics of analyte-ligand interaction ($k_a$ and $k_d$, the rates of complex formation and dissociation, $k_d/k_a=K_D$). The equilibrium phase provides information on the affinity of the analyte-ligand interaction ($K_D$).

BIAevaluation software provides comprehensive facilities for curve fitting using both numerical integration and global fitting algorithms. With suitable analysis of the data, separate rate and affinity constants for interaction can be obtained from simple BIAcore investigations. The range of affinities measurable by this technique is very broad ranging from mM to pM.

Epitope specificity is an important characteristic of a monoclonal antibody. Epitope mapping with BIAcore, in contrast to conventional techniques using radioimmunoassay, ELISA or other surface adsorption methods, does not require labeling or purified antibodies, and allows multi-site specificity tests using a sequence of several monoclonal antibodies. Additionally, large numbers of analyses can be processed automatically.

Pair-wise binding experiments test the ability of two MAbs to bind simultaneously to the same antigen. MAbs directed against separate epitopes will bind independently, whereas MAbs directed against identical or closely related epitopes will interfere with each other's binding. These binding experiments with BIAcore are straightforward to carry out.

For example, one can use a capture molecule to bind the first Mab, followed by addition of antigen and second MAb sequentially. The sensorgrams will reveal: 1. how much of the antigen binds to first Mab, 2. to what extent the second MAb binds to the surface-attached antigen, 3. if the second MAb does not bind, whether reversing the order of the pair-wise test alters the results.

Peptide inhibition is another technique used for epitope mapping. This method can complement pair-wise antibody binding studies, and can relate functional epitopes to structural features when the primary sequence of the antigen is known. Peptides or antigen fragments are tested for inhibition of binding of different MAbs to immobilized antigen. Peptides which interfere with binding of a given MAb are assumed to be structurally related to the epitope defined by that MAb.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., Sambrook et al., ed., Cold Spring Harbor Laboratory Press: (1989); *Molecular Cloning: A Laboratory Manual,* Sambrook et al., ed., Cold Springs Harbor Laboratory, New York (1992), DNA Cloning, D. N. Glover ed., Volumes I and II (1985); *Oligonucleotide Synthesis,* M. J. Gait ed., (1984); Mullis et al. U.S. Pat. No. 4,683,195; *Nucleic Acid Hybridization,* B. D. Hames & S. J. Higgins eds. (1984); *Transcription And Translation,* B. D. Hames & S. J. Higgins eds. (1984); *Culture Of Animal Cells,* R. I. Freshney, Alan R. Liss, Inc., (1987); *Immobilized Cells And Enzymes,* IRL Press, (1986); B. Perbal, *A Practical Guide To Molecular Cloning* (1984); the treatise, *Methods In Enzymology,* Academic Press, Inc., N.Y.; *Gene Transfer Vectors For Mammalian Cells,* J. H. Miller and M. P. Calos eds., Cold Spring Harbor Laboratory (1987); *Methods In Enzymology,* Vols. 154 and 155 (Wu et al. eds.); *Immunochemical Methods In Cell And Molecular Biology,* Mayer and Walker, eds., Academic Press, London (1987); *Handbook Of Experimental Immunology,* Volumes I-IV, D. M. Weir and C. C. Blackwell, eds., (1986); *Manipulating the Mouse Embryo,* Cold Spring Harbor Laboratory Press, Cold Spring Harbor, N.Y., (1986); and in Ausubel et al., *Current Protocols in Molecular Biology,* John Wiley and Sons, Baltimore, Md. (1989).

General principles of antibody engineering are set forth in *Antibody Engineering,* 2nd edition, C. A. K. Borrebaeck, Ed., Oxford Univ. Press (1995). General principles of protein engineering are set forth in *Protein Engineering, A Practical Approach,* Rickwood, D., et al., Eds., IRL Press at Oxford Univ. Press, Oxford, Eng. (1995). General principles of antibodies and antibody-hapten binding are set forth in: Nisonoff, A., *Molecular Immunology,* 2nd ed., Sinauer Associates, Sunderland, Mass. (1984); and Steward, M. W., *Antibodies, Their Structure and Function,* Chapman and Hall, New York, N.Y. (1984). Additionally, standard methods in immunology known in the art and not specifically described are generally followed as in *Current Protocols in Immunology,* John Wiley & Sons, New York; Stites et al. (eds), *Basic and Clinical— Immunology* (8th ed.), Appleton & Lange, Norwalk, Conn. (1994) and Mishell and Shuigi (eds), *Selected Methods in Cellular Immunology,* W.H. Freeman and Co., New York (1980).

Standard reference works setting forth general principles of immunology include *Current Protocols in Immunology,* John Wiley & Sons, New York; Klein, J., Immunology: *The Science of Self-Nonself Discrimination,* John Wiley & Sons, New York (1982); Kennett, R., et al., eds., *Monoclonal Antibodies, Hybridoma: A New Dimension in Biological Analy-* ses, Plenum Press, New York (1980); Campbell, A., "Monoclonal Antibody Technology" in Burden, R., et al., eds., *Laboratory Techniques in Biochemistry and Molecular Biology*, Vol. 13, Elsevere, Amsterdam (1984), *Kuby Immunnology* 4th ed. Ed. Richard A. Goldsby, Thomas J. Kindt and Barbara A. Osborne, H. Freemand & Co. (2000); Roitt, I., Brostoff, J. and Male D., *Immunology* 6th ed. London: Mosby (2001); Abbas A., Abul, A. and Lichtman, A., *Cellular and Molecular Immunology* Ed. 5, Elsevier Health Sciences Division (2005); Kontermann and Dubel, *Antibody Engineering*, Springer Verlan (2001); Sambrook and Russell, *Molecular Cloning: A Laboratory Manual*. Cold Spring Harbor Press (2001); Lewin, *Genes VIII*, Prentice Hall (2003); Harlow and Lane, *Antibodies: A Laboratory Manual*, Cold Spring Harbor Press (1988); Dieffenbach and Dveksler, *PCR Primer* Cold Spring Harbor Press (2003).

All of the references cited above, as well as all references cited herein, are incorporated herein by reference in their entireties.

EXAMPLES

Example 1

Identification of Human Anti-TNFα MAbs

Human anti-TNFα monoclonal antibodies (MAbs) were identified by methods described, e.g., U.S. Publ. No. 2002/0123057 A1, and as described further herein.

Step 1: The VH and VL genes from a mouse anti-TNFα MAb. were engineered into an Ig-H and Ig-K in vaccinia virus so that they could be expressed as chimeric human IgG1/kappa.

Step 2: A human Ig-H library was created where the CDR3 from a murine anti-TNFα antibody, was grafted on to a library of human VH genes. Every clone in the resulting Ig-H library contained a fixed CDR3 from a mouse anti-TNFα MAb, with diversity throughout the rest of the VH gene sequence.

Step 3A: The chimeric mouse Ig-H (Step 1) was used to select human Ig-Ks that can pair with the chimeric Ig-H and retain TNFα specific binding.

Step 3B: The chimeric mouse anti-TNFα Ig-K (Step 1) was used to select human Ig-Hs from the CDR3 grafted library (Step 2) that can pair with the chimeric Ig-K and retain TNFα specific binding.

Step 4A: The selected human Ig-Ks (Step 3A) were used to select human Ig-Hs that make a TNFα specific MAb.

Step 4B: The selected human Ig-Hs (Step 3B) were used to select human Ig-Ks that make a TNFα specific MAb Step 5: The V genes from the selected vaccinia recombinants were cloned into mammalian expression vectors containing the gamma I and kappa constant domains, creating full length gamma I heavy and kappa light chain genes. Recombinant antibody was produced by co-transfecting the plasmids containing the full length heavy and light chain genes into CHO cells.

Step 6: Recombinant antibody was purified by Protein A chromatography, and the antibody tested for specificity, affinity, and function.

Step 7: From the data obtained (Step 6), a lead first generation antibody was selected and optimized to improve affinity and function.

For screening, sets of mini vaccinia virus (vv) Ig-K gene libraries were generated, each containing a pool of 100-1000 individual VL gene recombinants in association with Cκ, by amplifying 100-1000 pfu from the parent Ig-K libraries in individual wells of 96 well plates. Each of the resulting mini libraries carried 100-1000 different VL genes at titers of approximately $10^6$ pfu.

The chimeric TNFα-specific Ig-H ("chIg-H") was screened in combination with the human Ig-K mini vv libraries. Thus, in a single well there were nominally 100-1000 distinct VH/VL combinations. Each assay well contained 100,000 cells which were infected at a multiplicity of infection (moi)=1 for Ig-H and Ig-K.

Following incubation for 72-96 hours, culture supernatants were sampled and tested by ELISA for capacity to bind to TNFα that had been coated onto an ELISA plate. Mini Ig-K libraries corresponding to positive wells were sampled from the master plate and replated at limiting dilution (e.g., 10 pfu/well).

Following second round screening, individual plaques from each positive well were picked and amplified. This step generated monoclonal vvIg-K which, in combination with the chimeric Ig-H described above, bound to TNFα.

HeLa cell monolayers were then coinfected with each monoclonal chIg-H and Ig-K pair. The resulting supernatants were tested for antigen binding to verify that correct pairs of VH and VL that encode for specific Ab were obtained. The VL genes which encode the human Ig-K proteins identified were then PCR amplified and subcloned into mammalian expression vectors for high level expression and further analysis.

To select human VH that can pair with the human VLs identified above the process was reversed. The selected human IG-Ks were used to screen mini-libraries of human Ig-H gene libraries, each containing a pool of 100-1000 individual VH gene recombinants in association with CH as described above.

Example 2

Selection of Ig-H and Ig-K Chains

The anti-TNFα chIg-H and Ig-K in vaccinia virus described above were used to screen libraries of human Ig-Ks and Ig-Hs.

Using the chimeric Ig-H, a panel of 5 human Ig-Ks was selected: L217, L218, L229, L230 and L250. The amino acid sequences of the selected VL proteins are shown in Table 8. Of note, all five of these Ig-Ks are encoded by nucleotide sequences derived from the human L2 germline gene.

Using the chimeric Ig-K, a panel of 11 human Ig-Hs was selected: H1102, H1103, H1104, H1118, H1117, H1119, H1120, H1121, H1122, H1194, H1195. The amino acid sequences of the selected human VH genes are shown in Table 7.

Using the Human VLs that had been selected with the chimeric VH to screen human Ig-H libraries, eight human Ig-Hs were selected. The sequences of these eight VHs is shown in Table 9. Of note, all eight human VHs were selected using L250, and all eight VHs are encoded by nucleotide sequences derived from the VH3-53 germline heavy chain gene.

A summary of the data generated with some of these eight human antibodies is also shown in Table 9. A number of selected MAbs demonstrated good affinity and good functional activity.

TABLE 9

TNFα Specific Human MAbs

| Clone Name | VH Number | Selected with | MAb Number | Affinity (nM) |
|---|---|---|---|---|
| 121 E1B | H1193 | L250 | 696 | 0.6 |
| 131 E11 | H1272 | L250 | 698 | 2.3 |
| 183 E9 | H1273 | L250 | 699 | 7.3 |
| 141 F2 | H1278 | L250 | 715 | 0.6 |
| 141 A10 | H1277 | L250 | 714 | 0.4 |
| 142 F2 | H1280 | L250 | 716 | >10 |
| 121 D11 | H1192 | L250 | 695 | 0.6 |
| 156 H7 | H1329 | L250 | 805 | 0.6 |

The commercially available chimeric anti-TNFα MAb Remicade® was used as a control. In this assay the affinity of Remicade® was 0.08 nM. The VH and VL nucleotide and amino acid sequences of the antibodies listed in Table 9 are set forth in Tables 6 and 7.

Example 3

Anti-TNFα MAbs Inhibit TNFα-Induced Cytotoxicity

Eight monoclonal antibodies were tested using a TNFα cytoxicity assay. WEHI 13VAR cells were utilized for the cytotoxicity assay because of their known senstivity to TNFα in the presence of Actinomycin D. At known concentrations of TNFα, treatment of WEHI 13VAR cells results in cell death. See e.g., Khabar, K., et al. *Immunology Letters,* 46:107-110 (1995).

WEHI-13VAR cells were incubated with TNFα at a standard concentration of 0.2 ng/ml in combination with various titrations of test monoclonal antibodies at 37° C. for 18 hours. The number of viable cells were measured using a Non-Radioactive Cell Proliferation Assay (Promega). For controls, cells were also treated as follows: (1) with TNFα (in the absence of antibody) at serial dilutions, starting at a concentration of 8 ng/ml; (2) in media alone; and (3) with 10% SDS (lysis control).

Antibodies that neutralized TNFα-induced cytotoxicity (cell death) resulted in more cells surviving in the presence of TNFα. In these cytotoxicity assays, the higher the OD, the greater the neutralization of TNFα has occurred. The levels of neutralization of TNFα-induced cell death in the presence of MAbs 695, 696, 592, 698, 699, 714, 715, 716, 805 and 696 at various titrations are shown in FIGS. 2A-C. Affinity optimization techniques were utilized, as described herein, to generate additional MAbs demonstrating higher levels of neutralization of TNFα.

Example 4

Improvement of the MAb Functional Activity by Optimization of VL L250

The lead human anti-TNFα MAbs identified above use the L250 light chain. This L250 light chain was mutagenized to produce antibodies with higher affinity to TNFα and higher functional activity, i.e. an increased capability to neutralize TNFα. The functional activity of MAbs 805, 714, 695 and 698 was improved by mutagenesis of the CDR3 of L250.

In order to introduce variability in the CDR3 of L250, we introduced NNK at a specific position, where N can be A, T, G, C and K is T or G. Using NNK, all 20 amino acids and 1 stop codon can be introduced at each position, and there are 32 possible combinations (4×4×2). All nine of the CDR3 residues in L250 were targeted, and changed 1 position at a time.

To make each library an anti-sense primer that encodes one amino acid of CDR3 replaced with NNK and included sequence complementary to the remainder of CDR3 and Framework 4 was paired with a sense primer that hybridizes in Framework 1 of L250 for a PCR reaction. Each PCR product encoded the entire VL domain, and had one amino acid position converted to NNK.

The PCR product was then cloned into a mammalian expression vector containing the constant domain of human gamma I (for VH mutants, see below), or kappa (for VL mutants), generating full length heavy or light chains. Clones were distributed into 96 well plate format, with 1 clone/well. Plasmid DNA was purified from each clone. To screen mutations in Ig-K, each kappa light chain clone was expressed with H11192 (mAb 695) by transfection in CHO cells. The antibodies containing mutated and Ig-K and H11192 were tested for binding to TNFα using an ELISA assay. Competition ELISA assays were also performed after incubation alone or in the presence of 0.3 nM TNFα or 1 nM TNFα. MAbs with an $IC_{50}$ higher than that of mAb 805 were selected and further characterized. When higher affinity mutant mAbs were identified, the mutants were sequenced, the resulting mutant MAbs were produced by larger scale transfection in CHO and the resulting MAbs tested for specificity, affinity and function in the cytotoxicity assay.

A summary of VL mutations within the CDR3 region of L250 resulting in increased affinity were identified and are shown in Table 10.

TABLE 10

VL Mutations

| Position # | Kabat # | Amino Acid (L250) | Mutant Amino Acid (MAb # with H1192) | New VL Number | Affinity of Mutant MAb (nM) |
|---|---|---|---|---|---|
| 1 | 89 | Q | | | |
| 2 | 90 | Q | | | |
| 3 | 91 | Y | W (855) | L332 (SEQ ID NO: 145) | 0.25 |
| 4 | 92 | H | F (812) | L308 (SEQ ID NO: 149) | 812 = 0.32 |
| | | | M (813) | L309 (SEQ ID NO: 153) | 813 = 0.42 |
| 5 | 93 | S | A (815) | L311 (SEQ ID NO: 157) | 0.36 |
| 6 | 94 | W | | | |
| 7 | 95 | P | | | |
| 8 | 96 | L | | | |
| 9 | 97 | T | | | |

The corresponding VH and VL sequences of the antibodies shown in Table 10 (855, 812, 813 and 815) are set forth in Table 4. The nucleotide and amino acid sequences of these corresponding VH and VL sequences are set forth in Tables 6-8.

Figure 3A:
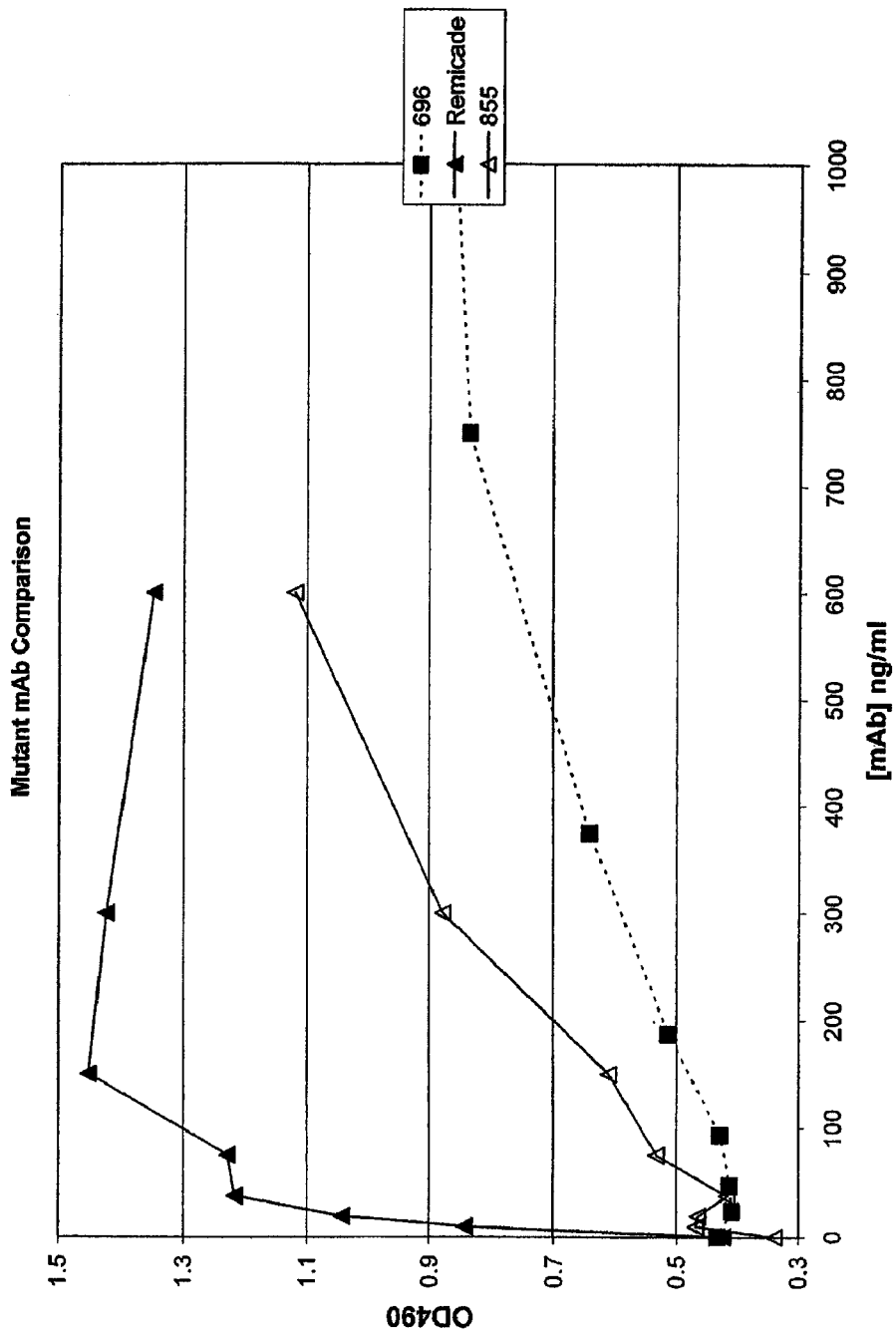
Figure 3B:
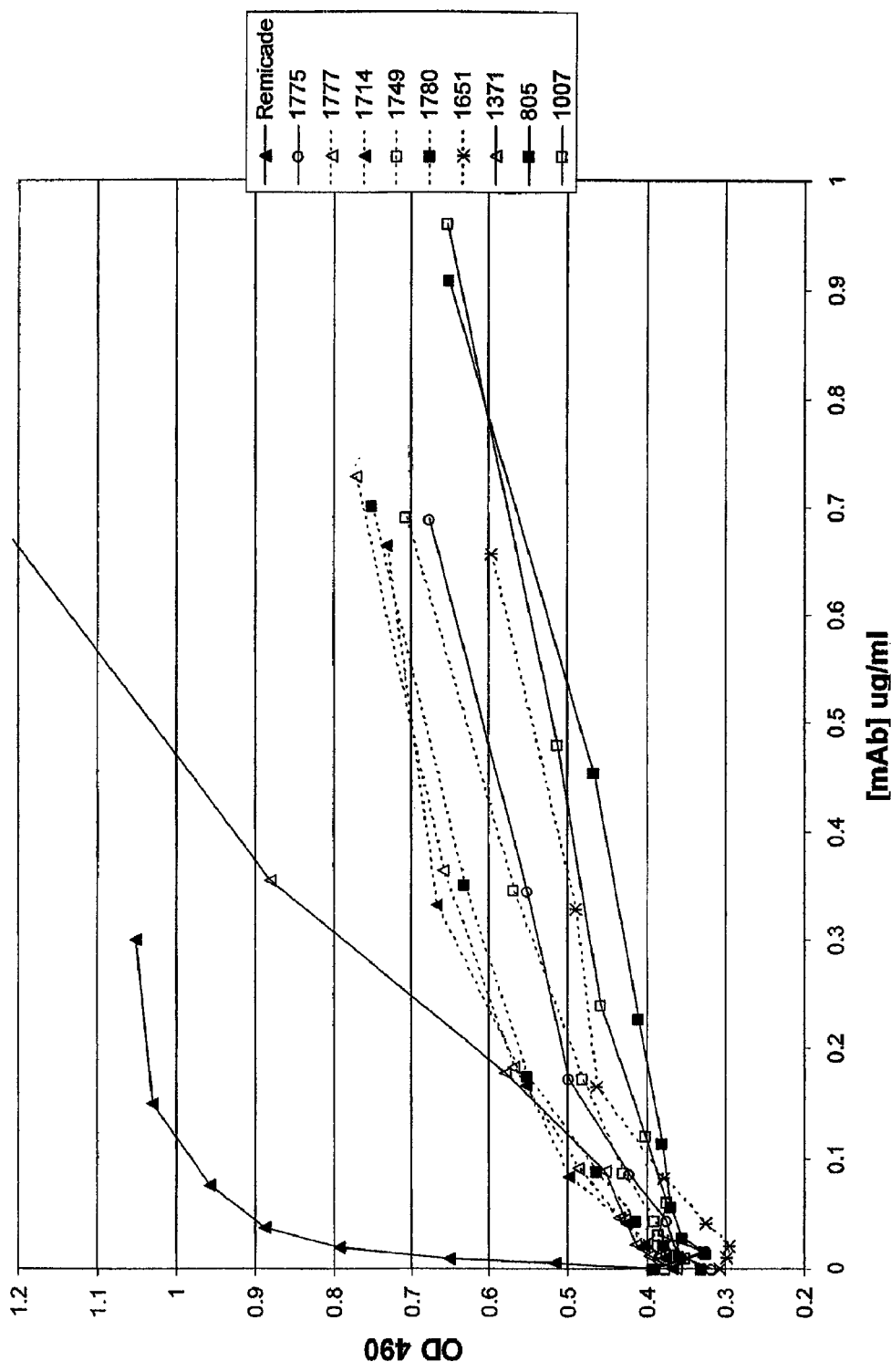

The mutant MAbs were tested in a cytotoxicity assay to confirm increased functional activity compared to parental MAb. As shown in FIG. 3A, MAb 855, containing a Y92W mutation, was significantly better than the parental MAb 695 (containing H1192 and L250) in the cytotoxicity assay. The other mutant MAbs listed in Table 10 showed higher functional activity in the cytotoxicity assay when compared with parental MAb. However, MAb 855 was preferred.

As a next step in the affinity improvement, we mutagenized the VH-CDR3 of H1192 and H1329 in a similar way to that described above for the mutagenesis of L250. Mutations of H1192 and H1328 that result in improved affinity when paired with L250 or L332 are summarized in Tables 11-14.

TABLE 11

Mutations of H1192 resulting in improved affinity when paired with L250

| Position # | Kabat # | Amino Acid (H1192) | Mutant Amino Acid (MAb # with L250) | New VH Number | Affinity of Mutant MAb (nM) |
|---|---|---|---|---|---|
| 1 | 95 | N | T (1028) | H1478 (SEQ ID NO: 35) | 0.32 |
|   |    |   | L (1029) | H1479 (SEQ ID NO: 37) | 0.36 |
| 2 | 96 | Y |   |   |   |
| 3 | 97 | Y | A (874) | H1373 (SEQ ID NO: 39) | 0.56 |
| 4 | 98 | G |   |   |   |
| 5 | 99 | S |   |   |   |
| 6 | 100 | T | L (892) | H1388 (SEQ ID NO: 41) | 0.43 |
| 7 | 100A | Y | F (1037) | F = H1482 (SEQ ID NO: 43) | F = 0.12 |
|   |      |   | M (1038) | M = H1483 (SEQ ID NO: 45) | M = 0.25 |
|   |      |   | L (1066) | L = H1487 (SEQ ID NO: 47) | L = 0.13 |
|   |      |   | H (1132) | H = H1518 (SEQ ID NO: 49) | H = 0.10 |
| 8 | 101 | D |   |   |   |
| 9 | 102 | Y |   |   |   |

The corresponding VH and VL sequences of the antibodies shown in Table 11 (1028, 1029, 874, 892, 1037, 1038, 1066 and 1132) are described in Table 4. The nucleotide and amino acid sequences of these corresponding VH and VL sequences are set forth in Tables 6-8. When the mutants shown above in Table 11 were expressed with L332, the improvements were additive.

TABLE 12

Combination of H1192 mutants with L332

| Position # | Kabat # | Amino Acid (H1192) | Mutant Amino Acid (MAb # with L332) | New VH Number | Affinity of Mutant MAb (nM) |
|---|---|---|---|---|---|
| 1 | 95 | N | T (1036) | H1478 (SEQ ID NO: 35) | 0.18 |
| 2 | 96 | Y |   |   |   |
| 3 | 97 | Y |   |   |   |
| 4 | 98 | G |   |   |   |
| 5 | 99 | S |   |   |   |
| 6 | 100 | T |   |   |   |
| 7 | 100A | Y | F (1042) | F = H1482 (SEQ ID NO: 43) | F = 0.07 |
|   |      |   | M (1043) | M = H1483 (SEQ ID NO: 45) | M = 0.31 |
|   |      |   | L (1067) | L = H1487 (SEQ ID NO: 47) | L = 0.12 |
|   |      |   | H (1131) | H = H1518 (SEQ ID NO: 49) | H = 0.13 |
|   |      |   | V (1210) | V = H1557 (SEQ ID NO: 51) | V = 0.14 |
| 8 | 101 | D |   |   |   |
| 9 | 102 | Y |   |   |   |

TABLE 13

Mutations of H1329 that result in improved affinity when paired with L332

| Position # | Kabat # | Amino Acid (H1329) | Mutant Amino Acid (MAb # with L332) | New VH Number | Affinity of Mutant MAb (nM) |
|---|---|---|---|---|---|
| 1 | 95 | N | T (1789) | H1694 (SEQ ID NO: 53) | |
| 2 | 96 | Y | | | |
| 3 | 97 | Y | | | |
| 4 | 98 | G | | | |
| 5 | 99 | S | | | |
| 6 | 100 | T | | | |
| 7 | 100A | Y | H (1371) | H = H1596 (SEQ ID NO: 55) | 1371 = 0.20 |
| | | | M (1775) | M = H1687 (SEQ ID NO: 57) | 1775 = 0.22 |
| | | | I (1777) | I = H1684 (SEQ ID NO: 59) | 1777 = 0.18 |
| | | | F (1714) | F = H1678 (SEQ ID NO: 61) | 1714 = 0.16 |
| | | | L (1780) | L = H1685 (SEQ ID NO: 63) | 1780 = 0.23 |
| 8 | 101 | D | | | |
| 9 | 102 | Y | | | |

The corresponding VH and VL sequences of the antibodies shown in Tables 12 and 13 are described in Table 4. The nucleotide and amino acid sequences of these corresponding VH and VL sequences are set forth in Tables 6-8.

Note that pairing H1329 with L332 creates MAb 1007, which has an affinity of 0.36 nM. Because of the striking similarity in the mutants that were isolated by mutagenesis of H1192 and H1329, we transferred selected mutants onto H1272 to see if these would also prove to be beneficial. As shown in Table 13, a number of transferred mutants resulted in an improvement in affinity.

TABLE 14

Transfer of mutants to H1272:

| Position # | Kabat # | Amino Acid (H1272) | Mutant Amino Acid (MAb # with L332) | New VH Number | Affinity of Mutant MAb (nM) |
|---|---|---|---|---|---|
| 1 | 95 | N | | | |
| 2 | 96 | Y | | | |
| 3 | 97 | Y | | | |
| 4 | 98 | G | | | |
| 5 | 99 | S | | | |
| 6 | 100 | T | | | |
| 7 | 100A | Y | H (1850) | H = H1727 (SEQ ID NO: 65) | H = 0.59 |
| | | | M (1874) | M = H1725 (SEQ ID NO: 67) | M = 0.38 |
| | | | F (1851) | F = H1728 (SEQ ID NO: 69) | F = 0.26 |
| | | | L (1852) | L = H1729 (SEQ ID NO: 225) | L = 0.41 |
| 8 | 101 | D | | | |
| 9 | 102 | Y | | | |

The corresponding VH and VL sequences of the antibodies shown in Table 14 are described in Table 4. The nucleotide and amino acid sequences of these corresponding VH and VL sequences are set forth in Tables 6-8.

Note that pairing H1272 with L332 creates MAb 1769, which has an affinity of 0.97 nM.

A summary and comparison of the binding affinities of the antibodies described in Tables 10-14 is set forth in Tables 3 and 4.

Example 4

Characterization of Mutant MAbs

Figure 3C:
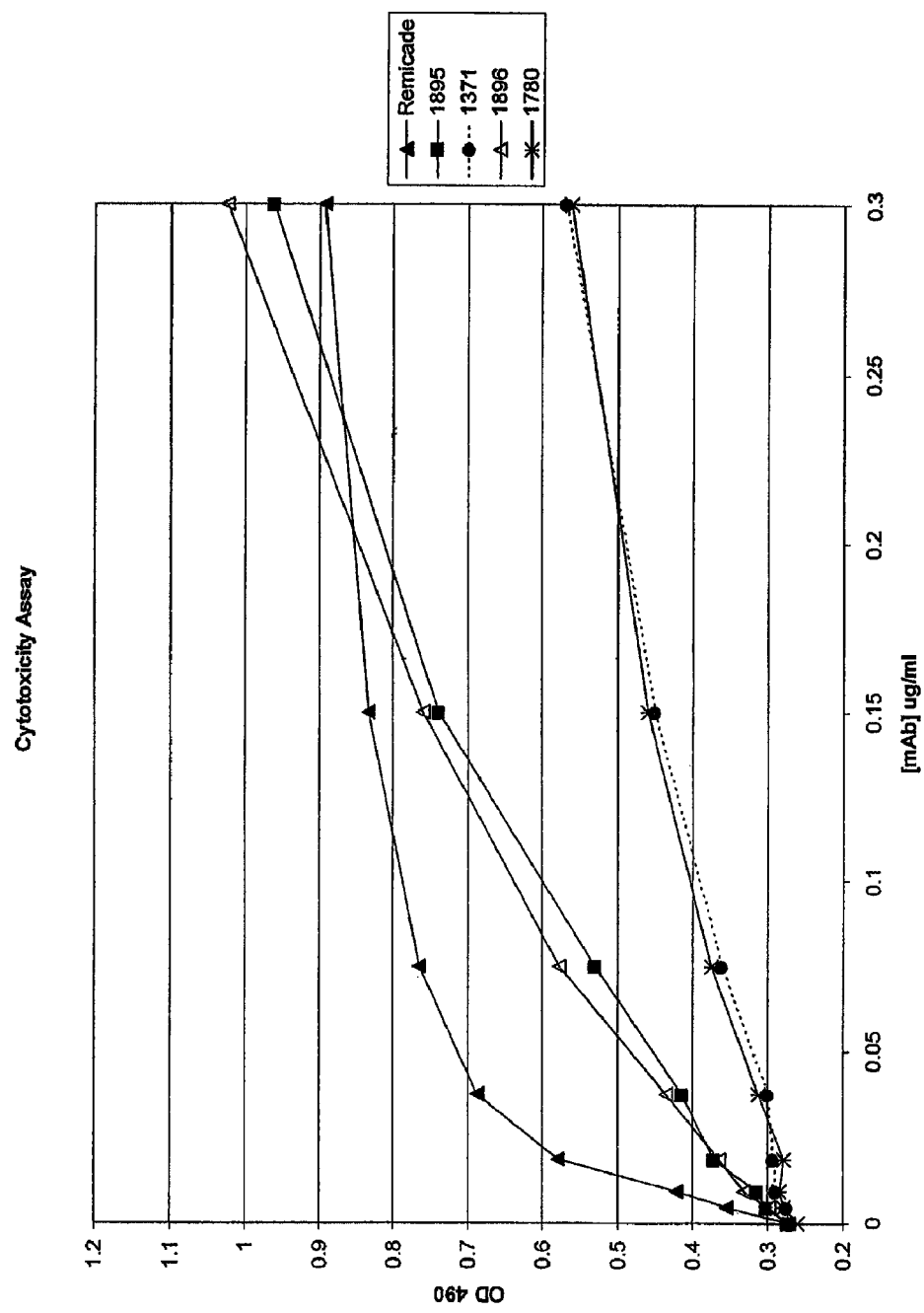

As shown above, the mutation of both VL and VH CDR3 resulted in MAbs that had significantly higher affinity and functional activity. To further improve these antibodies, additional mutagenesis was performed on the CDR1 and CDR2 of L332. A similar procedure to what was described above was employed to select higher affinity VLs. Selection of the mutant VL was carried out using both H1596 and H1685. We identified a G50N mutation that created the new VL, L459, that was significantly better than L332 (Table 15). As shown in FIG. 3C, this improvement in affinity also resulted in an improvement in functional activity in the cytotoxicity assay.

TABLE 15

Affinity of Mutant VL

| MAb | VH | VL | Affinity (nM) |
|---|---|---|---|
| Remicade ® | | | 0.08 |
| 1371 | H1596 | L332 | 0.20 |
| 1780 | H1685 | L332 | 0.23 |
| 1895 | H1596 | L459 | 0.09 |
| 1896 | H1685 | L459 | 0.08 |

In order to further improve this activity, we selected H1685 (H1329/L104) for further mutagenesis of the VH. Selected positions in CDR H1 and CDR H2 were targeted and randomized and screened as described above. Resulting mutants were paired with L459 and tested for affinity. Table 16 shows a summary of these results.

TABLE 16

Affinity of Mutant VH

| MAb | VH# | VH Mutation[1] | VL | Affinity (nM) |
|---|---|---|---|---|
| Remicade ® | | | | 0.08 |
| 1896 | H1685 | | L459 | 0.08 |
| 1988 | H1813 | G54I | L459 | 0.04 |
| 1989 | H1814 | G54V | L459 | 0.05 |
| 1999 | H1824 | A56I | L459 | 0.04 |
| 2006 | H1831 | M58H | L459 | 0.04 |
| 2019 | H1844 | A56V | L459 | 0.04 |

[1]Kabat Numbering System. "G54I" indicates that the wild type G at position 54 was mutated to I, etc.

Figure 3D:
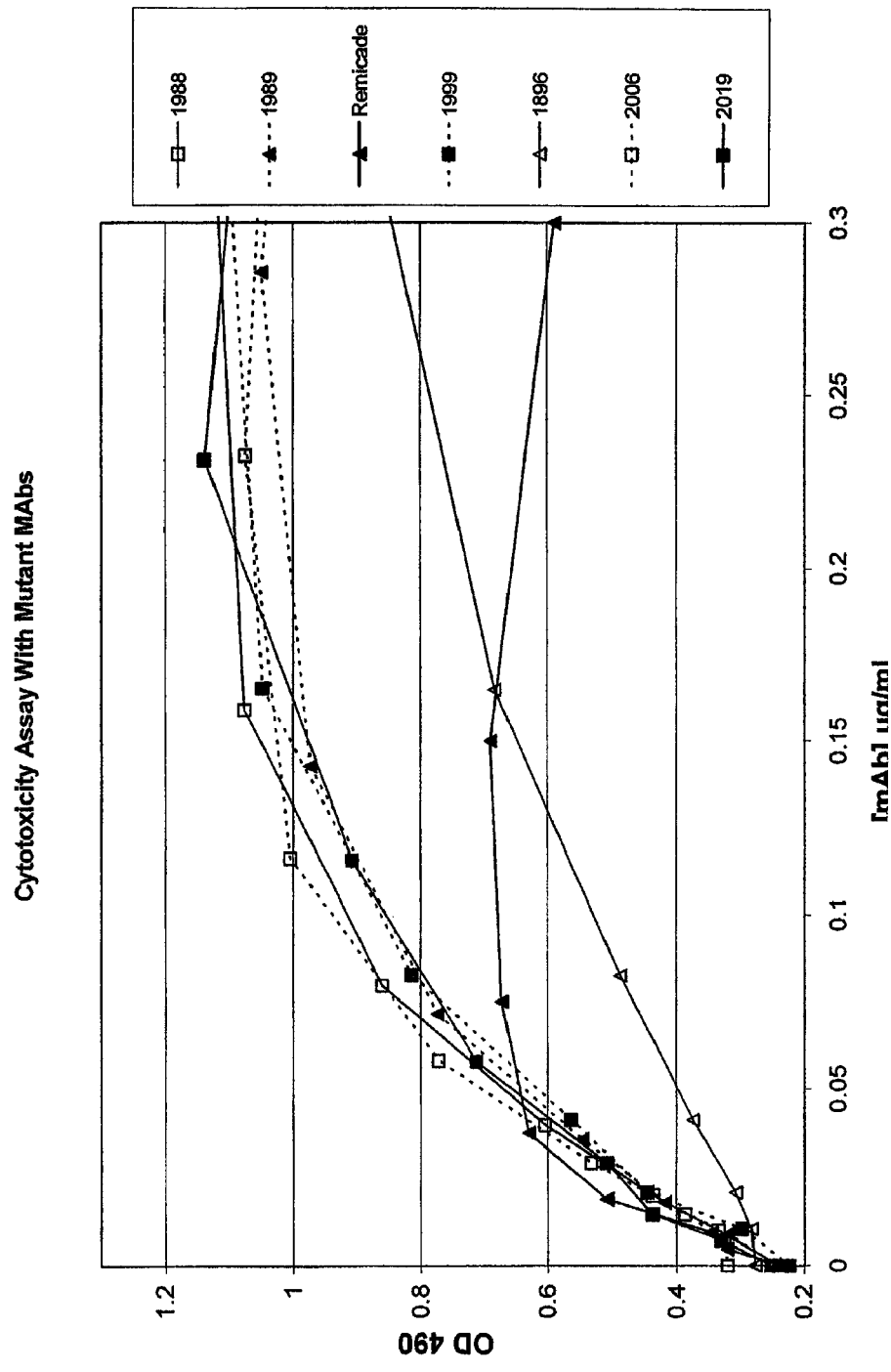

The resulting mutant antibodies were tested for enhanced functional activity in the cytotoxicity assay. As shown in FIG. 3D, all of the mutants demonstrated enhanced activity compared to MAb 1896.

To further improve these antibodies, additional mutagenesis was performed on the CDR2 of L459. A similar procedure to that described above was employed to select higher affinity VLs. In addition, in order to further reduce the chances of immunogenicity, we mutated two Framework 1 positions back to human germline (V9A/P14S). We identified a S52A mutation that created the new VL, L472 that was significantly better than L459. A VL containing just the V9A/P14S Framework substitutions was created (L471) and tested. A summary of affinity data for MAbs paired with L472 is shown in Table 17.

TABLE 17

| MAb | VH | VL | Affinity (nM) |
|---|---|---|---|
| Remicade ® | | | 0.06 |
| Humira ® | | | 0.09 |
| 2060 | H1844 | L471 | 0.02 |
| 2071 | H1844 | L472 | 0.01 |
| 2090 | H1813 | L472 | 0.02 |

Figure 3E:
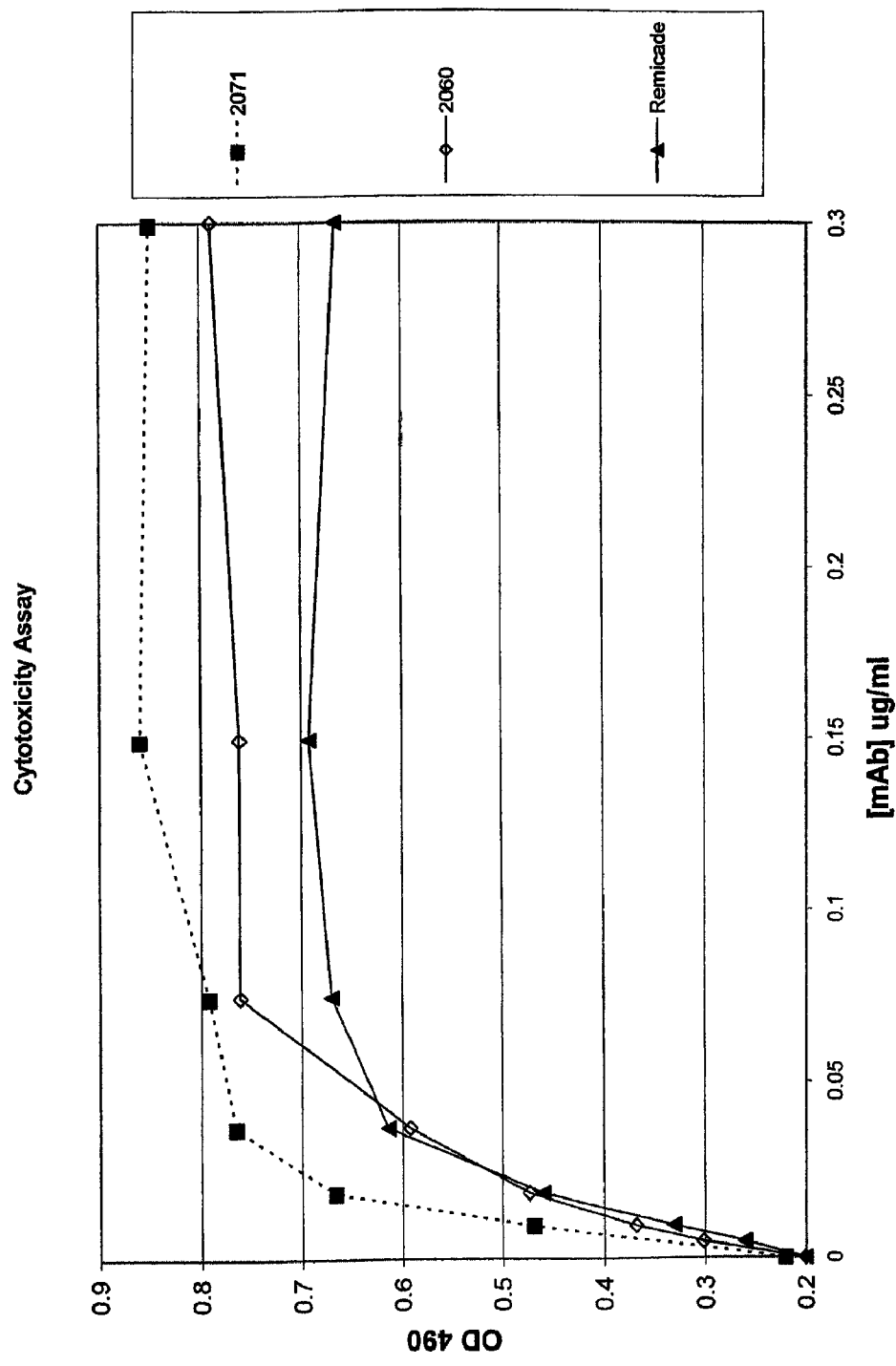
Figure 3F:
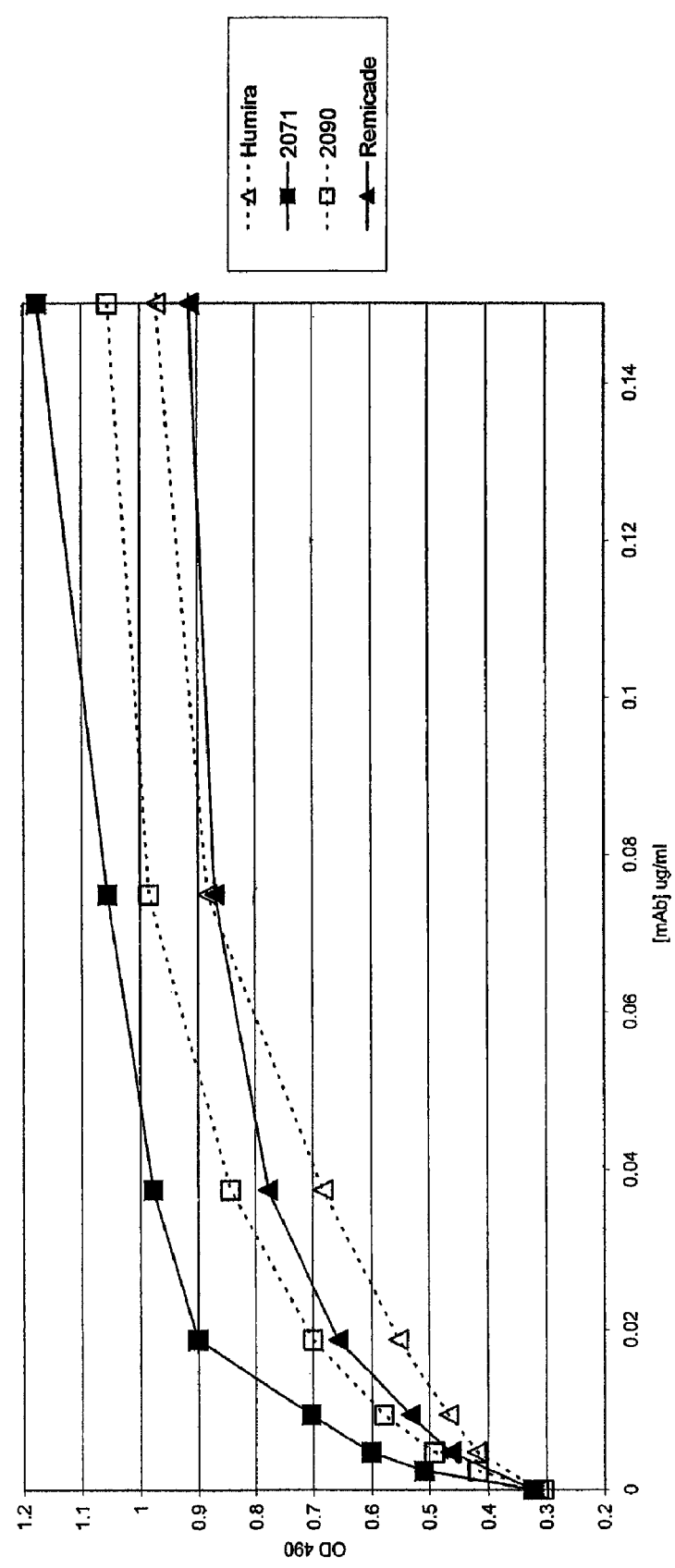

This enhanced affinity translated into enhanced functional activity in the cytotoxicity assay (FIG. 3E). In comparative cytotoxicity assays, MAb 2071 and 2090 were similar to each other, and superior to Remicade® and Humira® (FIG. 3F). The IC$_{50}$s in this cytotoxicity assay were: Remicade®=0.11; Humira®=0.18; MAb 2071=0.04; MAb 2090=0.09. MAbs 2071 and 2090 were tested by Biacore for affinity. As shown in FIG. 4, the affinity measured by Biacore is similar to the affinity measured by IC$_{50}$ ELISA, and superior to the affinity of Humira® and Remicade®.

Example 5

MAbs 2071 and 2090 Neutralize TNFα Binding to its Receptor

MAbs 2071 and 2090 were tested for their ability to neutralize TNFα binding to its receptors using a receptor blocking flow assay, as described in, for example, in Salfeld, et al., U.S. Pat. No. 6,090,382.

The receptor blocking flow assay utilizes human U937 cells which have TNFα receptors on the cell surface. A neutralizing MAb will block TNFα from binding to these receptors.

U937 cells were incubated with either MAb 2071 or MAb 2090 and TNFα on ice for 30 minutes. The cells were washed and then analyzed by flow cytometry using a secondary antibody capable of detecting binding of TNFα to the cell surface. A reduction in signal by flow cytometry indicates that TNFα binding has been neutralized. As shown in FIG. 5, MAbs 2071 and 2090 are able to neutralize TNFα binding in this assay at least as well as Remicade® and Humira®.

Example 6

MAbs 2071 and 2090 Inhibit TNFα-Induced Cell Surface Expression of Adhesion Molecules on HUVEC Cells MAbs 2071 and 2090 were tested for their ability to inhibit the TNFα-induced cell surface expression of adhesion molecules using human umbilical vein endothelial cells (HUVEC), as described in Scallon, B., et al., *The Journal of Pharmacology and Experimental Therapeutics*, 301(2): 418-426 (2002). Stimulation of HUVEC cells with TNFα induces surface expression of adhesion molecule E-selectin (CD62E and ELAM-1). The anti-TNFα antibodies Remicade® and Enbrel® have been shown to prevent TNFα from inducing the expression E-selectin.

50 µl of 20 ng/ml TNFα and 50 µl MAb (at a concentration of 1.0 to 0.1 nM) were added in media to HUVEC cells in a 96 well plate. The plate was incubate at 37° C. for 4 hrs. After incubation, expression of E-selectin was measured by flow cytometry. As shown in FIG. 6, MAbs 2071 and 2090 demonstrated greater inhibition of cell surface expression of adhesion molecules as compared to that of Remicade® and Humira®.

Example 7

MAbs 2071 and 2090 Inhibit TNFα-Induced Expression of IL-8 by Human Monocytes

MAbs 2071 and 2090 were tested for their ability to inhibit the TNFα-induced expression of IL-8 by human monocytes. See e.g., *FEBS Lett.* 307 p 97-101 (1992). A neutralizing MAb should prevent TNFα-induced WL8 expression. MAbs 2071 and 2090 were incubated with TNFα at room temperature for 30 minutes. Add the MAb/TNFα to 96 well plates containing U937 cells. Control wells contained media only (no IL8 induction) or TNF a only (IL8 induction). Cells were incubated for 6 hours at 37° C. IL-8 levels were assayed in supernatant by ELISA. As shown in FIG. 7, MAbs 2071 and 2090 demonstrate demonstrated greater inhibition of IL8 expression as compared to that of Remicade® and Humira®.

The nucleotide and amino acid sequences of the VHs and VL of MAbs 2071 and 2090 are shown in Tables 6 and 7.

The TNFα cytotoxicity assay was performed as described above in Example 3.

Example 8

Treatment of RA in Patients Using Anti-TNFα MAbs

The effects of anti-TNFα MAbs in the treatment of RA are evaluated in patients with active RA in randomized, double-blind, placebo-controlled trials. Patients are randomized to receive 1, 3, or 10 mg/kg anti-TNFα MAbs in an appropriate vehicle or placebo at weeks 0, 2, 6, and 14. Antibodies are also administered in combination with traditional disease-modifying anti-rheumatic drugs, such as methotrexate (MTX). Antibodies can be administered subcutaneously or intravenously.

Disease activity and response to therapy are followed clinically by the use of scaled measurements that are assessed at each visit. A number of instruments have been validated for use in RA. The American College of Rheumatology (ACR) preliminary definition of improvement in rheumatoid arthritis (ACR 20, 50, and 70, with the numbers referring to percentage of improvement) is used. For example, for a 20% improvement the following is required: >20% improvement in tender joint count and >20% improvement in swollen joint count. In addition >20% improvement in three of the following five categories is also required: (1) patient pain assessment; (2) patient global assessment; (3) physician global assessment; (4) patient self-assessed disability; and (5) acute-phase reactant (erythrocyte sedimentation rate or C-reactive protein).

What is claimed is:

1. An isolated antibody which specifically binds to human TNFα or an antigen binding fragment thereof, wherein the VH domain of said antibody or fragment thereof comprises an amino acid sequence which is either identical, or is identical except for one amino acid substitution in any one, two, or three CDRs within said VH domain, to a VH amino acid sequence selected from the group consisting of: SEQ ID NO: 3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO:55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 225, SEQ ID NO: 71, SEQ ID NO: 73, SEQ ID NO: 75, SEQ ID NO: 77, SEQ ID NO: 79, SEQ ID NO: 81, SEQ ID NO: 85, SEQ ID NO: 89, SEQ ID NO: 93, SEQ ID NO: 97, SEQ ID NO: 101, SEQ ID NO: 105, SEQ ID NO: 109, SEQ ID NO: 113, SEQ ID NO: 117 and SEQ ID NO: 121.

2. An isolated antibody which specifically binds to human TNFα or an antigen binding fragment thereof, wherein the VL domain of said antibody or fragment thereof comprises an amino acid sequence which is either identical, or is identical except for one amino acid substitution in any one two, or three CDRs within said VL domain, to a VL amino acid sequence selected from the group consisting of: SEQ ID NO: 125, SEQ ID NO: 129, SEQ ID NO: 133, SEQ ID NO: 137, SEQ ID NO: 141, SEQ ID NO: 145, SEQ ID NO: 149, SEQ ID NO: 153, SEQ ID NO: 157, SEQ ID NO: 161, SEQ ID NO: 165, and SEQ ID NO: 224.

3. An isolated antibody which specifically binds to human TNFα or an antigen binding fragment thereof, wherein the VH and VL domains of said antibody or fragment thereof comprise, respectively, amino acid sequences identical, or identical except for one amino acid substitution in any one, two, or three CDRs within said VH and VL domains, to VH and VL amino acid sequences selected from the group consisting of: SEQ ID NO: 3 and SEQ ID NO:141, SEQ ID NO:7 and SEQ ID NO:141, SEQ ID NO:11 and SEQ ID NO:141, SEQ ID NO:15 and SEQ ID NO:141, SEQ ID NO:19 and SEQ ID NO:141, SEQ ID NO:23 and SEQ ID NO:141, SEQ ID NO:27 and SEQ ID NO:141, SEQ ID NO:31 and SEQ ID NO:141, SEQ ID NO:3 and SEQ ID NO:145, SEQ ID NO:3 and SEQ ID NO:149, SEQ ID NO:3 and SEQ ID NO:153, 3 and SEQ ID NO:157, SEQ ID NO:35 and SEQ ID NO:141, SEQ ID NO:37 and SEQ ID NO:141, SEQ ID NO:39 and SEQ ID NO:141, SEQ ID NO:41 and SEQ ID NO:141, SEQ ID NO:43 and SEQ ID NO:141, SEQ ID NO:45 and SEQ ID NO:141, SEQ ID NO:47 and SEQ ID NO:141, SEQ ID NO:49 and SEQ ID NO:141, SEQ ID NO:35 and SEQ ID NO:145, SEQ ID NO:43 and SEQ ID NO:145, SEQ ID NO:45 and SEQ ID NO:145, SEQ ID NO:47 and SEQ ID NO:145, SEQ ID NO:49 and SEQ ID NO:145, SEQ ID NO:51 and SEQ ID NO:145, SEQ ID NO:53 and SEQ ID NO:145, SEQ ID NO:55 and SEQ ID NO:145, SEQ ID NO:57 and SEQ ID NO:145, SEQ ID NO:59 and SEQ ID NO:145, SEQ ID NO:61 and SEQ ID NO:145, SEQ ID NO:63 and SEQ ID NO:145, SEQ ID NO:65 and SEQ ID NO:145, SEQ ID NO:67 and SEQ ID NO:145, SEQ ID NO:69 and SEQ ID NO:145, SEQ ID NO:225 and SEQ ID NO:145, SEQ ID NO:55 and SEQ ID NO:161, SEQ ID NO:63 and SEQ ID NO:161, SEQ ID NO:71 and SEQ ID NO:161, SEQ ID NO:73 and SEQ ID NO:161, SEQ ID NO:75 and SEQ ID NO:161, SEQ ID NO:77 and SEQ ID NO:161, SEQ ID NO:79 and SEQ ID NO:161, SEQ ID NO:79 and SEQ ID NO:165, SEQ ID NO:71 and SEQ ID NO:165, and SEQ ID NO:79 and SEQ ID NO:224.

4. An isolated antibody which specifically binds to human TNFα or an antigen binding fragment thereof, wherein said antibody or fragment thereof comprises VL-CDR1, VL-CDR2, VL-CDR3, VH-CDR1, VH-CDR2, and VH-CDR3 amino acid sequences either identical, or identical except for one amino acid substitution in any one or more of said CDR sequences, to the following groups of VL-CDR1, VL-CDR2, VL-CDR3, VH-CDR1, VH-CDR2, and VH-CDR3 amino acid sequences:

VL-CDR1, VL-CDR2, and VL-CDR3 amino acid sequences SEQ ID NOs: 142, 143, and 144; and VH-CDR1, VH-CDR2, and VH-CDR3 amino acid sequences SEQ ID NOs: 28, 29, and 30; SEQ ID NOs: 8, 9, and 10; SEQ ID NOs: 12, 13, and 14; SEQ ID NOs: 16, 17, and 18; SEQ ID NOs: 20, 21, and 22; SEQ ID NOs: 24, 25, and 26; SEQ ID NOs: 4, 5, and 6; SEQ ID NOs: 32, 33, and 34; SEQ ID NOs: 4, 5, and 36; SEQ ID NOs: 4, 5, and 38; SEQ ID NOs: 4, 5, and 40; SEQ ID NOs: 4, 5, and 42; SEQ ID NOs: 4, 5, and 44; SEQ ID NOs: 4, 5, and 46; SEQ ID NOs: 4, 5, and 48; or SEQ ID NOs: 4, 5, and 50;

VL-CDR1, VL-CDR2, and VL-CDR3 amino acid sequences SEQ ID NOs: 146, 147, and 148; and VH-CDR1, VH-CDR2, and VH-CDR3 amino acid sequences SEQ ID NOs: 4, 5, and 6; SEQ ID NOs: 4, 5, and 36; SEQ ID NOs: 4, 5, and 44; SEQ ID NOs: 4, 5, and 46; SEQ ID NOs: 4, 5, and 48; SEQ ID NOs: 4, 5, and 50; SEQ ID NOs: 4, 5, and 46; SEQ ID NOs: 4, 5, and 48; SEQ ID NOs: 4, 5, and 52; SEQ ID NOs: 32, 33, and 54; SEQ ID NOs: 32, 33, and 56; SEQ ID NOs: 32, 33, and 58; SEQ ID NOs: 32, 33, and 60; SEQ ID NOs: 32, 33, and 62; SEQ ID NOs: 32, 33, and 64; SEQ ID NOs: 8, 9, and 66; SEQ ID NOs: 8, 9, and 68; SEQ ID NOs: 8, 9, and 70; or SEQ ID NOs: 32, 226, and 64;

VL-CDR1, VL-CDR2, and VL-CDR3 amino acid sequences SEQ ID NOs: 150, 151, and 152; and VH-CDR1, VH-CDR2, and VH-CDR3 amino acid sequences SEQ ID NOs: 4, 5, and 6;

VL-CDR1, VL-CDR2, and VL-CDR3 amino acid sequences SEQ ID NOs: 154, 155, and 156; and VH-CDR1, VH-CDR2, and VH-CDR3 amino acid sequences SEQ ID NOs: 4, 5, and 6;

VL-CDR1, VL-CDR2, and VL-CDR3 amino acid sequences SEQ ID NOs: 158, 159, and 160; and VH-CDR1, VH-CDR2, and VH-CDR3 amino acid sequences SEQ ID NOs: 4, 5, and 6;

VL-CDR1, VL-CDR2, and VL-CDR3 amino acid sequences SEQ ID NOs: 162, 163, and 164; and VH-CDR1, VH-CDR2, and VH-CDR3 amino acid sequences SEQ ID NOs: 32, 33, and 54; SEQ ID NOs: 32, 33, and 64; SEQ ID NOs: 32, 72, and 64; SEQ ID NOs: 32, 74, and 64; SEQ ID NOs: 32, 76, and 64; SEQ ID NOs: 32, 78, and 64; or SEQ ID NOs: 32, 80, and 64;

VL-CDR1, VL-CDR2, and VL-CDR3 amino acid sequences SEQ ID NOs: 166, 167, and 168; and VH-CDR1, VH-CDR2, and VH-CDR3 amino acid sequences SEQ ID NOs: 32, 80, and 64; or SEQ ID NOs: 32, 72 and 64; and VL-CDR1, VL-CDR2, and VL-CDR3 amino acid sequences SEQ ID NOs: 166, 163, and 168; and VH-CDR1, VH-CDR2, and VH-CDR3 amino acid sequences SEQ ID NOs: 32, 80, and 64.

5. The antibody or fragment thereof of claim 4, which specifically binds to an TNFα polypeptide or fragment thereof, or an TNFα variant polypeptide with an affinity characterized by a dissociation constant (KD) no greater than $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $5.7\times10^{-12}$ M, $8.4\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

6. The antibody or fragment thereof of claim 4, further comprising a heterologous polypeptide fused thereto.

7. A composition comprising the antibody or fragment thereof of claim 4, and a carrier.

8. The antibody or fragment thereof of claim 4, wherein said VL-CDR3 amino acid sequence is identical to SEQ ID NO: 144, except for an amino acid substitution that is Y→W at position 3; H→F at position 4; H→M at position 4; or S→A at position 5.

9. The antibody or fragment thereof of claim 4, wherein said VH-CDR3 amino acid sequence is identical to SEQ ID NO: 6, except for an amino acid substitution that is N→T at position 1; N→L at position 1; Y→A at position 3; T→L at position 6; Y→F at position 7; Y→M at position 7; Y→L at position 7; Y→H at position 7; or Y→V at position 7.

10. The antibody or fragment thereof of claim 4, wherein said VH-CDR3 amino acid sequence is identical to SEQ ID NO: 34, except for an amino acid substitution that is N→T at position 1; Y→H at position 7; Y→M at position 7; Y→I at position 7; Y→F at position 7; or Y→L at position 7.

11. The antibody or fragment thereof of claim 4, wherein said VH-CDR3 amino acid sequence is identical to SEQ ID NO: 10, except for an amino acid substitution that is Y→H at position 7; Y→M at position 7; Y→F at position 7; or Y→L at position 7.

12. The isolated antibody or fragment thereof of claim 1, wherein said amino acid sequence is identical, or is identical except for one amino acid substitution in any one, two, or three CDRs, to an amino acid sequence selected from the group consisting of SEQ ID NO: 71 and SEQ ID NO: 79.

13. The isolated antibody or fragment thereof of claim 2, wherein said amino acid sequence is identical, or is identical except for one amino acid substitution in any one, two, or three CDRs, to SEQ ID NO: 165.

14. The isolated antibody or fragment thereof of claim 3, wherein said VH and VL amino acid sequences, respectively, are identical, or are identical except for one amino acid substitution in any one, two, or three CDRs, to VH and VL amino acid sequences selected from the group consisting of SEQ ID NO: 79 and SEQ ID NO: 165; and SEQ ID NO: 71 and SEQ ID NO: 165.

15. The isolated antibody or fragment thereof of claim 4, wherein said VH-CDR1, VH-CDR2, and VH-CDR3 amino acid sequences are identical, or are identical except for one amino acid substitution in any one, two, or three CDRs, to amino acid sequences selected from the group consisting of SEQ ID NO: 32, 72, and 64; and SEQ ID NO: 32, 80, and 64.

16. The isolated antibody or fragment thereof of claim 4, wherein said VL-CDR1, VL-CDR2, and VL-CDR3 amino acid sequences are identical, or are identical except for one amino acid substitution in any one, two, or three CDRs, to SEQ ID NO: 166, 167, and 168.

17. The isolated antibody or fragment thereof of claim 4, wherein said VL-CDR1, VL-CDR2, VL-CDR3, VH-CDR1, VH-CDR2, and VH-CDR3, amino acid sequences are identical, or are identical except for one amino acid substitution in any one, two, or three CDRs to amino acid sequences selected from the group consisting of SEQ ID NOs: 166, 167, 168, 32, 72, and 64; and SEQ ID NOs: 166, 167, 168, 32, 80, and 64.

18. The antibody or fragment thereof of claim 14, which is an Fab fragment.

19. The antibody or fragment thereof of claim 14, which is an Fab' fragment.

20. The antibody or fragment thereof of claim 14, which is an F(ab')2 fragment.

21. The antibody or fragment thereof of claim 14, which is an Fv fragment.

22. The antibody or fragment thereof of claim 14, which is a single chain antibody.

23. The antibody or fragment thereof of claim 14, which comprises a light chain constant region selected from the group consisting of a human kappa constant region and a human lambda constant region.

24. The antibody or fragment thereof of claim 14, which comprises at least a heavy chain constant region or fragment thereof.

25. The antibody or fragment thereof of claim 24, wherein said heavy chain constant region or fragment thereof is human IgG1, IgG2, IgG3 or IgG4.

26. The antibody or fragment thereof of claim 25, wherein said IgG4 is mutagenized to remove glycosylation sites.

27. The antibody or fragment thereof of claim 14, which preferentially binds to a human TNFα polypeptide or fragment thereof, relative to a murine TNFα polypeptide or fragment thereof or a non-human primate TNFα polypeptide or fragment thereof.

28. The antibody or fragment thereof of claim 14, which binds to human TNFα polypeptide or fragment thereof, and also binds to a non-human primate TNFα polypeptide or fragment thereof.

29. The antibody or fragment thereof of claim 28, wherein said TNFα is inhibited from binding to its receptor.

30. The antibody or fragment thereof of claim 14, wherein said antibody is conjugated to an agent selected from the group consisting of cytotoxic agent, a therapeutic agent, cytostatic agent, a biological toxin, a prodrug, a peptide, a protein, an enzyme, a virus, a lipid, a biological response modifier, pharmaceutical agent, a lymphokine, a heterologous antibody or fragment thereof, a detectable label, polyethylene glycol (PEG), and a combination of two or more of any said agents.

31. The antibody or fragment thereof of claim 30, wherein said cytotoxic agent is selected from the group consisting of a radionuclide, a biotoxin, an enzymatically active toxin, a cytostatic or cytotoxic therapeutic agent, an immunologically active ligand, a biological response modifier, or a combination of two or more of any said cytotoxic agents.

32. The antibody or fragment thereof of claim 30, wherein said detectable label is selected from the group consisting of an enzyme, a fluorescent label, a chemiluminescent label, a bioluminescent label, a radioactive label, or a combination of two or more of any said detectable labels.

* * * * *